(12) United States Patent
Brockschnieder et al.

(10) Patent No.: US 12,390,508 B2
(45) Date of Patent: Aug. 19, 2025

(54) BRAIN NATRIURETIC PEPTIDE ENGRAFTED ANTIBODIES

(71) Applicant: Boehringer Ingelheim International GmbH, Ingelheim am Rhein (DE)

(72) Inventors: Damian Brockschnieder, Haan (DE); Jan Tebbe, Cologne (DE); Andreas Wilmen, Cologne (DE); Frank Wunder, Wuppertal (DE)

(73) Assignee: BOEHRINGER INGELHEIM INTERNATIONAL GMBH (DE)

( * ) Notice: Subject to any disclaimer, the term of this patent is extended or adjusted under 35 U.S.C. 154(b) by 1192 days.

(21) Appl. No.: 17/046,648

(22) PCT Filed: Apr. 10, 2019

(86) PCT No.: PCT/EP2019/059101
§ 371 (c)(1),
(2) Date: Oct. 9, 2020

(87) PCT Pub. No.: WO2019/197475
PCT Pub. Date: Oct. 17, 2019

(65) Prior Publication Data
US 2021/0147504 A1  May 20, 2021

(30) Foreign Application Priority Data
Apr. 12, 2018 (EP) .................................. 18167106

(51) Int. Cl.
| A61K 38/00 | (2006.01) |
| A61K 39/00 | (2006.01) |
| A61P 9/12 | (2006.01) |
| C07K 14/58 | (2006.01) |
| C07K 16/00 | (2006.01) |
| A61P 9/04 | (2006.01) |

(52) U.S. Cl.
CPC ............... *A61K 38/00* (2013.01); *A61P 9/12* (2018.01); *C07K 14/58* (2013.01); *C07K 16/00* (2013.01); *A61K 2039/505* (2013.01); *A61P 9/04* (2018.01); *C07K 2317/21* (2013.01); *C07K 2317/24* (2013.01); *C07K 2317/565* (2013.01); *C07K 2317/94* (2013.01); *C07K 2318/10* (2013.01); *C07K 2319/31* (2013.01)

(58) Field of Classification Search
CPC ........................ C07K 16/00; C07K 2317/21; C07K 2317/24; C07K 2317/565; C07K 2318/10; C07K 2319/31; C07K 14/58; C07K 2317/567; C07K 2317/94; C07K 2317/52; C07K 2319/00; A61K 38/00; A61K 2039/505; A61P 9/12; A61P 9/04
See application file for complete search history.

(56) References Cited

U.S. PATENT DOCUMENTS

| 4,399,216 A | 8/1983 | Axel |
| 4,510,245 A | 4/1985 | Cousens |
| 4,634,665 A | 1/1987 | Axel |
| 4,816,397 A | 3/1989 | Boss |
| 4,968,615 A | 11/1990 | Koszinowski |
| 5,168,062 A | 12/1992 | Stinski |
| 5,179,017 A | 1/1993 | Axel |
| 5,288,931 A | 2/1994 | Chang |
| 7,112,660 B1 | 9/2006 | Domingues |
| 7,521,424 B2 | 4/2009 | Rosen |
| 7,705,043 B2 | 4/2010 | Alonso-alija et al. |
| 7,781,470 B2 | 8/2010 | Alonso-alija et al. |
| 8,796,324 B2 | 8/2014 | Bruggemeier et al. |
| 9,193,777 B2 | 11/2015 | Burnett, Jr. |
| 9,687,476 B2 | 6/2017 | Fürstner et al. |
| 9,993,476 B2 | 6/2018 | Follmann et al. |
| 2003/0045474 A1 | 3/2003 | Sailer |
| 2004/0253242 A1 | 12/2004 | Bowdish |

(Continued)

FOREIGN PATENT DOCUMENTS

| CN | 103087191 A | 5/2013 |
| CN | 103649116 A | 3/2014 |

(Continued)

OTHER PUBLICATIONS

Mezo, A.R., et al. (2012). "Atrial Natriuretic Peptide-Fc, ANP-Fc, Fusion Proteins: Semisynthesis, In Vitro Activity and Pharmacokinetics in Rats," American Chemical Society, 23: 518-526.

(Continued)

*Primary Examiner* — Olga N Chernyshev
(74) *Attorney, Agent, or Firm* — MORRISON & FOERSTER LLP

(57) ABSTRACT

The present invention relates to an antibody or a fragment thereof comprising at least one heterologous amino acid sequence incorporated within at least one CDR region of said antibody or fragment thereof, wherein said at least one heterologous amino acid sequence comprises an N-terminal linker sequence (Ntls), a Brain Natriuretic Peptide (BNP) and a C-terminal linker sequence (Ctls). Optionally, at least a portion of said at least one CDR region is replaced by said at least one heterologous amino acid sequence incorporated therein. The present invention further relates to such antibody or fragment thereof for use in a method for treatment, a composition comprising such antibody or fragment thereof, a nucleic acid or a mixture of nucleic acids encoding such antibody or fragment thereof, a host cell comprising such nucleic acid or such mixture of nucleic acids and to a process for producing such antibody or fragment thereof.

Figure 1:
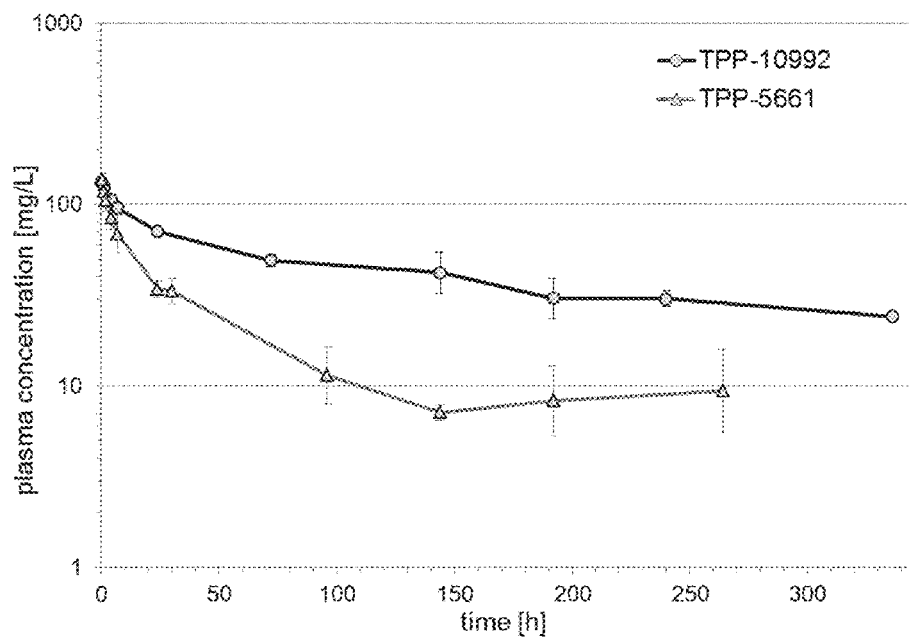

17 Claims, 13 Drawing Sheets
Specification includes a Sequence Listing.

(56) References Cited

U.S. PATENT DOCUMENTS

| | | |
|---|---|---|
| 2007/0292411 A1 | 12/2007 | Salcedo |
| 2010/0310561 A1 | 12/2010 | Canada |
| 2012/0114659 A1 | 5/2012 | Waterman |
| 2014/0148390 A1 | 5/2014 | Haupts |
| 2014/0154743 A1 | 6/2014 | Levy |
| 2021/0079056 A1 | 3/2021 | Brockschnieder |
| 2021/0139555 A1 | 5/2021 | Mayer-Bartschmid et al. |

FOREIGN PATENT DOCUMENTS

| | | |
|---|---|---|
| EP | 2432489 B1 | 10/2016 |
| WO | 0006568 A1 | 2/2000 |
| WO | 0006569 A1 | 2/2000 |
| WO | 0119355 A2 | 3/2001 |
| WO | 0119776 A2 | 3/2001 |
| WO | 0119778 A1 | 3/2001 |
| WO | 0119780 A2 | 3/2001 |
| WO | 0119780 A3 | 9/2001 |
| WO | 0119776 A3 | 11/2001 |
| WO | 0242301 A1 | 5/2002 |
| WO | 02070462 A1 | 9/2002 |
| WO | 02070510 A2 | 9/2002 |
| WO | 02078612 A2 | 10/2002 |
| WO | 02070510 A3 | 1/2003 |
| WO | 03095451 A1 | 11/2003 |
| WO | 2005060642 A2 | 7/2005 |
| WO | 2005082004 A2 | 9/2005 |
| WO | 2005060642 A3 | 10/2005 |
| WO | 2006107124 A1 | 10/2006 |
| WO | 2008079995 A2 | 7/2008 |
| WO | 2008079995 A3 | 8/2008 |
| WO | 2005082004 A3 | 10/2008 |
| WO | 2008136611 A1 | 11/2008 |
| WO | 2008154226 A1 | 12/2008 |
| WO | 2009033094 A2 | 3/2009 |
| WO | 2010054007 A1 | 5/2010 |
| WO | 2010105770 A1 | 9/2010 |
| WO | 2010117760 A2 | 10/2010 |
| WO | 2010117760 A3 | 11/2010 |
| WO | 2010135541 A2 | 11/2010 |
| WO | 2011104322 A1 | 9/2011 |
| WO | 2011147809 A1 | 12/2011 |
| WO | 2012004258 A1 | 1/2012 |
| WO | 2012028647 A1 | 3/2012 |
| WO | 2012059549 A1 | 5/2012 |
| WO | 2015006337 A2 | 1/2015 |
| WO | 2016071212 A1 | 5/2016 |

OTHER PUBLICATIONS

Peng, J., et al. (Apr. 25, 2018). "Preparation of anti hCG single domain antibodies using antigen binding peptide engrafted antibody technology," Chinese Journal of Biotechnology, 34(4): 569-577. English translation of abstract only.

Anand-Srivastava, M.B. (Jun. 2005). "Natriuretic peptide receptor-C signaling and regulation," Peptides 26(6): 1044-1059.

Anker, S.D. et al. (Mar. 21, 2015). "Ularitide for the treatment of acute decompensated heart failure: from preclinical to clinical studies," Eur Heart J. 36 (12): 715-723.

Baliga, R.S. et al. (Jul. 2014). "Intrinsic defence capacity and therapeutic potential of natriuretic peptides in pulmonary hypertension associated with lung fibrosis," British Journal of Pharmacology 171(14): 3463-3475.

Buglioni, A. et al. (2016). "New Pharmacological Strategies to Increase cGMP," Annu Rev .Med. 67: 229-243.

Dahrouj, M. et al. (Jan. 2013). "C-Type Natriuretic Peptide Protects the Retinal Pigment Epithelium against Advanced Glycation End Product-Induced Barrier Dysfunction." J Pharmacol Exp Ther. 344 (1): 96-102.

Edelson, J.D. et al. (Apr. 2013). "In vitro and in vivo pharmacological profile of PL-3994, a novel cyclic peptide Hept-cyclo(Cys-His-Phe-D-Ala-Gly-Arg-D-Nle-Asp-Arg-Ile-Ser-Cys)-Tyr-[Argmimetic]-NH2) natriuretic peptide receptor-A agonist that is resistant to neutral endopeptidase and acts as a bronchodilator," Pulmonary Pharmacology & Therapeutics 26: 229-238.

Hunt, P.J. et al. (1994). "Bioactivity and Metabolism of C-Type Natriuretic Peptide in Normal Man*" Journal of Clinical Endocrinology and Metabolism, 78(6):1428-1435.

International Search Report mailed Oct. 17, 2019 for PCT International Application No. PCT/EP2019/059101, filed Apr. 10, 2019, 4 pages.

Kimura, K. et al. (2007). "ANP is cleared much faster than BNP in patients with congestive heart failure," Eur J Clin Pharmacol, 63:699-702.

Kimura, T. et al. (2016). "C-type natriuretic peptide ameliorates pulmonary fibrosis by acting on lung fibroblasts in mice," Respiratory Research, 17(19):1-17.

Knowles, J.W. et al. (2001). "Pressure-independent enhancement of cardiac hypertrophy in natriuretic peptide receptor A-deficient mice," J.Clin. Invest. 107(8): 975-984.

Lee, C. et al. (2007). "Pharmacokinetic and pharmacodynamic study of a novel chimeric natriuretic peptide, CD-NP, in the normal dog," BMC Pharmacology 7 (Suppl I): P38.

Lumsden, N.G. et al. (2010). "C-type Natriuretic Peptide (CNP): Cardiovascular Roles and Potential as a Therapeutic Target," Current Pharmaceutical Design, 16:4080-4088.

McKie, P. et al. (2010) "CD-NP: An Innovative Designer Natriuretic Peptide Activator of Particulate Guanylyl Cyclase Receptors for Cardiorenal Disease," Curr Heart Fail Rep, 7:93-99.

McKie, P.M. et al. (Dec. 2010). "A Novel Atrial Natriuretic Peptide Based Therapeutic in Experimental Angiotensin II Mediated Acute Hypertension," Hypertension 56 (6): 1152-1159.

Mitaka, C. et al. (2014) "Effects of atrial natriuretic peptide on inter-organ crosstalk among the kidney, lung, and heart in a rat model of renal ischemia-reperfusion injury," Intensive Care Medicine Experimental, 2(28):1-17.

Moyes, A.J. et al. (2014), "Endothelial C-type natriuretic peptide maintains vascular homeostasis," The Journal of Clinical Investigation, 124(9):4039-4051.

Pan, S. et al. (Jul. 7, 2009). "Biodesign of a renal-protective peptide based on alternative splicing of B-type natriuretic peptide," PNAS 106 (27): 11282-11287.

Potter, L. et al. (2009) "Natriuretic Peptides: Their Structures, Receptors, Physiologic Functions and Therapeutic Applications," Handb Exp Pharmacol., 191:341-66.

Wang, W. et al. (Nov. 2004). "AlbuBNP, a Recombinant B-TypeNatriuretic Peptide and Human Serum Albumin Fusion Hormone, asa Long-Term Therapy of Congestive Heart Failure," Pharmaceutical Research, Springer 21(11):2105-2110.

Wendt, D. J. et al. (Apr. 2015). "Neutral Endopeptidase-Resistant C-Type Natriuretic Peptide Variant Represents a New Therapeutic Approach for Treatment of Fibroblast Growth Factor Receptor 3-Related Dwarfism," J. Pharmacol Exp Ther. 353: 132-149.

Werner, F. et al. (2016) "Endothelial actions of atrial natriuretic peptide prevent pulmonary hypertension in mice," Basic Res Cardiol 111(22):1-16.

Woods, R. (2004) "Cardioprotective Functions of Atrial Natriuretic Peptide and B-Type Natriuretic Peptide: A Brief Review," Clinical and Experimental Pharmacology and Physiology, 31:791-794.

Yasoda, A. et al. (2009). "Effects of natriuretic peptides on endochondral bone growth," Clinical Calcium, 17(7):103-108. English Abstract.

Fillippovic O. B. et al., Biochemical basis for human life activity. Textbook for for college-level.—M.: Vlados, 2005.—407 p. il.; see p. 49-50 and 70. (Partial English Translation only.).

Roitt A. et al. (2000), Immunology. Translation from English—M.: Mir, 2000.—592 p. ill.; p. 150. (Partial English Translation only.).

Šarošina I. A. et al. (2003). "The role of natriuretic peptides for the diagnosis of heart failure," Russian Journal of Cardiology, N 2(40): 81-86.

Alaoui-Ismaili, M.H. et al. (2009). "Design of Second Generation Therapeutic Recombinant Bone Morphogenetic Proteins," Cytokine Growth Factor Rev. 20:501-507.

(56) References Cited

OTHER PUBLICATIONS

Bernier, V. et al. (2004, e-pub. Aug. 23, 2004). "Pharmacological Chaperone Action on G-protein-coupled Receptors," Curr. Opin. Pharmacol. 4:528-533.

Bhattacharya, R. et al. (Mar. 15, 2017). "Impact of Genetic Variations on Three Dimensional Structure and Function of Proteins," PLoS ONE 12(3):e0171355, 22 pages.

Fenton, A. W. et al. (2020, e-pub. Jun. 7, 2020). "Rheostat Positions: A New Classification of Protein Positions Relevant to Pharmacogenomics," Medicinal Chemistry Research 29:1133-1146.

Guo, H. H. et al. (Jun. 22, 2004). "Protein Tolerance to Random Amino Acid Change," PNAS 101(25):9205-9210.

International Search Report and Written Opinion, mailed May 17, 2019, for PCT Application No. PCT/EP2019/059101, filed Apr. 10, 2019, 10 pages.

International Search Report and Written Opinion, mailed May 20, 2019, for PCT Application No. PCT/EP2019/059103, filed Apr. 10, 2019, 11 pages.

Teng, S. et al. (2010, e-pub. Feb. 4, 2011). "Structural Assessment of the Effects of Amino Acid Substitutions on Protein Stability and Protein-Protein Interaction," Int J Comput Biol Drug Des. 3(4):334-349.

Tobi, D. et al. (Dec. 14, 2005). "Structural Changes Involved in Protein Binding Correlate with Intrinsic Motions of Proteins in the Unbound State," PNAS 102(52):18908-18913.

Tokuriki, N. et al. (2009, e-pub. Sep. 16, 2009). "Stability Effects of Mutations and Protein Evolvability," Curr. Opin. Struc. Biol. 19:596-604.

Ulloa-Aguirre, A. et al. (2004). "Pharmacologic Rescue of Conformationally-Defective Proteins: Implications for the Treatment of Human Disease," Traffic 5:821-837.

BRAIN NATRIURETIC PEPTIDE ENGRAFTED ANTIBODIES

CROSS REFERENCE TO RELATED APPLICATIONS

This application is a national stage application under 35 U.S.C. § 371 of International Application No. PCT/EP2019/059101, filed internationally on Apr. 10, 2019, which claims the benefit of priority to European Application No. 18167106.6, filed Apr. 12, 2018.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052044500SUBSEQLIST.TXT, date recorded: May 26, 2022, size: 215,279 bytes).

FIELD OF THE INVENTION

The present invention relates to an antibody or a fragment thereof comprising at least one heterologous amino acid sequence incorporated within at least one CDR region of said antibody or fragment thereof, wherein said at least one heterologous amino acid sequence comprises an N-terminal linker sequence (Ntls), a Brain Natriuretic Peptide (BNP) and a C-terminal linker sequence (Ctls). Optionally, at least a portion of said at least one CDR region is replaced by said at least one heterologous amino acid sequence incorporated therein. At least 12 amino acid residues are present between amino acid residue HC (heavy chain) res25 according to Kabat and the first amino acid residue of the BNP in case of an incorporation of said heterologous amino acid sequence within CDRH1; amino acid residue HC res51 according to Kabat and the first amino acid residue of the BNP in case of an incorporation of said heterologous amino acid sequence within CDRH2; amino acid residue HC res92 according to Kabat and the first amino acid residue of the BNP in case of an incorporation of said heterologous amino acid sequence within CDRH3; amino acid residue LC (light chain) res26 according to Kabat and the first amino acid residue of the BNP in case of an incorporation of said heterologous amino acid sequence within CDRL1; amino acid residue LC res49 according to Kabat and the first amino acid residue of the BNP in case of an incorporation of said heterologous amino acid sequence within CDRL2; and/or amino acid residue LC res88 according to Kabat and the first amino acid residue of the BNP in case of an incorporation of said heterologous amino acid sequence within CDRL3. Additionally, at least 9 amino acid residues are present between the last amino acid residue of the BNP and amino acid residue HC res35a according to Kabat in case of an incorporation of said heterologous amino acid sequence within CDRH1; amino acid residue HC res57 according to Kabat in case of an incorporation of said heterologous amino acid sequence within CDRH2; amino acid residue HC res106 according to Kabat in case of an incorporation of said heterologous amino acid sequence within CDRH3; amino acid residue LC res 32 according to Kabat in case of an incorporation of said heterologous amino acid sequence within CDRL1; amino acid residue LC res57 according to Kabat in case of an incorporation of said heterologous amino acid sequence within CDRL2; and/or amino acid residue LC res98 according to Kabat in case of an incorporation of said heterologous amino acid sequence within CDRL3. The present invention further relates to such antibody or fragment thereof for use in a method for treatment, a composition comprising such antibody or fragment thereof, a nucleic acid or a mixture of nucleic acids encoding such antibody or fragment thereof, a host cell comprising such nucleic acid or such mixture of nucleic acids and to a process for producing such antibody or fragment thereof.

BACKGROUND OF THE INVENTION

Natriuretic peptides are a family of three structurally related peptides with neurohumoral actions. Atrial Natriuretic Peptide (ANP) is a peptide of 28 amino acids comprising a central ring structure formed by a disulfide bridge between cysteine residues 7 and 23. Human ANP is expressed as a 153 amino acid long pre-pro-hormone in atrial myocyte cells. Signal peptide cleavage yields the prohormone form, which is subsequently further cleaved into the mature ANP and the N-terminal remnant, known as NT-proANP. Similar to ANP, also Brain Natriuretic Peptide (BNP) and C-Type Natriuretic Peptide (CNP) are produced from precursor proteins and comprise a central ring structure. ANP is mainly produced and released by cardiomyocytes of the left and right heart atria, whereas BNP is mainly produced by cardiomyocytes of the ventricles. CNP is synthesized by endothelial cells of blood vessels. Apart from these locations natriuretic peptides are also produced in smaller amounts in other parts of the body, e.g., in brain, kidney and adrenal gland. Natriuretic peptides are encoded by three separate genes, NPPA, NPPB, and NPPC. The amino acid sequences of the three peptides are highly conserved in mammals (Potter et al., Handb Exp Pharmacol. 2009; (191):341-66). Yet, significant sequence modifications of natriuretic peptides such as truncations, amino acid exchanges as well chimeric fusions (e.g. CD-NP (McKie et al., Curr Heart Fail Rep. 2010 September; 7 (3): 93-9)) have been described to result in potent natriuretic peptides that activate or bind to cellular receptors and can elicit relevant physiological effects.

Natriuretic peptides bind to three different, membrane-bound receptor types—NPR-A, NPR-B, and NPR-C—thereby mediating their biological effects. ANP and BNP bind with greatest affinity to NPR-A; in contrast, CNP has the highest affinity for the NPR-B receptor. NPR-A and NPR-B comprise a (particulate) guanylate cyclase domain (pGC) whose enzymatic activity causes an increase in (intracellular) cyclic guanosine monophosphate (cGMP). As a second messenger, cGMP regulates diverse cellular processes. The NPR-C receptor exhibits no guanylate cyclase activity and is also termed “clearance” receptor, as it can bind natriuretic peptides, which leads to their degradation by endocytosis. An additional signaling function of the NPR-C receptor via modulation of cAMP has been described (Anand-Srivastava, Peptides. 2005 June; 26 (6): 1044-59).

The cardiac hormones ANP and BNP are excreted upon stretching of the ventricles and atria, e.g. due to excessive plasma volume. They exert vasodilating effects via relaxation of vascular smooth muscle and lead to a reduction in blood pressure. In the kidney ANP causes i.a. an increase in urinary excretion (diuresis), as well as an increase in the concentration of sodium ions in the urine (natriuresis). ANP is considered to constitute a compensatory antagonist of the renin-angiotensin-aldosterone system (RAAS), which is over-activated in a number of cardiovascular diseases. In addition, ANP exerts other neuro-humoral effects, including an inhibitory effect on the sympathetic nervous system, as well as a complex regulatory effect on the baroreflex (Woods et al., Clin Exp Pharmacol Physiol. 2004 November; 31 (11): 791-4). For ANP, as well as BNP and CNP, anti-inflammatory, anti-hypertrophic and anti-fibrotic effects have been demonstrated in animal models for different diseases (e.g. Knowles et al., 2001, J. Clin. Invest. 107: 975-984; Dahrouj et al., J Pharmacol Exp Ther. 2013 January; 344 (1): 96-102; Baliga et al., Br J Pharmacol. 2014 July; 171 (14): 3463-75; Mitaka et al. Intensive Care Med Exp. 2014 December; 2 (1): 28; Werner et al., Basic Res Cardiol. 2016 March; 111 (2): 22; Kimura et al., Respir Res. 2016 Feb. 19; 17: 19). Activation of NPR-B by CNP is plays a significant role in bone growth (Yasoda et al., Clin. Calcium. 2009 July; 19 (7): 1003-8) and vascular endothelium integrity (Moyes et al., J Clin Invest. 2014 September; 124 (9): 4039-51).

The broad spectrum of physiological effects of natriuretic peptides and their receptors make them attractive targets in drug discovery (Lumsden et al., Curr Pharm Des. 2010; 16 (37): 4080-8; Buglioni et al., Annu Rev Med. 2016; 67: 229-43). For example, the natriuretic cGMP system may be suppressed under various pathophysiological conditions, which may result in hypertension, increased cell proliferation, fibrosis, inflammation, endothelial dysfunction, diabetes, metabolic syndrome, atherosclerosis, cardiac insufficiency, myocardial infarction, pulmonary hypertension, ocular and renal diseases, bone disorders, stroke and/or sexual dysfunction.

A major hurdle for the therapeutic use of natriuretic peptides is their very short plasma half-life of only a few minutes in the organism (Hunt et al., J Clin Endocrinol Metab. 1994 June; 78 (6): 1428-35; Kimura et al., Eur J Clin Pharmacol. 2007 July; 63 (7): 699-702). In addition to endocytosis by the NPR-C receptor, the natriuretic peptides are efficiently proteolytically degraded by the enzymes neprilysin (NEP) and insulin degrading enzyme (IDE). The associated short-term biological effects of administered natriuretic peptides have restricted their therapeutic use primarily to acute indications. For example, infusions of recombinant carperitide (ANP) and nesiritide (BNP) are approved for the treatment of acute decompensated heart failure in different countries.

The treatment of chronic diseases would be greatly facilitated by the provision of NPR-A and NPR-B agonists with increased plasma half-lives, higher proteolytic stability and prolonged duration of action.

In recent years, several natriuretic peptide derivatives and variants have been described, e.g., CD-NP (McKie et al., Curr Heart Fail Rep. 2010 September; 7 (3): 93-9), ZD100/MANP (McKie et al., Hypertension. 2010 December; 56 (6): 1152-9), PL-3994 (Edelson et al., Pulm Pharmacol Ther. 2013 April; 26 (2): 229-38), Ularitide (Anker et al., Eur Heart J. 2015 Mar. 21; 36 (12): 715-2), ANX-042 (Pan et al., Proc Natl Acad Sci USA. 2009 Jul. 7; 106 (27): 11282-7) and BMN-111 (Wendt et al., J. Pharmacol Exp Ther. 2015 April; 353 (1): 132-49). The half-life of CD-NP is about 18.5 min (Lee et al., BMC Pharmacology 2007, 7 (Suppl I): P38). Further ANP and CNP derivatives are disclosed in U.S. Pat. No. 9,193,777 and EP 2 432 489 A, respectively.

In addition, natriuretic peptide fusions including Fc fusions, albumin fusion and PEGylated natriuretic peptides have been described. Natriuretic peptide-Fc fusions are for example disclosed in US 2010/0310561, WO 2008/154226, WO 2010/117760, WO 2006/107124, WO 2008/136611 and WO 2008/079995. Natriuretic peptide-albumin fusions are disclosed in U.S. Pat. No. 7,521,424 and US 2014/0148390 and PEGylated natriuretic peptides are disclosed in US 2014/0148390.

WO 2005/060642 describes the generation of ANP and BNP peptide engrafted antibody libraries obtained by inserting ANP or BNP with two randomized flanking amino acids on both ends into the CDRH3 region of a human tetanus toxoid specific antibody. Similarly, WO 2005/082004 discloses the generation of an ANP mimetic engrafted antibody library obtained by replacing the entire original CDRH3 region of a 2G12 antibody with an ANP mimetic peptide flanked by two random amino acid residues on either side. Neither one of WO 2005/060642 and WO 2005/082004 discloses any specific natriuretic peptide engrafted antibodies, let alone functionally characterizes such antibodies.

OBJECTS OF THE INVENTION

In view of the prior art it is an object of the present invention to provide novel natriuretic peptide receptor agonists with increased stability in serum as compared to naturally occurring wild type natriuretic peptides.

SUMMARY OF THE INVENTION

The above stated object is achieved by the teaching of the subject independent claims. The present inventors have surprisingly found that biologically active natriuretic peptide variants with significantly increased stability in serum as compared to naturally occurring wild type natriuretic peptides can be obtained by incorporating a natriuretic peptide amino acid sequence into one of the CDR regions of an immunoglobulin molecule or a fragment thereof, despite the short length and high sequence conservation of immunoglobulin CDR regions, which impose considerable conformational restrains to the incorporation of biologically active peptides. However, the activity of natriuretic peptides incorporated within an immunoglobulin CDR region was shown to vary considerably. The present inventors have found that the decisive factor for a successful incorporation yielding a biologically active natriuretic peptide variant is the number of amino acid residues between the incorporated natriuretic peptide and the nearest neighboring CDR-framework junctions N-terminal and C-terminal from the incorporated natriuretic peptide. Below a certain number of N-terminal and C-terminal flanking amino acid residues between natriuretic peptide and neighboring CDR-framework junctions only natriuretic peptide immunoglobulin fusion constructs with no or drastically reduced biological activity were obtained. Specific linker sequences flanking the incorporated natriuretic peptide were found to be especially advantageous for achieving high peptide activity, good expression levels and/or low protein fragmentation levels.

Thus, in a first aspect, the present invention relates to an antibody or a fragment thereof comprising at least one heterologous amino acid sequence incorporated within at least one CDR region of said antibody or fragment thereof, wherein said at least one heterologous amino acid sequence comprises an N-terminal linker sequence (Ntls), a natriuretic peptide and a C-terminal linker sequence (Ctls), wherein optionally at least a portion of said at least one CDR region is replaced by said at least one heterologous amino acid sequence incorporated therein, and wherein a) at least 12 amino acid residues are present between
   i) amino acid residue HC res25 according to Kabat (in the heavy chain having the amino acid sequence of SEQ ID NO 65 this corresponds to res S25) and the first amino acid residue of the natriuretic peptide in case of an incorporation of said heterologous amino acid sequence within CDRH1;

ii) amino acid residue HC res51 according to Kabat (in the heavy chain having the amino acid sequence of SEQ ID NO 65 this corresponds to res 151) and the first amino acid residue of the natriuretic peptide in case of an incorporation of said heterologous amino acid sequence within CDRH2;

iii) amino acid residue HC res92 according to Kabat (in the heavy chain having the amino acid sequence of SEQ ID NO 65 this corresponds to res C96) and the first amino acid residue of the natriuretic peptide in case of an incorporation of said heterologous amino acid sequence within CDRH3;

iv) amino acid residue LC res26 according to Kabat (in the light chain having the amino acid sequence of SEQ ID NO 66 this corresponds to res S25) and the first amino acid residue of the natriuretic peptide in case of an incorporation of said heterologous amino acid sequence within CDRL1;

v) amino acid residue LC res49 according to Kabat (in the light chain having the amino acid sequence of SEQ ID NO 66 this corresponds to res Y51) and the first amino acid residue of the natriuretic peptide in case of an incorporation of said heterologous amino acid sequence within CDRL2; and/or vi) amino acid residue LC res88 according to Kabat (in the light chain having the amino acid sequence of SEQ ID NO 66 this corresponds to res C90) and the first amino acid residue of the natriuretic peptide in case of an incorporation of said heterologous amino acid sequence within CDRL3; and wherein b) at least 9 amino acid residues are present between the last amino acid residue of the natriuretic peptide and i) amino acid residue HC res35a according to Kabat (in the heavy chain having the amino acid sequence of SEQ ID NO 65 this corresponds to res M34) in case of an incorporation of said heterologous amino acid sequence within CDRH1;

ii) amino acid residue HC res57 according to Kabat (in the heavy chain having the amino acid sequence of SEQ ID NO 65 this corresponds to res T58) in case of an incorporation of said heterologous amino acid sequence within CDRH2;

iii) amino acid residue HC res106 according to Kabat (in the heavy chain having the amino acid sequence of SEQ ID NO 65 this corresponds to res G111) in case of an incorporation of said heterologous amino acid sequence within CDRH3;

iv) amino acid residue LC res 32 according to Kabat (in the light chain having the amino acid sequence of SEQ ID NO 66 this corresponds to res D34) in case of an incorporation of said heterologous amino acid sequence within CDRL1;

v) amino acid residue LC res57 according to Kabat (in the light chain having the amino acid sequence of SEQ ID NO 66 this corresponds to res G59) in case of an incorporation of said heterologous amino acid sequence within CDRL2; and/or vi) amino acid residue LC res98 according to Kabat (in the light chain having the amino acid sequence of SEQ ID NO 66 this corresponds to res F102) in case of an incorporation of said heterologous amino acid sequence within CDRL3.

In further aspects, the present invention relates to such antibody or fragment thereof for use in a method for treatment, a composition comprising such antibody or fragment thereof, a nucleic acid or a mixture of nucleic acids encoding such antibody or fragment thereof, a host cell comprising such nucleic acid or such mixture of nucleic acids and to a process for producing such antibody or fragment thereof.

DETAILED DESCRIPTION OF THE INVENTION

The present invention may be understood more readily by reference to the following detailed description of the invention and the examples included therein.

In a first aspect, the present invention relates to an antibody or a fragment thereof comprising at least one heterologous amino acid sequence incorporated within at least one CDR region of said antibody or fragment thereof, wherein said at least one heterologous amino acid sequence comprises an N-terminal linker sequence (Ntls), a natriuretic peptide and a C-terminal linker sequence (Ctls), wherein optionally at least a portion of said at least one CDR region is replaced by said at least one heterologous amino acid sequence incorporated therein.

The present inventors have found that biologically active natriuretic peptide variants with significantly increased stability in serum as compared to naturally occurring wild type natriuretic peptides can be obtained by incorporating a natriuretic peptide amino acid sequence into one of the CDR regions of an immunoglobulin molecule or a fragment thereof. This finding was entirely unexpected. As is well known in the art, the short length and high sequence conservation of immunoglobulin CDR regions, which are especially pronounced in CDRL1, CDRL2, CDRL3, CDRH1 and CDRH2, impose considerable conformational restrains to the incorporation of biologically active peptides, and the surrounding immunoglobulin sequences may negatively affect expression, folding and/or biological activity of the incorporated peptide. Indeed, the present inventors have found that the activity of natriuretic peptides incorporated within an immunoglobulin CDR region varied considerably depending on the exact way the natriuretic peptide engrafted antibody was constructed. The decisive factor for a successful incorporation yielding a functional, i.e. biologically active natriuretic peptide variant was shown to be the number of amino acid residues between the incorporated natriuretic peptide and the nearest neighboring CDR-framework junctions N-terminal and C-terminal from the incorporated natriuretic peptide. Below a certain number of N-terminal and C-terminal flanking amino acid residues between natriuretic peptide and the neighboring CDR-framework junctions no biologically active natriuretic peptide immunoglobulin fusion constructs were obtained.

The terms “incorporated”, “inserted”, “integrated”, “engrafted” and “embedded” as well as “incorporation”, “insertion”, “integration”, “engrafting” and “embedding” are used interchangeably herein. Within the context of the present invention, these terms refer to the generation of hybrid polynucleic acids or hybrid polypeptides by the introduction of a heterologous sequence into the original sequence of an antibody or an antibody fragment. Such an incorporation may be done by any means. Typically, the antibody or fragment thereof comprising a natriuretic peptide flanked by an N-terminal and a C-terminal linker sequence is generated by recombinant DNA technology and expression as described herein.

Incorporation of the natriuretic peptide flanked by an N-terminal and a C-terminal linker sequence into a CDR region of the original antibody or antibody fragment sequence may result in the deletion of at least a portion of said CDR region. For instance, cloning of a nucleic acid sequence encoding said heterologous amino acid sequence comprising an N-terminal linker sequence, a natriuretic peptide and a C-terminal linker sequence may be performed such that part of the CDR encoding sequence is replaced by the incorporated heterologous nucleic acid sequence. In particular other embodiments, the incorporation of the heterologous amino acid sequence comprising the natriuretic peptide does not result in the deletion of amino acid residues of the CDR region into which the heterologous amino acid sequence is inserted.

Within the context of the present invention, the term "heterologous amino acid sequence" refers to an amino acid sequence that does not originate from the initial "empty" antibody or fragment thereof, into which it is incorporated. Engrafting of the heterologous amino acid sequence into an antibody or fragment thereof thus yields an engineered, recombinant antibody molecule composed of amino acid sequences of different origin.

The term "natriuretic peptide" refers to peptides that can induce natriuresis, the excretion of sodium by the kidneys. Natriuretic peptides include Atrial Natriuretic Peptide (ANP), Brain Natriuretic Peptide (BNP), C-Type Natriuretic Peptide (CNP), Dendroaspis natriuretic peptide (DNP) and Urodilatin. Natriuretic peptides within the meaning of the present invention may be of any origin. Natriuretic peptides include natural natriuretic peptides such as wild type natriuretic peptides and mutant versions thereof as well as homolog natriuretic peptides of a different species. The term however also encompasses engineered natriuretic peptides such as engineered chimeric variants of distinct natriuretic peptides. It is known that the usage of codons is different between species. Thus, when expressing a heterologous protein in a target cell, it may be necessary, or at least helpful, to adapt the nucleic acid sequence to the codon usage of the target cell. Methods for designing and constructing derivatives of a given protein are well known to anyone of ordinary skill in the art.

In particular embodiments, the natriuretic peptide is selected from a wild type natriuretic peptide of any species and a functional variant of any such wild type natriuretic peptide. Within the context of the present invention, the term "functional variant of a natriuretic peptide" or "functional natriuretic peptide variant" refers to a natriuretic peptide of any origin, including natural and engineered peptides, that differs in the amino acid sequence and/or the nucleic acid sequence encoding the amino acid sequence of a given natriuretic peptide, such as a wild type natriuretic peptide of a given species, but is still functionally active. Within the context of the present invention, the term "functionally active" refers to the ability of a natriuretic peptide variant to perform the biological functions of a naturally occurring natriuretic peptide, in particular a wild type natriuretic peptide. In particular, "functionally active" means that the natriuretic peptide variant is able to bind to its respective receptor. In case of NPR-A and NPR-B ligands, "functionally active" particularly means the ability to mediate an increase in (intracellular) cyclic guanosine monophosphate (cGMP) by binding to one or both of these receptors.

In particular embodiments, the functional natriuretic peptide variant is able to perform one or more biological functions of a given natriuretic peptide, such as a wild type natriuretic peptide of any given species to at least about 50%, particularly to at least about 60%, to at least about 70%, to at least about 80%, and most particularly to at least about 90%, wherein the one or more biological functions include, but are not limited to, binding of the natriuretic peptide to its respective receptor and/or induction of an increase in intracellular cGMP.

The functional activity of natriuretic peptides can be measured by any methods including in vitro methods that make it possible either to measure the increase of (intracellular) cyclic guanosine monophosphate (cGMP), or to measure changes in cellular processes regulated by cGMP, including the methods described in Examples 3 and 5. In particular embodiments, a (non-engrafted) natriuretic peptide variant is considered functionally active, if its $EC_{50}$ value as determined by the fluorescence assay described in Example 3 is below 500 nM, more particularly below 250 nM, more particularly below 150 nM, more particularly below 100 nM, more particularly below 50 nM, most particularly below 25 nM.

Incorporation of such a functional natriuretic peptide variant into one of the CDR regions of an immunoglobulin molecule or a fragment thereof as described herein yields a natriuretic peptide engrafted immunoglobulin with natriuretic peptide functional activity and significantly increased stability in serum as compared to the non-engrafted functional natriuretic peptide variant as shown in the Examples. An natriuretic peptide engrafted immunoglobulin is considered biologically active (i.e. functional), if it gives a significant positive signal in any method that measures the increase of (intracellular) cyclic guanosine monophosphate (cGMP) either directly or indirectly by assessing changes in cellular processes regulated by cGMP. In particular, the functional activity of a natriuretic peptide engrafted immunoglobulin may be assessed by the methods described in Examples 3 and 5. In case of natriuretic peptide engrafted immunoglobulins, significance is typically assessed based on i) comparison to a negative sample such as an empty immunoglobulin scaffold, e.g. construct #209, an antibody comprising SEQ ID NO 65 and SEQ ID NO 66, TPP-5657, ii) comparison to a positive sample, e.g. construct #117, an antibody comprising SEQ ID NO 67 and SEQ ID NO 66, TPP-5661, and iii) dose dependency.

Even though the functional natriuretic peptide variant according to the present invention may contain any number of mutations comprising additions, deletions and/or substitutions of one or more amino acids in comparison to the reference natriuretic peptide, a functional natriuretic peptide variant will typically maintain key features of the corresponding natriuretic peptide, such as key residues within the central ring domain. Conserved residues of natriuretic peptides are for instance described in Lincoln R. Potter et al. (Handb Exp Pharmacol. 2009; (191): 341-366). Thus, in particular embodiments, the functional natriuretic peptide variant shares at least 60%, at least 65%, at least 70%, at least 75%, at least 80%, at least 85%, at least 90% or at least 95% sequence identity with the sequence shown below:

(SEQ ID NO: 91)

$X_1CFGX_2X_3X_4DRIX_5X_6X_7SX_8LGC$ wherein $X_1$ and $X_5$ are G or S;

$X_3$ is R or K;

$X_6$ is A or S; and $X_2$, $X_4$, $X_7$ and $X_8$ may be any amino acid.

In principle, natriuretic peptides of any type may be incorporated within a CDR region of an immunoglobulin or fragment thereof as described herein. In particular, the present inventors have found that the findings for one type of natriuretic peptide regarding both minimal requirements for satisfactory biological activity of the engrafted natriuretic peptide and especially suitable N-terminal and C-terminal amino acid sequences may be conferred to other types of natriuretic peptides. Without wishing to be bound by theory it is hypothesized that these similar requirements for successful embedding of a natriuretic peptide within an immunoglobulin molecule among different natriuretic peptide types may be due to structural similarities and/or mechanisms of action within the natriuretic peptide family.

In particular embodiments, the natriuretic peptide is selected from the group consisting of human ANP having the sequence of SEQ ID NO 23, human BNP having the sequence of SEQ ID NO 24, human CNP having the sequence of SEQ ID NO 25 and a peptide having at least 60%, 65%, 70%, 75%, 80%, 85%, 90%, 95% or at least 98% sequence identity with any one of SEQ ID NOs 23 to 25. Again, the natriuretic peptide having a sequence deviating from wild type human natriuretic peptides ANP, BNP and CNP may be of any natural origin, e.g. a mutant version of a wild type human natriuretic peptide, or a homolog of a different species, or an engineered natriuretic peptide. Methods for designing and constructing peptide variants are well known to anyone of ordinary skill in the art.

In particular such embodiments, the natriuretic peptide having at least 60%, 65%, 70%, 75%, 80%, 85%, 90%, 95% or at least 98% sequence identity with any one of SEQ ID NOs 23 to 25 is a functional natriuretic peptide variant.

"Percent (%) sequence identity" with respect to a reference polynucleotide or polypeptide sequence, respectively, is defined as the percentage of nucleic acid or amino acid residues, respectively, in a candidate sequence that are identical to the nucleic acid or amino acid residues, respectively, in the reference polynucleotide or polypeptide sequence, respectively, after aligning the sequences and optionally introducing gaps, if necessary, to achieve the maximum percent sequence identity. Conservative substitutions are not considered as part of the sequence identity. In particular embodiments, any gaps introduced in the candidate sequence and/or the reference sequence may in total not amount to more than 50%, more than 40%, more than 30%, more than 25%, more than 20%, more than 15% or more than 10% of the total amount of residues of the reference sequence. In particular embodiments, the percentage sequence identity is determined without introducing any gaps into the candidate or the reference sequence (i.e. using an ungapped alignment). Alignment for purposes of determining percent amino acid sequence identity can be achieved in various ways that are well within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The natriuretic peptide that shares a given percentage of sequence identity with a given reference natriuretic peptide, e.g., human BNP having the amino acid sequence of SEQ ID NO 24, may contain one or more mutations comprising an addition, a deletion and/or a substitution of one or more amino acids in comparison to the reference natriuretic peptide. According to the teaching of the present invention, said deleted, added and/or substituted amino acids may be consecutive amino acids or may be interspersed over the length of the amino acid sequence of the natriuretic peptide that shares a given percentage of sequence identity with a reference natriuretic peptide, e.g., human BNP having the amino acid sequence of SEQ ID NO 24. On the DNA level, the nucleic acid sequences encoding the natriuretic peptide that shares a given percentage of sequence identity with a given reference natriuretic peptide may differ to a larger extent due to the degeneracy of the genetic code.

According to the teaching of the present invention, any number of amino acids may be added, deleted, and/or substituted, as long as the stipulated amino acid sequence identity with the reference natriuretic peptide is adhered to. In particular embodiments, the stipulated amino acid sequence identity is adhered to and the natriuretic peptide variant is biologically active, i.e. is a functional natriuretic peptide variant. Preferably, the biologic activity of the natriuretic peptide that shares a given percentage of sequence identity with a given reference natriuretic peptide, e.g., human BNP having the amino acid sequence as found in SEQ ID NO 24, is reduced by less than 90%, less than 80%, less than 70%, less than 60%, less than 50%, less than 25% or less than 10% compared to said reference natriuretic peptide as measured in the above described assay.

The term "antibody", as used herein, is intended to refer to immunoglobulin molecules, particularly dimeric immunoglobulin molecules comprised of four polypeptide chains—two heavy (H) chains and two light (L) chains which are typically inter-connected by disulfide bonds. Each heavy chain is comprised of a heavy chain variable region (abbreviated herein as VH) and a heavy chain constant region. The heavy chain constant region can comprise e.g. three domains CH1, CH2 and CH3. Each light chain is comprised of a light chain variable region (abbreviated herein as VL) and a light chain constant region. The light chain constant region is comprised of one domain (CL). The VH and VL regions can be further subdivided into regions of hypervariability, termed complementarity determining regions (CDR), interspersed with regions that are more conserved, termed framework regions (FR). Each VH and VL is typically composed of three CDRs and four FRs arranged from amino-terminus to carboxy-terminus e.g. in the following order: FR1, CDR1, FR2, CDR2, FR3, CDR3, FR4.

As used herein, the term "Complementarity Determining Regions" (CDRs; e.g., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (e.g. about residues 24-34 (CDRL1), 50-56 (CDRL2) and 89-97 (CDRL3) in the light chain variable domain and 31-35 (CDRH1), 50-65 (CDRH2) and 95-102 (CDRH3) in the heavy chain variable domain; (Kabat et al., Sequences of Proteins of Immulological Interest, 5th Ed. Public Health Service, National Institutes of Health, Bethesda, MD. (1991)) and/or those residues from a "hypervariable loop" (e.g. about residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain (Chothia and Lesk; J Mol Biol 196: 901-917 (1987)). In some instances, a complementarity determining region can include amino acids from both a CDR region defined according to Kabat and a hypervariable loop.

Depending on the amino acid sequence of the constant domain of their heavy chains, intact antibodies can be assigned to different "classes". There are five major classes of intact antibodies: IgA, IgD, IgE, IgG, and IgM, and several of these maybe further divided into "subclasses" (isotypes), e.g., IgG1, IgG2, IgG3, IgG4, IgA1, and IgA2. Within the context of the present invention, the term "antibody" includes immunoglobulin molecules of any primary class—including IgG, IgE, IgM, IgD, IgA and IgY—and any subclass—including, IgG1, IgG2, IgG3, IgG4, IgA1 and Ig A2—isolated from nature or prepared by recombinant means and includes all conventionally known antibodies. A preferred class of immunoglobulins for use in the present invention is IgG. The term "antibody" also extends to other protein scaffolds that are able to orient antibody CDR inserts into the same active binding conformation as that found in natural antibodies such that binding of the target antigen observed with these chimeric proteins is maintained relative to the binding activity of the natural antibody from which the CDRs were derived.

Within the context of the present invention, the term "fragment" of an antibody/immunoglobulin refers to any part of an antibody/immunoglobulin that comprises at least one CDR region. Particularly, the antibody fragment according to the present invention retains the ability to increase the serum half-life of a biologically active peptide, preferably a natriuretic peptide, incorporated therein. Antibody fragments according to the present invention include Fab, Fab', Fab'-SH, F(ab')2, and Fv fragments; diabodies; single domain antibodies (Dabs); linear antibodies; single-chain antibody molecules (scFv); and disulfide-stabilized Fv antibody fragments (dsFv); as well as multispecific antibodies formed from antibody fragments and fragments comprising a VL or VH domain, which are prepared from intact immunoglobulins or prepared by recombinant means.

The F(ab')$_2$ or Fab may be engineered to minimize or completely remove the intermolecular disulfide interactions that occur between the CH1 and CL domains. Antibody fragments according to the present invention may comprise the variable region(s) alone or in combination with the entirety or a portion of the following: hinge region, CH1, CH2, CH3 and CL domains. Also included are antibody fragments comprising any combination of variable region(s) with a hinge region, CH1, CH2, CH3 and CL domain.

The antibody or fragment thereof constitutes a scaffold that confers stability to the natriuretic peptide incorporated therein. For example, the serum half-life of a natriuretic peptide incorporated within the CDR region of an antibody as described herein may be increased as compared to that of a naturally occurring natriuretic peptide.

Principally, the heterologous amino acid sequence comprising the natriuretic peptide may be incorporated within any immunoglobulin molecule or fragment thereof. In particular, immunoglobulins of any species (including but not limited to human, bovine, murine, rat, pig, dog, shark, *lama* and camel) and any primary class and subclass may be used according to the present invention. For therapeutic use a human or humanized antibody may however be preferable. Within the context of the present invention, the term "human antibody" refers to antibodies having the amino acid sequence of a human immunoglobulin and includes antibodies isolated from human immunoglobulin libraries, from human B cells, or from animals transgenic for one or more human immunoglobulin as well as synthetic human antibodies. In particular embodiments the amino acid light chain and heavy chain sequences of the variable domain derive from human germline sequences LV 1-40 and HV 3-23, respectively (for more information see Example 1).

Within the context of the present invention, the term "humanized antibody" or "humanized antibody fragment" refers to an antibody or fragment thereof that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

The antibody or fragment thereof according to the present invention may be monospecific, bispecific, trispecific or of greater multispecificity.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment, the term "comprising" as used throughout the application and in particular within the claims may be replaced by the term "consisting of".

In the context of the present invention, the term "about" or "approximately" means within 80% to 120%, alternatively within 90% to 110%, including within 95% to 105% of a given value.

In the antibody or fragment thereof according to the invention, a) at least 12 amino acid residues are present between i) amino acid residue HC res25 according to Kabat (in the heavy chain having the amino acid sequence of SEQ ID NO 65 this corresponds to res S25) and the first amino acid residue of the natriuretic peptide in case of an incorporation of the heterologous amino acid sequence within CDRH1;

ii) amino acid residue HC res51 according to Kabat (in the heavy chain having the amino acid sequence of SEQ ID NO 65 this corresponds to res 151) and the first amino acid residue of the natriuretic peptide in case of an incorporation of the heterologous amino acid sequence within CDRH2;

iii) amino acid residue HC res92 according to Kabat (in the heavy chain having the amino acid sequence of SEQ ID NO 65 this corresponds to res C96) and the first amino acid residue of the natriuretic peptide in case of an incorporation of the heterologous amino acid sequence within CDRH3;

iv) amino acid residue LC res26 according to Kabat (in the light chain having the amino acid sequence of SEQ ID NO 66 this corresponds to res S25) and the first amino acid residue of the natriuretic peptide in case of an incorporation of the heterologous amino acid sequence within CDRL1;

v) amino acid residue LC res49 according to Kabat (in the light chain having the amino acid sequence of SEQ ID NO 66 this corresponds to res Y51) and the first amino acid residue of the natriuretic peptide in case of an incorporation of the heterologous amino acid sequence within CDRL2; and/or vi) amino acid residue LC res88 according to Kabat (in the light chain having the amino acid sequence of SEQ ID NO 66 this corresponds to res C90) and the first amino acid residue of the natriuretic peptide in case of an incorporation of the heterologous amino acid sequence within CDRL3;

and b) at least 9 amino acid residues are present between the last amino acid residue of the natriuretic peptide and i) amino acid residue HC res35a according to Kabat (in the heavy chain having the amino acid sequence of SEQ ID NO 65 this corresponds to res M34) in case of an incorporation of the heterologous amino acid sequence within CDRH1;

ii) amino acid residue HC res57 according to Kabat (in the heavy chain having the amino acid sequence of SEQ ID NO 65 this corresponds to res T58) in case of an incorporation of the heterologous amino acid sequence within CDRH2;

iii) amino acid residue HC res106 according to Kabat (in the heavy chain having the amino acid sequence of SEQ ID NO 65 this corresponds to res G111) in case of an incorporation of the heterologous amino acid sequence within CDRH3;

iv) amino acid residue LC res 32 according to Kabat (in the light chain having the amino acid sequence of SEQ ID NO 66 this corresponds to res D34) in case of an incorporation of the heterologous amino acid sequence within CDRL1;

v) amino acid residue LC res57 according to Kabat (in the light chain having the amino acid sequence of SEQ ID NO 66 this corresponds to res G59) in case of an incorporation of the heterologous amino acid sequence within CDRL2; and/or vi) amino acid residue LC res98 according to Kabat (in the light chain having the amino acid sequence of SEQ ID NO 66 this corresponds to res F102) in case of an incorporation of the heterologous amino acid sequence within CDRL3.

The denomination of the above listed amino acid residues refers to the amino acid position in the original immunoglobulin molecule before incorporation of the heterologous amino acid sequence. Within the context of the present invention, the above listed amino acid residues are referred to as "reference amino acids" or "reference aa". These reference amino acid residues lie at or near CDR framework junctions but do not necessarily correspond to standard CDR border definitions (standard CDR border definitions are amino acid residues S25 and W36 for CDRH1; S49 and R67 for CDRH2; K98 and W108 for CDRH3; C22 and W37 for CDRL1; Y51 and G59 for CDRL2; C90 and F102 for CDRL3. Jarasch and Skerra, Proteins 2017 January; 85 (1): 65-71).

The nearest neighboring reference aa N-terminal from the inserted natriuretic peptide plus the amino acid stretch present between said reference aa and the first amino acid residue of the inserted natriuretic peptide are herein referred to as "N-terminal sequence". The N-terminal sequence comprises the Ntls. In particular embodiments, the N-terminal sequence consists of the Ntls plus the neighboring N-terminal reference aa.

The amino acid stretch present between the last amino acid residue of the inserted natriuretic peptide and the nearest neighboring reference aa C-terminal from the inserted natriuretic peptide plus and said reference aa are herein referred to as "C-terminal sequence". The C-terminal sequence comprises the Ctls. In particular embodiments, the C-terminal sequence consists of the Ctls plus the neighboring C-terminal reference aa.

In particular embodiments, the Ntls comprises a GS linker sequence; a PN linker sequence; an amino acid sequence which is part of a human IgG antibody scaffold or a sequence that shares at least 80% sequence identity therewith, particularly an amino acid sequence which is part of the fab domain scaffold of a human IgG antibody or a sequence that shares at least 80% sequence identity therewith, more particularly the sequence of any one of SEQ ID NOs 1, 2 or 4, or a sequence that shares at least 80% sequence identity with any one of SEQ ID NOs 1, 2 or 4; the sequence of any one of SEQ ID NOs 6, 7, 9, 11, 13, 15, 16, 17, 19 or 21; or a sequence that shares at least 60%, at least 70%, at least 80%, at least 90% or at least 95% sequence identity with any one of SEQ ID NO 6, 7, 9, 11, 13, 15, 16, 17, 19 or 21. The Ntls may also comprise any combination of the above listed amino acid sequences.

In particular such embodiments, the Ntls comprises a GS linker sequence; a PN linker sequence; an amino acid sequence which is part of a human IgG antibody scaffold or a sequence that shares at least 80% sequence identity therewith, particularly an amino acid sequence which is part of the fab domain scaffold of a human IgG antibody or a sequence that shares at least 80% sequence identity therewith, more particularly the sequence of any one of SEQ ID NOs 1, 2 or 4, or a sequence that shares at least 80% sequence identity with any one of SEQ ID NOs 1, 2 or 4; the sequence of any one of SEQ ID NOs 6, 7, 9, 11, 13, 15 or 21; a sequence that shares at least 60%, at least 70%, at least 80%, at least 90%, or at least 95% sequence identity with any one of SEQ ID NO 6, 7, 9, 11, 13, 15, or 21; or any combination thereof.

In particular embodiments, the Ctls comprises a GS linker sequence; a PN linker sequence; an amino acid sequence which is part of a human IgG antibody scaffold or a sequence that shares at least 80% sequence identity therewith, particularly an amino acid sequence which is part of the fab domain scaffold of a human IgG antibody or a sequence that shares at least 80% sequence identity therewith, more particularly the sequence of any one of SEQ ID NOs 1, 3 or 5, or a sequence that shares at least 80% sequence identity with any one of SEQ ID NOs 1, 3 or 5; the sequence of any one of SEQ ID NOs 6, 8, 10, 12, 14, 15, 17, 18, 19, 20 or 22; or a sequence that shares at least 60%, at least 70%, at least 80%, at least 90% or at least 95% sequence identity with any one of SEQ ID NOs 6, 8, 10, 12, 14, 15, 17, 18, 19, 20 or 22. The Ctls may also comprise any combination of the above listed amino acid sequences.

In particular embodiments, the Ctls comprises a GS linker sequence; a PN linker sequence; an amino acid sequence which is part of a human IgG antibody scaffold or a sequence that shares at least 80% sequence identity therewith, particularly an amino acid sequence which is part of the fab domain scaffold of a human IgG antibody or a sequence that shares at least 80% sequence identity therewith, more particularly the sequence of any one of SEQ ID NOs 1, 3 or 5, or a sequence that shares at least 80% sequence identity with any one of SEQ ID NOs 1, 3 or 5; the sequence of any one of SEQ ID NOs 6, 8, 10, 12, 14, 15, 20 or 22; a sequence that shares at least 60%, at least 70%, at least 80%, at least 90% or at least 95% sequence identity with any one of SEQ ID NOs 6, 8, 10, 12, 14, 15, 20 or 22; or any combination thereof.

In particular embodiments the sequence identity between the sequence comprised in the Ntls and/or the Ctls and any one of SEQ ID NOs 1 to 22 is at least 60%, particularly at least 65%, at least 70%, at least 75%, at least 80%, at least 85%, at least 90%, at least 95% or 100%.

Within the context of the present invention the term "GS linker sequence" refers to a peptide linker comprising mainly glycine and serine residues. Particularly, at least 60%, at least 65%, at least 70%, at least 75%, at least 80%, at least 85%, at least 90%, at least 95% or 100% of the amino acid residues of the GS linker sequence according to the present invention are selected from glycine and serine residues. The GS linker sequence according to the present invention may for example comprise from 1 to 30 amino acid residues in total. Particularly, the GS linker sequence according to the present invention does not comprise more than 3, 2 or 1 amino acid residue(s) other than glycine or serine.

Within the context of the present invention the term "PN linker sequence" refers to a peptide linker comprising mainly proline and asparagine residues. Particularly, at least 60%, at least 65%, at least 70%, at least 75%, at least 80%, at least 85%, at least 90%, at least 95% or 100% of the amino acid residues of the PN linker sequence according to the present invention are selected from proline and asparagine residues. The PN linker sequence according to the present invention may for example comprise from 1 to 30 amino acid residues in total. Particularly, the PN linker sequence according to the present invention does not comprise more than 3, 2 or 1 amino acid residue(s) other than proline or asparagine. Other amino acid residues that may be present in a PN linker sequence according to the present invention are for instance lysine or glutamic acid residues.

In particular embodiments, the linker sequence comprised in the Ntls and/or the Ctls and selected from a GS linker sequence; a PN linker sequence; a human IgG antibody scaffold linker sequence; a human IgG fab domain scaffold sequence; a sequence that shares at least 80% sequence identity with the human IgG antibody scaffold linker sequence, the human IgG fab domain scaffold sequence or the sequence of any one of SEQ ID NOs 1 to 5; and a sequence that shares at least 60% sequence identity with any one of SEQ ID NOs 6 to 22, comprises at least 1, 2, 3, 4, 5, 6, 7, 8, 9 or 10 amino acid residues. The linker sequence comprised in the Ntls and/or the Ctls may for instance comprise up to 30, 28, 26, 25, 24, 23, 22, 21, 20, 19, 18, 17, 16, 15, 14, 13, 12, 11 or 10 amino acid residues.

In the case of linkers comprising a sequence of a human IgG antibody scaffold or a sequence that shares at least 80% sequence identity therewith, it may be particularly advantageous to use a sequence of a scaffold region which is adjacent to the CDR into which the heterologous amino acid sequence is incorporated. For example, the Ntls and/or the Ctls may comprise a linker comprising an amino acid sequence that is part of framework region FRH2 or FRH3 in case the heterologous amino acid sequence is incorporated within the CDRH2 domain. Similarly, the Ntls and/or the Ctls may comprise a linker comprising an amino acid sequence that is part of framework region FRL2 or FRL3 in case the heterologous amino acid sequence is incorporated within the CDRL2 region.

In particular embodiments, the Ntls consists of a GS linker sequence; a PN linker sequence; an amino acid sequence which is part of a human IgG antibody scaffold or a sequence that shares at least 80% sequence identity therewith, particularly an amino acid sequence which is part of the fab domain scaffold of a human IgG antibody or a sequence that shares at least 80% sequence identity therewith, more particularly the sequence of any one of SEQ ID NOs 1, 2 or 4 or a sequence that shares at least 80% sequence identity with any one of SEQ ID NOs 1, 2 or 4; the sequence of any one of SEQ ID NOs 6, 7, 9, 11, 13, 15, 16, 17, 19 or 21; a sequence that shares at least 60%, at least 70%, at least 80%, at least 90% or at least 95% sequence identity with any one of SEQ ID NOs 6, 7, 9, 11, 13, 15, 16, 17, 19 or 21; or any combination thereof.

In particular embodiments, the Ctls consists of a GS linker sequence; a PN linker sequence; an amino acid sequence which is part of a human IgG antibody scaffold or a sequence that shares at least 80% sequence identity therewith, particularly an amino acid sequence which is part of the fab domain scaffold of a human IgG antibody or a sequence that shares at least 80% sequence identity therewith, more particularly the sequence of any one of SEQ ID NOs 1, 3 or 5 a sequence that shares at least 80% sequence identity with any one of SEQ ID NOs 1, 3 or 5; the sequence of any one of SEQ ID NOs 6, 8, 10, 12, 14, 15, 17, 18, 19, 20 or 22; a sequence that shares at least 60%, at least 70%, at least 80%, at least 90% or at least 95% sequence identity with any one of SEQ ID NOs 6, 8, 10, 12, 14, 15, 17, 18, 19, 20 or 22; or any combination thereof.

In particular embodiments, both the Ntls and the Ctls comprise at least one of the above listed linker sequences or any combination thereof. In principle, any of the above listed Ntls linker sequences may be combined with any of the above listed Ctls linker sequences. In particular, any linker sequence may be combined with a GS linker. As a non-limiting example, a GS Ctls linker may be combined with an Ntls linker comprising the sequence of any one of SEQ ID NOs 6, 9 or 15 or a sequence that shares at least 60% sequence identity with any one of SEQ ID NOs 6, 9 or 15. A further non-limiting example is a GS Ntls linker combined with a Ctls linker comprising the sequence of SEQ ID NO 15 or a sequence that shares at least 60% sequence identity therewith.

The above listed linker sequences have proven particularly advantageous for achieving good natriuretic peptide activities, given a sufficient total length of the N-terminal and C-terminal flanking sequences. Without wishing to be bound by theory, it is believed that the above listed linker peptide stretches result in a conformation/folding that contributes to a favorable state of the system in presentation of a biologically active natriuretic peptide to its respective receptor with minimal sterical hindrance.

In particular embodiments, i) the Ntls comprises a GS linker sequence; a PN linker sequence; the sequence of SEQ ID NOs 2, 4, 9, 11, 13 or 15; a sequence that shares at least 60% sequence identity with SEQ ID NOs 2, 4, 9, 11, 13 or 15; or any combination thereof and ii) the Ctls comprises a GS linker sequence; a PN linker sequence; the sequence of SEQ ID NOs 3, 5, 12, 14, 15 or 20; a sequence that shares at least 60% sequence identity with SEQ ID NOs 3, 5, 12, 14, 15 or 20; or any combination thereof. These linker sequences have proven particularly useful as they not only achieve high natriuretic peptide activities but also good expression levels in recombinant expression and are not prone to protein fragmentation upon expression (see Table 9).

In particular embodiments, the Ntls and the Ctls each comprise a GS linker sequence; the Ntls and the Ctls each comprise a PN linker sequence; the Ntls and the Ctls each comprise an amino acid sequence which is part of a human IgG antibody scaffold or a sequence that shares at least 80% sequence identity therewith, particularly an amino acid sequence which is part of the fab domain scaffold of a human IgG antibody or a sequence that shares at least 80% sequence identity therewith, more particularly the Ntls comprises the sequence of any one of SEQ ID NOs 1, 2 or 4 or a sequence that shares at least 80% sequence identity with any one of SEQ ID NOs 1, 2 or 4 and the Ctls comprises the sequence of any one of SEQ ID NOs 1, 3 or 5 or a sequence that shares at least 80% sequence identity therewith; the Ntls and the Ctls each comprise the sequence of SEQ ID NO 6 or a sequence that shares at least 60% sequence identity therewith; the Ntls comprises the sequence of SEQ ID NO 7 or a sequence that shares at least 60% sequence identity therewith and the Ctls comprises the sequence of SEQ ID NO 8 or a sequence that shares at least 60% sequence identity therewith; the Ntls comprises the sequence of SEQ ID NO 9 or a sequence that shares at least 60% sequence identity therewith and the Ctls comprises the sequence of SEQ ID NO 10 or a sequence that shares at least 60% sequence identity therewith; the Ntls comprises the sequence of SEQ ID NO 11 or a sequence that shares at least 60% sequence identity therewith and the Ctls comprises the sequence of SEQ ID NO 12 or a sequence that shares at least 60% sequence identity therewith; the Ntls comprises the sequence of SEQ ID NO 13 or a sequence that shares at least 60% sequence identity therewith and the Ctls comprises the sequence of SEQ ID NO 14 or a sequence that shares at least 60% sequence identity therewith; the Ntls and the Ctls each comprise the sequence of SEQ ID NO 15 or a sequence that shares at least 60% sequence identity therewith; the Ntls comprises the sequence of SEQ ID NO 16 or a sequence that shares at least 60% sequence identity therewith and the Ctls comprises the sequence of SEQ ID NO 17 or a sequence that shares at least 60% sequence identity therewith; the Ntls comprises the sequence of SEQ ID NO 17 or a sequence that shares at least 60% sequence identity therewith and the Ctls comprises the sequence of SEQ ID NO 18 or a sequence that shares at least 60% sequence identity therewith; the Ntls and the Ctls each comprise the sequence of SEQ ID NO 19 or a sequence that shares at least 60% sequence identity therewith; the Ntls comprises the sequence of SEQ ID NO 9 or a sequence that shares at least 60% sequence identity therewith and the Ctls comprises the sequence of SEQ ID NO 20 or a sequence that shares at least 60% sequence identity therewith; or the Ntls comprises the sequence of SEQ ID NO 21 or a sequence that shares at least 60% sequence identity therewith and the Ctls comprises the sequence of SEQ ID NO 22 or a sequence that shares at least 60% sequence identity therewith.

In particular such embodiments, the Ntls and the Ctls each comprise a GS linker sequence; the Ntls and the Ctls each comprise a PN linker sequence; the Ntls and the Ctls each comprise an amino acid sequence which is part of a human IgG antibody scaffold or a sequence that shares at least 80% sequence identity therewith, particularly an amino acid sequence which is part of the fab domain scaffold of a human IgG antibody or a sequence that shares at least 80% sequence identity therewith, more particularly the Ntls comprises the sequence of any one of SEQ ID NOs 1, 2 or 4 or a sequence that shares at least 80% sequence identity with any one of SEQ ID NOs 1, 2 or 4 and the Ctls comprises the sequence of any one of SEQ ID NOs 1, 3 or 5 or a sequence that shares at least 80% sequence identity therewith; the Ntls and the Ctls each comprise the sequence of SEQ ID NO 6 or a sequence that shares at least 60% sequence identity therewith; the Ntls comprises the sequence of SEQ ID NO 7 or a sequence that shares at least 60% sequence identity therewith and the Ctls comprises the sequence of SEQ ID NO 8 or a sequence that shares at least 60% sequence identity therewith; the Ntls comprises the sequence of SEQ ID NO 9 or a sequence that shares at least 60% sequence identity therewith and the Ctls comprises the sequence of SEQ ID NO 10 or a sequence that shares at least 60% sequence identity therewith; the Ntls comprises the sequence of SEQ ID NO 11 or a sequence that shares at least 60% sequence identity therewith and the Ctls comprises the sequence of SEQ ID NO 12 or a sequence that shares at least 60% sequence identity therewith; the Ntls comprises the sequence of SEQ ID NO 13 or a sequence that shares at least 60% sequence identity therewith and the Ctls comprises the sequence of SEQ ID NO 14 or a sequence that shares at least 60% sequence identity therewith; the Ntls and the Ctls each comprise the sequence of SEQ ID NO 15 or a sequence that shares at least 60% sequence identity therewith; the Ntls comprises the sequence of SEQ ID NO 9 or a sequence that shares at least 60% sequence identity therewith and the Ctls comprises the sequence of SEQ ID NO 20 or a sequence that shares at least 60% sequence identity therewith; or the Ntls comprises the sequence of SEQ ID NO 21 or a sequence that shares at least 60% sequence identity therewith and the Ctls comprises the sequence of SEQ ID NO 22 or a sequence that shares at least 60% sequence identity therewith.

In particular such embodiments, the Ntls and the Ctls each comprise a GS linker sequence; the Ntls and the Ctls each comprise a PN linker sequence; the Ntls comprises the sequence of SEQ ID NO 2 or a sequence that shares at least 80% sequence identity therewith and the Ctls comprises the sequence of SEQ ID NO 3 or a sequence that shares at least 80% sequence identity therewith; the Ntls comprises the sequence of SEQ ID NO 4 or a sequence that shares at least 80% sequence identity therewith and the Ctls comprises the sequence of SEQ ID NO 5 or a sequence that shares at least 80% sequence identity therewith; the Ntls comprises the sequence of SEQ ID NO 11 or a sequence that shares at least 60% sequence identity therewith and the Ctls comprises the sequence of SEQ ID NO 12 or a sequence that shares at least 60% sequence identity therewith; the Ntls comprises the sequence of SEQ ID NO 13 or a sequence that shares at least 60% sequence identity therewith and the Ctls comprises the sequence of SEQ ID NO 14 or a sequence that shares at least 60% sequence identity therewith; the Ntls and the Ctls each comprise the sequence of SEQ ID NO 15 or a sequence that shares at least 60% sequence identity therewith; or the Ntls comprises the sequence of SEQ ID NO 9 or a sequence that shares at least 60% sequence identity therewith and the Ctls comprises the sequence of SEQ ID NO 20 or a sequence that shares at least 60% sequence identity therewith. These linker combinations have proven particularly useful for achieving high natriuretic peptide activities, good expression levels in recombinant expression and minimal or no protein fragmentation, as shown in Table 9.

In particular embodiments, the Ntls further comprises an anchoring element A1 at its C terminal end and/or the Ctls further comprises an anchoring element A2 at its N terminal end, wherein A1 and A2 predominantly comprise glycine and serine residues. In particular embodiments, A1 and/or A2 comprise at least 1, 2, 3, 4, or 5 amino acid residues. A1 and/or A2 may comprise up to 10, 9, 8, 7, 6 or 5 amino acid residues in total. In particular embodiments, at least 60%, at least 70%, at least 80%, at least 90%, or 100% of the amino acid residues of A1 and/or A2 are selected from glycine and serine residues. Particularly A1 and/or A2 do/does not comprise more than 3, 2 or 1 amino acid residue other than glycine or serine.

In particular embodiments the Ntls consists of i) an anchoring element A1 at its C terminal end and ii) a GS linker sequence; a PN linker sequence; an amino acid sequence which is part of a human IgG antibody scaffold or a sequence that shares at least 80% sequence identity therewith, particularly an amino acid sequence which is part of the fab domain scaffold of a human IgG antibody or a sequence that shares at least 80% sequence identity therewith, more particularly the sequence of any one of SEQ ID NOs 1, 2 or 4 or a sequence that shares at least 80% sequence identity with any one of SEQ ID NOs 1, 2 or 4; the sequence of any one of SEQ ID NOs 6, 7, 9, 11, 13, 15, 16, 17, 19 or 21; a sequence that shares at least 60% sequence identity with any one of SEQ ID NO 6, 7, 9, 11, 13, 15, 16, 17, 19 or 21; or any combination thereof.

In particular embodiments, the Ctls consists of i) an anchoring element A2 at its N terminal end and ii) a GS linker sequence; a PN linker sequence; an amino acid sequence which is part of a human IgG antibody scaffold or a sequence that shares at least 80% sequence identity therewith, particularly an amino acid sequence which is part of the fab domain scaffold of a human IgG antibody or a sequence that shares at least 80% sequence identity therewith, more particularly the sequence of any one of SEQ ID NOs 1, 3 or 5 a sequence that shares at least 80% sequence identity with any one of SEQ ID NOs 1, 3 or 5; the sequence of any one of SEQ ID NOs 6, 8, 10, 12, 14, 15, 17, 18, 19, 20 or 22; a sequence that shares at least 60% sequence identity with any one of SEQ ID NOs 6, 8, 10, 12, 14, 15, 17, 18, 19, 20 or 22; or any combination thereof.

In particular embodiments, the Ntls and/or the Ctls comprise(s) at least 3, 4, 5, 6, 7, 8, 9 or 10 amino acid residues in total. The Ntls and/or the Ctls may for instance comprise up to 30, 28, 26, 25, 24, 23, 22, 21, 20, 19, 18, 17, 16, 15, 14, 13, 12, 11 or 10 amino acid residues in total.

In particular embodiments, the amino acid stretch present between
i) amino acid residue HC res25 according to Kabat and the first amino acid residue of the natriuretic peptide in case of an incorporation of said heterologous amino acid sequence within CDRH1;
ii) amino acid residue HC res51 according to Kabat and the first amino acid residue of the natriuretic peptide in case of an incorporation of said heterologous amino acid sequence within CDRH2;
iii) amino acid residue HC res92 according to Kabat and the first amino acid residue of the natriuretic peptide in case of an incorporation of said heterologous amino acid sequence within CDRH3;
iv) amino acid residue LC res26 according to Kabat and the first amino acid residue of the natriuretic peptide in case of an incorporation of said heterologous amino acid sequence within CDRL1;
v) amino acid residue LC res49 according to Kabat and the first amino acid residue of the natriuretic peptide in case of an incorporation of said heterologous amino acid sequence within CDRL2; and/or
vi) amino acid residue LC res88 according to Kabat and the first amino acid residue of the natriuretic peptide in case of an incorporation of said heterologous amino acid sequence within CDRL3 comprises the sequence of any one of SEQ ID NOs 26 to 38 or a sequence having at least 80%, 85%, 90%, 95% or at least 98% sequence identity with any one of SEQ ID NOs 26 to 38.

In particular embodiments, the amino acid stretch present between the last amino acid residue of the natriuretic peptide and
i) amino acid residue HC res35a according to Kabat in case of an incorporation of said heterologous amino acid sequence within CDRH1;
ii) amino acid residue HC res57 according to Kabat in case of an incorporation of said heterologous amino acid sequence within CDRH2;
iii) amino acid residue HC res106 according to Kabat in case of an incorporation of said heterologous amino acid sequence within CDRH3;
iv) amino acid residue LC res 32 according to Kabat in case of an incorporation of said heterologous amino acid sequence within CDRL1;
v) amino acid residue LC res57 according to Kabat in case of an incorporation of said heterologous amino acid sequence within CDRL2; and/or
vi) amino acid residue LC res98 according to Kabat in case of an incorporation of said heterologous amino acid sequence within CDRL3 comprises the sequence of any one of SEQ ID NOs 39 to 51 or a sequence having at least 80%, 85%, 90%, 95% or at least 98% sequence identity with any one of SEQ ID NOs 39 to 51.

In particular embodiments, the heterologous amino acid sequence consists of the Ntls, the natriuretic peptide and the Ctls.

In particular embodiments, the amino acid stretch present between
i) amino acid residue HC res25 according to Kabat and amino acid residue HC res35a according to Kabat in case of an incorporation of said heterologous amino acid sequence within CDRH1;
ii) amino acid residue HC res51 according to Kabat and amino acid residue HC res57 according to Kabat in case of an incorporation of said heterologous amino acid sequence within CDRH2;
iii) amino acid residue HC res92 according to Kabat and amino acid residue HC res106 according to Kabat in case of an incorporation of said heterologous amino acid sequence within CDRH3;
iv) amino acid residue LC res26 according to Kabat and amino acid residue LC res 32 according to Kabat in case of an incorporation of said heterologous amino acid sequence within CDRL1;
v) amino acid residue LC res49 according to Kabat and amino acid residue LC res57 according to Kabat in case of an incorporation of said heterologous amino acid sequence within CDRL2; and/or
vi) amino acid residue LC res88 according to Kabat and amino acid residue LC res98 according to Kabat in case of an incorporation of said heterologous amino acid sequence within CDRL3 comprises the sequence of any one of SEQ ID NOs 52 to 64 or a sequence having at least 80%, 85%, 90%, 95% or at least 98% sequence identity with any one of SEQ ID NOs 52 to 64.

In particular embodiments, the antibody or fragment thereof comprises at least two natriuretic peptides. In particular embodiments, both natriuretic peptides are comprised in a heterologous amino acid sequence further comprising an Ntls and a Ctls and incorporated within a CDR region of said antibody or fragment thereof, as described herein. The at least two natriuretic peptides may be incorporated within the two corresponding CDR regions of two light chains or two heavy chains or the at least two natriuretic peptides may be incorporated within two separate CDR regions. The at least two natriuretic peptides may be the same or different. In particular such embodiments, the antibody or fragment thereof comprises at least two different natriuretic peptides that are incorporated within at least two CDR regions.

Due to the dimeric structure of antibody molecules, the insertion of one nucleic acid sequence encoding the heterologous amino acid sequence (Ntls-natriuretic peptide-Ctls) into the nucleic acid encoding either the light or the heavy chain of an immunoglobulin molecule typically yields an antibody protein carrying two natriuretic peptides located in the corresponding CDR regions of the two identical light or the two identical heavy chains. However, it is also envisaged to insert two natriuretic peptide encoding nucleic acids into two different CDR encoding regions of the nucleic acid sequences encoding the light and/or the heavy chain, thereby yielding an antibody molecule with four natriuretic peptides located in two corresponding CDR pairs of the dimeric antibody. Also encompassed are dimeric immunoglobulin molecules whose light chains and/or heavy chains are not identical, for instance including dimeric antibodies carrying a single natriuretic peptide as well as dimeric antibodies carrying two different natriuretic peptides in two corresponding CDR regions of the two light or the two heavy chains.

In particular embodiments, natriuretic peptides are inserted in the CDRH1 and CDRH2, CDRH1 and CDRH3, CDRH2 and CDRH3, CDRH1 and CDRL1, CDRH1 and CDRL2, CDRH1 and CDRL3, CDRH2 and CDRL1, or CDRH2 and CDRL2. In particular embodiments, the antibody or fragment thereof comprises one ANP and one BNP molecule; one ANP and one CNP molecule; or one BNP and one CNP molecule.

In particular embodiments, the natriuretic peptide comprised in the at least one heterologous amino acid sequence incorporated within at least one CDR region of said antibody or fragment thereof is an BNP and the antibody or fragment thereof comprises at least one further natriuretic peptide. In particular embodiments, the at least one further natriuretic peptide is also comprised in a heterologous amino acid sequence further comprising an Ntls and a Ctls and incorporated within a CDR region of said antibody or fragment thereof. In particular embodiments, the BNP and the at least one further natriuretic peptide are incorporated within two corresponding CDR regions of either the two light or the two heavy chains of the antibody or fragment thereof. In particular other embodiments, the BNP and the at least one further natriuretic peptide are incorporated within at least two separate CDR regions. Particularly, said at least one further natriuretic peptide is selected from ANP, BNP and CNP, more particularly from ANP and CNP.

The "empty" antibody molecule not harboring a heterologous amino acid sequence comprising a natriuretic peptide which is composed of two heavy chains having the sequence of SEQ ID NO 65 and two light chains having the sequence of SEQ ID NO 66 is termed TPP-5657. In particular embodiments, an antibody molecule composed of two heavy chains having the sequence of SEQ ID NO 65 or a sequence having at least 80%, at least 85%, at least 90% or at least 95% sequence identity therewith and two light chains having the sequence of SEQ ID NO 66 or a sequence having at least 80%, at least 85%, at least 90% or at least 95% sequence identity therewith serves as the initial or parental antibody, into which the heterologous amino acid sequence comprising the natriuretic peptide is incorporated. In particular such embodiments, the heterologous amino acid sequence comprising the natriuretic peptide is incorporated within a CDR region of one or both heavy chains of such antibody molecule.

In particular such embodiments, the heavy chain(s) comprising the at least one heterologous amino acid sequence incorporated within at least one of its CDR regions has the sequence of any one of SEQ ID NOs 67 to 79 or a sequence having at least 80%, at least 85%, at least 90% or at least 95% sequence identity with any one of SEQ ID NOs 67 to 79. In particular embodiments, the antibody according to the present invention is composed of two identical heavy chains having the sequence of any one of SEQ ID NOs 67 to 79 or a sequence having at least 80%, at least 85%, at least 90% or at least 95% sequence identity with any one of SEQ ID NOs 67 to 79 and two identical light chains having the sequence of SEQ ID NO 66 or a sequence having at least 80%, at least 85%, at least 90% or at least 95% sequence identity therewith.

In particular other embodiments, the heterologous amino acid sequence comprising the natriuretic peptide is incorporated within a CDR region of one or both light chains of such antibody molecule. In particular such embodiments, the light chain(s) comprising the at least one heterologous amino acid sequence incorporated within at least one of its CDR regions has(have) the sequence of any one of SEQ ID NOs 80 or 81 a sequence having at least 80%, at least 85%, at least 90% or at least 95% sequence identity with any one of SEQ ID NOs 80 or 81. In particular embodiments, the antibody according to the present invention is composed of two identical light chains having the sequence of any one of SEQ ID NOs 80 or 81 or a sequence having at least 80%, at least 85%, at least 90% or at least 95% sequence identity with any one of SEQ ID NOs 80 or 81 and two identical heavy chains having the sequence of SEQ ID NO 65 or a sequence having at least 80%, at least 85%, at least 90% or at least 95% sequence identity therewith.

The table below depicts the heavy and light chain composition of exemplary antibodies according to the present invention.

TABLE 1

Exemplary natriuretic peptide engrafted antibody constructs

| TPP-Number | Heavy Chain | Light Chain |
|---|---|---|
| TPP-5661 | SEQ ID NO 67 | SEQ ID NO 66 |
| TPP-10274 | SEQ ID NO 68 | SEQ ID NO 66 |
| TPP-10282 | SEQ ID NO 69 | SEQ ID NO 66 |
| TPP-10283 | SEQ ID NO 70 | SEQ ID NO 66 |
| TPP-10290 | SEQ ID NO 71 | SEQ ID NO 66 |
| TPP-10294 | SEQ ID NO 72 | SEQ ID NO 66 |
| TPP-10765 | SEQ ID NO 73 | SEQ ID NO 66 |
| TPP-10845 | SEQ ID NO 74 | SEQ ID NO 66 |
| TPP-10847 | SEQ ID NO 75 | SEQ ID NO 66 |
| TPP-10992 | SEQ ID NO 76 | SEQ ID NO 66 |
| TPP-13054 | SEQ ID NO 77 | SEQ ID NO 66 |
| TPP-13061 | SEQ ID NO 78 | SEQ ID NO 66 |
| TPP-13230 | SEQ ID NO 79 | SEQ ID NO 66 |
| TPP-10355 | SEQ ID NO 65 | SEQ ID NO 80 |
| TPP-10361 | SEQ ID NO 65 | SEQ ID NO 81 |
| TPP-9902 | SEQ ID NO 442 | SEQ ID NO 66 |
| TPP-11156 | SEQ ID NO 443 | SEQ ID NO 66 |
| TPP-18034 | SEQ ID NO 444 | SEQ ID NO 66 |
| TPP-12897 | SEQ ID NO 445 | SEQ ID NO 447 |
| TPP-12377 | SEQ ID NO 445 | SEQ ID NO 66 |
| TPP-9465 | SEQ ID NO 446 | SEQ ID NO 66 |

Antibodies of the present invention or fragments thereof include naturally occurring purified products, products of chemical synthetic procedures, and products produced by recombinant techniques. Depending on its origin, the antibody or fragment thereof according to the present invention may be glycosylated or non-glycosylated.

For example, standard recombinant DNA methodologies may be used to prepare and/or obtain nucleic acids encoding the heavy and light chains, incorporate these nucleic acids into expression vectors and introduce the vectors into host cells for recombinant expression (see, for example, Sambrook, Fritsch and Maniatis (eds.), Molecular Cloning; A Laboratory Manual, Second Edition, Cold Spring Harbor, N.Y., (1989); Ausubel, F. M. et al. (eds.) Current Protocols in Molecular Biology, Greene Publishing Associates, (1989); Goeddel, Gene Expression Technology, Methods in Enzymology 185, Academic Press, San Diego, Calif. (1990); and U.S. Pat. No. 4,816,397 by Boss et al.).

Thus, in a second aspect, the present invention relates to a nucleic acid or a mixture of nucleic acids encoding the antibody or fragment thereof according to the present invention. These nucleic acid sequences may be optimized in certain cases for mammalian expression. DNA molecules of the invention are not limited to the sequences disclosed herein, but also include variants thereof.

The present invention further provides recombinant nucleic acid constructs comprising one or more of the nucleic acid sequences according to the present invention. The recombinant nucleic acid construct according to the present invention may for instance comprise a nucleic acid vector, such as a plasmid, into which a nucleic acid molecule encoding an antibody or fragment thereof according to the present invention has been inserted. It is understood that the design of the expression vector, including the selection of regulatory sequences is affected by factors such as the choice of the host cell, the desired protein expression level and whether constitutive or inducible expression is desired.

Useful expression vectors for bacterial use may be constructed by inserting one or more nucleic acid sequences according to the present invention together with suitable translation initiation and termination signals in operable reading phase with a functional promoter. Bacterial expression vectors typically comprise one or more phenotypic selectable markers and an origin of replication to ensure maintenance of the vector and, if desirable, to provide amplification within the bacterial host. Bacterial expression vectors may comprise elements derived from commercially available plasmids such as the well-known cloning vector pBR322 (ATCC 37017). A number of bacterial expression vectors may be advantageously selected depending upon the use intended of the expressed antibody or fragment thereof. For example, if a large quantity of such antibody is desired, vectors mediating high level expression of antibody fusion proteins that are readily purified may be desirable.

Recombinant nucleic acid constructs intended for antibody expression in a eukaryotic host cell may comprise regulatory sequences that are able to control the expression of an open reading frame in a eukaryotic cell, preferably a promoter and a polyadenylation signal. Promoters and polyadenylation signals are preferably selected to be functional within the specific cell type intended for antibody expression. Examples of suitable promoters include but are not limited to promoters from Cytomegalovirus (CMV), such as the strong CMV immediate early promoter, Simian Virus 40 (SV40), Mouse Mammary Tumor Virus (MMTV), Human Immunodeficiency Virus (HIV), such as the HIV Long Terminal Repeat (LTR) promoter, Moloney virus, Epstein Barr Virus (EBV), adenovirus (e.g., the adenovirus major late promoter (AdMLP)), polyoma and from Rous Sarcoma Virus (RSV), the synthetic CAG promoter composed of the CMV early enhancer element, the promoter, the first exon and the first intron of chicken beta-actin gene and the splice acceptor of the rabbit beta globin gene, as well as promoters from mammalian genes such as actin, myosin, hemoglobin, muscle creatine, and metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals include but are not limited to the bovine growth hormone (BGH) polyadenylation site, SV40 polyadenylation signals and LTR polyadenylation signals.

In addition, the recombinant nucleic acid sequence may comprise one or more enhancer sequences. The enhancer can be, for example, an enhancer of mammalian actin, myosin, hemoglobin, muscle creatine or a viral enhancer, e.g. an enhancer from CMV, RSV, SV40 or EBV. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

Regulatory sequences and codons are generally species dependent, so in order to maximize protein production, the regulatory sequences and codons are preferably selected to be effective in the species/cell type intended for antibody expression. The person skilled in the art can produce recombinant DNA molecules that are functional in a given subject species.

The mammalian recombinant expression vectors can also include origins of replication and selectable markers (see e.g., U.S. Pat. Nos. 4,399,216, 4,634,665 and 5,179,017). Suitable selectable markers include genes that confer resistance to drugs such as G418, puromycin, hygromycin, blasticidin, zeocin/bleomycin or methotrexate or selectable marker that exploit auxotrophies such as Glutamine Synthetase on a host cell into which the vector has been introduced. For example, the dihydrofolate reductase (DHFR) gene confers resistance to methotrexate, the neo gene confers resistance to G418, the bsd gene from *Aspergillus terreus* confers resistance to blasticidin, puromycin N-acetyl-transferase confers resistance to puromycin, the Sh ble gene product confers resistance to zeocin, and resistance to hygromycin is conferred by the *E. coli* hygromycin resistance gene (hyg or hph). Selectable markers like DHFR or Glutamine Synthetase are also useful for amplification techniques in conjunction with MTX and MSX.

In some embodiments, the nucleic acid sequences encoding the heavy and light chains are inserted into separate vectors. In other embodiments, the nucleic acid sequences encoding the heavy and light chains are inserted into the same vector. In addition, the nucleic acid sequences encoding variable regions of the heavy and/or light chains can be converted, for example, to nucleic acid sequences encoding full-length antibody chains, Fab fragments, or to scFv. The VL- or VH-encoding DNA fragment can be operatively linked, (such that the amino acid sequences encoded by the two DNA fragments are in-frame) to another DNA fragment encoding, for example, an antibody constant region or a flexible linker. As an example, to create a polynucleotide sequence that encodes a scFv, the VH- and VL-encoding nucleic acids can be operatively linked to another fragment encoding a flexible linker such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554). The sequences of human heavy chain and light chain constant regions are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

In particular embodiments, the nucleic acid sequences encoding the heavy chain into which the heterologous amino acid sequence comprising the natriuretic peptide is incorporated comprises the sequence of any one of SEQ ID NOs 82 or 83 or a sequence having at least 80%, at least 85%, at least 90% or at least 95% sequence identity with any one of SEQ ID NOs 82 or 83. In particular such embodiments, the nucleic acid sequence encoding the light chain comprises the sequence of SEQ ID NO 84 or a sequence having at least 80%, at least 85%, at least 90% or at least 95% sequence identity therewith.

In a third aspect, the present invention relates to a host cell comprising the nucleic acid or the mixture of nucleic acids according to the present invention. Within the context of the present invention, the terms "host cell", "host cell line", and "host cell culture" are used interchangeably and refer to cells into which an exogenous nucleic acid has been introduced, including the progeny of such cells. Host cells include "transformants", "transformed cells", "transfectants", "transfected cells", and "transduced cells", which include the primary transformed/transfected/transduced cell and progeny derived therefrom without regard to the number of passages. Progeny may not be completely identical in nucleic acid content to a parent cell, and the comprised exogenous nucleic acid may contain mutations. Mutant progeny that have the same function or biological activity as screened or selected for in the originally transformed cell are included herein.

Transfection of the expression vector into a host cell can be carried out using standard techniques such as electroporation, nucleofection, calcium-phosphate precipitation, lipofection, polycation-based transfection such as polyethlylenimine (PEI)-based transfection and DEAE-dextran transfection.

Suitable host cells include prokaryotic and eukaryotic cells. Examples for prokaryotic host cells are e.g. bacteria and include but are not limited to *Escherichia coli, Bacillus subtilis, Salmonella typhimurium* and various species within the genera *Pseudomonas, Streptomyces*, and *Staphylococcus*.

Non limiting examples of eukaryotic hosts cells include yeasts, insects and insect cells, plants and plant cells, transgenic animals and mammalian cells. Suitable mammalian host cells for antibody expression include Chinese Hamster Ovary (CHO cells) such as CHO-K1, CHO-S, CHO-K1SV (including dhfr-CHO cells, described in Urlaub and Chasin, (1980) Proc. Natl. Acad. Sci. USA 77:4216-4220 and Urlaub et al., Cell. 1983 June; 33(2):405-12, used with a DHFR selectable marker, e.g., as described in R. J. Kaufman and P. A. Sharp (1982) Mol. Biol. 159:601-621; and other knockout cells exemplified in Fan et al., Biotechnol Bioeng. 2012 April; 109(4):1007-15), NSO myeloma cells, COS cells, HEK293 cells, HKB11 cells, BHK21 cells, CAP cells, EB66 cells, and SP2 cells.

Expression may also be transient or semi-stable in expression systems such as HEK293, HEK293T, HEK293-EBNA, HEK293E, HEK293-6E, HEK293-Freestyle, HKB11, Expi293F, 293EBNALT75, CHO Freestyle, CHO—S, CHO-K1, CHO-K1SV, CHOEBNALT85, CHOS-XE, CHO-3E7 or CAP-T cells (for instance Durocher et al., Nucleic Acids Res. 2002 Jan. 15; 30(2):E9).

In a fourth aspect, the present invention relates to a process for producing an antibody or fragment thereof, comprising culturing the host cell according to the present invention. Particularly, the host cell according to the present invention is cultured under conditions suitable for expression of the antibody or fragment thereof.

Antibody expression may be constitutive or regulated (e.g., inducible). For inducible antibody expression the host cell according to the present invention is typically grown to an appropriate cell density followed by de-repression/induction of the selected promoter by appropriate means (e.g., temperature shift or chemical induction such as addition or removal of small molecule inductors such as tetracycline in conjunction with Tet system) and culturing of the host cell for an additional period.

In particular embodiments, the process for producing an antibody or fragment thereof according to the present invention further comprises the step of recovering the antibody or fragment thereof from the host cell culture. Cells may for instance be harvested by centrifugation, disrupted by physical or chemical means, and the antibody or fragment thereof may be further purified from the resulting crude extract. In some embodiments, the expression vector is designed such that the expressed antibody or fragment thereof is secreted into the culture medium in which the host cells are grown. In that case, the antibody or fragment thereof can be directly recovered from the culture medium using standard protein purification methods.

In particular embodiments, the process according to the present invention further comprises the step of purifying the recovered antibody or fragment thereof. Particularly, the antibody is purified (1) to greater than 90% as determined e.g. by analytical chromatography or by SDS-Capillary Gel electrophoresis (for example on a Caliper LabChip GXII, GX 90 or Biorad Bioanalyzer device), and, more particularly, purification yields an antibody homogeneity of at least about 92.5%, 95%, 98% or 99%; alternatively, the antibody is purified (2) to a degree sufficient to obtain at least 15 residues of N-terminal or internal amino acid sequence, or (3) to homogeneity by SDS-PAGE under reducing or non-reducing conditions using Coomassie blue or, preferably, silver stain.

Antibodies or fragments thereof according to the present invention can be recovered and purified from recombinant cell cultures by well-known methods including, but not limited to ammonium sulfate or ethanol precipitation, acid extraction, Protein A chromatography, Protein G chromatography, size exclusion chromatography, anion or cation exchange chromatography, phospho-cellulose chromatography, hydrophobic interaction chromatography, affinity chromatography, hydroxylapatite chromatography and lectin chromatography. High performance liquid chromatography ("HPLC") can also be employed for purification (see, e.g., Colligan, Current Protocols in Immunology, or Current Protocols in Protein Science, John Wiley & Sons, NY, N.Y., (1997-2001), e.g., Chapters 1, 4, 6, 8, 9, 10).

In a fifth aspect, the present invention relates to a composition comprising the antibody or fragment thereof according the present invention. Particularly, the composition according to the present invention is a pharmaceutical composition suitable for use in a method for treatment, wherein the antibody or fragment thereof according to the present invention is contained in an amount effective to achieve the intended purpose, i.e. prevention or treatment of a particular disease state.

The composition optionally further comprises at least one pharmaceutically acceptable excipient. In the context of the present invention, the term "excipient" refers to a natural or synthetic substance formulated alongside the active ingredient of a medication. Suitable excipients include antiadherents, binders, coatings, disintegrants, flavors, colors, lubricants, glidants, sorbents, preservatives and sweeteners. Specific examples of pharmaceutically acceptable excipients include but are not limited to saline, buffered saline, dextrose, and water. In the context of the present invention, the term "pharmaceutically acceptable" refers to molecular entities and other ingredients of pharmaceutical compositions that are physiologically tolerable and do not typically produce untoward reactions when administered to a mammal (e.g., human). The term "pharmaceutically acceptable" may also mean approved by a regulatory agency of a Federal or a state government or listed in the U.S. Pharmacopeia or other generally recognized pharmacopeia for use in mammals, and, more particularly, in humans.

The composition according to the present invention may further comprise one or more further therapeutically active agents.

The pharmaceutical composition may be in the form of a solution, a suspension, an enteric coated capsule, a lyophilized powder or any other form suitable for the intended use.

Pharmaceutical compositions for oral administration can be formulated using pharmaceutically acceptable excipients well known in the art in dosages suitable for oral administration. Such excipients enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methylcellulose, hydroxypropylmethylcellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores can be provided with suitable coatings such as concentrated sugar solutions, which may also contain gum arabic, talc, polyvinyl pyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, i.e. dosage.

Pharmaceutical preparations that can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of a therapeutically active agent. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active agent may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the therapeutically active agent to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a salt and can be formed with acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 7.5 that is combined with buffer prior to use.

Further details on techniques for formulation and administration may be found in the latest edition of Remington's Pharmaceutical Sciences (Ed. Maack Publishing Co, Easton, Pa.).

After preparation of a pharmaceutical composition comprising the antibody or fragment thereof according to the present invention, it may be placed in an appropriate container and labeled for treatment of an indicated condition. For administration of the antibody or fragment according to the present invention, such labeling would include amount, frequency and method of administration.

The present invention further provides pharmaceutical packs and kits comprising one or more containers filled with one or more of the ingredients of the aforementioned compositions according to the present invention. Associated with such container(s) can be a notice in the form prescribed by a governmental agency regulating the manufacture, use or sale of pharmaceuticals or biological products, reflecting approval by the agency of the manufacture, use or sale of the product for human administration.

In a sixth aspect, the present invention relates to the antibody or fragment thereof according to the present invention or the composition according to the present invention for use in a method for treatment.

Particularly, such method for treatment involves administering to a subject in need thereof a therapeutically effective amount of the antibody or fragment thereof according to the present invention. The subject may be a human or non-human animal (e.g., rabbit, rat, mouse, dog, monkey or other lower-order primate).

Within the context of the present invention, the term "therapeutically effective amount" is defined as the amount of an antibody or fragment thereof according to the present invention that is sufficient to prevent or alleviate disease symptoms of any of the disorders and diseases mentioned herein—either as a single dose or according to a multiple dose regimen, alone or in combination with other agents. In particular embodiments, said "therapeutically effective amount" is toxicologically tolerable. The determination of an effective dose is well within the capability of those skilled in the art. The therapeutically effective amount of a therapeutic agent usually largely depends on particular patient characteristics such as age, weight, gender and disease state, time, frequency and route of administration, drug combination(s), and the nature of the disorder being treated. Common dosage amounts for antibodies vary from 0.1 to 100,000 micrograms, up to a total dose of about 10 g, depending upon the route of administration.

General guidance for its determination can be found, for example, in the publications of the International Conference on Harmonization and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament that may be determined using methods well known in the art and found in the foregoing references. In brief, therapeutic efficacy and toxicity of therapeutic agents may be determined in cell culture assays or in animal models, e.g., as ED50 (the dose therapeutically effective in 50% of the population) and LD50 (the dose lethal to 50% of the population), respectively. The dose ratio between ED50 and LD50 is the therapeutic index.

The antibody or fragment thereof according to the present invention is suitable for treatment and/or prophylaxis of cardiovascular, renal, pulmonary, skeletal, ocular, thromboembolic and fibrotic diseases and disorders, dwarfism, achondroplasia as well as other cGMP-related and/or natriuretic peptide responsive disorders. Thus, in particular embodiments, the antibody or fragment thereof is for use in the treatment and/or prophylaxis of any one of these disorders and diseases or any combination thereof.

The antibody or fragment thereof according to the present invention can therefore be used in medicaments for treatment and/or prophylaxis of cardiovascular disorders, for example arterial and pulmonary hypertension, resistant and refractory hypertension, acute and chronic heart failure, coronary heart disease, Bronchiolitis obliterans Syndrome (BOS), tumor related and oncological diseases, graft versus host disease, sickle cell disease, stable and unstable angina pectoris, peripheral and cardiac vascular disorders, arrhythmias, atrial and ventricular arrhythmias and impaired conduction, for example atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation, for example pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenosis, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for treatment and/or prophylaxis of erectile dysfunction and female sexual dysfunction.

In the context of the present invention, the term "heart failure" encompasses both acute and chronic forms of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure, heart failure with preserved ejection fraction (HFpEF), heart failure with reduced ejection fraction (HFrEF) and acute phases of worsening of existing chronic heart failure (worsening heart failure).

In addition, the antibody or fragment thereof according to the present invention can also be used for treatment and/or prophylaxis of arteriosclerosis, peripheral artery disease (PAD), impaired lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity and of combined hyperlipidaemias and metabolic syndrome.

The antibody or fragment thereof according to the present invention can additionally be used for treatment and/or prophylaxis of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The antibody or fragment thereof according to the present invention is also suitable for treating urological disorders, for example benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic overactive bladder (OAB) and (IC), incontinence (UI), for example mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The antibody or fragment thereof according to the present invention is also suitable for treatment and/or prophylaxis of kidney disorders, in particular of acute and chronic renal insufficiency and acute and chronic renal failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerular and arterioles, tubular dilatation, hyperphosphatemia and/or need for dialysis. The present invention also encompasses the use of the antibody or fragment thereof according to the present invention for treatment and/or prophylaxis of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

In addition, the antibody or fragment thereof according to the present invention are also suitable for treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke). Bronchiolitis obliterans Syndrom (BOS), and cystic fibrosis (CF).

The antibody or fragment thereof according to the present invention is also suitable for control of central nervous system disorders characterized by disturbances of the NO/cGMP system. It is suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis. It is also suitable for treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

The antibody or fragment thereof according to the present invention is additionally also suitable for controlling cerebral blood flow and thus represent effective agents for controlling migraine. It is also suitable for the prophylaxis and control of sequelae of cerebral infarct (Apoplexia cerebri) such as stroke, cerebral ischaemias and skull-brain trauma. It can likewise be used for controlling states of pain and tinnitus.

In addition, the antibody or fragment according to the present invention has anti-inflammatory action and can therefore be used as anti-inflammatory agents for treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the antibody or fragment thereof according to the present invention can also be used for treatment and/or prophylaxis of autoimmune diseases.

The antibody or fragment thereof is also suitable for treatment and/or prophylaxis of fibrotic disorders of the internal organs, for example the lung, the heart, the kidney, the reproductive system, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, uterine fibroids, endometriosis, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarcoidosis).

The antibody or fragment thereof according to the present invention is also suitable for controlling postoperative scarring, for example as a result of glaucoma operations.

The antibody or fragment thereof according to the present invention can likewise be used cosmetically for ageing and keratinized skin.

Moreover, the antibody or fragment thereof according to the present invention is suitable for treatment and/or prophylaxis of hepatitis, neoplasms, osteoporosis, glaucoma and gastroparesis.

The antibody or fragment thereof according to the present invention is moreover suitable for treatment and/or prophylaxis of eye disorders such as ophthalmic diseases responsive to natriuretic peptides, retina disorders, glaucoma including primary open angle glaucoma (POAG), angle closure glaucoma, and congenital/developmental glaucoma, retinopathies, ocular trauma, optic neuropathies, ocular hypertension, elevated intraocular pressure, diabetic retinopathy, macular degeneration (AMD), age-related eye diseases, macular oedema, scleritis, uveitis, dry eye, corneal epithelial abrasion, corneal ulcer.

Moreover, the antibody or fragment thereof according to the present invention is suitable for the treatment of bone and cartilage disorders such as bone and cartilage diseases responsive to natriuretic peptides, arthritis, degenerative diseases of cartilage tissue, osteoarthritis, cartilage degeneration, bone fractures, skeletal dysplasias, achondroplasia, osteoporosis, osteogenesis imperfecta, Paget disease of bone (PDB), metabolic bone disease, age-related bone diseases, osteomyelitis, osteonecrosis, rickets, osteomalacia, growth plate injuries and diseases, joint and bone replacement associated defects, Marfan syndrome, sports injuries, muscular dystrophies, Duchenne muscular dystrophy.

Thus, in another aspect, the present invention relates to the use of the antibody or fragment thereof according to the present invention for treatment and/or prophylaxis of disorders, in particular the disorders mentioned above.

In particular embodiments, the antibody or fragment thereof according to the present invention is for use in a method for treatment and/or prophylaxis of heart failure, angina pectoris, hypertension, pulmonary hypertension, ischaemias, vascular disorders, renal insufficiency, thromboembolic disorders, fibrotic disorders, skeletal and bone disorders, ocular disorders and arteriosclerosis.

In another aspect, the present invention relates to the use of antibody or fragment thereof according to the present invention for production of a medicament for treatment and/or prophylaxis of disorders, especially of the aforementioned disorders.

In particular embodiments, the present invention relates to the use of the antibody or fragment thereof according to the present invention for production of a medicament for treatment and/or prophylaxis of heart failure, angina pectoris, hypertension, pulmonary hypertension, ischaemias, vascular disorders, renal insufficiency, thromboembolic disorders, fibrotic disorders, dementia illness, arteriosclerosis, skeletal and bone disorders, ocular disorders, dwarfism, achondroplasia and erectile dysfunction.

In another aspect, the present invention relates to a method for treatment and/or prophylaxis of disorders, in particular the disorders mentioned above, using an effective amount of at least one antibody or fragment thereof according to the present invention.

In particular embodiments, the present invention relates to a method for treatment and/or prophylaxis of heart failure, angina pectoris, hypertension, pulmonary hypertension, ischaemias, vascular disorders, renal insufficiency, thromboembolic disorders, fibrotic disorders, tumor and oncological diseases, skeletal and bone disorders, ocular disorders, dwarfism, achondroplasia and arteriosclerosis using an effective amount of at least one antibody or fragment thereof according to the present invention.

An antibody of the invention or fragment thereof according to the present invention may be administered as the sole pharmaceutical agent or in combination with one or more additional therapeutic agents, and in some instances the antibody might itself be modified. For example, an antibody or fragment thereof could be conjugated to a chemical entity e.g., to further increase efficacy, stability and/or half-life. Particularly, the antibody or fragment thereof according to the present invention may be PEGylated and/or HESylated.

Thus, in particular embodiments, the antibody or fragment thereof according to the present invention is used in combination with at least one additional therapeutic agent in a method of treatment, in particular for the above cited purposes.

The present invention further provides pharmaceutical combinations comprising at least one antibody or fragment thereof according to the present invention and at least one additional therapeutic agent.

Within the context of the present invention, the term "pharmaceutical combination" is used as known to persons skilled in the art, it being possible for such combination to be a fixed combination, a non-fixed combination or a kit-of-parts.

Within the context of the present invention, the term "fixed combination" is used as known to persons skilled in the art and is defined as a combination wherein, for example, a first active ingredient, such as one or more antibody or fragment thereof according to the present invention, and a further active ingredient are present together in one unit dosage or in one single entity, e.g., a single dosage formulation. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture. The present invention thus provides such pharmaceutical compositions comprising at least one antibody or fragment thereof and at least one additional therapeutic agent, in particular for use in treatment and/or prophylaxis of the aforementioned disorders.

Within the context of the present invention, the terms "non-fixed combination" and "kit-of-parts" are used as known to persons skilled in the art and are defined as a combination wherein a first active ingredient and a further active ingredient are present in more than one unit, e.g., in separate dosage formulations. One example of a non-fixed combination or kit-of-parts is a combination wherein the first active ingredient and the further active ingredient are present separately.

It is possible for the components of the non-fixed combination or kit-of-parts to be administered separately, sequentially, simultaneously, concurrently or chronologically staggered.

The antibody or fragment thereof according to the present invention may be administered simultaneously with, prior to or after said further therapeutically active agent. In the context of the present invention, the term "simultaneously with" means administration of the antibody or fragment thereof according to the present invention and the at least one further therapeutically active agent on the same day, more particularly within 12 hours, more particularly within 2 hours.

In particular embodiments, administration of the antibody or fragment thereof according to the present invention and the at least one further therapeutically active agent occurs within eight consecutive weeks, more particularly within one to six consecutive weeks. The antibody or fragment thereof according to the present invention and the at least one further therapeutically active agent may be administered via the same route or via different routes.

The antibody or fragment thereof according to the present invention may for instance be combined with known agents of the same indication treatment group, such as agents used for the treatment and/or prophylaxis of diseases and/or conditions associated with hypertension, heart failure, pulmonary hypertension, COPD, asthma, cystic fibrosis, achondroplasia, hyperphosphatemia, chronic kidney disease (CKD), soft tissue calcification, chronic kidney disease associated calcification, non-chronic kidney disease associated calcification, media calcifications including Moenckeberg's medial sclerosis, atherosclerosis, intima calcification, CKD associated heart hypertrophy, CKD associated renal dystrophy, osteoporosis, post-menopausal osteoporosis, diabetes mellitus II, chronic renal disease, aging, hypophosphaturia, hyperparathyroidism, Vitamin D disorders, Vitamin K deficiency, Vitamin K-antagonist coagulants, Kawasaki disease, ACDC (arterial calcification due to deficiency of CD73), GACI (generalized arterial calcification of infancy), IBGC (idiopathic basal ganglia calcification), PXE (pseudoxanthoma elasticum), rheumatoid arthritis, Singleton-Merten syndrome, P-thalassemia, calciphylaxis, heterotrophic ossification, preterm placental calcification, calcification of the uterus, calcified uterine fibroids, morbus fahr, mircocalcification and calcification of the aortic valve.

Preferred examples of suitable further therapeutic agents to be combined with the antibody or fragment thereof according to the present invention:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil, tadalafil, udenafil, desantafil, avanafil, mirodenafil, lodenafil or PF-00489791;

antithrombotic agents, by way of example and with preference from the group of the platelet aggregation inhibitors, the anticoagulants or the profibrinolytic substances;

hypotensive active ingredients, by way of example and with preference from the group of the calcium antagonists, angiotensin All antagonists, ACE inhibitors, NEP-inhibitors, vasopeptidase-inhibitors, endothelin antagonists, renin inhibitors, alpha-receptor blockers, beta-receptor blockers, mineralocorticoid receptor antagonists, rho-kinase-inhibitors and the diuretics;

antiarrhythmic agents, by way of example and with preference from the group of sodium channel blocker, beta-receptor blocker, potassium channel blocker, calcium antagonists, If-channel blocker, digitalis, parasympatholytics (vagoliytics), sympathomimetics and other antiarrhythmics as adenosin, adenosine receptor agonists as well as vernakalant;

positive-inotropic agents, by way of example cardiac glycoside (Dogoxin), beta-adrenergic and dopaminergic agonists, such as isoprenalin, adrenalin, noradrenalin, dopamin or dobutamin;

vasopressin-rezeptor-antagonists, by way of example and with preference from the group of conivaptan, tolvaptan, lixivaptan, mozavaptan, satavaptan, SR-121463, RWJ 676070 or BAY 86-8050, as well as the compounds described in WO 2010/105770, WO2011/104322 and WO 2016/071212;

active ingredients which alter lipid metabolism, for example and with preference from the group of the thyroid receptor agonists, PCSK9 inhibitors, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

anti-inflammatory agents, for example and with preference from the group of the gluco-corticoids, such as, by way of example and preferably, prednison, prednisolon, methylprednisolon, triamcinolon, dexamethason, beclomethason, betamethason, flunisolid, budesonid or fluticason as well as the non-steroidal anti-inflammatory agents (NSAIDs), by way of example and preferably, acetyl salicylic acid (aspirin), ibuprofen and naproxen, 5-amino salicylic acid-derivates, leukotriene-antagonists, TNF-alpha-inhibitors and chemokine-receptor antagonists, such as CCR1, 2 and/or 5 inhibitors;

agents that inhibit the signal transductions cascade, for example and with preference from the group of the kinase inhibitors, by way of example and preferably, from the group of the tyrosine kinase and/or serine/threonine kinase inhibitors;

agents, that inhibit the degradation and modification of the extracellular matrix, for example and with preference from the group of the inhibitors of the matrix-metalloproteases (MMPs), by way of example and preferably, inhibitors of chymasee, stromelysin, collagenases, gelatinases and aggrecanases (with preference from the group of MMP-1, MMP-3, MMP-8, MMP-9, MMP-10, MMP-11 and MMP-13) as well as of the metallo-elastase (MMP-12) and neutrophil-elastase (HNE), as for example sivelestat or DX-890;

agents, that block the binding of serotonin to its receptor, for example and with preference antagonists of the 5-HT2b-receptor;

anti-fibrotic agents, for example and with preference, nintedanib, pirfenidone, adenosine A2b receptor antagonists, sphingosine-1-phosphate receptor 3 (S1P3) antagonists, autotaxin-inhibitors, lysophosphatidic acid receptor 1 (LPA-1) and lysophosphatidic acid receptor 2 (LPA-2) antagonists, lysyloxidase (LOX) inhibitors, lysyloxidase-like-2 inhibitors, CTGF inhibitors, IL-13 antagonists, integrin antagonists, TGF-beta antagonists, inhibitors of wnt signaling, CCR2-antagonists;

agents, that act as bronchodilators, for example and with preference antagonists of the 5-HT2b-receptor; β2("beta two")-adrenergic agonists (short- and long-acting), anticholinergics, and theophylline;

agents that are antagonists of cytokines and chemokines, for example and with preference antagonists of TGF-beta, CTGF, IL-1, IL-4, IL-5, IL-6, IL-8, IL-13, IL-25, IL-33, TSLP and integrins;

organic nitrates and NO-donators, for example and with preference sodium nitroprussid, nitro-glycerine, isosorbid mononitrate, isosorbid dinitrate, molsidomine or SIN-1, as well as inhaled NO;

NO-independent, but heme-dependent stimulators of the soluble guanylate cyclase, for example and with preference the compounds described in WO 00/06568, WO 00/06569, WO 02/42301, WO 03/095451, WO 2011/147809, WO 2012/004258, WO 2012/028647 and WO 2012/059549;

NO-independent and heme-independent activators of the soluble guanylate cyclase, for example and with preference the compounds described in WO 01/19355, WO 01/19776, WO 01/19778, WO 01/19780, WO 02/070462 and WO 02/070510;

agents, that stimulate the synthesis of cGMP, for example sGC modulators, for example and with preference riociguat, cinaciguat, vericiguat;

prostacyclin-analogs or IP receptor agonists, for example and with preference iloprost, beraprost, treprostinil, epoprostenol or Selexipag;

endothelin receptor antagonists, for example and with preference Bosentan, Darusentan, Ambrisentan oder Sitaxsentan;

agents, that inhibit soulble epoxidhydrolase (sEH), for example and with preference N,N'-Di-cyclohexyl urea, 12-(3-Adamantan-1-yl-ureido)-dodecanic acid or 1-Adamantan-1-yl-3-{5-[2-(2-ethoxyethoxy)ethoxy]pentyl}-urea;

agents that interact with glucose metabolism, for example and with preference insuline, biguanide, thiazolidinedione, sulfonyl urea, acarbose, DPP4 inhibitors, GLP-1 analogs or SGLT-1 inhibitors;

natriuretic peptides, for example and with preference Atrial Natriuretic Peptide (ANP, Carperitide), Brain Natriuretic Peptide (BNP, Nesiritide), C-Type Natriuretic Peptide (CNP) or urodilatin;

natriuretic peptide derivatives, for example and with preference vosoritide, cenderitide, PL 3994 activators of the cardiac myosin, for example and with preference omecamtiv mecarbil (CK-1827452);

calcium-sensitizers, for example and with preference levosimendan;

agents that affect the energy metabolism of the heart, for example and with preference etomoxir, dichloroacetat, ranolazine or trimetazidine, full or partial adenosine A1 receptor agonists such as GS-9667 (formerly known as CVT-3619), capadenoson and neladenoson;

agents that affect the heart rate, for example and with preference ivabradin.

Antithrombotic agents are preferably understood to mean compounds from the group of the platelet aggregation inhibitors, the anticoagulants or the profibrinolytic substances.

In particular embodiments, the antibody or fragment thereof according to the present invention is administered in combination with a platelet aggregation inhibitor, by way of example and with preference aspirin, clopidogrel, prasugrel, ticagrelor, ticlopidin or dipyridamole.

In particular embodiments, the antibody or fragment thereof according to the present invention is administered in combination with a thrombin inhibitor, by way of example and with preference ximelagatran, dabigatran, melagatran, bivalirudin or clexane.

In particular embodiments, the antibody or fragment thereof according to the present invention is administered in combination with a GPIIb/IIIa antagonist such as, by way of example and with preference, tirofiban or abciximab.

In particular embodiments, the antibody or fragment thereof according to the present invention is administered in combination with a factor Xa inhibitor, by way of example and with preference rivaroxaban, DU-176b, apixaban, betrixaban, otamixaban, fidexaban, razaxaban, letaxaban, eribaxaban, fondaparinux, idraparinux, PMD-3112, darexaban (YM-150), KFA-1982, EMD-503982, MCM-17, MLN-1021, DX 9065a, DPC 906, JTV 803, SSR-126512 or SSR-128428.

In particular embodiments, the antibody or fragment thereof according to the present invention is administered in combination with heparin or with a low molecular weight (LMW) heparin derivative.

In particular embodiments, the antibody or fragment thereof according to the present invention is administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, rho-kinase inhibitors and the diuretics.

In particular embodiments, the antibody or fragment thereof according to the present invention is administered in combination with a calcium antagonist, by way of example and with preference nifedipine, amlodipine, verapamil or diltiazem.

In particular embodiments, the antibody or fragment thereof according to the present invention is administered in combination with an alpha-1-receptor blocker, by way of example and with preference prazosin.

In particular embodiments, the antibody or fragment thereof according to the present invention is administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In particular embodiments, the antibody or fragment thereof according to the present invention is administered in combination with an angiotensin AII antagonist, by way of example and with preference losartan, candesartan, valsartan, telmisartan or embusartan or a dual angiotensin AII antagonist/neprilysin-inhibitor, by way of example and with preference LCZ696 (valsartan/sacubitril).

In particular embodiments, the antibody or fragment thereof according to the present invention is administered in combination with an ACE inhibitor, by way of example and with preference enalapril, captopril, lisinopril, ramipril, delapril, fosinopril, quinopril, perindopril or trandopril.

In particular embodiments, the antibody or fragment thereof according to the present invention is administered in combination with an endothelin antagonist, by way of example and with preference bosentan, darusentan, ambrisentan or sitaxsentan.

In particular embodiments, the antibody or fragment thereof according to the present invention is administered in combination with a renin inhibitor, by way of example and with preference aliskiren, SPP-600 or SPP-800.

In particular embodiments, the antibody or fragment thereof according to the present invention is administered in combination with a mineralocorticoid receptor antagonist, by way of example and with preference finerenone, spironolactone or eplerenone.

In particular embodiments, the antibody or fragment thereof according to the present invention is administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In particular embodiments, the antibody or fragment thereof according to the present invention is administered in combination with a CETP inhibitor, by way of example and with preference dalcetrapib, anacetrapib, torcetrapib (CP-529 414), JTT-705 or CETP vaccine (Avant).

In particular embodiments, the antibody or fragment thereof according to the present invention is administered in combination with a thyroid receptor agonist, by way of example and with preference D-thyroxine, 3,5,3'-triiodothyronine (T3), CGS 23425 or axitirome (CGS 26214).

In particular embodiments, the antibody or fragment thereof according to the present invention is administered in combination with an HMG-CoA reductase inhibitor from the class of statins, by way of example and with preference lovastatin, simvastatin, pravastatin, fluvastatin, atorvastatin, rosuvastatin or pitavastatin.

In particular embodiments, the antibody or fragment thereof according to the present invention is administered in combination with a squalene synthesis inhibitor, by way of example and with preference BMS-188494 or TAK-475.

In particular embodiments, the antibody or fragment thereof according to the present invention is administered in combination with an ACAT inhibitor, by way of example and with preference avasimibe, melinamide, pactimibe, eflucimibe or SMP-797.

In particular embodiments, the antibody or fragment thereof according to the present invention is administered in combination with an MTP inhibitor, by way of example and with preference implitapide, BMS-201038, R-103757 or JTT-130.

In particular embodiments, the antibody or fragment thereof according to the present invention is administered in combination with a PPAR-gamma agonist, by way of example and with preference pioglitazone or rosiglitazone.

In particular embodiments, the antibody or fragment thereof according to the present invention is administered in combination with a PPAR-delta agonist, by way of example and with preference GW 501516 or BAY 68-5042.

In particular embodiments, the antibody or fragment thereof according to the present invention is administered in combination with a cholesterol absorption inhibitor, by way of example and with preference ezetimibe, tiqueside or pamaqueside.

In particular embodiments, the antibody or fragment thereof according to the present invention is administered in combination with a lipase inhibitor, a preferred example being orlistat.

In particular embodiments, the antibody or fragment thereof according to the present invention is administered in combination with a polymeric bile acid adsorbent, by way of example and with preference cholestyramine, colestipol, colesolvam, CholestaGel or colestimide.

In particular embodiments, the antibody or fragment thereof according to the present invention is administered in combination with a bile acid reabsorption inhibitor, by way of example and with preference ASBT (=IBAT) inhibitors, for example AZD-7806, S-8921, AK-105, BARI-1741, SC-435 or SC-635.

In particular embodiments, the antibody or fragment thereof according to the present invention is administered in combination with a lipoprotein(a) antagonist, by way of example and with preference, gemcabene calcium (CI-1027) or nicotinic acid.

In particular embodiments, the antibody or fragment thereof according to the present invention is administered in combination with a lipoprotein(a) antagonist, by way of example and with preference, gemcabene calcium (CI-1027) or nicotinic acid.

In particular embodiments, the antibody or fragment thereof according to the present invention is administered in combination with sGC modulators, by way of example and with preference, riociguat, cinaciguat or vericiguat.

In particular embodiments, the antibody or fragment thereof according to the present invention is administered in combination with an agent affecting the glucose metabolism, by way of example and with preference, insulin, a sulfonyl urea, acarbose, DPP4 inhibitors, GLP-1 analogs or SGLT-1 inhibitors.

In particular embodiments, the antibody or fragment thereof according to the present invention is administered in combination with a TGFbeta antagonist, by way of example and with preference pirfenidone, nintedanib or fresolimumab.

In particular embodiments, the antibody or fragment thereof according to the present invention is administered in combination with a CCR2 antagonist, by way of example and with preference CCX-140.

In particular embodiments, the antibody or fragment thereof according to the present invention is administered in combination with a TNFalpha antagonist, by way of example and with preference adalimumab.

In particular embodiments, the antibody or fragment thereof according to the present invention is administered in combination with a galectin-3 inhibitor, by way of example and with preference GCS-100.

In particular embodiments, the antibody or fragment thereof according to the present invention is administered in combination with a Nrf-2 inhibitor, by way of example and with preference bardoxolone.

In particular embodiments, the antibody or fragment thereof according to the present invention is administered in combination with a BMP-7 agonist, by way of example and with preference THR-184.

In particular embodiments, the antibody or fragment thereof according to the present invention is administered in combination with a NOX1/4 inhibitor, by way of example and with preference GKT-137831.

In particular embodiments, the antibody or fragment thereof according to the present invention is administered in combination with a medicament which affects the vitamin D metabolism, by way of example and with preference calcitriol, alfacalcidol, doxercalciferol, maxacalcitol, paricalcitol, cholecalciferol or paracalcitol.

In particular embodiments, the antibody or fragment thereof according to the present invention is administered in combination with a cytostatic agent, by way of example and with preference cyclophosphamide.

In particular embodiments, the antibody or fragment thereof according to the present invention is administered in combination with an immunosuppressive agent, by way of example and with preference ciclosporin.

In particular embodiments, the antibody or fragment thereof according to the present invention is administered in combination with a phosphate binder, by way of example and with preference colestilan, sevelamer hydrochloride and sevelamer carbonate, Lanthanum and lanthanum carbonate.

In particular embodiments, the antibody or fragment thereof according to the present invention is administered in combination with renal proximal tubule sodium-phosphate co-transporter, by way of example and with preference, niacin or nicotinamide.

In particular embodiments, the antibody or fragment thereof according to the present invention is administered in combination with a calcimimetic for therapy of hyperparathyroidism.

In particular embodiments, the antibody or fragment thereof according to the present invention is administered in combination with agents for iron deficit therapy, by way of example and with preference iron products.

In particular embodiments, the antibody or fragment thereof according to the present invention is administered in combination with agents for the therapy of hyperurikaemia, by way of example and with preference allopurinol or rasburicase.

In particular embodiments, the antibody or fragment thereof according to the present invention is administered in combination with glycoprotein hormone for the therapy of anaemia, by way of example and with preference erythropoietin.

In particular embodiments, the antibody or fragment thereof according to the present invention is administered in combination with biologics for immune therapy, by way of example and with preference abatacept, rituximab, eculizumab or belimumab.

In particular embodiments, the antibody or fragment thereof according to the present invention is administered in combination with vasopressin antagonists (group of the vaptanes) for the treatment of heart failure, by way of example and with preference tolvaptan, conivaptan, lixivaptan, mozavaptan, satavaptan or relcovaptan.

In particular embodiments, the antibody or fragment thereof according to the present invention is administered in combination with Jak inhibitors, by way of example and with preference ruxolitinib, tofacitinib, baricitinib, CYT387, GSK2586184, lestaurtinib, pacritinib (SB1518) or TG101348.

In particular embodiments, the antibody or fragment thereof according to the present invention is administered in combination with prostacyclin analogs for therapy of microthrombi.

In particular embodiments, the antibody or fragment thereof according to the present invention is administered in combination with an alkali therapy, by way of example and with preference sodium bicarbonate.

In particular embodiments, the antibody or fragment thereof according to the present invention is administered in combination with an mTOR inhibitor, by way of example and with preference everolimus or rapamycin.

In particular embodiments, the antibody or fragment thereof according to the present invention is administered in combination with an NHE3 inhibitor, by way of example and with preference AZD1722 or tenapanor.

In particular embodiments, the antibody or fragment thereof according to the present invention is administered in combination with an eNOS modulator, by way of example and with preference sapropterin.

In particular embodiments, the antibody or fragment thereof according to the present invention is administered in combination with a CTGF inhibitor, by way of example and with preference FG-3019.

The antibody or fragment thereof for use in a method for treatment according to the present invention may be formulated in any conventional manner using one or more physiologically acceptable carriers or excipients. The antibody or fragment thereof according to the present invention may be administered by any suitable means, which can vary, depending on the type of disorder to be treated. Possible administration routes include enteral (e.g., oral), parenteral (e.g., intravenous, intra-arterial, intraperitoneal, intramuscular, subcutaneous, intracardiac, intraventricular, intrathecal, intramedullary, intralesional), intrapulmonary and intranasal administration. In addition, an antibody or fragment thereof according to the present invention may be administered by pulse infusion, with, e.g., declining doses of the antibody or fragment thereof. Preferably, the dosing is given by injections, most preferably intravenous or subcutaneous injections, depending in part on whether the condition is acute or chronic. The amount to be administered will depend on a variety of factors such as the clinical symptoms, sex, age, and/or weight of the individual, whether other drugs are administered, and others. The skilled artisan will recognize that the route of administration will vary depending on the disorder or condition to be treated.

Methods of parenteral delivery include topical, intra-arterial, intratumoral, intramuscular, subcutaneous, intramedullary, intrathecal, intraventricular, intravenous, intraperitoneal, or intranasal administration.

In particular embodiments, the method for treatment comprises a single or multiple administrations of the antibody or fragment thereof or the pharmaceutical composition comprising the same. The single dose of the administrations may be the same or different. In particular, the method for treatment comprises 1, 2, 3, 4, 5 or 6 administrations of the antibody or fragment thereof according to the present invention, preferably wherein the multiple administrations occur within one to six consecutive months. The antibody or fragment thereof according to the present invention may for instance be administered every 3 to 4 days, every week, once every two weeks, or once every three weeks, depending on its half-life and clearance rate.

SHORT DESCRIPTION OF FIGURES

FIG. 1: Mean plasma concentrations of TPP-10992 and TPP-5661 after intravenous administration of 5 mg/kg in rat.

Figure 2:
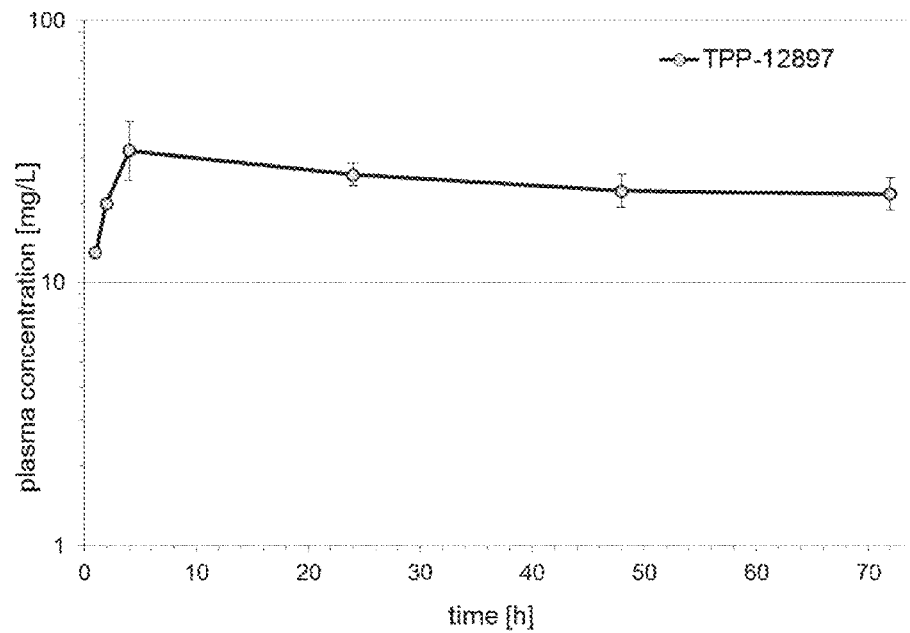

FIG. 2: Mean plasma concentrations of TPP-12897 after intraperitoneal administration of 5 mg/kg in mice.

Figure 3:
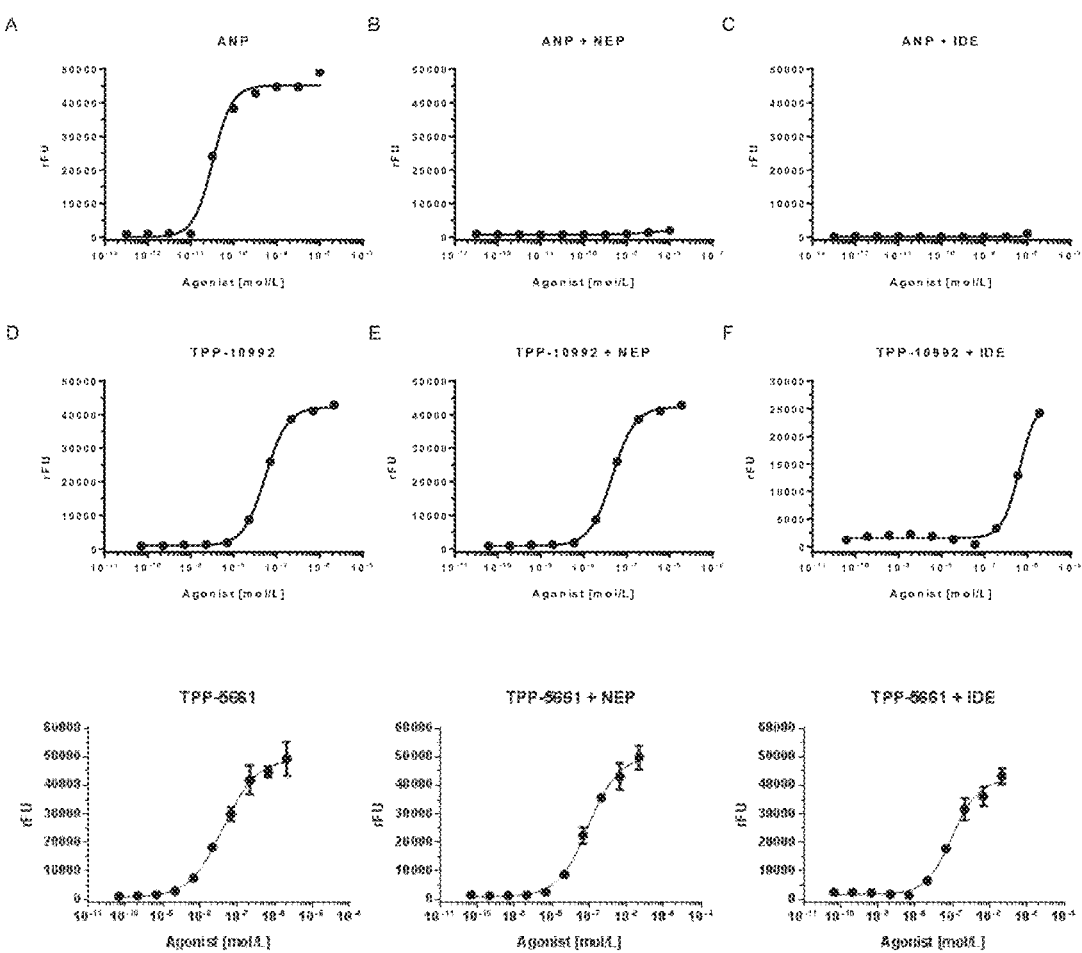

FIG. 3: Stability of ANP (A-C), TPP-10992 (D-F) and TPP-5661 (G-I) against proteolytic degradation. ANP, TPP-10992 and TPP-5661 activity were tested on the stable rat ANP receptor cell line directly (A, D, G), or after 4 h incubation at 37° C. with 0.6 µg/ml NEP (B, E, H) or 0.6 µg/ml IDE (C, F, I).

Figure 4:
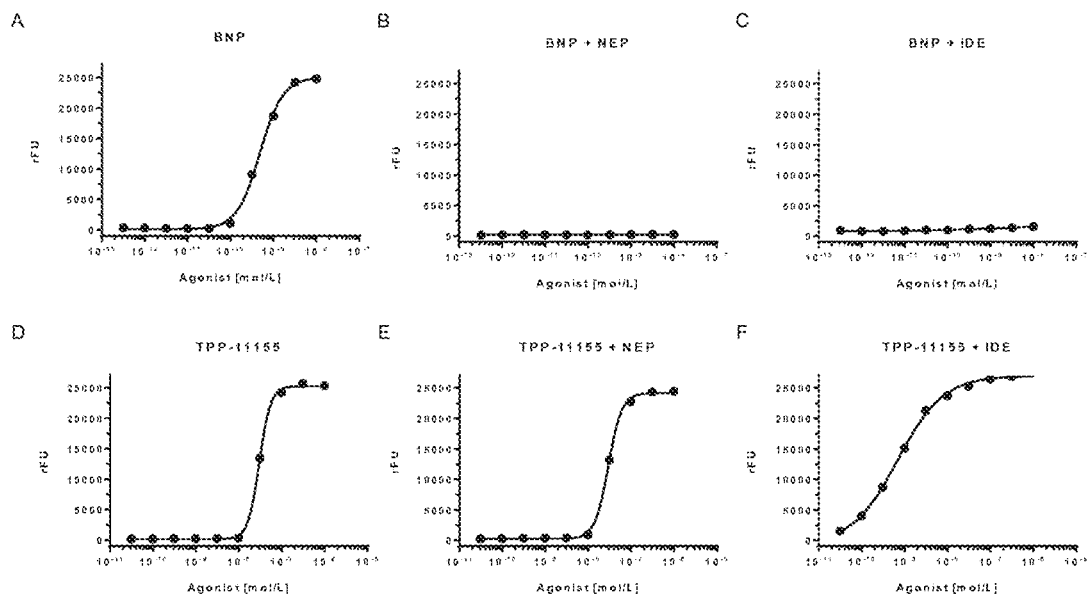

FIG. 4: Stability of BNP (A-C) and TPP-11155 (D-F) against proteolytic degradation. BNP and TPP-11155 activity were tested on the stable rat BNP receptor cell line directly (A, D), or after 4 h incubation at 37° C. with 0.6 µg/ml NEP (B, E) or 0.6 µg/ml IDE (C, F).

Figure 5:
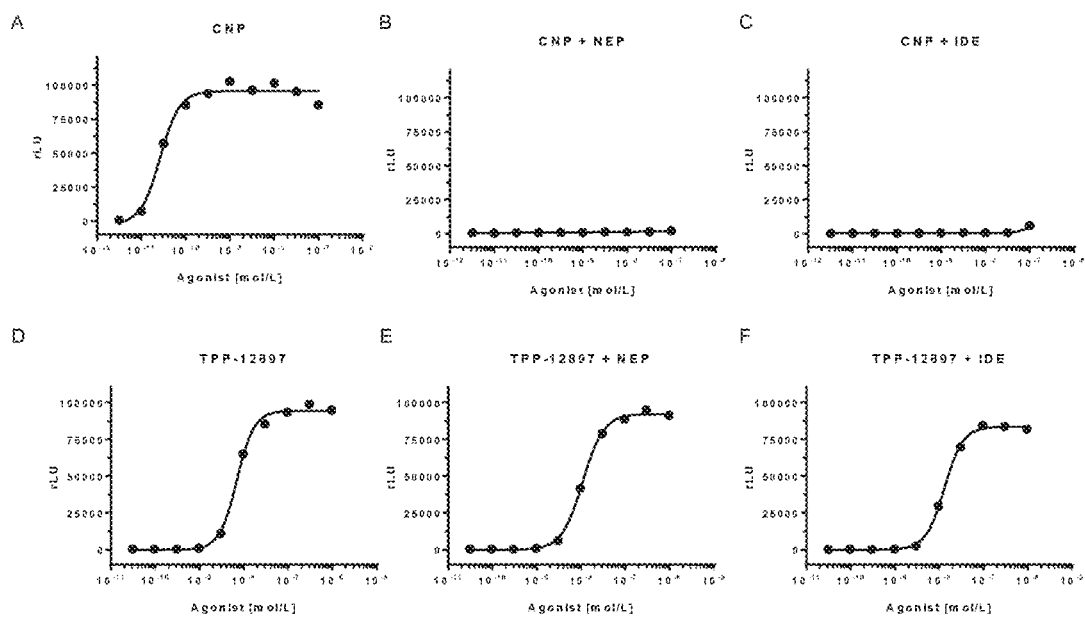

FIG. 5: Stability of CNP (A-C) and TPP-12897 (D-F) against proteolytic degradation. CNP and TPP-11155 activity were tested on the stable rat CNP receptor cell line directly (A, D), or after 4 h incubation at 37° C. with 0.6 µg/ml NEP (B, E) or 0.6 µg/ml IDE (C, F).

Figure 6:
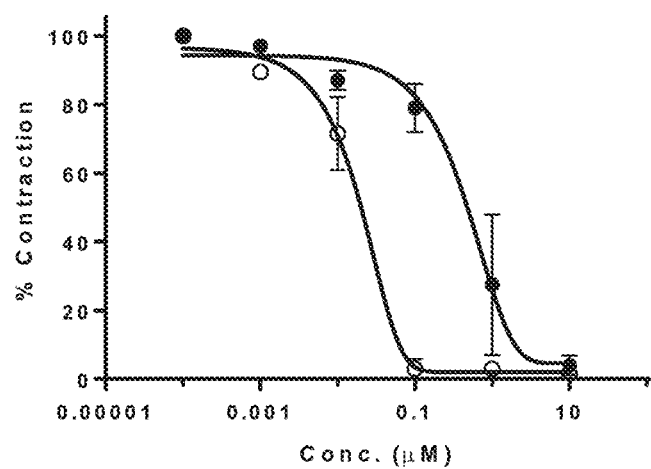

FIG. 6: ANP Peptide and TPP-10992 induced vasodilation dose-response curves in PE-contracted aortic rings. Concentration-response curves (0.0001-10 µM; n=3 Rats) to the ANP peptide (open circles) and TPP-10992 (closed circles) in endothelium-intact rat aortic rings contracted by phenylephrine (1 µM). Experimental values were calculated relative to the maximal changes from the contraction produced by phenylephrine in each tissue, which was taken as 100%. Potency of ANP peptide and TPP-10992 were −7.4 and −6.7 respectively (log $EC_{50}$ values). Data represent the mean±S.E.M. of 2 experiments.

Figure 7:
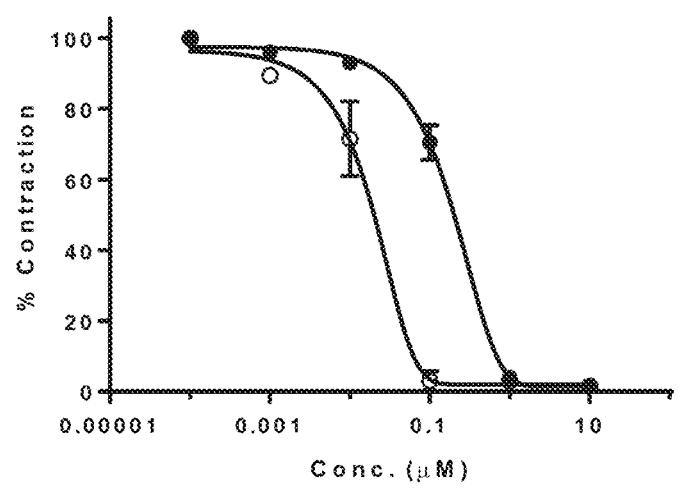

FIG. 7: ANP Peptide and TPP-5661 induced vasodilation dose-response curves in PE-contracted aortic rings. Concentration-response curves (0.0001-10 µM; n=3 Rats) to the ANP peptide (open circles) and TPP-5661 (closed circles) in endothelium-intact rat aortic rings contracted by phenylephrine (1 µM). Experimental values were calculated relative to the maximal changes from the contraction produced by phenylephrine in each tissue, which was taken as 100%. Potency of ANP peptide and TPP-5661 were −7.4 and −6.5 respectively (log $EC_{50}$ values). Data represent the mean±S.E.M. of 2 experiments.

Figure 8:
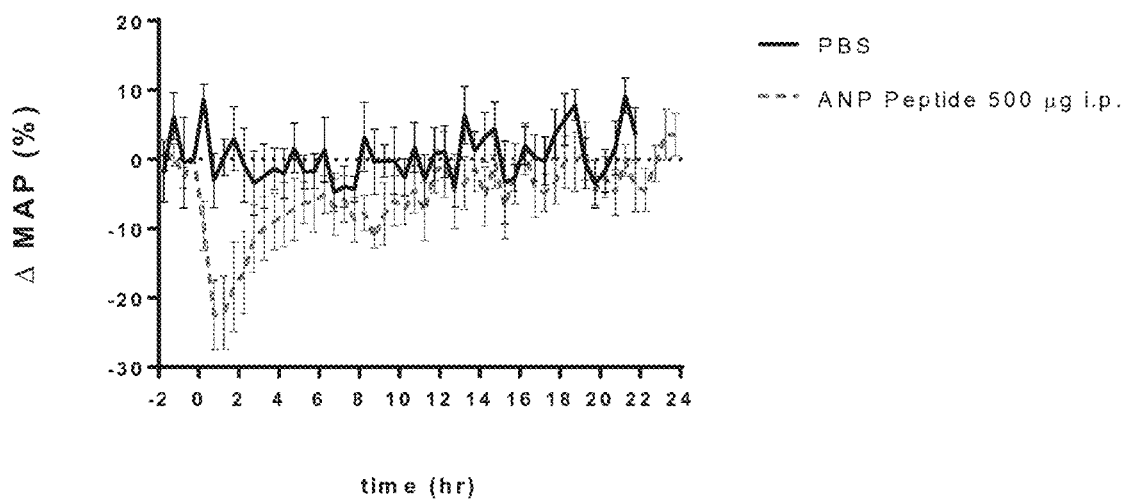

FIG. 8: Hemodynamic effect of ANP in conscious rats. Rat ANP was given intraperitoneally at 0 hours. A 500 µg dose of ANP resulted in an approximately 25% drop in mean arterial blood pressure (MAP) with a duration of effect around 6-8 hours.

Figure 9:
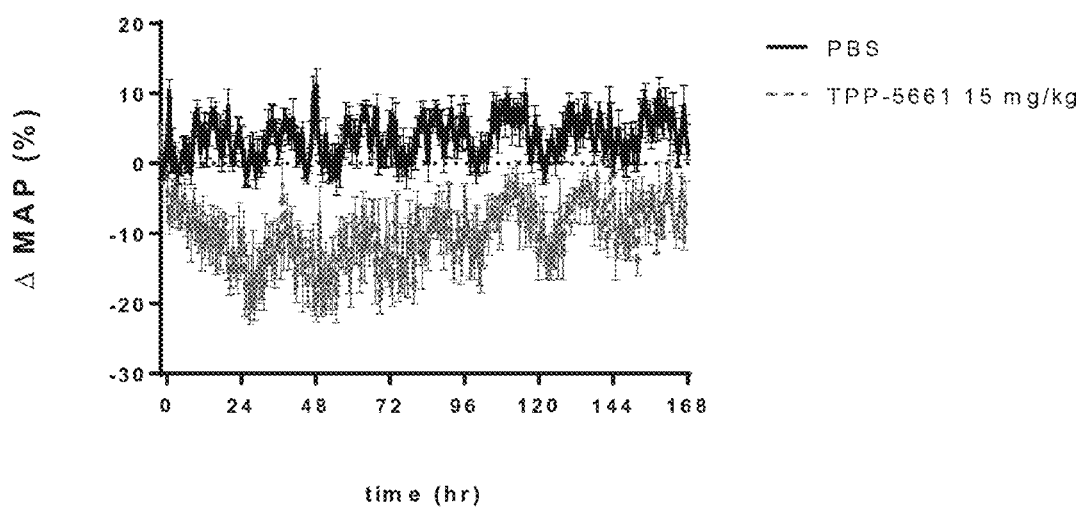

FIG. 9: Hemodynamic effect TPP-5661 in conscious rats. TPP-5661 was given intraperitoneally at 0 hours. A 15 mg/kg dose resulted in an approximately 20% reduction in mean arterial blood pressure (MAP) with maximum effect at 24-48 hours post application and a duration of effect greater than 6 days.

Figure 10:
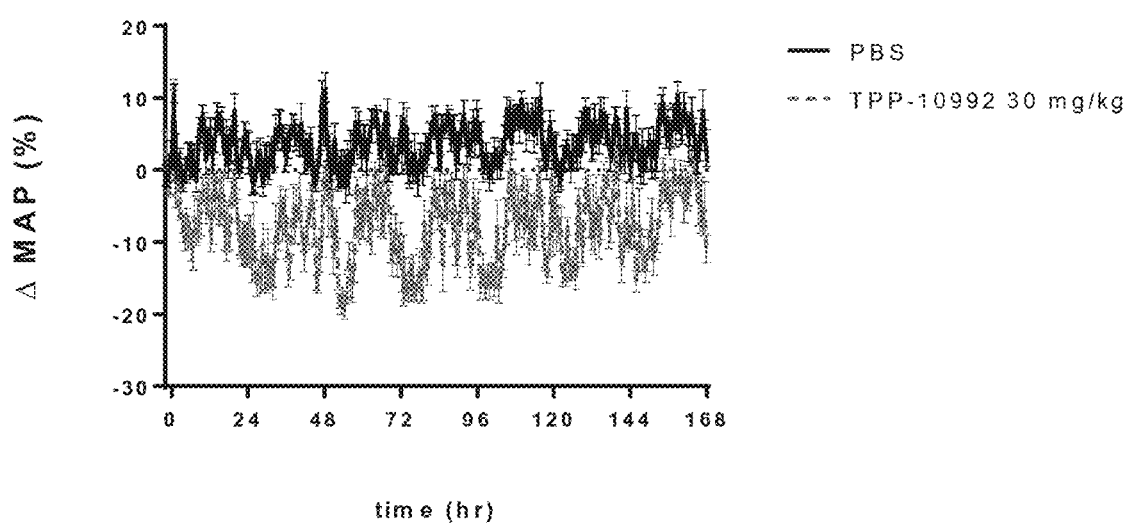

FIG. 10: Hemodynamic effect TPP-10992 in conscious rats. TPP-10992 was given intraperitoneally at 0 hours. A 30 mg/kg dose resulted in an approximately 20% reduction in mean arterial blood pressure (MAP) with maximum effect at 48 hours post application and a duration of effect greater than 6 days.

Figure 11:
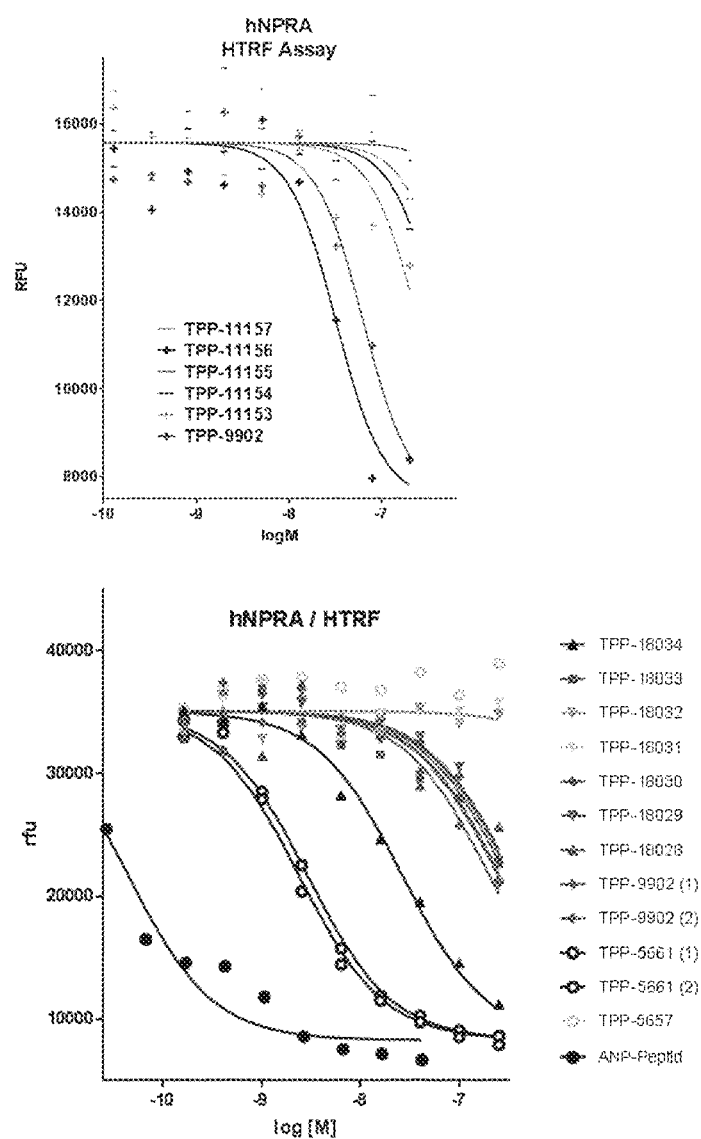

FIG. 11: Activity of BNP engrafted antibody constructs on hNPRA cells. The activity of purified compound samples on stable hNPRA-CHO k1 cells was assessed by comparison to reference sample TPP-5661 and TPP-5657. Samples were tested in dilution series in quadruplets.

Figure 12:
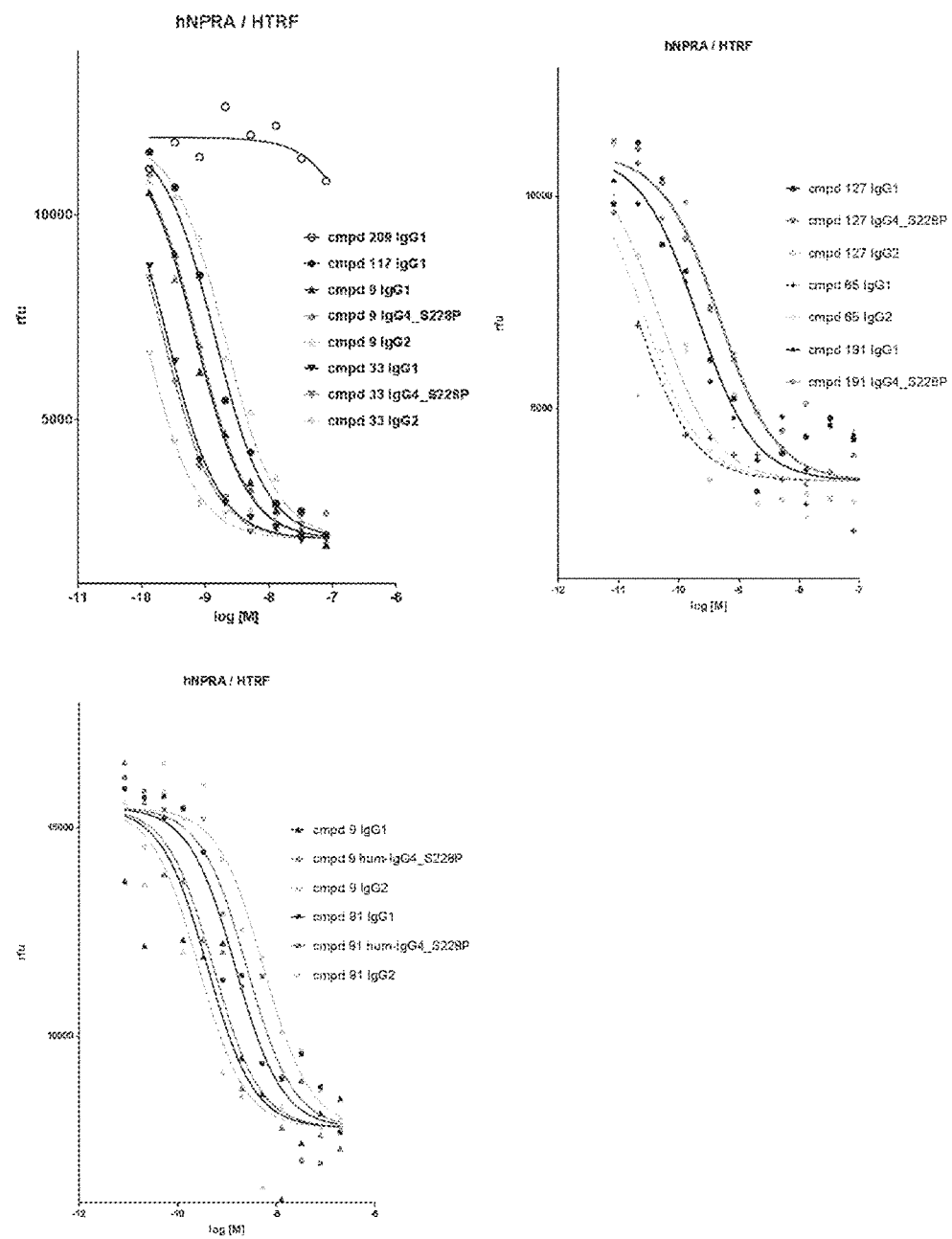

FIG. 12: Different human IgG isotypes provide equally suitable antibody scaffolds. Exemplary activity determination of compounds 9, 33, 65, 91, 127 and 191 IgG1 (TPP-10294, TPP-10277, TPP-10279, TPP-10282, TPP-10269 and TPP-10355, respectively), IgG2 and IgG4 isotypes. The activity of purified compound samples on stable hNPRA-CHO k1 cells was assessed by comparison to reference samples compound 117 human IgG1 TPP-5661 and compound 209 human IgG1 TPP-5657. Samples were tested in dilution series in quadruplets.

Figure 13:
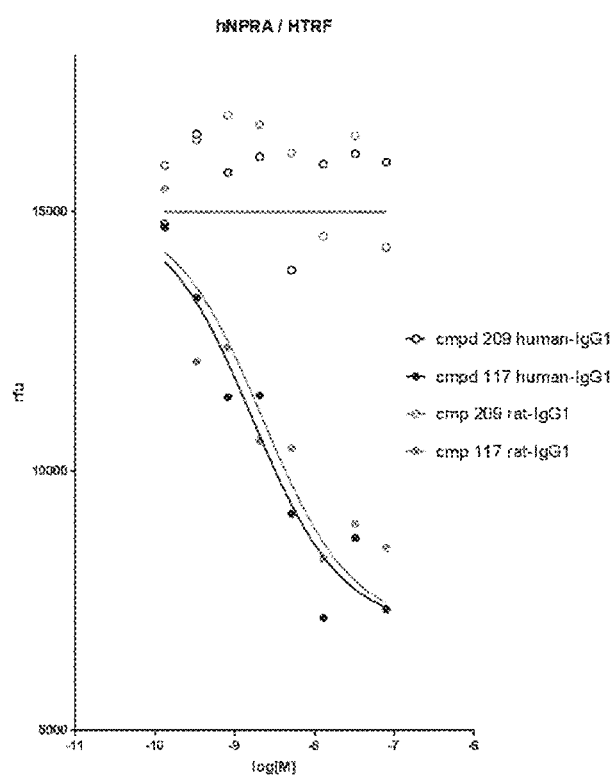
Figure 13:
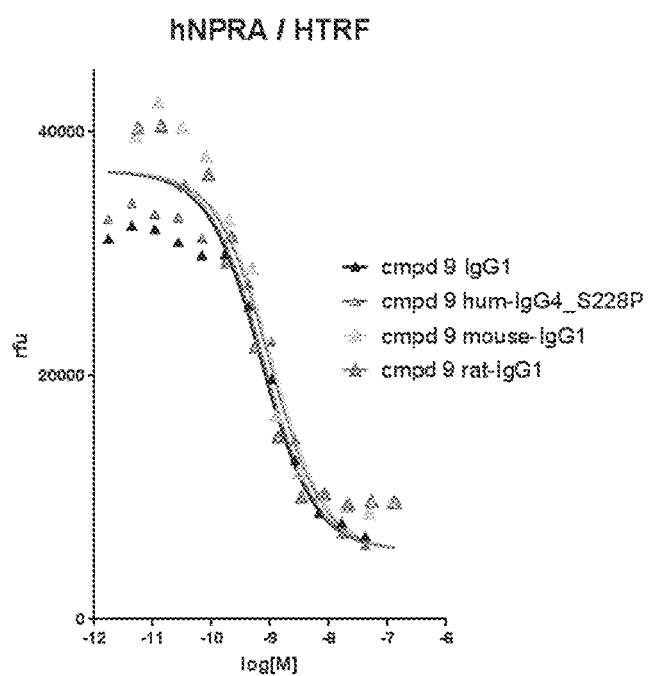

FIG. 13: Equally suitable IgG antibody scaffolds originated from different species. Exemplary activity determination of compound 117 human IgG1 (TPP-5661) and compound 9 human IgG1 (TPP-10294) and their non-human IgG1 counterparts. The activity of purified compound samples on stable hNPRA-CHO k1 cells was assessed by comparison to reference sample compound 209 human IgG1 (TPP-5657). Samples were tested in dilution series in quadruplets.

Figure 14:
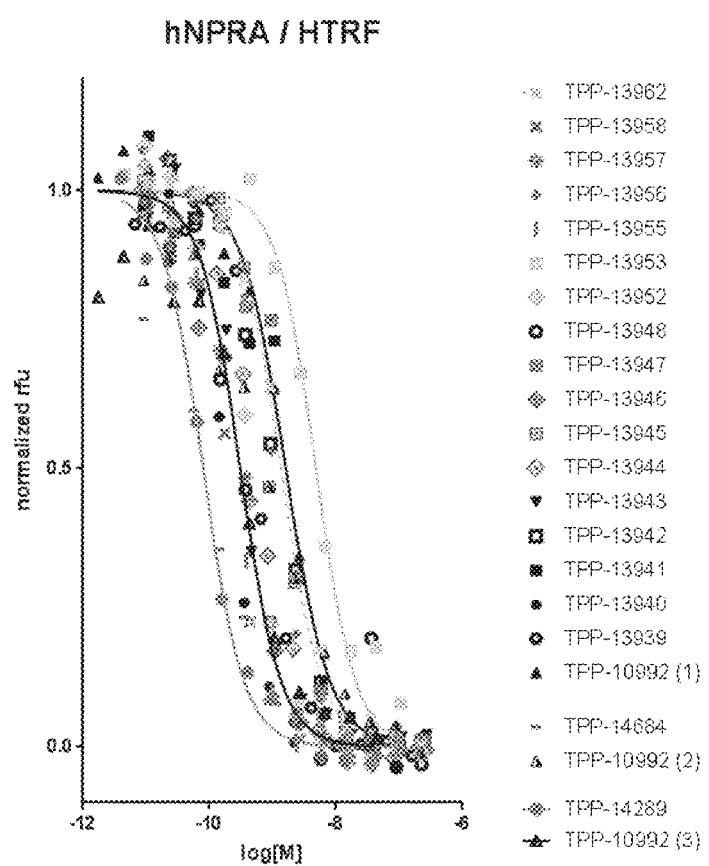

FIG. 14: Equally suitable human IgG antibody scaffolds originated from different germline sequences. The activity of purified compound samples on stable hNPRA-CHO k1 cells was assessed by comparison to reference sample TPP-10992. Samples were tested in dilution series in quadruplets.

Figure 15:
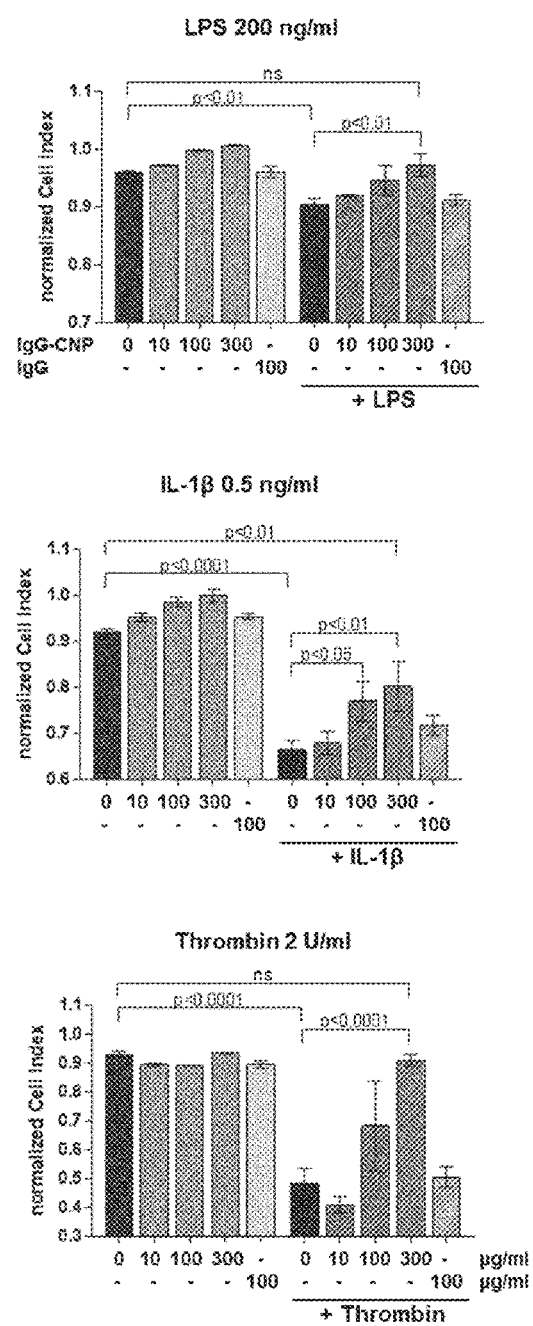

FIG. 15: Protective effects of TPP-12899 against LPS, IL-1β and thrombin induced endothelial barrier permeability as assessed by real-time impedance measurement.

Figure 16:
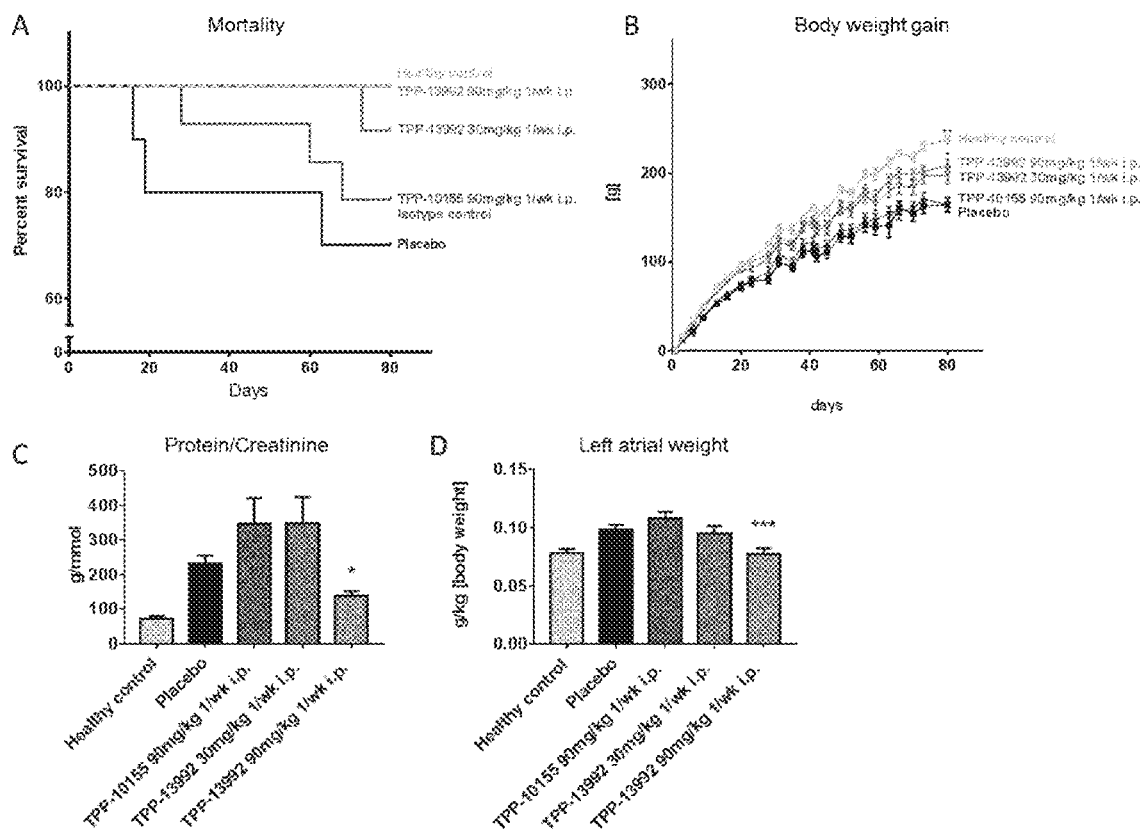

FIG. 16: Therapeutic effects of TPP-13992 on survival (A), body weight gain (B), urinary protein/creatinine ratio (C) and left atrial weight (D); (n=8-12 (healthy control n=5), mean±SEM, One-Way ANOVA vs TPP-10155 (isotype specific control antibody).

Figure 17:
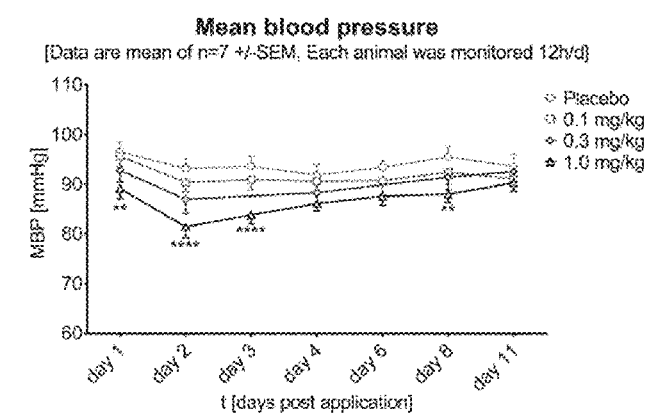
Figure 17:
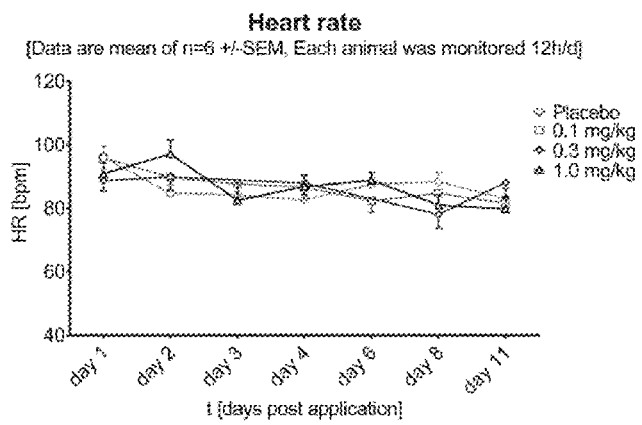

FIG. 17: Hemodynamic assessment after Placebo, 0.1, 0.3 and 1.0 mg/kg of TPP-10992. TPP-10992 shows a dose-dependent and long-lasting (>5d) reduction in blood pressure.p<0.01, **p<0.0001 in comparison to placebo group using an One-way ANOVA test for repeated measurements followed by Tukey's multiple comparison test.

EXAMPLES

Example 1: Construction of Candidate TPP-5661

Candidate TPP-5661 was designed by fusion of a heterologous amino acid sequence comprising a Ntls, wild type rat ANP and a Ctls to the C-terminus of HV 3-23 (SEQ ID NO 85) by substituting the two C-terminal residues of HV 3-23 by the two N-terminal residues of the heterologous amino acid sequence and to the N-terminus of IGHJ1 (SEQ ID NO 86) by substituting the nine N-terminal residues of IGHJ1 by the 9 C-terminal residues of the heterologous amino acid sequence. The corresponding full length heavy chain sequence of SEQ ID NO 67 further comprises amino acid sequence Constant-H (SEQ ID NO 87).

Pairing of the full length heavy chain sequence of SEQ ID NO 67 harboring the inserted rat ANP (rANP) with the full length light chain sequence of SEQ ID NO 66 built by combining sequences LV 1-40 (SEQ ID NO 88), IGLJ2 (SEQ ID NO 89) and Constant-L (SEQ ID NO 90) yields the full IgG candidate TPP-5661 (see Table 1).

Shown below is the full length heavy chain sequence (SEQ ID NO 67); the incorporated heterologous amino acid sequence (Ntls-rANP-Ctls) is underlined; sequences derived from HV 3-23 and IGHJ1 are shown in bold:

EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYC<u>TS</u>

<u>VHQETKKYQSSPDGGSGGSLRRSSCFGGRIDRIGAQSGLGCNSFRYGSY</u>

<u>SYTYNYEWHVDVWGQ</u>GTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPG

The designed and synthesized antibody construct was cloned according to well-known methods in the art and confirmed by DNA sequencing using plasmid specific oligonucleotides.

Example 2: Insertion of NPs within Antibody-CDRs Results in an Increased Serum Half-Life Determination of In Vivo Pharmacokinetic Parameters Pharmacokinetic parameters of TPP-10992 (SEQ ID NO 76 and SEQ ID NO 66) and TPP-5661 (SEQ ID NO 67 and SEQ ID NO 66) were determined after intravenous administration of 5 mg/kg to male Wistar rats (n=3). TPP-10992 and TPP-5661 were given as a bolus injection via the tail vein. Blood samples were collected from the jugular vein via previously implanted catheters in time intervals up to 14 days (336 hours). Generated EDTA-plasma was stored at −20° C. until further analysis.

The quantification of TPP-10992 and TPP-5661 in plasma samples was performed employing an anti-human IgG ELISA (enzyme-linked immunosorbent assay) format. Pharmacokinetic parameters were calculated from plasma concentration time profiles using non-compartmental data analysis.

Mean plasma concentrations of TPP-10992 and TPP-5661 after intravenous administration over time are graphically depicted in FIG. 1.

Mean clearance and terminal half-life of TPP-10992 and TPP-5661 are summarized in Table 2 below.

TABLE 2

Mean clearance (CL) and terminal half-life ($t_{1/2}$) of TPP-10992 and TPP-5661 after intravenous administration of 5 mg/kg in rat.

| Analyte | | TPP-5661 | TPP-10992 |
|---|---|---|---|
| CL | [mL/h/kg] | 0.62 | 0.27 |
| $t_{1/2}$ | [h] | 297 | 184 |

Determination of In Vivo Pharmacokinetic Parameters Pharmacokinetic parameters of TPP-12897 were determined after intraperitoneal administration to female Balb/c mice (n=3). Blood samples were collected from 15 minutes up to 72 hours post application. Generated EDTA-plasma was stored at −20° C. until further analysis. The quantification of TPP-12897 in plasma samples was performed by an anti-human IgG (Immunoglobulin G) ELISA format.

Pharmacokinetic parameters were calculated from plasma concentration time profiles using non-compartmental data analysis.

Mean plasma concentrations of TPP-12897 after intraperitoneal administration over time are graphically depicted in FIG. 2.

Mean area under the curve (AUC) and terminal half-life of TPP-12897 are summarized in Table 3 below.

TABLE 3

Mean area under the curve (AUC) and terminal half-life ($t_{1/2}$) of TPP-12897 after intraperitoneal administration of 5 mg/kg in mice.

| Analyte | | TPP-12897 |
|---|---|---|
| AUC | [mg · h/L] | 7705 |
| $t_{1/2}$ | [h] | 194 |

Example 3: In Vitro, Ex Vivo and In Vivo Potency of NP Engrafted Antibodies

Activity Data of ANP Engrafted Antibodies in NPR-A Receptor Cell Line

A luminescence-based rat ANP receptor (NPR-A) cell line was generated as described previously (Wunder et al. (2013), *Eur J Pharmacol.* 698: 131). Accordingly, a fluorescence-based rat ANP receptor (NPR-A) cell line was generated by co-transfecting a CHO cell line, stably expressing the fluorescent calcium sensor protein GCaMP6, with plasmid constructs encoding CNGA2 (cGMP biosensor) and rat NPR-A.

ANP receptor GCaMP6 cells were cultured for one day on black, clear-bottom 384-well microtiter plates (2500 cells/well). After removal of the cell culture medium reporter cells were loaded for 20 min with Tyrode (130 mM NaCl, 5 mM KCl, 2 mM $CaCl_2$, 20 mM HEPES, 1 mM $MgCl_2$, 4.8 mM $NaHCO_3$ at pH 7.4) containing a black masking dye at 37° C. and 5% $CO_2$. IBMX (0.2 mM) was used to prevent cGMP degradation by endogenous phosphodiesterases.

Fluorescence measurements (3 min, kinetic mode) were directly started upon agonist addition. Receptor ligands were added in Tyrode containing a black masking dye and 0.1% BSA. Measurements were done on a FLIPR Tetra®.

ANP (Bachem, H-2100) stimulated concentration-dependent fluorescence signals on the NPR-A cell line with an $EC_{50}$ values of 0.22 nM. TPP-5661 and TPP-10992 stimulated the rat ANP receptor reporter cell line with $EC_{50}$ values of 17 nM and 180 nM, respectively. The control antibody construct TPP-5657 did not significantly stimulate the NPR-A cell line (tested up to the max. concentration of 460 nM).

To determine the sensitivity towards proteolytic degradation, the activity of receptor ligands was also characterized after 4 hours incubation with 0.6 µg/ml neutral endopeptidase (NEP, R&D Systems, 1182-ZNC) or 0.6 µg/ml insulin degrading enzyme (IDE, Merck, 407241-50UG) at 37° C.

FIG. 3 graphically depicts the stability of ANP (A-C), TPP-10992 (D-F) and TPP-5661 (G-I) against proteolytic degradation. As shown in FIG. 3, the natriuretic peptide ANP (Bachem, H-2100) showed high sensitivity towards degradation by NEP and IDE. In contrast, TPP-5661 and TPP-10992 showed high resistance to proteolytic degradation by NEP and IDE.

Activity Data of BNP Engrafted Antibodies in NPR-A Receptor Cell Line

A luminescence-based rat BNP receptor (NPR-A) cell line was generated as described previously (Wunder et al. (2013), *Eur J Pharmacol.* 698: 131). Accordingly, a fluorescence-based rat BNP receptor (NPR-A) cell line was generated by co-transfecting a CHO cell line, stably expressing the fluorescent calcium sensor protein GCaMP6, with plasmid constructs encoding CNGA2 (cGMP biosensor) and rat NPR-A.

BNP receptor GCaMP6 cells were cultured for one day on black, clear-bottom 384-well microtiter plates (2500 cells/well). After removal of the cell culture medium reporter cells were loaded for 20 min with Tyrode (130 mM NaCl, 5 mM KCl, 2 mM $CaCl_2$, 20 mM HEPES, 1 mM $MgCl_2$, 4.8 mM $NaHCO_3$ at pH 7.4) containing a black masking dye at 37° C. and 5% $CO_2$. IBMX (0.2 mM) was used to prevent cGMP degradation by endogenous phosphodiesterases.

Fluorescence measurements (3 min, kinetic mode) were directly started upon agonist addition. Receptor ligands were added in Tyrode containing a black masking dye and 0.1% BSA. Measurements were done on a FLIPR Tetra®.

BNP (Bachem, H-5968) stimulated concentration-dependent fluorescence signals on the NPR-A cell line with an $EC_{50}$ value of 2.9 nM. TPP-9902, TPP-11153, TPP-1154, TPP-11155, TPP-11156 and TPP-11157 stimulated the rat BNP receptor reporter cell line with $EC_{50}$ values of 2.3 µM, >1.9 µM, 7 nM, 12 nM, 1.2 µM and 11 nM, respectively. The control antibody construct TPP-5657 did not significantly stimulate the NPR-A cell line (tested up to the max. concentration of 460 nM).

To determine the sensitivity towards proteolytic degradation, the activity of receptor ligands was also characterized after 4 hours incubation with 0.6 µg/ml neutral endopeptidase (NEP, R&D Systems, 1182-ZNC) or 0.6 µg/ml insulin degrading enzyme (IDE, Merck, 407241-50UG) at 37° C. The natriuretic peptide BNP (Bachem, H-5968) showed high sensitivity towards degradation by NEP and IDE. In contrast, TPP-11155 and TPP-11157 showed high resistance to proteolytic degradation by NEP and IDE.

FIG. 4 graphically depicts the stability of BNP (A-C) and TPP-11155 (D-F) against proteolytic degradation.

Activity Data of CNP Engrafted Antibodies in NPR-B Receptor Cell Line

A luminescence-based rat CNP receptor (NPR-B) reporter cell line was generated and luminescence measurements were performed as described previously (Wunder et al. (2013), Eur J Pharmacol. 698: 131).

CNP receptor cells (2500 cells/well) were cultured for 1 day on opaque 384-well microtiter plates. After removal of the cell culture medium, cells were loaded for 3 h with 2.5 µg/ml coelenterazine in $Ca^{2+}$-free Tyrode (130 mM NaCl, 5 mM KCl, 20 mM HEPES, 1 mM $MgCl_2$, 4.8 mM $NaHCO_3$ at pH 7.4) at 37° C. and 5% $CO_2$. Receptor ligands were added for 10 min in $Ca^{2+}$-free Tyrode containing 0.1% BSA. IBMX (0.2 mM) was used to prevent cGMP degradation by endogenous phosphodiesterases Immediately before adding calcium ions (final concentration 3 mM), luminescence measurements were started by using a charge-coupled device (CCD) camera in a light tight box. Luminescence was monitored continuously for 50 s.

CNP (Bachem, H-1296) stimulated concentration-dependent luminescence signals on the rat NPR-B cell line with an $EC_{50}$ value of 0.024 nM. TPP-9465, TPP-12377, TPP-12378, TPP-12897 and TPP-12899 stimulated the rat CNP receptor reporter cell line with $EC_{50}$ values of 5.2 nM, 4.1 nM, 25 nM, 10 nM and 3.2 nM, respectively. TPP-12374 stimulated the rat CNP receptor reporter cell line with $EC_{50}$ values of 150 nM, and TPP-12375, TPP-12376 showed only weak indication of activity.

To determine the sensitivity towards proteolytic degradation, the activity of receptor ligands was also characterized after 4 hours incubation with 0.6 µg/ml neutral endopeptidase (NEP, R&D Systems, 1182-ZNC) or 0.6 µg/ml insulin degrading enzyme (IDE, Merck, 407241-50UG) at 37° C.

In contrast to the natriuretic peptide CNP (Bachem, H-1296), TPP-12377, TPP-12897 and TPP-12899 showed high resistance to proteolytic degradation by NEP and IDE.

FIG. 5 graphically depicts the stability of CNP (A-C) and TPP-12897 (D-F) against proteolytic degradation.

Activity Data of ANP Engrafted Antibodies Determined with Isolated Rat Aortic Rings All experiments were conducted in accordance with institutional guidelines and approved by the local committee on animal experiments. Male Sprague-Dawley rats (weighing 250-300 g) were anesthetized with pentobarbital sodium (40 mg/kg i.p.), killed by decapitation, and exsanguinated. The thoracic aorta was excised and placed in ice-cold Krebs buffer of the following composition: 130 mM NaCl, 14.9 mM $NaHCO_3$, 5.5 mM dextrose, 4.7 mM KCl, 1.18 mM $KH_2PO_4$, 1.17 mM $MgSO_4 7H_2O$, and 1.6 mM $CaCl_2 2H_2O$. The vessel was pinned in a Sylgard Petri dish filled with chilled Krebs' solution, cleaned of fat and connective tissue, and cut into ring segments of approximately 3 to 4 mm in length. Aortic rings were vertically mounted in 50-ml chambers (ADIinstruments) containing Krebs' solution at 37° C. continuously bubbled with a mixture of 95% $O_2$ and 5% $CO_2$. Changes in isometric force were recorded using a PowerLab data acquisition system (software Lab Chart 7.0)

After the equilibration period, aortic rings were challenged with 80 mM KCl to check tissue viability. Next, the endothelial integrity of the preparations was determined by verifying the responsiveness to acetylcholine (ACh, 1 µM) in vessels pre-contracted with Phenylephrine (PE, 1 µM). After wash-out and a period of equilibration, Phenylephrine (PE, 1 µM) was used to induce contraction, thereafter natriuretic peptides and natriuretic peptide engrafted IgGs were evaluated for vasorelaxation. Rat ANP peptide (ADH-GM-10057T, Santai Labs) was used as a reference.

As shown in FIG. 6, both ANP peptide and TPP-10992 induced dose-dependent vasodilation in PE-contracted aortic rings.

As shown in FIG. 7, both ANP peptide and TPP-5661 induced dose-dependent vasodilation in PE-contracted aortic rings.

Activity Data of ANP Engrafted Antibodies Obtained in Conscious Rats

Blood pressure and heart rate were monitored in freely moving conscious animals by radiotelemetry (Data Sciences International). Female spontaneously hypertensive rats (SHR/N Crl BR, Charles River) with a body weight of 210-300 g were used for these studies. All animals were housed in individual cages at 22-24° C. ambient temperature and maintained on a 12-hour light/dark cycle with free access to standard laboratory rat chow and water ad libitum. Telemeter (HD-10, DSI) implantation was performed a minimum of 14 days before animals were used for blood pressure measurements. Surgery was performed under aseptic conditions. After shaving the abdominal wall, a midline abdominal incision was made, and the fluid-filled sensor catheter was inserted upstream into the exposed descending aorta between the iliac bifurcation and the renal arteries. According to the DSI guidelines the tip of the telemetric catheter was located caudal to the renal arteries and secured by tissue adhesive. The transmitter body was affixed to the inner peritoneal wall before closure of the abdomen. For postsurgical protection against infections and pain a single dosage of an antibiotic (Oxytetracyclin® 10%, 60 mg/kg s.c., 0.06 ml/100 g body weight, Beta-Pharma GmbH & Co, Germany) and analgesic were injected (Rimadyl®, 4 mg/kg s.c., Pfizer, Germany). Telemetric data acquisition was performed by DSI software was predefined to sample hemodynamic data for 10 seconds repeated every 5 minutes. Data collection was started at least 2 hours before drug administration and finished after completion of measurement cycles. Data are expressed as % of basal values±SEM of at least 4 animals per group. The basal value for each animal was calculated as the average of the values measured in two hours prior to substance application (7:00-9:00 AM). Data are then expressed as averages every half hour, starting 15 minutes post application. All animals were treated with a single intraperitoneal (ip) application of test substances dissolved in phosphate buffered saline (PBS). Drug administration took place at 9:00 AM (0 hours).

The hemodynamic effect of ANP peptide is graphically depicted in FIG. 8. The hemodynamic effect of TPP-5661 is graphically depicted in FIG. 9. The hemodynamic effect of TPP-10992 is graphically depicted in FIG. 10.

Example 4: Generation of Different NP Engrafted Antibody Constructs

For constructs with a natriuretic peptide incorporation in a CDR region other than CDRH3 a presumably functionally neutral CDRH3 was designed by fusion of the three residues stretch Leu Thr Gly (IGHD7-27*01) to the C-terminus of HV 3-23 and the N-terminus of IGHJ1 (compare Example 1). The corresponding full length heavy chain sequence of SEQ ID NO 65 further comprises amino acid sequence Constant-H (SEQ ID NO 87).

Pairing of the full length heavy chain sequence of SEQ ID NO 65 without any natriuretic peptide insertion with the full length light chain sequence of SEQ ID NO 66 described in Example 1 yields the synthetic and presumably neutral IgG negative control TPP-5657.

The designed and synthesized antibody construct was cloned according to well-known methods in the art and confirmed by DNA sequencing using plasmid specific oligonucleotides.

Starting from this antibody scaffold, the following ANP engrafted antibody constructs were generated.

TABLE 4

Design of ANP engrafted antibody constructs

| Cmpd | TPP | Insertion Site | SEQ ID NO comprised in Ntls | SEQ ID NO comprised in Ctls | # aa N-term[1] | # aa C-term[2] |
|---|---|---|---|---|---|---|
| 1 | TPP-13057 | CDRH1 | | | 6 | 2 |
| 2 | TPP-13056 | CDRH1 | | | 9 | 5 |

TABLE 4-continued

Design of ANP engrafted antibody constructs

| Cmpd | TPP | Insertion Site | SEQ ID NO comprised in Ntls | SEQ ID NO comprised in Ctls | # aa N-term[1] | # aa C-term[2] |
|---|---|---|---|---|---|---|
| 3 | TPP-13055 | CDRH1 | | | 12 | 8 |
| 4 | TPP-13054 | CDRH1 | | | 15 | 11 |
| 5 | TPP-12545 | CDRH1 | | | 18 | 10 |
| 6 | TPP-10454 | CDRH1 | | | 19 | 17 |
| 7 | TPP-10453 | CDRH1 | | | 19 | 17 |
| 8 | TPP-11172 | CDRH1 | 6 | | 20 | 17 |
| 9 | TPP-10294 | CDRH1 | | | 23 | 14 |
| 10 | TPP-12547 | CDRH1 | | | 23 | 14 |
| 11 | TPP-11171 | CDRH1 | 6 | | 24 | 13 |
| 12 | TPP-10841 | CDRH2 | | | 3 | 3 |
| 13 | TPP-10842 | CDRH2 | | | 7 | 7 |
| 14 | TPP-11009 | CDRH2 | | | 8 | 9 |
| 15 | TPP-11008 | CDRH2 | | | 10 | 11 |
| 16 | TPP-11018 | CDRH2 | | | 11 | 14 |
| 17 | TPP-10775 | CDRH2 | | | 12 | 8 |
| 18 | TPP-10767 | CDRH2 | | | 13 | 12 |
| 19 | TPP-11012 | CDRH2 | 9 | | 14 | 9 |
| 20 | TPP-10774 | CDRH2 | 13 | 14 | 14 | 10 |
| 21 | TPP-11007 | CDRH2 | | | 14 | 11 |
| 22 | TPP-11179 | CDRH2 | | | 14 | 14 |
| 23 | TPP-10773 | CDRH2 | 13 | 14 | 15 | 10 |
| 24 | TPP-10770 | CDRH2 | 1 | 1 | 15 | 12 |
| 25 | TPP-10766 | CDRH2 | | | 15 | 14 |
| 26 | TPP-10772 | CDRH2 | 13 | 14 | 16 | 11 |
| 27 | TPP-11005 | CDRH2 | | | 16 | 11 |
| 28 | TPP-11006 | CDRH2 | | | 16 | 11 |
| 29 | TPP-11017 | CDRH2 | | | 16 | 14 |
| 30 | TPP-11169 | CDRH2 | 9 | 10 | 16 | 15 |
| 31 | TPP-11181 | CDRH2 | | | 16 | 15 |
| 32 | TPP-11182 | CDRH2 | | | 16 | 17 |
| 33 | TPP-10277 | CDRH2 | 9 | 10 | 17 | 11 |
| 34 | TPP-12553 | CDRH2 | 9 | 10 | 17 | 11 |
| 35 | TPP-12554 | CDRH2 | 9 | 10 | 17 | 11 |
| 36 | TPP-12555 | CDRH2 | 9 | 10 | 17 | 11 |
| 37 | TPP-12542 | CDRH2 | 9 | 10 | 17 | 11 |
| 38 | TPP-12543 | CDRH2 | 9 | 10 | 17 | 11 |
| 39 | TPP-12544 | CDRH2 | 9 | 10 | 17 | 11 |
| 40 | TPP-13058 | CDRH2 | 9 | 10 | 17 | 11 |
| 41 | TPP-13059 | CDRH2 | 9 | 10 | 17 | 11 |
| 42 | TPP-13060 | CDRH2 | 9 | 20 | 17 | 11 |
| 43 | TPP-13061 | CDRH2 | 9 | 20 | 17 | 11 |
| 44 | TPP-13062 | CDRH2 | 9 | 10 | 17 | 11 |
| 45 | TPP-13063 | CDRH2 | 9 | 10 | 17 | 11 |
| 46 | TPP-13064 | CDRH2 | 9 | 10 | 17 | 11 |
| 47 | TPP-13065 | CDRH2 | 9 | 10 | 17 | 11 |
| 48 | TPP-13066 | CDRH2 | 9 | 10 | 17 | 11 |
| 49 | TPP-12546 | CDRH2 | 9 | 10 | 17 | 11 |
| 50 | TPP-10452 | CDRH2 | 13 | 14 | 17 | 12 |
| 51 | TPP-10846 | CDRH2 | 4 | 5 | 17 | 12 |
| 52 | TPP-10852 | CDRH2 | | | 17 | 12 |
| 53 | TPP-10851 | CDRH2 | 6 | | 17 | 13 |
| 54 | TPP-10769 | CDRH2 | 1 | 1 | 17 | 14 |
| 55 | TPP-10765 | CDRH2 | | | 17 | 14 |
| 56 | TPP-11180 | CDRH2 | | | 17 | 15 |
| 57 | TPP-11177 | CDRH2 | | | 17 | 17 |
| 58 | TPP-11178 | CDRH2 | | | 17 | 17 |
| 59 | TPP-11176 | CDRH2 | 17 | 18 | 17 | 17 |
| 60 | TPP-10278 | CDRH2 | 9 | 10 | 18 | 12 |
| 61 | TPP-10847 | CDRH2 | 4 | 5 | 18 | 13 |
| 62 | TPP-11004 | CDRH2 | | | 18 | 13 |
| 63 | TPP-10844 | CDRH2 | 2 | 3 | 18 | 13 |
| 64 | TPP-10853 | CDRH2 | | | 18 | 13 |
| 65 | TPP-10279 | CDRH2 | 9 | 10 | 18 | 13 |
| 66 | TPP-11170 | CDRH2 | 9 | 10 | 18 | 13 |
| 67 | TPP-11010 | CDRH2 | 9 | | 18 | 13 |
| 68 | TPP-11011 | CDRH2 | 9 | | 18 | 13 |
| 69 | TPP-10764 | CDRH2 | | | 18 | 14 |
| 70 | TPP-11183 | CDRH2 | | | 18 | 17 |
| 71 | TPP-11175 | CDRH2 | 16 | 17 | 18 | 17 |
| 72 | TPP-11016 | CDRH2 | 15 | | 19 | 12 |

TABLE 4-continued

Design of ANP engrafted antibody constructs

| Cmpd | TPP | Insertion Site | SEQ ID NO comprised in Ntls | SEQ ID NO comprised in Ctls | # aa N-term[1] | # aa C-term[2] |
|---|---|---|---|---|---|---|
| 73 | TPP-11015 | CDRH2 | 15 | | 19 | 14 |
| 74 | TPP-10451 | CDRH2 | 13 | 14 | 19 | 14 |
| 75 | TPP-10768 | CDRH2 | 1 | 1 | 19 | 14 |
| 76 | TPP-10848 | CDRH2 | 4 | 5 | 19 | 14 |
| 77 | TPP-11003 | CDRH2 | | | 19 | 14 |
| 78 | TPP-11002 | CDRH2 | | | 19 | 14 |
| 79 | TPP-10843 | CDRH2 | 2 | 3 | 19 | 14 |
| 80 | TPP-10845 | CDRH2 | 2 | 3 | 19 | 14 |
| 81 | TPP-10284 | CDRH2 | | | 19 | 14 |
| 82 | TPP-10446 | CDRH2 | 11 | 12 | 19 | 14 |
| 83 | TPP-10447 | CDRH2 | | | 19 | 14 |
| 84 | TPP-10854 | CDRH2 | | | 19 | 14 |
| 85 | TPP-11014 | CDRH2 | 15 | | 19 | 15 |
| 86 | TPP-10849 | CDRH2 | 6 | 6 | 19 | 15 |
| 87 | TPP-10850 | CDRH2 | 6 | | 19 | 15 |
| 88 | TPP-11013 | CDRH2 | | | 20 | 14 |
| 89 | TPP-10771 | CDRH2 | 1 | 1 | 20 | 15 |
| 90 | TPP-10287 | CDRH2 | 1 | 1 | 20 | 15 |
| 91 | TPP-10282 | CDRH2 | | | 20 | 15 |
| 92 | TPP-10285 | CDRH2 | | | 20 | 15 |
| 93 | TPP-10286 | CDRH2 | | | 20 | 15 |
| 94 | TPP-10283 | CDRH2 | | | 20 | 15 |
| 95 | TPP-11168 | CDRH2 | 9 | 10 | 20 | 15 |
| 96 | TPP-10857 | CDRH2 | | | 20 | 15 |
| 97 | TPP-10856 | CDRH2 | | | 20 | 15 |
| 98 | TPP-10855 | CDRH2 | | | 20 | 15 |
| 99 | TPP-10281 | CDRH3 | | | 10 | 3 |
| 100 | TPP-10280 | CDRH3 | | | 10 | 8 |
| 101 | TPP-10583 | CDRH3 | | | 12 | 10 |
| 102 | TPP-10582 | CDRH3 | 7 | | 14 | 12 |
| 103 | TPP-10270 | CDRH3 | 7 | 8 | 15 | 18 |
| 104 | TPP-10264 | CDRH3 | 7 | 8 | 16 | 14 |
| 105 | TPP-10581 | CDRH3 | | | 16 | 14 |
| 106 | TPP-10263 | CDRH3 | 7 | 8 | 17 | 15 |
| 107 | TPP-10271 | CDRH3 | 7 | 8 | 17 | 18 |
| 108 | TPP-10262 | CDRH3 | 7 | 8 | 18 | 16 |
| 109 | TPP-10272 | CDRH3 | 7 | 8 | 18 | 18 |
| 110 | TPP-10261 | CDRH3 | 7 | 8 | 19 | 17 |
| 111 | TPP-10289 | CDRH3 | | | 19 | 17 |
| 112 | TPP-10273 | CDRH3 | 7 | 8 | 19 | 18 |
| 113 | TPP-10260 | CDRH3 | 7 | 8 | 20 | 17 |
| 114 | TPP-10275 | CDRH3 | 9 | 10 | 20 | 17 |
| 115 | TPP-10580 | CDRH3 | | | 20 | 18 |
| 116 | TPP-10274 | CDRH3 | 7 | 8 | 20 | 18 |
| 117 | TPP-5661 | CDRH3 | 7 | 8 | 20 | 18 |
| 118 | TPP-13226 | CDRH3 | 7 | 8 | 18 | 16 |
| 119 | TPP-13227 | CDRH3 | 7 | 8 | 18 | 16 |
| 120 | TPP-13228 | CDRH3 | 7 | 22 | 20 | 18 |
| 121 | TPP-13229 | CDRH3 | 7 | 22 | 20 | 18 |
| 122 | TPP-13230 | CDRH3 | 21 | 22 | 20 | 18 |
| 123 | TPP-13231 | CDRH3 | 21 | 22 | 20 | 18 |
| 124 | TPP-10276 | CDRH3 | 9 | 10 | 20 | 18 |
| 125 | TPP-10290 | CDRH3 | | | 20 | 18 |
| 126 | TPP-10445 | CDRH3 | 11 | 12 | 20 | 18 |
| 127 | TPP-10269 | CDRH3 | 7 | 8 | 20 | 18 |
| 128 | TPP-10288 | CDRH3 | 2 | 3 | 20 | 18 |
| 129 | TPP-10265 | CDRH3 | 7 | 8 | 20 | 19 |
| 130 | TPP-10268 | CDRH3 | 7 | 8 | 21 | 19 |
| 131 | TPP-10593 | CDRH3 | 19 | | 22 | 20 |
| 132 | TPP-11174 | CDRH3 | 6 | 12 | 22 | 20 |
| 133 | TPP-10266 | CDRH3 | 7 | 8 | 22 | 20 |
| 134 | TPP-11173 | CDRH3 | 6 | 12 | 22 | 20 |
| 135 | TPP-10444 | CDRH3 | 11 | 12 | 22 | 20 |
| 136 | TPP-10267 | CDRH3 | 7 | 8 | 24 | 22 |
| 137 | TPP-10443 | CDRH3 | 11 | 12 | 24 | 22 |
| 138 | TPP-11163 | CDRL1 | 6 | | 16 | 14 |
| 139 | TPP-10360 | CDRL1 | | | 19 | 13 |
| 140 | TPP-10462 | CDRL1 | | | 20 | 18 |
| 141 | TPP-10460 | CDRL1 | | | 21 | 19 |
| 142 | TPP-10461 | CDRL1 | | | 21 | 19 |
| 143 | TPP-11161 | CDRL1 | 6 | 6 | 21 | 19 |
| 144 | TPP-11162 | CDRL1 | 6 | | 21 | 19 |

TABLE 4-continued

Design of ANP engrafted antibody constructs

| Cmpd | TPP | Insertion Site | SEQ ID NO comprised in Ntls | SEQ ID NO comprised in Ctls | # aa N-term[1] | # aa C-term[2] |
|---|---|---|---|---|---|---|
| 145 | TPP-10359 | CDRL1 |  |  | 23 | 14 |
| 146 | TPP-10824 | CDRL2 |  |  | 1 | 6 |
| 147 | TPP-10825 | CDRL2 |  |  | 5 | 10 |
| 148 | TPP-11019 | CDRL2 |  |  | 12 | 16 |
| 149 | TPP-11021 | CDRL2 |  |  | 13 | 17 |
| 150 | TPP-11020 | CDRL2 |  |  | 13 | 17 |
| 151 | TPP-10789 | CDRL2 |  |  | 14 | 14 |
| 152 | TPP-11022 | CDRL2 |  |  | 15 | 19 |
| 153 | TPP-10829 | CDRL2 | 4 | 5 | 16 | 15 |
| 154 | TPP-10835 | CDRL2 |  |  | 16 | 15 |
| 155 | TPP-10788 | CDRL2 |  |  | 16 | 16 |
| 156 | TPP-10571 | CDRL2 | 15 | 15 | 17 | 16 |
| 157 | TPP-10830 | CDRL2 | 4 | 5 | 17 | 16 |
| 158 | TPP-10790 | CDRL2 |  |  | 17 | 16 |
| 159 | TPP-10573 | CDRL2 |  | 19 | 17 | 16 |
| 160 | TPP-10827 | CDRL2 | 2 | 3 | 17 | 16 |
| 161 | TPP-10572 | CDRL2 | 19 |  | 17 | 16 |
| 162 | TPP-10836 | CDRL2 |  |  | 17 | 16 |
| 163 | TPP-10834 | CDRL2 | 6 |  | 17 | 17 |
| 164 | TPP-10787 | CDRL2 |  |  | 18 | 16 |
| 165 | TPP-10831 | CDRL2 | 4 | 5 | 18 | 17 |
| 166 | TPP-10828 | CDRL2 | 2 | 3 | 18 | 17 |
| 167 | TPP-10826 | CDRL2 | 2 | 3 | 18 | 17 |
| 168 | TPP-10837 | CDRL2 |  |  | 18 | 17 |
| 169 | TPP-10361 | CDRL2 |  |  | 19 | 17 |
| 170 | TPP-11023 | CDRL2 | 11 | 12 | 19 | 18 |
| 171 | TPP-10838 | CDRL2 |  |  | 19 | 18 |
| 172 | TPP-10840 | CDRL2 |  |  | 19 | 18 |
| 173 | TPP-10839 | CDRL2 |  |  | 19 | 18 |
| 174 | TPP-10832 | CDRL2 | 6 |  | 19 | 19 |
| 175 | TPP-10833 | CDRL2 | 6 |  | 19 | 19 |
| 176 | TPP-11024 | CDRL2 | 11 | 12 | 20 | 19 |
| 177 | TPP-10353 | CDRL3 |  |  | 2 | 2 |
| 178 | TPP-10780 | CDRL3 |  |  | 14 | 9 |
| 179 | TPP-10786 | CDRL3 |  |  | 16 | 10 |
| 180 | TPP-10779 | CDRL3 |  |  | 16 | 11 |
| 181 | TPP-10778 | CDRL3 |  |  | 16 | 13 |
| 182 | TPP-10783 | CDRL3 | 11 | 12 | 17 | 11 |
| 183 | TPP-10785 | CDRL3 |  |  | 18 | 12 |
| 184 | TPP-10776 | CDRL3 |  |  | 18 | 13 |
| 185 | TPP-10777 | CDRL3 |  |  | 18 | 13 |
| 186 | TPP-10784 | CDRL3 |  |  | 18 | 14 |
| 187 | TPP-10782 | CDRL3 | 11 | 12 | 19 | 13 |
| 188 | TPP-10352 | CDRL3 | 7 | 8 | 19 | 14 |
| 189 | TPP-10356 | CDRL3 |  |  | 19 | 14 |
| 190 | TPP-10354 | CDRL3 |  |  | 19 | 14 |
| 191 | TPP-10355 | CDRL3 |  |  | 19 | 14 |
| 192 | TPP-10781 | CDRL3 | 11 | 12 | 19 | 15 |
| 193 | TPP-10436 | CDRL3 | 7 | 8 | 20 | 14 |
| 194 | TPP-10440 | CDRL3 | 11 | 12 | 20 | 14 |
| 195 | TPP-10442 | CDRL3 |  |  | 20 | 14 |
| 196 | TPP-10351 | CDRL3 | 7 | 8 | 20 | 15 |
| 197 | TPP-10348 | CDRL3 | 7 | 8 | 20 | 15 |
| 198 | TPP-10358 | CDRL3 |  |  | 20 | 15 |
| 199 | TPP-11167 | CDLR3 | 6 | 12 | 21 | 15 |
| 200 | TPP-10438 | CDRL3 | 11 | 12 | 21 | 15 |
| 201 | TPP-10439 | CDRL3 | 11 | 12 | 21 | 15 |
| 202 | TPP-10441 | CDRL3 |  |  | 21 | 15 |
| 203 | TPP-10349 | CDRL3 | 7 | 8 | 21 | 16 |
| 204 | TPP-10350 | CDRL3 | 7 | 8 | 22 | 17 |
| 205 | TPP-10437 | CDRL3 | 11 | 12 | 23 | 17 |
| 206 | TPP-11166 | CDRL3 | 6 | 12 | 24 | 18 |
| 207 | TPP-10362 | CDRL3 | 6 | 6 | 24 | 20 |
| 208 | TPP-10363 | CDRL3 | 6 | 6 | 24 | 20 |
| 209 | TPP-5657 | no |  |  | na | n |

[1]The number of amino acid residues present between the respective N-terminal reference amino acid residue and the first amino acid of the inserted natriuretic peptide;
[2]The number of amino acid residues present between the last amino acid of the inserted natriuretic peptide and the respective C-terminal reference amino acid residue Table 4 cont.: Design of ANP engrafted antibody constructs

| Cmpd | TPP | N-terminal sequence[3] | C-terminal sequence[4] |
|---|---|---|---|
| 1 | TPP-13057 | SGFTFSS (SEQ ID NO: 92) | YAM |
| 2 | TPP-13056 | SGFTFGSGSG (SEQ ID NO: 93) | GSGSGM (SEQ ID NO: 94) |
| 3 | TPP-13055 | SGFTFGSGSGSGS (SEQ ID NO: 95) | SGSGSGSGM (SEQ ID NO: 96) |
| 4 | TPP-13054 | SGFTFGSGSGSGGSGG (SEQ ID NO: 97) | GGSGGSGSGSGM (SEQ ID NO: 98) |
| 5 | TPP-12545 | SGFTFGSGSGSGSGGGSGG (SEQ ID NO: 99) | GSGSGGSGSGM (SEQ ID NO: 100) |
| 6 | TPP-10454 | SPAVVYIEILDRHPDGGSGG (SEQ ID NO: 101) | GSGREVPISNGSGFVVAM (SEQ ID NO: 102) |
| 7 | TPP-10453 | SGAVVYIEILDRHPDGGSGG (SEQ ID NO: 103) | GSGREVPISNGSGFVVAM (SEQ ID NO: 102) |
| 8 | TPP-11172 | SSSDRSALLKSKLRALLTAPR (SEQ ID NO: 104) | GSGREVPISNGSGFVVAM (SEQ ID NO: 102) |
| 9 | TPP-10294 | SGFTFGSGSGSGSGSGSPDGGSGG (SEQ ID NO: 105) | GSYGSGSGSGSGSGM (SEQ ID NO: 106) |
| 10 | TPP-12547 | SGFTFGSGSGSGSGSGSPDGGSGG (SEQ ID NO: 105) | GSYGSGSGSGSGSGM (SEQ ID NO: 106) |
| 11 | TPP-11171 | SGFTFSSDRSALLKSKLRALLTAPR (SEQ ID NO: 107) | GSGSGSGSGSGSGM (SEQ ID NO: 108) |
| 12 | TPP-10841 | ISGS (SEQ ID NO: 109) | GGST (SEQ ID NO: 110) |
| 13 | TPP-10842 | ISGSGSGS (SEQ ID NO: 111) | GSGSGGST (SEQ ID NO: 112) |
| 14 | TPP-11009 | ISGSGSGSG (SEQ ID NO: 113) | GSSGSGSGST (SEQ ID NO: 114) |
| 15 | TPP-11008 | ISGSGSGSGSG (SEQ ID NO: 115) | GSSGSGSGSGST (SEQ ID NO: 116) |
| 16 | TPP-11018 | ISGSGSGSGSGG (SEQ ID NO: 117) | GEKEKEKVSTAVGST (SEQ ID NO: 118) |
| 17 | TPP-10775 | ISGSAVVNGGSGG (SEQ ID NO: 119) | GKIAIGGST (SEQ ID NO: 120) |
| 18 | TPP-10767 | ISGPNPNKNPNPGG (SEQ ID NO: 121) | GSNENPNPNPGST (SEQ ID NO: 122) |
| 19 | TPP-11012 | ISGSVVVTSHGGSGG (SEQ ID NO: 123) | GGSGSGSGST (SEQ ID NO: 124) |
| 20 | TPP-10774 | ISGSAVVNVRGGSGG (SEQ ID NO: 125) | GGDKIAIGGST (SEQ ID NO: 126) |
| 21 | TPP-11007 | ISGSGSGSGSGSSGG (SEQ ID NO: 127) | GSSGSGSGSGST (SEQ ID NO: 116) |
| 22 | TPP-11179 | ISGLAVQIRRGGSGG (SEQ ID NO: 128) | GGSGRETLTLYVGST (SEQ ID NO: 129) |
| 23 | TPP-10773 | ISGSAVVNVRAGGSGG (SEQ ID NO: 130) | GGDKIAIGGST (SEQ ID NO: 126) |
| 24 | TPP-10770 | ISGSYAMSWVRGGSGG (SEQ ID NO: 131) | GSYAMSWVRQGST (SEQ ID NO: 132) |
| 25 | TPP-10766 | ISGPNPNKNPNPNPGG (SEQ ID NO: 133) | GSNPNENPNPNPGST (SEQ ID NO: 134) |
| 26 | TPP-10772 | ISGSAVVNVRADGGSGG (SEQ ID NO: 135) | GSGDKIAIGGST (SEQ ID NO: 136) |

-continued

Table 4 cont.: Design of ANP engrafted antibody constructs

| Cmpd | TPP | N-terminal sequence[3] | C-terminal sequence[4] |
|---|---|---|---|
| 27 | TPP-11005 | ISGSGSGSGSPDGGSGG (SEQ ID NO: 137) | GSSGSGSGSGST (SEQ ID NO: 116) |
| 28 | TPP-11006 | ISGSGSGSGSGSGGSGG (SEQ ID NO: 138) | GSSGSGSGSGST (SEQ ID NO: 116) |
| 29 | TPP-11017 | ISGSGSGSGSGSGGSGG (SEQ ID NO: 138) | GEKEKEKVSTAVGST (SEQ ID NO: 118) |
| 30 | TPP-11169 | ISGSVVVTSHQAPGSGG (SEQ ID NO: 139) | GSGEKKKLKSLAYGST (SEQ ID NO: 140) |
| 31 | TPP-11181 | ISGRYNILKIQKVGSGG (SEQ ID NO: 141) | GGSGEYLITYQIMGST (SEQ ID NO: 142) |
| 32 | TPP-11182 | ISGRQLLFCRVTLGSGG (SEQ ID NO: 143) | GGSGEQAYPEYLITYGST (SEQ ID NO: 144) |
| 33 | TPP-10277 | ISVVVTSHQAPGEGGSGG (SEQ ID NO: 145) | GEKKKLKSLAST (SEQ ID NO: 146) |
| 34 | TPP-12553 | ISGVVTSHQAPGEGGSGG (SEQ ID NO: 147) | GEKKKLKSLAST (SEQ ID NO: 146) |
| 35 | TPP-12554 | ISVVVTSHQAPGEGGSGG (SEQ ID NO: 145) | GEKKKLKSLGST (SEQ ID NO: 148) |
| 36 | TPP-12555 | ISVVVTSHQAPGEGGSGG (SEQ ID NO: 145) | GEKKKLKSGGST (SEQ ID NO: 149) |
| 37 | TPP-12542 | ISGVVTSHQAPGEGGSGG (SEQ ID NO: 147) | GEKKKLKSGGST (SEQ ID NO: 149) |
| 38 | TPP-12543 | ISGSVTSHQAPGEGGSGG (SEQ ID NO: 150) | GEKKKLKSGGST (SEQ ID NO: 149) |
| 39 | TPP-12544 | ISGSVTSHQAPGEGGSGG (SEQ ID NO: 150) | GEKKKGKSGGST (SEQ ID NO: 151) |
| 40 | TPP-13058 | ISVVVTSHQAPGSGGSGG (SEQ ID NO: 152) | GEKKKLKSLAST (SEQ ID NO: 146) |
| 41 | TPP-13059 | ISVVVTSHQAPTSGGSGG (SEQ ID NO: 153) | GEKKKLKSLAST (SEQ ID NO: 146) |
| 42 | TPP-13060 | ISVVVTSHQSPTPGGSGG (SEQ ID NO: 154) | GGSTPLKSLAST (SEQ ID NO: 155) |
| 43 | TPP-13061 | ISVVVTSHQAPGEGGSGG (SEQ ID NO: 145) | GGSTPLKSLAST (SEQ ID NO: 155) |
| 44 | TPP-13062 | ISVVVTSHQAPGEGGSGG (SEQ ID NO: 145) | GSTPKLKSLAST (SEQ ID NO: 156) |
| 45 | TPP-13063 | ISVVVTSHQSPTPGGSGG (SEQ ID NO: 154) | GEKKKLKSLAST (SEQ ID NO: 146) |
| 46 | TPP-13064 | ISVVVTSHPTPGEGGSGG (SEQ ID NO: 157) | GEKKKLKSLAST (SEQ ID NO: 146) |
| 47 | TPP-13065 | ISVVVTSHQAPSPGSTGG (SEQ ID NO: 158) | GEKKKLKSLAST (SEQ ID NO: 146) |
| 48 | TPP-13066 | ISVVVTSHQANGSGGSGG (SEQ ID NO: 159) | GEKKKLKSLAST (SEQ ID NO: 146) |
| 49 | TPP-12546 | ISVVVTSHQAPGEGGSGG (SEQ ID NO: 145) | GEKKKLKSLAST (SEQ ID NO: 146) |
| 50 | TPP-10452 | ISGSAVVNVRAPDGGSGG (SEQ ID NO: 160) | GSKGDKIAIGGST (SEQ ID NO: 161) |
| 51 | TPP-10846 | ISTSASLAITGPDGGSGG (SEQ ID NO: 162) | GSDRFSGSKSGST (SEQ ID NO: 163) |

Table 4 cont.: Design of ANP engrafted antibody constructs

| Cmpd | TPP | N-terminal sequence[3] | C-terminal sequence[4] |
|---|---|---|---|
| 52 | TPP-10852 | ISGFILPIEVYPDGGSGG (SEQ ID NO: 164) | GSKVRFDYDLFST (SEQ ID NO: 165) |
| 53 | TPP-10851 | ISSALLKSKLRALLTAPG (SEQ ID NO: 166) | GGSGSGSGSGSGST (SEQ ID NO: 167) |
| 54 | TPP-10769 | ISGSYAMSWVRQAGGSGG (SEQ ID NO: 168) | GSSSYAMSWVRQGST (SEQ ID NO: 169) |
| 55 | TPP-10765 | ISGPNPNKNPNPNPGSGG (SEQ ID NO: 170) | GSNPNENPNPNPGST (SEQ ID NO: 134) |
| 56 | TPP-11180 | IHPLQNRWALWFFKGSGG (SEQ ID NO: 171) | GGSGNLRLISKFDTVT (SEQ ID NO: 172) |
| 57 | TPP-11177 | ISGSVTIFSLATNEGSGG (SEQ ID NO: 173) | GGSGKTTWHRISVFGGST (SEQ ID NO: 174) |
| 58 | TPP-11178 | IYLEGKIDYGEYMDGSGG (SEQ ID NO: 175) | GGSNVRRQATTIIADNIT (SEQ ID NO: 176) |
| 59 | TPP-11176 | ISGSVQGIINFEQKGSGG (SEQ ID NO: 177) | GGSGPVKVWGSIKGGGST (SEQ ID NO: 178) |
| 60 | TPP-10278 | ISGVVVTSHQAPGEGGSGG (SEQ ID NO: 179) | GEKKKLKSLAGST (SEQ ID NO: 180) |
| 61 | TPP-10847 | ISGTSASLAITGPDGGSGG (SEQ ID NO: 181) | GSDRFSGSKSGGST (SEQ ID NO: 182) |
| 62 | TPP-11004 | ISGSGSGSGSGSPDGGSGG (SEQ ID NO: 183) | GSSGSGSGSGSGST (SEQ ID NO: 184) |
| 63 | TPP-10844 | ISGTYISNVNHKPDGGSGG (SEQ ID NO: 185) | GSNTKVDKKVEGST (SEQ ID NO: 186) |
| 64 | TPP-10853 | ISGGFILPIEVYPDGGSGG (SEQ ID NO: 187) | GSKVRFDYDLFGST (SEQ ID NO: 188) |
| 65 | TPP-10279 | ISGSVVVTSHQAPGGGSGG (SEQ ID NO: 189) | GEKKKLKSLAYGST (SEQ ID NO: 190) |
| 66 | TPP-11170 | ISGSVVVTSHQAPGGGSGG (SEQ ID NO: 189) | GEKPKPKPLAYGST (SEQ ID NO: 191) |
| 67 | TPP-11010 | ISGSVVVTSHQAPGGGSGG (SEQ ID NO: 189) | GSSGSGSGSGSGST (SEQ ID NO: 184) |
| 68 | TPP-11011 | ISGSVVVTSHQAPGGGSGG (SEQ ID NO: 189) | GSGSGSGSGSGGST (SEQ ID NO: 192) |
| 69 | TPP-10764 | ISGPNPNKNPNPNPGGSGG (SEQ ID NO: 193) | GSNPNENPNPNPGST (SEQ ID NO: 134) |
| 70 | TPP-11183 | ISGDIYLAINITNGEGSGG (SEQ ID NO: 194) | GGSGDIYLAINITNGEST (SEQ ID NO: 195) |
| 71 | TPP-11175 | ISGSATKAVSVLKGDGSGG (SEQ ID NO: 196) | GGSGVQGIINFEQKGGST (SEQ ID NO: 197) |
| 72 | TPP-11016 | ISGSVPKEKEKEKVSTAVGG (SEQ ID NO: 198) | GSGSGSGSGSGST (SEQ ID NO: 199) |
| 73 | TPP-11015 | ISGSVPKEKEKEKVSTAVGG (SEQ ID NO: 198) | GSGSGSGSGSGSGST (SEQ ID NO: 200) |
| 74 | TPP-10451 | ISGSSGAVVNVRAPDGGSGG (SEQ ID NO: 201) | GSKGDKIAIWTTGST (SEQ ID NO: 202) |
| 75 | TPP-10768 | ISGSYAMSWVRQAPDGGSGG (SEQ ID NO: 203) | GSSSYAMSWVRQGST (SEQ ID NO: 169) |
| 76 | TPP-10848 | ISGSTSASLAITGPDGGSGG (SEQ ID NO: 204) | GSDRFSGSKSGGGST (SEQ ID NO: 205) |

Table 4 cont.: Design of ANP engrafted antibody constructs

| Cmpd | TPP | N-terminal sequence[3] | C-terminal sequence[4] |
|---|---|---|---|
| 77 | TPP-11003 | ISGSGSGSGSGSGPDGGSGG (SEQ ID NO: 206) | GSGSGSGSGSGSGST (SEQ ID NO: 200) |
| 78 | TPP-11002 | ISGSGSGSGSGSSPDGGSGG (SEQ ID NO: 448) | GSYSGSGSGSGSGST (SEQ ID NO: 208) |
| 79 | TPP-10843 | ISTQTYISNVNHKPDGGSGG (SEQ ID NO: 209) | GSNTKVDKKVEPKST (SEQ ID NO: 210) |
| 80 | TPP-10845 | ISGSTYISNVNHKPDGGSGG (SEQ ID NO: 211) | GSNTKVDKKVEGGST (SEQ ID NO: 212) |
| 81 | TPP-10284 | ISGPNPNPNPNPNPDGGSGG (SEQ ID NO: 213) | GSNPNPNPNPNPGST (SEQ ID NO: 214) |
| 82 | TPP-10446 | ISAVQVKLELGHRPDGGSGG (SEQ ID NO: 215) | GSNHLRSEKLTFNST (SEQ ID NO: 216) |
| 83 | TPP-10447 | ISGFILPIEVYFKPDGGSGG (SEQ ID NO: 217) | GSPRKVRFDYDLFST (SEQ ID NO: 218) |
| 84 | TPP-10854 | ISGSGFILPIEVYPDGGSGG (SEQ ID NO: 219) | GSKVRFDYDLFGGST (SEQ ID NO: 220) |
| 85 | TPP-11014 | ISGSVPKEKEKEKVSTAVGG (SEQ ID NO: 198) | GSYGSGSGSGSGSGST (SEQ ID NO: 221) |
| 86 | TPP-10849 | ISDRSALLKSKLRALLTAPR (SEQ ID NO: 222) | GSDRSALLKSKLRAST (SEQ ID NO: 223) |
| 87 | TPP-10850 | ISDRSALLKSKLRALLTAPG (SEQ ID NO: 224) | GGSGSGSGSGSGSGST (SEQ ID NO: 225) |
| 88 | TPP-11013 | ISGSSDKTHTSPPSPDGGSGG (SEQ ID NO: 226) | GSKTHTSPPSPGGST (SEQ ID NO: 227) |
| 89 | TPP-10771 | ISGSYAMSWVRQASPDGGSGG (SEQ ID NO: 228) | GSYSSYAMSWVRGGST (SEQ ID NO: 229) |
| 90 | TPP-10287 | ISGSYAMSWVRQASPDGGSGG (SEQ ID NO: 228) | GSYSSYAMSWVRQGST (SEQ ID NO: 230) |
| 91 | TPP-10282 | ISGSGSGSGSGSGSPDGGSGG (SEQ ID NO: 231) | GSYGSGSGSGSGSGST (SEQ ID NO: 221) |
| 92 | TPP-10285 | ISGSPNPNPNPNPSPDGGSGG (SEQ ID NO: 232) | GSYPNPNPNPNPSGST (SEQ ID NO: 233) |
| 93 | TPP-10286 | ISGPNPNKNPNPNSPDGGSGG (SEQ ID NO: 234) | GSYNPNENPNPNPGST (SEQ ID NO: 235) |
| 94 | TPP-10283 | ISGPNPNPNPNPNSPDGGSGG (SEQ ID NO: 236) | GSYNPNPNPNPNPGST (SEQ ID NO: 237) |
| 95 | TPP-11168 | ISGSVVVTSHQAPGGSGGSGG (SEQ ID NO: 238) | GSGEKKKLKSLAYGST (SEQ ID NO: 140) |
| 96 | TPP-10857 | ISGSVVYIEILDRHPDGGSGG (SEQ ID NO: 239) | GSGREVPISNGSGGST (SEQ ID NO: 240) |
| 97 | TPP-10856 | ISGAVVYIEILDRHPDGGSGG (SEQ ID NO: 241) | GSGREVPISNGSGGST (SEQ ID NO: 240) |
| 98 | TPP-10855 | ISPAVVYIEILDRHPDGGSGG (SEQ ID NO: 242) | GSGREVPISNGSGFST (SEQ ID NO: 243) |
| 99 | TPP-10281 | CAKSPDGGSGG (SEQ ID NO: 244) | GSYG (SEQ ID NO: 245) |
| 100 | TPP-10280 | CAKSPDGGSGG (SEQ ID NO: 244) | GSYQHWGQG (SEQ ID NO: 246) |
| 101 | TPP-10583 | CAKVHQETGGSGG (SEQ ID NO: 247) | GSWHVQHWGQG (SEQ ID NO: 248) |

Table 4 cont.: Design of ANP engrafted antibody constructs

| Cmpd | TPP | N-terminal sequence[3] | C-terminal sequence[4] |
|---|---|---|---|
| 102 | TPP-10582 | CAKVHQETPDGGSGG (SEQ ID NO: 249) | GSYEWHVQHWGQG (SEQ ID NO: 250) |
| 103 | TPP-10270 | CTSVHQETKKYQSSGG (SEQ ID NO: 251) | GSYSYTYNYEWHVDVWGQG (SEQ ID NO: 252) |
| 104 | TPP-10264 | CTSVHQETSSPDGGSGG (SEQ ID NO: 253) | GSYSYEWHVDVWGQG (SEQ ID NO: 254) |
| 105 | TPP-10581 | CAKTHTSPPSPDGGSGG (SEQ ID NO: 255) | GSSPPSPYFQHWGQG (SEQ ID NO: 256) |
| 106 | TPP-10263 | CTSVHQETKSSPDGGSGG (SEQ ID NO: 257) | GSYSNYEWHVDVWGQG (SEQ ID NO: 258) |
| 107 | TPP-10271 | CTSVHQETKKYQSSPDGG (SEQ ID NO: 259) | GSYSYTYNYEWHVDVWGQG (SEQ ID NO: 252) |
| 108 | TPP-10262 | CTSVHQETKKSSPDGGSGG (SEQ ID NO: 260) | GSYSNYEWHVDVWGQG (SEQ ID NO: 261) |
| 109 | TPP-10272 | CTSVHQETKKYQSSGGSGG (SEQ ID NO: 262) | GSYSYTYNYEWHVDVWGQG (SEQ ID NO: 252) |
| 110 | TPP-10261 | CTSVHQETKKQSSPDGGSGG (SEQ ID NO: 263) | GSYSYYNYEWHVDVWGQG (SEQ ID NO: 264) |
| 111 | TPP-10289 | CAKVHPNPNPNPNPDGGSGG (SEQ ID NO: 265) | GSNPNPNPNPHVDVWGQG (SEQ ID NO: 266) |
| 112 | TPP-10273 | CTSVHQETKKYQSSPDGGSG (SEQ ID NO: 267) | GSYSYTYNYEWHVDVWGQG (SEQ ID NO: 252) |
| 113 | TPP-10260 | CTSVHQETKKYQSSPDGGSGG (SEQ ID NO: 268) | GSYSYYNYEWHVDVWGQG (SEQ ID NO: 264) |
| 114 | TPP-10275 | CAKLTVVVTSHQAPGEGGSGG (SEQ ID NO: 269) | GEKKKLKSLAYFQHWGQG (SEQ ID NO: 270) |
| 115 | TPP-10580 | CAKSSDKTHTSPPSPDGGSGG (SEQ ID NO: 271) | GSKTHTSPPSPYFQHWGQG (SEQ ID NO: 272) |
| 116 | TPP-10274 | CTSVHQETKKYQSSPDGGSGG (SEQ ID NO: 268) | GSYSYTYNYEWHVDVWGQG (SEQ ID NO: 252) |
| 117 | TPP-5661 | CTSVHQETKKYQSSPDGGSGG (SEQ ID NO: 268) | GSYSYTYNYEWHVDVWGQG (SEQ ID NO: 252) |
| 118 | TPP-13226 | CAKVETKKYQSSPDGGSGG (SEQ ID NO: 273) | GSYSYTYNYEVQHWGQG (SEQ ID NO: 274) |
| 119 | TPP-13227 | CAKVHTKKYQSSPDGGSGG (SEQ ID NO: 275) | GSYSYTYNYHVQHWGQG (SEQ ID NO: 276) |
| 120 | TPP-13228 | CAKLTVETKKYQSSPDGGSGG (SEQ ID NO: 277) | GSYSYTYNYEWHVQHWGQG (SEQ ID NO: 278) |
| 121 | TPP-13229 | CAKLTAETKKYQSSPDGGSGG (SEQ ID NO: 279) | GSYSYTYNYENYFQHWGQG (SEQ ID NO: 280) |
| 122 | TPP-13230 | CAKGITGTKKYQSSPDGGSGG (SEQ ID NO: 281) | GSYSYTYNYAEYFQHWGQG (SEQ ID NO: 282) |
| 123 | TPP-13231 | CAKGITGTKKYQSSPDGGSGG (SEQ ID NO: 281) | GSYDYVWGSYAYFQHWGQG (SEQ ID NO: 283) |
| 124 | TPP-10276 | CAKLTSVVVTSHQAPGGGSGG (SEQ ID NO: 284) | GEKKKLKSLAYYFQHWGQG (SEQ ID NO: 285) |
| 125 | TPP-10290 | CAKVHPNPNPNPNSPDGGSGG (SEQ ID NO: 286) | GSYNPNPNPNPHVDVWGQG (SEQ ID NO: 287) |
| 126 | TPP-10445 | CAKLTQVKLELGHRPDGGSGG (SEQ ID NO: 288) | GSNHLRSEKLTYFQHWGQG (SEQ ID NO: 289) |

Table 4 cont.: Design of ANP engrafted antibody constructs

| Cmpd | TPP | N-terminal sequence[3] | C-terminal sequence[4] |
|---|---|---|---|
| 127 | TPP-10269 | CAKVHQETKKYQSSPDGGSGG (SEQ ID NO: 290) | GSYSYTYNYEWHVQHWGQG (SEQ ID NO: 278) |
| 128 | TPP-10288 | CAKTQTYISNVNHKPDGGSGG (SEQ ID NO: 291) | GSNTKVDKKAEYFQHWGQG (SEQ ID NO: 292) |
| 129 | TPP-10265 | CTSVHQETKKYQSSPDGGSGG (SEQ ID NO: 268) | GSYSYTTYNYEWHVDVWGQG (SEQ ID NO: 293) |
| 130 | TPP-10268 | CATSVHQETKKYQSSPDGGSGG (SEQ ID NO: 294) | GSYSYTYNYEWHVDVWGQG (SEQ ID NO: 295) |
| 131 | TPP-10593 | CAKLTAEEWKKKYEKEKEKNKGS (SEQ ID NO: 296) | GGSGGSGGSGGAEYFQHWGQG (SEQ ID NO: 297) |
| 132 | TPP-11174 | CADSSDRSALLKSKLRALLTAPR (SEQ ID NO: 298) | GSNHLRSEKLTFNYFQHWGQG (SEQ ID NO: 299) |
| 133 | TPP-10266 | CTSVHQETKKYQYQSSPDGGSGG (SEQ ID NO: 300) | GSYSYTYTYNYEWHVDVWGQG (SEQ ID NO: 301) |
| 134 | TPP-11173 | CAKLTDRSALLKSKLRALLTAPR (SEQ ID NO: 302) | GSNHLRSEKLTFNYFQHWGQG (SEQ ID NO: 299) |
| 135 | TPP-10444 | CAKLTAVQVKLELGHRPDGGSGG (SEQ ID NO: 303) | GSNHLRSEKLTFNYFQHWGQG (SEQ ID NO: 299) |
| 136 | TPP-10267 | CTSVHQETKKYQSSYQSSPDGGSGG (SEQ ID NO: 304) | GSYSYTYSYTYNYEWHVDVWGQG (SEQ ID NO: 305) |
| 137 | TPP-10443 | CAKLTAVQVKLELGHRAQPDGGSGG (SEQ ID NO: 306) | GSPVNHLRSEKLTFNYFQHWGQG (SEQ ID NO: 307) |
| 138 | TPP-11163 | SSSNIGSKLRALLTAPR (SEQ ID NO: 308) | GSGSGGSGGSGSGYD (SEQ ID NO: 309) |
| 139 | TPP-10360 | SGSGSGSGSGSGSPDGGSGG (SEQ ID NO: 29) | GSYGSGGSGSGSGD (SEQ ID NO: 310) |
| 140 | TPP-10462 | SSLGQIQLTIRHSSPDGGSGG (SEQ ID NO: 311) | GSNKLIVVVHASRNLIGYD (SEQ ID NO: 312) |
| 141 | TPP-10460 | SPLGQIQLTIRHSSQPDGGSGG (SEQ ID NO: 313) | GSRNKLIVVVHASRNLIAYD (SEQ ID NO: 314) |
| 142 | TPP-10461 | SSLGQIQLTIRHSSQPDGGSGG (SEQ ID NO: 315) | GSRNKLIVVVHASRNLIGYD (SEQ ID NO: 316) |
| 143 | TPP-11161 | SSSNIGSALLKSKLRALLTAPR (SEQ ID NO: 317) | GSSDRSALLKSKLRALLTAD (SEQ ID NO: 318) |
| 144 | TPP-11162 | SSSNIGSALLKSKLRALLTAPR (SEQ ID NO: 317) | GSGSGGSGGSGGSGSGSGYD (SEQ ID NO: 319) |
| 145 | TPP-10359 | SSSNIGSGSGSGSGSGSPDGGSGG (SEQ ID NO: 320) | GSYGSGGSGSGSGYD (SEQ ID NO: 321) |
| 146 | TPP-10824 | YG | NSNRPSG (SEQ ID NO: 322) |
| 147 | TPP-10825 | YGGSGS (SEQ ID NO: 323) | GSGSNSNRPSG (SEQ ID NO: 324) |
| 148 | TPP-11019 | YGKTHTSPPSPGG (SEQ ID NO: 325) | GGKTHTSPPSPGNRPSG (SEQ ID NO: 326) |
| 149 | TPP-11021 | YGSGSGSGSGSGGG (SEQ ID NO: 327) | GGKTHTSPPSPSGNRPSG (SEQ ID NO: 328) |
| 150 | TPP-11020 | YGSKTHTSPPSPGG (SEQ ID NO: 329) | GGKTHTSPPSPSGNRPSG (SEQ ID NO: 328) |
| 151 | TPP-10789 | YGSGSGSGSGGGSGG (SEQ ID NO: 330) | GSGGSGSGSGNRPSG (SEQ ID NO: 331) |

-continued

Table 4 cont.: Design of ANP engrafted antibody constructs

| Cmpd | TPP | N-terminal sequence[3] | C-terminal sequence[4] |
|---|---|---|---|
| 152 | TPP-11022 | YGSSDKTHTSPPSPGG (SEQ ID NO: 332) | GGSGSGSGGSGSGSGNRPSG (SEQ ID NO: 333) |
| 153 | TPP-10829 | YTSASLAITGPDGGSGG (SEQ ID NO: 334) | GSDRFSGSKSGNRPSG (SEQ ID NO: 335) |
| 154 | TPP-10835 | YGFILPIEVYPDGGSGG (SEQ ID NO: 336) | GSKVRFDYDLFNRPSG (SEQ ID NO: 337) |
| 155 | TPP-10788 | YGSGSGSGSGSGGGSGG (SEQ ID NO: 338) | GSGSGGSGSGSGNRPSG (SEQ ID NO: 339) |
| 156 | TPP-10571 | YGVPKEKEKEKVSTAVGG (SEQ ID NO: 340) | GSAPLEVPKEKEKEKVG (SEQ ID NO: 341) |
| 157 | TPP-10830 | YGTSASLAITGPDGGSGG (SEQ ID NO: 342) | GSDRFSGSKSGGNRPSG (SEQ ID NO: 343) |
| 158 | TPP-10790 | YGGSGSGSGSGPDGGSGG (SEQ ID NO: 344) | GSGSGGSGSGSGNRPSG (SEQ ID NO: 339) |
| 159 | TPP-10573 | YGSGSGSGSGSGSGSGGG (SEQ ID NO: 345) | GSYEKEKEKNKTLKNVG (SEQ ID NO: 346) |
| 160 | TPP-10827 | YGTYISNVNHKPDGGSGG (SEQ ID NO: 347) | GSNTKVDKKVEGNRPSG (SEQ ID NO: 348) |
| 161 | TPP-10572 | YGAEEWKKKYEKEKEKGG (SEQ ID NO: 349) | GSGSGSGSGSGSGSGSG (SEQ ID NO: 350) |
| 162 | TPP-10836 | YGGFILPIEVYPDGGSGG (SEQ ID NO: 351) | GSKVRFDYDLFGNRPSG (SEQ ID NO: 352) |
| 163 | TPP-10834 | YGSALLKSKLRALLTAPG (SEQ ID NO: 353) | GSDGSGGSGSGSNRPSG (SEQ ID NO: 354) |
| 164 | TPP-10787 | YGSGSGSGSGSGPDGGSGG (SEQ ID NO: 355) | GSGSGGSGSGSGNRPSG (SEQ ID NO: 339) |
| 165 | TPP-10831 | YGGTSASLAITGPDGGSGG (SEQ ID NO: 356) | GSDRFSGSKSGGGNRPSG (SEQ ID NO: 357) |
| 166 | TPP-10828 | YGGTYISNVNHKPDGGSGG (SEQ ID NO: 358) | GSNTKVDKKVEGGNRPSG (SEQ ID NO: 359) |
| 167 | TPP-10826 | YTQTYISNVNHKPDGGSGG (SEQ ID NO: 360) | GSNTKVDKKVEPKNRPSG (SEQ ID NO: 361) |
| 168 | TPP-10837 | YGGGFILPIEVYPDGGSGG (SEQ ID NO: 362) | GSKVRFDYDLFGGNRPSG (SEQ ID NO: 363) |
| 169 | TPP-10361 | YGSGSGSGSGSGSPDGGSGG (SEQ ID NO: 364) | GSYGSGGSGSGSGNRPSG (SEQ ID NO: 365) |
| 170 | TPP-11023 | YGSQVKLELGHRAPDGGSGG (SEQ ID NO: 366) | GSVNHLRSEKLTSGNRPSG (SEQ ID NO: 367) |
| 171 | TPP-10838 | YPAVVYIEILDRHPDGGSGG (SEQ ID NO: 368) | GSGREVPISNGSGFNRPSG (SEQ ID NO: 369) |
| 172 | TPP-10840 | YGGVVYIEILDRHPDGGSGG (SEQ ID NO: 370) | GSGREVPISNGSGGNRPSG (SEQ ID NO: 371) |
| 173 | TPP-10839 | YGAVVYIEILDRHPDGGSGG (SEQ ID NO: 372) | GSGREVPISNGSGGNRPSG (SEQ ID NO: 371) |
| 174 | TPP-10832 | YGSRSALLKSKLRALLTAPR (SEQ ID NO: 373) | GSDGSGSGGSGSGSGNRPSG (SEQ ID NO: 374) |
| 175 | TPP-10833 | YGSRSALLKSKLRALLTAPG (SEQ ID NO: 375) | GSDGSGSGGSGSGSGNRPSG (SEQ ID NO: 374) |
| 176 | TPP-11024 | YGSAVQVKLELGHRPDGGSGG (SEQ ID NO: 376) | GSNHLRSEKLTFNSGNRPSG (SEQ ID NO: 377) |

Table 4 cont.: Design of ANP engrafted antibody constructs

| Cmpd | TPP | N-terminal sequence[3] | C-terminal sequence[4] |
|---|---|---|---|
| 177 | TPP-10353 | CQS | VVF |
| 178 | TPP-10780 | CGSGSGSGPDGGSGG (SEQ ID NO: 378) | GSGSGSGSGF (SEQ ID NO: 379) |
| 179 | TPP-10786 | CQSYDILPIEPDGGSGG (SEQ ID NO: 380) | GSRFDYDGVVF (SEQ ID NO: 381) |
| 180 | TPP-10779 | CGSGSGSGSGPDGGSGG (SEQ ID NO: 382) | GSGSGSGSGSGF (SEQ ID NO: 383) |
| 181 | TPP-10778 | CGSGSGSGSGSGGGSGG (SEQ ID NO: 384) | GSGSGSGSGSGSGF (SEQ ID NO: 385) |
| 182 | TPP-10783 | CQSYDKLELGHPDGGSGG (SEQ ID NO: 386) | GSHLRSEKGVVF (SEQ ID NO: 387) |
| 183 | TPP-10785 | CQSYDILPIEVYPDGGSGG (SEQ ID NO: 388) | GSKVRFDYDGVVF (SEQ ID NO: 389) |
| 184 | TPP-10776 | CGSGSGSGSGSGPDGGSGG (SEQ ID NO: 390) | GSGSGSGSGSGSGF (SEQ ID NO: 385) |
| 185 | TPP-10777 | CGSGSGSGSGSGSDGGSGG (SEQ ID NO: 391) | GSGSGSGSGSGSGF (SEQ ID NO: 385) |
| 186 | TPP-10784 | CQSYDGFILPIEVYGGSGG (SEQ ID NO: 392) | GSKVRFDYDLFGVVF (SEQ ID NO: 393) |
| 187 | TPP-10782 | CQSYDKLELGHRAPDGGSGG (SEQ ID NO: 394) | GSVNHLRSEKGVVF (SEQ ID NO: 395) |
| 188 | TPP-10352 | CQVHQETKKYQSSPDGGSGG (SEQ ID NO: 396) | GSYSYTYNYEWHVVF (SEQ ID NO: 397) |
| 189 | TPP-10356 | CGSGSGSGSGSGSPDGGSGG (SEQ ID NO: 398) | GSYGSGSGSGSGSGF (SEQ ID NO: 399) |
| 190 | TPP-10354 | CQSYDPNPNPNPNPDGGSGG (SEQ ID NO: 400) | GSNPNPNPNPSGVVF (SEQ ID NO: 401) |
| 191 | TPP-10355 | CAAWNPNPNPNPNGGSGG (SEQ ID NO: 402) | GSNPNPNPNPNVF (SEQ ID NO: 403) |
| 192 | TPP-10781 | CQSYDQVKLELGHRAGGSGG (SEQ ID NO: 404) | GSVNHLRSEKLTGVVF (SEQ ID NO: 405) |
| 193 | TPP-10436 | CQSVHQETKKYQSSPDGGSGG (SEQ ID NO: 406) | GSYSYTYNYEWHVVF (SEQ ID NO: 397) |
| 194 | TPP-10440 | CQSYDQVKLELGHRPDGGSGG (SEQ ID NO: 407) | GSNHLRSEKLTGVVF (SEQ ID NO: 408) |
| 195 | TPP-10442 | CQSYDGFILPIEVYPDGGSGG (SEQ ID NO: 409) | GSKVRFDYDLFGVVF (SEQ ID NO: 393) |
| 196 | TPP-10351 | CTSVHQETKKYQSSPDGGSGG (SEQ ID NO: 268) | GSYSYTYNYEWHVDVF (SEQ ID NO: 410) |
| 197 | TPP-10348 | CQSVHQETKKYQSSPDGGSGG (SEQ ID NO: 406) | GSYSYTYNYEWHVVVF (SEQ ID NO: 411) |
| 198 | TPP-10358 | CGGSGSGSGSGSGSPDGGSGG (SEQ ID NO: 412) | GSYGSGSGSGSGSGGF (SEQ ID NO: 413) |
| 199 | TPP-11167 | CQCQSYDSSALLKSKLRALLTAPR (SEQ ID NO: 414) | GSVNHLRSEKLTGVVF (SEQ ID NO: 405) |
| 200 | TPP-10438 | CQSAVQVKLELGHRAPDGGSGG (SEQ ID NO: 415) | GSVNHLRSEKLTFNVF (SEQ ID NO: 416) |
| 201 | TPP-10439 | CQSYDQVKLELGHRAPDGGSGG (SEQ ID NO: 417) | GSVNHLRSEKLTGVVF (SEQ ID NO: 405) |

Table 4 cont.: Design of ANP engrafted antibody constructs

| Cmpd | TPP | N-terminal sequence[3] | C-terminal sequence[4] |
|---|---|---|---|
| 202 | TPP-10441 | CQSYDGFILPIEVYFPDGGSGG (SEQ ID NO: 418) | GSRKVRFDYDLFGVVF (SEQ ID NO: 419) |
| 203 | TPP-10349 | CQSYVHQETKKYQSSPDGGSGG (SEQ ID NO: 420) | GSYSYTYNYEWHVGVVF (SEQ ID NO: 421) |
| 204 | TPP-10350 | CQSYDVHQETKKYQSSPDGGSGG (SEQ ID NO: 422) | GSYSYTYNYEWHVSGVVF (SEQ ID NO: 423) |
| 205 | TPP-10437 | CQSYDAVQVKLELGHRAPDGGSGG (SEQ ID NO: 424) | GSVNHLRSEKLTFNGVVF (SEQ ID NO: 425) |
| 206 | TPP-11166 | CQCQSYDSSDRSALLKSKLRALLTAPR (SEQ ID NO: 426) | GSGGSVNHLRSEKLTGVVF (SEQ ID NO: 427) |
| 207 | TPP-10362 | CQSYDSSDRSALLKSKLRALLTAPR (SEQ ID NO: 426) | GSDRSALLKSKLRALLTAVVF (SEQ ID NO: 428) |
| 208 | TPP-10363 | CQSYDSSDRSALLKSKLRALLTAPE (SEQ ID NO: 429) | GSDRSALLKSKLRALLTAVVF (SEQ ID NO: 428) |
| 209 | TPP-5657 | | |

[3]The N-terminal sequence corresponds to the nearest neighboring reference aa N-terminal from the inserted natriuretic peptide plus the amino acid stretch present between said reference aa and the first amino acid residue of the inserted natriuretic peptide

[4]The C-terminal sequence corresponds the amino acid stretch present between the last amino acid residue of the inserted natriuretic peptide and the nearest neighboring reference aa C-terminal from the inserted natriuretic peptide plus and said reference aa In addition, the following BNP engrafted human IgG1 antibody constructs were generated starting from the antibody scaffold TPP-5657.

TABLE 5

Design of BNP engrafted antibody constructs

| Cmpd | TPP | Insertion Site | # aa N-term[1] | # aa C-term[2] | BNP | Corresp. ANP Cpd[3] |
|---|---|---|---|---|---|---|
| B1 | TPP-9902 | CTSVHQETKKYQSSPDGGSGG (SEQ ID NO: 268) | GSYSYTYNYEWHVDVWGQG (SEQ ID NO: 252) | 18 | Hum28aa | #117 |
| B2 | TPP-11153 | CTSVHQETKKYQSSPDGGSGGSG (SEQ ID NO: 430) | GGSYSYTYNYEWHVDVWGQG (SEQ ID NO: 431) | 19 | Hum25aa | |
| B3 | TPP-11154 | CTSVHQETKKYQSSPDGGSGG (SEQ ID NO: 268) | GSYSYTYNYEWHVDVWGQG (SEQ ID NO: 252) | 18 | Rat28aa | #117 |
| B4 | TPP-11155 | CTSVHQETKKYQSSPDGG (SEQ ID NO: 259) | SYSYTYNYEWHVDVWGQG (SEQ ID NO: 432) | 17 | Rat32aa | |
| B5 | TPP-11156 | ISGSVVVTSHQAPGGGSGG (SEQ ID NO: 189) | GEKKKLKSLAYGST (SEQ ID NO: 190) | 13 | Hum28aa | #65 |
| B6 | TPP-11157 | ISGSVVVTSHQAPGGGSGG (SEQ ID NO: 189) | GEKKKLKSLAYGST (SEQ ID NO: 190) | 13 | Rat28aa | #65 |
| B7 | TPP-18029 | SGFTFGSGSGSGSGSGSPDGGSGG (SEQ ID NO: 105) | GSYGSGSGSGSGSGM (SEQ ID NO: 106) | 14 | Hum28aa | #9 |
| B8 | TPP-18031 | ISGS (SEQ ID NO: 109) | GGST (SEQ ID NO: 110) | 3 | Hum28aa | #12 |
| B9 | TPP-18032 | ISGSGSGS (SEQ ID NO: 111) | GSGSGGST (SEQ ID NO: 112) | 7 | Hum28aa | #13 |
| B10 | TPP-18033 | ISGSTYISNVNHKPDGGSGG (SEQ ID NO: 211) | GSNTKVDKKVEGGST (SEQ ID NO: 212) | 14 | Hum28aa | #80 |

TABLE 5-continued

Design of BNP engrafted antibody constructs

| | | | | | | | |
|---|---|---|---|---|---|---|---|
| B11 | TPP-18028 | ISGPNPNPNPNPNSPDGGSGG (SEQ ID NO: 236) | GSYNPNPNPNPNPGST (SEQ ID NO: 237) | 15 | Hum28aa | #94 | |
| B12 | TPP-18034 | CAKGITGTKKYQSSPDGGSGG (SEQ ID NO: 281) | GSYSYTYNYAEYFQHWGQG (SEQ ID NO: 282) | 18 | Hum28aa | #122 | |
| B13 | TPP-18030 | CAAWNPNPNPNPNPNGGSGG (SEQ ID NO: 402) | GSNPNPNPNPNPNVF (SEQ ID NO: 403) | 14 | Hum28aa | #191 | |

| Cmpd | TPP | N-terminal sequence[3] | C-terminal sequence[4] |
|---|---|---|---|
| B1 | TPP-9902 | CTSVHQETKKYQSSPDGGSGG | GSYSYTYNYEWHVDVWGQG |
| B2 | TPP-11153 | CTSVHQETKKYQSSPDGGSGGSG | GGSYSYTYNYEWHVDVWGQG |
| B3 | TPP-11154 | CTSVHQETKKYQSSPDGGSGG | GSYSYTYNYEWHVDVWGQG |
| B4 | TPP-11155 | CTSVHQETKKYQSSPDGG | SYSYTYNYEWHVDVWGQG |
| B5 | TPP-11156 | ISGSVVVTSHQAPGGGSGG | GEKKKLKSLAYGST |
| B6 | TPP-11157 | ISGSVVVTSHQAPGGGSGG | GEKKKLKSLAYGST |
| B7 | TPP-18029 | SGFTFGSGSGSGSGSGSPDGGSGG | GSYGSGSGSGSGSGM |
| B8 | TPP-18031 | ISGS | GGST |
| B9 | TPP-18032 | ISGSGSGS | GSGSGGST |
| B10 | TPP-18033 | ISGSTYISNVNHKPDGGSGG | GSNTKVDKKVEGGST |
| B11 | TPP-18028 | ISGPNPNPNPNPNSPDGGSGG | GSYNPNPNPNPNPGST |
| B12 | TPP-18034 | CAKGITGTKKYQSSPDGGSGG | GSYSYTYNYAEYFQHWGQG |
| B13 | TPP-18030 | CAAWNPNPNPNPNPNGGSGG | GSNPNPNPNPNPNVF |

[1]The number of amino acid residues present between the respective N-terminal reference amino acid residue and the first amino acid of the inserted natriuretic peptide;
[2]The number of amino acid residues present between the last amino acid of the inserted natriuretic peptide and the respective C-terminal reference amino acid residue
[3]Corresponding ANP Cpd. refers to an ANP engrafted antibody construct with the same integration locus and comprising the same N-terminal and C-terminal sequence
[3]The N-terminal sequence corresponds to the nearest neighboring reference aa N-terminal from the inserted natriuretic peptide plus the amino acid stretch present between said reference aa and the first amino acid residue of the inserted natriuretic peptide
[4]The C-terminal sequence corresponds the amino acid stretch present between the last amino acid residue of the inserted natriuretic peptide and the nearest neighboring reference aa C-terminal from the inserted natriuretic peptide plus and said reference aa In addition, the following CNP engrafted human IgG1 antibody constructs were generated.

TABLE 6

Design of CNP engrafted antibody constructs

| Cmpd | TPP | Insertion Site | SEQ ID NO comprised in Ntls | SEQ ID NO comprised in Ctls | # aa N-term[1] | # aa C-term[2] | µg/ml pcs | % purity pcs | Corresp. ANP Cpd[3] |
|---|---|---|---|---|---|---|---|---|---|
| C1 | TPP-9465 | CDRH3 | 7 | 8 | 21 | 23 | 69-242 | 97 | |
| C2 | TPP-12374 | CDRL3 | 11 | 12 | 20 | 20 | 212 | | |
| C3 | TPP-12375 | CDRH3 | 7 | 8 | 21 | 23 | 6 | | |
| C4 | TPP-12376 | CDRH3 | 7 | 8 | 20 | 22 | 7 | | |
| C5 | TPP-12377 | CDRH3 | 8 | | 21 | 23 | 7 | | |

TABLE 6-continued

Design of CNP engrafted antibody constructs

| | | | | | | | | | |
|---|---|---|---|---|---|---|---|---|---|
| C6  | TPP-12378 | CDRH2 | 9  | 10 | 19 | 18 | 3   |     | #9   |
| C13 | TPP-18036 | CDRH1 |    |    | 23 | 14 | 259 | 100 | #12  |
| C14 | TPP-18038 | CDRH2 |    |    | 3  | 3  | 0   |     | #12  |
| C15 | TPP-18039 | CDRH2 |    |    | 7  | 7  | 301 | 100 | #13  |
| C16 | TPP-18040 | CDRH2 | 2  | 3  | 19 | 14 | 300 | 100 | #80  |
| C17 | TPP-18035 | CDRH2 |    |    | 20 | 15 | 243 | 100 | #94  |
| C18 | TPP-18041 | CDRH3 | 21 | 22 | 20 | 18 | 287 | 100 | #122 |
| C19 | TPP-18037 | CDRL3 |    |    | 19 | 14 | 246 | 100 | #191 |

| Cmpds based on TPP-12377: | | Difference vs. TPP-12377 | | |
|---|---|---|---|---|
| C7  | TPP-12895 | LC_G99E |         |    |
| C8  | TPP-12896 | LC_G99L | 101-131 |    |
| C9  | TPP-12897 | LC_S98D | 198-304 |    |
| C10 | TPP-12898 | LC_S98G | 147-258 |    |
| C11 | TPP-12899 | LC_A33Y | 165-197 | 82 |
| C12 | TPP-12900 | LC_A33E | 109-195 |    |

[1] The number of amino acid residues present between the respective N-terminal reference amino acid residue and the first amino acid of the inserted natriuretic peptide;
[2] The number of amino acid residues present between the last amino acid of the inserted natriuretic peptide and the respective C-terminal reference amino acid residue
[3] Corresponding ANP Cpd. refers to an ANP engrafted antibody construct with the same integration locus and comprising the same N-terminal and C-terminal sequence Table 6 cont.: Design of CNP engrafted antibody constructs

| Cmpd | TPP | N-terminal sequence[3] | C-terminal sequence[4] |
|---|---|---|---|
| C1 | TPP-9465  | CTSVHQETKKYQSSPDGGSGGS (SEQ ID NO: 433) | GSGGYGSYSYTYNYEWHVDVWGQG (SEQ ID NO: 434) |
| C2 | TPP-12374 | CQSYDQVKLELGHRAGGSGGS (SEQ ID NO: 435)  | GSGGSGSVNHLRSEKLTGVVF (SEQ ID NO: 436)    |
| C3 | TPP-12375 | CTSVHQETKKYQSSPDGGSGGS (SEQ ID NO: 433) | GSGGSGSYSYTYNYEWHVDVWGQG (SEQ ID NO: 437) |
| C4 | TPP-12376 | CTSVHQETKKYQSSPDGGSGG (SEQ ID NO: 268)  | GGGSGSYSYTYNYEWHVDVWGQG (SEQ ID NO: 438)  |
| C5 | TPP-12377 | CTSVHQETKKYQSSPYKGANKK (SEQ ID NO: 439) | GSGGSGSYSYTYNYEWHVDVWGQG (SEQ ID NO: 437) |
| C6 | TPP-12378 | ISGSVVVTSHQAPGGGSGGS (SEQ ID NO: 440)   | GSGGSGEKKKLKSLAYGST (SEQ ID NO: 441)      |

[3] The N-terminal sequence corresponds to the nearest neighboring reference aa N-terminal from the inserted natriuretic peptide plus the amino acid stretch present between said reference aa and the first amino acid residue of the inserted natriuretic peptide of the inserted natriuretic peptide and the nearest
[4] The C-terminal sequence corresponds the amino acid stretch present between the last amino acid residue neighboring reference aa C-terminal from the inserted natriuretic peptide plus and said reference aa

Example 5: In Vitro Activities of Generated Constructs

All constructs were expressed transiently in HEK293 cells according to well-known methods in the art, targeting a cell density of about 2×10^6 cells/ml, a total DNA concentration of about 1 μg/ml for the two plasmids encoding the light and heavy chain and a 5 day incubation for the expression.

Raw compound samples (rcs) were expressed in a culture volume of 0.4 ml, and the supernatant separated by centrifugation was directly used for testing. The compound concentration was assessed by an IgG-Fc quantification ELISA according to well-known methods in the art. Briefly, 1:1500 diluted supernatant and a 2-fold dilution series of Human Reference Serum (Bethyl, RS-110-4) starting with 400 ng/ml were immobilized in black Maxisorp 384 micro titer plates (MTP) coated with anti-human Fc [Sigma 12136] in a 1:440 dilution in 1× coating buffer (Candor, 121125) for 1 h, 37° C. After blocking with 100% SMART Block (Candor, 113125) anti-human Fc-HRP [Sigma, A0170] was applied in a 1:10000 dilution for the detection of antibodies in rcs and reference samples. Dose curves of the reference sample were used for the quantitative assessment of compound concentrations shown in Tables 7 and 8, column "μg/ml rcs". All samples were applied in quadruplets.

Isolated compound samples (ics) were generated by 1-step purification via protein-A from 6 ml expression culture and according to well-known methods in the art. Acid eluates were neutralized by addition of 8% (v/v) 1M Tris/HCl pH 9.0, quantified via absorption at 280 nm and normalized to a concentration of 125 nM.

Purified compound samples (pcs) were generated by 2-step purification via protein-A and subsequent SEC in PBS buffer from expression culture of at least 35 ml. Values shown in Tables 7 and 8, column "μg/ml pcs", refer to the compound concentration in the expression culture supernatant determined by analytical Protein A chromatography.

All activities shown in Tables 7 and 8 were measured on cells with heterologous over expression of human NPRA (hNPRA) by use of a cGMP quantification assay conducted according to manufacturer's instructions (cisbio; 62GM2PEH). In brief, the assay quantifies cGMP in buffered solution or cell-culture supernatants based on the competition between cGMP produced by the cell as result of the NPRA stimulation through the (natriuretic peptide) sample and d2 labelled cGMP for binding to a Cryptate labelled antibody. Sample cGMP and d2 labeled cGMP compete for binding to a limited number of sites on Cryptate labeled anti-cGMP antibodies, and consequently, HTRF® specific fluorescent signal (i.e. energy transfer) is inversely proportional to the concentration of cGMP in the sample.

Dose-response curve data were analyzed with GraphPad Prism (version 7.00 for Windows, GraphPad Software, La Jolla California USA) and EC50 were fitted according to $Y=Bottom+(Top-Bottom)/(1+10^{((LogEC50-X)*HillSlope)})$ applying constraints for bottom, top and slope (shared value for all data sets of the respective experiment).

The raw compound sample activity on stable hNPRA-CHO k1 cells was first assessed by comparison to the negative control TPP-5657 and to a positive sample, in particular TPP-5661. Controls and rcs were tested in quadruplets in two concentrations with a relative dilution factor of 5 aiming for a fluorescent signal (s) in the dynamic range of the assay. The assay window was defined as the difference in signal of inactive (max. signal, s_max) and highly active samples (min. signal, s_min), and for both compound concentrations the activity in % was calculated as $100*(s\_max-s)/(s\_max-s\_min)$. Values listed in Table 7, columns "activity rcs" and "stdev activity rcs", represent the average of the results for the two concentrations and the respective standard deviation. Rcs signals less than half of the signal of the reference compound TPP-5661 (36%) were assessed as not active (n.a.).

The activity of several raw compound samples on stable hNPRA-CHO k1 cells was reassessed by comparison to reference sample TPP-5661 in 2.5-fold dilution series (8 concentrations) starting with a 5-fold dilution. The "log EC50" fit value as activity measure of the rcs was set in relation to the corresponding value of the reference rcs TPP-5661 by calculating the delta "log EC50"_compound– "log EC50"_TPP-5661; resulting values are listed in Table 7, column "rel. activity rcs". Notably, the compound concentrations in the rcs was not considered, and consequently given values are influenced by compound activity and concentration in equal measure. All samples were applied in quadruplets.

The activity of isolated compound samples on stable hNPRA-CHO k1 cells was assessed by EC50 determination and comparison to reference sample TPP-5661. Samples were tested in 2.5-fold dilution series from 80 nM to 0.13 nM. The log EC50 fit value as activity measure of the ics was set in relation to the corresponding value of the reference ics TPP-5661 (−8.8) by calculating the delta log EC50_compound–log EC50_TPP-5661; resulting values are listed in Table 7, column "rel. log EC50 ics". All samples were applied in quadruplets.

The activity of purified compound samples on stable hNPRA-CHO k1 cells was assessed in multiple experiments by EC50 determination and comparison to reference sample TPP-5661. Samples were tested in dilution series at least in quadruplets. Values listed in Table 7, columns "rel. log EC50 pcs 1, 3 and 4" result from 5-fold dilution series (>4 concentrations) starting with 20 or 25 nM. Values listed in Table 7, column "rel. log EC50 pcs 2" result from 10-fold dilution series (4 concentrations) starting with 25 nM. Values listed in Table 7, columns "rel. log EC50 pcs 5, 6, 7, 8 and 9" result from 2.5-fold dilution series, with 8 or 12 concentrations starting with 40 to 200 nM, respectively. The log EC50 fit value as activity measure of the pcs was set in relation to the corresponding value of the reference TPP-5661 in the respective experiment (in average −9.2, standard deviation 0.5) by calculating the delta log EC50_compound–log EC50_TPP-5661.

The activity of purified compound samples on transient hNPRA-HEK293 cells was assessed in three experiments by EC50 determination and comparison to reference sample TPP-5661. Samples were tested in 5-fold dilution series from 1000 nM to 0.013 nM. The log EC50 fit value as activity measure of the pcs was set in relation to the corresponding value of the reference TPP-5661 in the respective experiment (average of three experiments −9.0, standard deviation 0.4) by calculating the delta log EC50_compound–log EC50_TPP-5661; resulting values are listed in Table 7, columns "rel. log EC50*pcs". All samples were applied in duplicates.

A summarized qualitative assessment of the activity of compounds is given in the column "qualit. activity", values listed in column "average rel. log EC50" were calculated as average of given rel. log EC50 values. Compounds showing an EC50 values>50-fold of the reference compound TPP-5661, meaning average rel. log EC50>1.7, were qualitatively assessed as not active ("−"), compounds showing a relative log EC50 between 0.7 and 1.7 were assessed as active ("+"), compounds showing a relative log EC50<0.7 were assessed as very active ("++"); highest activities were observed at relative log EC50 below −0.7 ("+++"). Compounds showing an activity in rcs without confirmation as ics or pcs are marked with an unified "y", and compounds assessed as not active ("n.a." in column "activity rcs") probably due to their very low expression level (≤1 µg/ml, "n.e." in column "µg/ml rcs") are marked accordingly.

TABLE 7

Expression levels and activities of atrial natriuretic peptide engrafted antibody constructs

| Compound | # aa N-term[1] | # aa C-term[2] | µg/ml rcs | µg/ml pcs | % purity pcs | activity rcs | stdev activity rcs | rel. activity rcs | rel. log-EC50 ics | rel. log-EC50 pcs 1 | rel. log-EC50 pcs 2 | rel. log-EC50 pcs 3 | rel. log-EC50 pcs 4 | rel. log-EC50 pcs 5 | rel. log-EC50 pcs 6 | rel. log-EC50 pcs 7 | rel. log-EC50 pcs 8 | rel. log-EC50 pcs 9 | rel TABLE 7-continued Expression levels and activities of atrial natriuretic peptide engrafted antibody constructs

| Compound | # aa N-term[1] | # aa C-term[2] | µg/ml rcs | µg/ml pcs | % purity pcs | activity rcs | stdev activity rcs | rel. activity res | rel. log-EC50 ics | rel. log-EC50 pcs 1 | rel. log-EC50 pcs 2 | rel. log-EC50 pcs 3 | rel. log-EC50 pcs 4 | rel. log-EC50 pcs 5 | rel. log-EC50 pcs 6 | rel. log-EC50 pcs 7 | rel. log-EC50 pcs 8 | rel. log-EC50 pcs 9 | rel. log-EC50* pcs | rel. log-EC50* pcs | rel. log-EC50* pcs | qualit. activity | average rel log-EC50 |
|---|---|---|---|---|---|---|---|---|---|---|---|---|---|---|---|---|---|---|---|---|---|---|---|
| #50 | 17 | 12 | 9.0 | 87 | 97 | 66% | 21% | −1.0 | | | 0.0 | −0.4 | | | | | | | | | | ++ | −0.2 |
| #51 | 17 | 12 | 6.4 | n.d. | n.d. | 44% | 39% | | | | | | | | | | | | | | | y | |
| #52 | 17 | 12 | 7.6 | n.d. | n.d. | 26% | 20% | | | | | | | | | | | | | | | y | |
| #53 | 17 | 13 | n.d. | n.d. | n.d. | 69% | 5% | | | | | | | | | | | | | | | y | |
| #54 | 17 | 14 | n.e | 75 | n.d. | n.a. | | | | | | | | | | | | | | | | n.e | |
| #55 | 17 | 14 | 8.8 | 271 | 95 | 72% | 40% | −0.9 | | | | | | −0.9 | −0.4 | 0.2 | | | | | | ++ | −0.4 |
| #57 | 17 | 17 | 13.0 | n.d. | n.d. | 48% | 1% | | | | | | | | | | | | | | | y | |
| #58 | 17 | 17 | 33.0 | n.d. | n.d. | 45% | 9% | | | | | | | | | | | | | | | y | |
| #59 | 17 | 17 | 31.0 | n.d. | n.d. | 87% | 4% | −1.1 | 0.0 | | | | | | | | | | | | | ++ | 0.0 |
| #60 | 18 | 12 | 4.1 | 367 | 90 | 53% | 31% | | | | 0.0 | −0.5 | | | | | | | | | | ++ | −0.3 |
| #61 | 18 | 13 | n.e | 334 | 97 | n.a. | | | | | | | | 0.0 | −0.9 | | | | | | | ++ | −0.5 |
| #62 | 18 | 13 | 11.0 | n.d. | n.d. | 36% | 14% | | 1.5 | | | | | | | | | | | | | + | 1.5 |
| #63 | 18 | 13 | 9.5 | 239 | 96 | 70% | 22% | | | | | | | −0.1 | | | | | | | | ++ | −0.1 |
| #64 | 18 | 13 | 5.3 | n.d. | n.d. | 51% | 18% | | | | | | | | | | | | | | | y | |
| #65 | 18 | 13 | 1.2 | 253 | 86 | 69% | 17% | | | −0.5 | −0.3 | | −1.2 | −0.9 | | | | | | | | +++ | −0.7 |
| #66 | 18 | 13 | 38.0 | n.d. | n.d. | 87% | 4% | −0.5 | 0.2 | | | | | | | | | | | | | ++ | 0.2 |
| #67 | 18 | 13 | 4.8 | n.d. | n.d. | 35% | 17% | −1.1 | 0.7 | | | | | | | | | | | | | ++ | 0.7 |
| #68 | 18 | 13 | 9.2 | n.d. | n.d. | 48% | 13% | | | | | | | | | | | | | | | y | |
| #69 | 18 | 14 | 7.1 | n.d. | n.d. | 66% | 11% | −1.0 | 0.3 | | | | | | | | | | | | | ++ | 0.3 |
| #70 | 18 | 17 | n.e | n.d. | n.d. | 30% | 2% | | | | | | | | | | | | | | | y | |
| #71 | 18 | 17 | 27.0 | n.d. | n.d. | 89% | 2% | −0.5 | −0.6 | | | | | | | | | | | | | ++ | −0.6 |
| #72 | 19 | 12 | 11.0 | n.d. | n.d. | 82% | 0% | −1.5 | 0.1 | | | | | | | | | | | | | ++ | 0.1 |
| #73 | 19 | 14 | 9.4 | n.d. | n.d. | 71% | 0% | −1.4 | −0.2 | | | | | | | | | | | | | ++ | −0.2 |
| #74 | 19 | 14 | 3.8 | 142 | 97 | 67% | 7% | −1.0 | | | 0.0 | 0.3 | | | | | | | | | | ++ | 0.2 |
| #75 | 19 | 14 | 4.4 | 50 | 49 | 95% | 8% | | | | | | −0.4 | | | | | | | | | ++ | −0.4 |
| #76 | 19 | 14 | 11.0 | 299 | 97 | 56% | 2% | | | | | | | 0.2 | −0.8 | | | | | | | ++ | −0.3 |
| #77 | 19 | 14 | 13.0 | n.d. | n.d. | 38% | 6% | | 1.1 | | | | | | | | | | | | | + | 1.1 |
| #78 | 19 | 14 | 14.0 | n.d. | n.d. | 55% | 38% | | 1.0 | | | | | | | | | | | | | + | 1.0 |
| #79 | 19 | 14 | 5.5 | n.d. | n.d. | 67% | 26% | | | | | | | | | | | | | | | y | |
| #80 | 19 | 14 | 5.4 | 214 | 95 | 67% | 19% | | | | | | | −0.4 | −0.8 | | | | | | | ++ | −0.6 |
| #81 | 19 | 14 | 6.2 | n.d. | n.d. | 64% | 10% | | | | | | | | | | | | | | | y | |
| #82 | 19 | 14 | 1.6 | n.d. | n.d. | 57% | 9% | | | | | | | | | | | | | | | y | |
| #83 | 19 | 14 | n.e | n.d. | n.d. | 22% | 40% | | | | | | | | | | | | | | | y | |
| #84 | 19 | 14 | 11.0 | n.d. | n.d. | 45% | 30% | | | | | | | | | | | | | | | y | |
| #85 | 19 | 15 | 4.5 | n.d. | n.d. | 74% | 27% | −1.2 | −0.9 | | | | | | | | | | | | | +++ | −0.9 |
| #87 | 19 | 15 | 42.0 | n.d. | n.d. | 90% | 13% | | | | | | | | | | | | | | | y | |
| #89 | 20 | 15 | n.e | 85 | n.d. | n.a. | | | | | | | | | | | | | | | | n.e | |
| #90 | 20 | 15 | n.e | 68 | 50 | 52% | 18% | | | 0.9 | 0.5 | | 0.4 | | | | | | | | | ++ | 0.6 |
| #91 | 20 | 15 | 3.4 | 275 | 99 | 30% | 26% | −0.3 | | 0.3 | −0.2 | | 0.1 | 0.2 | | | | | | | | ++ | 0.1 |
| #92 | 20 | 15 | 2.3 | n.d. | n.d. | n.a. | | −0.3 | 0.6 | | | | | | | | | | | | | ++ | 0.6 |
| #93 | 20 | 15 | 4.1 | 286 | 98 | 70% | 4% | −0.8 | | | | | | −0.8 | | | | | | | | +++ | −0.8 |
| #94 | 20 | 15 | 12.0 | 318 | 98 | 83% | 17% | −0.8 | | | | | | −0.8 | | | | | | | | +++ | −0.8 |
| #95 | 20 | 15 | 38.0 | n.d. | n.d. | 81% | 16% | | | | | | | | | | | | | | | y | |
| #96 | 20 | 15 | 7.3 | n.d. | n.d. | n.a. | | | | | | | | | | | | | | | | – | |
| #97 | 20 | 15 | 8.3 | n.d. | n.d. | 26% | 17% | | | | | | | | | | | | | | | y | |
| #98 | 20 | 15 | 7.7 | n.d. | n.d. | 40% | 14% | | | | | | | | | | | | | | | y | |

TABLE 7-continued

Expression levels and activities of atrial natriuretic peptide engrafted antibody constructs

| Compound | # aa N-term[1] | # aa C-term[2] | µg/ml rcs | µg/ml pcs | % purity pcs | activ- ity rcs | stdev activ- ity rcs | rel. activ- ity res | rel. log- EC50 ics | rel. log- EC50 pcs 1 | rel. log- EC50 pcs 2 | rel. log- EC50 pcs 3 | rel. log- EC50 pcs 4 | rel. log- EC50 pcs 5 | rel. log- EC50 pcs 6 | rel. log- EC50 pcs 7 | rel. log- EC50 pcs 8 | rel. log- EC50 pcs 9 | rel. log- EC50* pcs | rel. log- EC50* pcs | rel. log- EC50* pcs | qualit. activity | average rel log- EC50 |
|---|---|---|---|---|---|---|---|---|---|---|---|---|---|---|---|---|---|---|---|---|---|---|---|
| #99 | 10 | 3 | 44.0 | 257 | 100 | n.a. | | | | | n.a. | n.a. | | | | | | | | | | − | n.a. |
| #100 | 10 | 8 | 88.0 | 188 | 99 | n.a. | | | | | n.a. | n.a. | | | | | | | | | | − | n.a. |
| #101 | 12 | 10 | 83.0 | n.d. | n.d. | n.a. | | | | | | | | | | | | | | | | − | |
| #102 | 14 | 12 | 16.0 | n.d. | n.d. | 20% | 7% | | | | | | | | | | | | | | | y | |
| #103 | 15 | 18 | 7.7 | 101 | 85 | 50% | 8% | | | | 0.7 | | −0.1 | | | | | | | | | ‡ | 0.3 |
| #104 | 16 | 14 | 15.0 | 137 | 98 | n.a. | | | | | 1.0 | 2.3 | | | | | | | | | | ? | 1.7 |
| #106 | 17 | 15 | 30.0 | n.d. | n.d. | 20% | 2% | | | | | | | | | | | | | | | y | |
| #107 | 17 | 18 | 8.8 | n.d. | n.d. | 50% | 19% | | | | | | | | | | | | | | | y | |
| #108 | 18 | 16 | 37.0 | n.d. | n.d. | 68% | 7% | | | | | | | | | | | | | | | y | |
| #109 | 18 | 18 | 4.6 | n.d. | n.d. | 62% | 20% | | | | | | | | | | | | | | | y | |
| #110 | 19 | 17 | 34.0 | 238 | 100 | 45% | 25% | | | | −0.4 | 1.1 | | | | | | | | | | ‡ | 0.4 |
| #111 | 19 | 17 | 41.0 | 296 | 98 | 80% | 3% | | | | −0.4 | 0.2 | | | | | | | | | | ‡ | −0.1 |
| #112 | 19 | 18 | 3.9 | n.d. | n.d. | 31% | 30% | | | | | | | | | | | | | | | y | |
| #113 | 20 | 17 | 44.0 | n.d. | n.d. | 52% | 2% | | | | | | | | | | | | | | | ‡ | |
| #114 | 20 | 17 | 26.0 | 219 | 76 | 94% | 4% | | | | 0.5 | 0.1 | | | | | | | | | | ‡ | 0.3 |
| #116 | 20 | 18 | 9.4 | 247 | 84 | 71% | 11% | | | | −0.3 | −0.2 | | | | | | | | | | ‡ | −0.1 |
| #117 | 20 | 18 | 12.9 | 238 | 92 | 36% | 30% | | | | 0.0 | 0.0 | | | | | | | | | | + | 0.0 |
| #118 | 18 | 16 | n.d. | 191 | n.d. | n.d. | | 0.0 | | 0.0 | | | | | | | | | −0.2 0.0 | | | ‡ | −0.1 |
| #119 | 18 | 16 | n.d. | 171 | n.d. | n.d. | | | | | | | | | | | | −0.1 | | | | ‡ | −0.1 |
| #120 | 20 | 18 | n.d. | 200 | n.d. | n.d. | | | | | | | | | | | | −0.2 | | | | ‡ | −0.2 |
| #121 | 20 | 18 | n.d. | 253 | n.d. | n.d. | | | | | | | | | | | | −0.3 | | | | ‡ | −0.3 |
| #122 | 20 | 18 | n.d. | 115 | n.d. | n.d. | | | | | | | | | | | | −0.2 | | | | ‡ | −0.2 |
| #123 | 20 | 18 | n.d. | 153 | n.d. | n.d. | | | | | | | | | | | | −0.3 | | | | ‡ | −0.3 |
| #124 | 20 | 18 | 41.0 | 320 | 99 | 77% | 23% | | | | | | | | | | | −0.1 | | | | ‡ | −0.1 |
| #125 | 20 | 18 | 18.0 | 203 | 90 | 84% | 16% | | | | −0.8 | −0.1 | | | | | | | | | | y | −0.5 |
| #126 | 20 | 18 | 17.0 | 119 | 92 | 80% | 2% | | | | | | −0.7 | | | | | | 0.0 0.0 | 0.0 | | ‡ | −0.3 |
| #127 | 20 | 18 | 35.0 | 291 | 96 | 95% | 2% | | | | 0.5 | | | | | | | | −0.5 | −0.5 | −0.5 | y | −0.3 |
| #128 | 20 | 19 | 64.0 | n.d. | n.d. | 93% | 99% | | | | | | | | | | | | | | | y | |
| #129 | 20 | 19 | 28.0 | n.d. | n.d. | 78% | 12% | | | | | | | | | | | | | | | y | |
| #130 | 21 | 19 | 33.0 | n.d. | n.d. | 89% | 5% | | | | | | | | | | | | | | | y | |
| #132

TABLE 7-continued

Expression levels and activities of atrial natriuretic peptide engrafted antibody constructs

| Compound | # aa N-term[1] | # aa C-term[2] | µg/ml rcs | µg/ml pcs | % purity pcs | activity rcs | stdev activity rcs | rel. activity rcs | rel. log-EC50 ics | rel. log-EC50 pcs 1 | rel. log-EC50 pcs 2 | rel. log-EC50 pcs 3 | rel. log-EC50 pcs 4 | rel. log-EC50 pcs 5 | rel. log-EC50 pcs 6 | rel. log-EC50 pcs 7 | rel. log-EC50 pcs 8 | rel. log-EC50 pcs 9 | rel. log-EC50* pcs | rel. log-EC50* pcs | rel. log-EC50* pcs | qualit. activity | average rel. log-EC50 |
|---|---|---|---|---|---|---|---|---|---|---|---|---|---|---|---|---|---|---|---|---|---|---|---|
| #158 | 17 | 16 | 10.0 | n.d. | n.d. | n.a. | | | | | | | | | | | | | | | | | ++ | |
| #159 | 17 | 16 | 4.9 | n.d. | n.d. | 55% | 22% | -0.6 | | | | | | | | | | | | | | ++ | |
| #160 | 17 | 16 | 2.8 | n.d. | n.d. | 34% | 22% | -1.3 | | | | | | | | | | | | | | y | |
| #161 | 17 | 16 | 4.9 | n.d. | n.d. | 34% | 9% | -0.7 | | | | | | | | | | | | | | ++ | |
| #162 | 17 | 16 | n.e | n.d. | n.d. | n.a. | | | | | | | | | | | | | | | | n.e | |
| #163 | 17 | 17 | n.d. | 84 | 85 | n.d. | | | | | | | | 0.6 | | | | | | | | ++ | 0.6 |
| #164 | 18 | 16 | 3.0 | n.d. | n.d. | 53% | 28% | -0.8 | -0.1 | | | | | | | | | | | | | ++ | -0.1 |
| #165 | 18 | 17 | 3.5 | n.d. | n.d. | 20% | 34% | | | | | | | | | | | | | | | y | |
| #166 | 18 | 17 | 4.1 | n.d. | n.d. | 44% | 13% | | | | | | | | | | | | | | | y | |
| #167 | 18 | 17 | n.e | 48 | n.d. | n.a. | | | | | | | | | | | | | | | | y | |
| #168 | 18 | 17 | n.e | n.d. | n.d. | 20% | 16% | -0.1 | | | | | | -0.1 | | | | | | | | n.e | -0.1 |
| #169 | 19 | 17 | 2.8 | 78 | 99 | n.a. | | | | | | | | | | | | | | | | ++ | |
| #170 | 19 | 18 | n.e | n.d. | n.d. | n.a. | | | | | | | | | | | | | | | | n.e | |
| #171 | 19 | 18 | n.e | n.d. | n.d. | n.a. | | | | | | | | | | | | | | | | n.e | |
| #172 | 19 | 18 | n.e | n.d. | n.d. | n.a. | | | | | | | | | | | | | | | | n.e | |
| #173 | 19 | 18 | n.e | 73 | n.d. | n.a. | | | | | | | | | | | | | | | | + | |
| #174 | 19 | 19 | n.d. | 105 | 82 | n.d. | | | | | | | | 1.3 | 0.1 | | | | | | | ++ | 1.3 |
| #175 | 19 | 19 | n.e | n.d. | n.d. | n.a. | | | | | | | | 0.3 | | | | | | | | n.e | 0.2 |
| #176 | 20 | 19 | 41.0 | 262 | 100 | 67% | 33% | | | | | | | | | | | | | | | - | |
| #177 | 2 | 2 | 16.0 | n.d. | n.d. | n.a. | | | | | n.a. | n.a. | | | | | | | | | | y | n.a. |
| #178 | 14 | 9 | 51.0 | n.d. | n.d. | n.a. | | | | | | | | | | | | | | | | - | |
| #179 | 16 | 10 | 18.0 | n.d. | n.d. | 37% | 6% | | | | | | | | | | | | | | | y | |
| #180 | 16 | 11 | 21.0 | n.d. | n.d. | 79% | 7% | | | | | | | | | | | | | | | y | |
| #181 | 16 | 13 | 2.5 | n.d. | n.d. | 73% | 19% | | | | | | | | | | | | | | | y | |
| #182 | 17 | 11 | 36.0 | n.d. | n.d. | 21% | 16% | | | | | | | | | | | | | | | y | |
| #183 | 18 | 12 | 10.0 | 100 | 100 | 50% | 3% | | | | | | | | | | | | | | | y | |
| #184 | 18 | 13 | 17.0 | 81 | 100 | 72% | 1% | | | | | | | | | | | | | | | y | |
| #185 | 18 | 13 | 20.0 | 77 | 96 | 45% | 22% | | | | | | | | | | | | | | | y | |
| #186 | 18 | 14 | 35.0 | 217 | 95 | 85% | 10% | | | | | | | | | | | | | | | y | |
| #187 | 19 | 13 | 15.0 | n.d. | n.d. | 77% | 8% | | -1.1 | | | | | | | | | | | | | +++ | -1.1 |
| #188 | 19 | 14 | 16.0 | 102 | 99 | 59% | 4% | | -1.0 | | | | | | | | | | | | | y | |
| #189 | 19 | 14 | 41.0 | n.d. | n.d. | 64% | 13% | | | | | | | | | | | | | | | y | |
| #190 | 19 | 14 | 29.0 | 248 | 99 | 94% | 8% | 0.1 | | | -0.6 | 0.2 | -0.3 | | | | | | | | | ++ | -0.2 |
| #191 | 19 | 15 | 70.0 | n.d. | n.d. | 90% | 14% | -1.0 | | | | | | | | | | | | | | +++ | -1.0 |
| #192 | 19 | 14 | 2.7 | n.d. | n.d. | 33% | 37% | | | | | | | | | | | | | | | y | |
| #193 | 20 | 14 | 32.0 | 98 | 97 | 75% | 3% | | | | | | | | | | | | | | | y | |
| #194 | 20 | 14 | 20.0 | 43 | 97 | 34% | 12% | | | | | | | | | | | | | | | ++ | |
| #195 | 20 | 14 | n.e | n.d. | n.d. | n.a. | | | | | | | | | | | | | | | | n.e | |
| #196 | 20 | 15 | 5.5 | 18 | n.d. | 54% | 20% | | | | | | | | | | | | | | | y | |
| #197 | 20 | 15 | 14.0 | 57 | 100 | 52% | 21% | | | | | | | | | | | | | | | y | |
| #198 | 20 | 15 | 7.3 | n.d. | n.d. | 29% | 12% | | | | | | | | | | | | | | | y | |
| #199 | 21 | 15 | 33.0 | 97 | n.d. | 78% | 7% | | | | | | | | | | | | | | | y | |
| #200 | 21 | 15 | 51.0 | 134 | 97 | 87% | 6% | -0.3 | | | 0.1 | -0.3 | | | | | | | | | | ++ | -0.1 |
| #201 | 21 | 15 | 16.0 | 29 | n.d. | 58% | 3% | | | | | | | | | | | | | | | y | |
| #202 | 21 | 15 | n.d. | n.d. | n.d. | n.d. | | | | | | | | | | | | | | | | | |
| #203 | 21 | 16 | 3.1 | 17 | n.d. | 33% | 2% | | | | | | | | | | | | | | | y | |

TABLE 7-continued

Expression levels and activities of atrial natriuretic peptide engrafted antibody constructs

| Compound | # aa N-term[1] | # aa C-term[2] | µg/ml rcs | µg/ml pcs | % purity pcs | activity rcs | stdev activity rcs | rel. activity res | rel. log-EC50 rcs | rel. log-EC50 pcs 1 | rel. log-EC50 pcs 2 | rel. log-EC50 pcs 3 | rel. log-EC50 pcs 4 | rel. log-EC50 pcs 5 | rel. log-EC50 pcs 6 | rel. log-EC50 pcs 7 | rel. log-EC50 pcs 8

No conclusive data for compounds #104 and #135 were obtained. 12 compounds (#54, #61, #89, #139, #162, #168, #170, #171, #172, #173, #176, #196) showed very low expression levels (≤1 µg/ml in rcs) and consequently no activity; activity of #61 was shown after compound preparation (pcs). 7 compounds (#7, #24, #70, #83, #90, #154, #167) showed in most cases low activity as rcs, although their expression level was very low; the activity of #24 and #90 was confirmed by compound preparation (pcs). No activity was observed in rcs of compounds #18, #26, #29, #92, #96, #101, #104, #158, #164, #179; however, the activity of compounds #18, #92, #158, #164 was shown using higher concentrations (rel. activity rcs); the lack of activity of #26 was thereby confirmed.

TABLE 8

| Compound | TPP | # aa N-term[1] | # aa C-term[2] | µg/ml pcs | % purity pcs | qualit. activity on hNPRA | qualit. activity of corresp. ANP cpd.[3] |
|---|---|---|---|---|---|---|---|
| B1 | TPP-9902 | 20 | 18 | 304 | 96 | ++ | ++ |
| B2 | TPP-11153 | 22 | 19 | 202 | 99 | + | |
| B3 | TPP-11154 | 20 | 18 | 205 | 100 | − | ++ |
| B4 | TPP-11155 | 17 | 17 | 226 | 97 | − | |
| B5 | TPP-11156 | 18 | 13 | 115 | 75 | ++ | +++ |
| B6 | TPP-11157 | 18 | 13 | 125 | 93 | − | +++ |
| B7 | TPP-18029 | 23 | 14 | 265 | 99 | + | ++ |
| B8 | TPP-18031 | 3 | 3 | 260 | 99 | − | − |
| B9 | TPP-18032 | 7 | 7 | 262 | 99 | − | − |
| B10 | TPP-18033 | 19 | 14 | 310 | 98 | + | ++ |
| B11 | TPP-18028 | 20 | 15 | 74 | 99 | + | +++ |
| B12 | TPP-18034 | 20 | 18 | 315 | 97 | ++ | ++ |
| B13 | TPP-18030 | 19 | 14 | 304 | 100 | + | ++ |
| #209 | TPP-5657 | na | na | 402 | 100 | − | − |

[1]The number of amino acid residues present between the respective N-terminal reference amino acid residue and the first amino acid of the inserted natriuretic peptide;
[2]The number of amino acid residues present between the last amino acid of the inserted natriuretic peptide and the respective C-terminal reference amino acid residue
[3]Corresponding ANP Cpd. refers to an ANP engrafted antibody construct with the same integration locus and comprising the same N-terminal and C-terminal sequence Purified compound samples were tested as described in Example 3 in quadruplets in dilution series on stable hNPRA-CHO k1 cells. The activities of BNP engrafted antibody constructs are graphically depicted in FIG. 11.

TPP-11156, TPP-9902 and TPP-11153 showed significant activity on hNPRA cells in contrast to TPP-1154, TPP-11155, and TPP-11157. Opposed results were observed on rNPRA with EC50<20 nM for TPP-1154, TPP-11155, and TPP-11157, and EC50>1 µM for TPP-9902, TPP-11153, and TPP-11156 (see Example 3). This can be explained by the presence of a human BNP sequence in TPP-11156, TPP-9902 and TPP-11153, whereas TPP-1154, TPP-11155, and TPP-11157 comprise a rat BNP sequence (see Table 5). In contrast to all other human BNP engrafted antibody constructs, TPP-18031 and TPP-18032 with low numbers of additional amino acids N- and C-terminal to BNP showed no activity on hNPRA.

Example 6: Specific Linker Sequences are Particularly Advantageous for Achieving Good Homogeneity and Expression Levels The purity of purified compound samples (Example 5, Table 7, column "% purity pcs") was determined by capillary Gel Electrophoresis according to manufacturer's instructions (LabChip GX, Caliper Life Sciences) under reduced conditions. The purity in % was calculated as sum of peak areas corresponding to the intact light and heavy chain relative to the sum of all peaks observed.

Ntls sequences comprising a GS linker sequence, a PN linker sequence or the sequence of SEQ ID NOs 2, 4, 9, 11, 13 or 15 and Ctls sequences comprising a GS linker sequence, a PN linker sequence or the sequence of SEQ ID NOs 3, 5, 12, 14, 15 or 20 have proven particularly useful as they not only achieve high natriuretic peptide activities (provided that at least 12 amino acid residues are present between the respective N-terminal reference amino acid residue and the first amino acid of the inserted natriuretic peptide) but also good expression levels (in contrast to e.g., sequences used in compounds #186, #195 and #202) and (in contrast to e.g., sequences used in compounds 6 and 7) a low degree of inhomogeneity (see Table 9). With linker sequences comprising a GS linker sequence as well as linker sequences comprising a PN linker sequence very good purities of 98% in average were observed. Similarly good values were observed for compounds with linkers comprising sequences of SEQ ID NOs 2, 3, 4, 5, 9, 11, 12, 13, 14, 15 and 20. Notably, the Ntls having the sequence of SEQ ID NO 9 resulted only in combination with the Ctls having the sequence of SEQ ID NO 20 in compounds with very good purity; compounds with a combination of the Ntls having the sequence of SEQ ID NO 11 and the Ctls having the sequence of SEQ ID NO 12 showed only very good purity when SEQ ID NO 11 was flanked by Asp (D) on the N-terminal side and not by Thr (T) or Val (V) and when the SEQ ID NO 12 VNHLRSEKLT was flanked by Gly (G) on the C-terminal side but not by Tyr (Y) or Phe (F) as in compounds #126 and #135.

TABLE 9

Ntls and Ctls effects on antibody purity (excerpt of Table 7)

| Cpd | TPP | Insertion Site | SEQ ID NO comprised in Ntls | SEQ ID NO comprised in Ctls | # aa N-term[1] | # aa C-term[2] |
|---|---|---|---|---|---|---|
| 2 | TPP-13056 | CDRH1 | GS | GS | 9 | 5 |
| 3 | TPP-13055 | CDRH1 | GS | GS | 12 | 8 |
| 4 | TPP-13054 | CDRH1 | GS | GS | 15 | 10 |
| 5 | TPP-12545 | CDRH1 | GS | GS | 18 | 10 |
| 9 | TPP-10294 | CDRH1 | GS | GS | 23 | 14 |

TABLE 9-continued

Ntls and Ctls effects on antibody purity (excerpt of Table 7)

| | | | | | | |
|---|---|---|---|---|---|---|
| 10 | TPP-12547 | CDRH1 | GS | GS | 23 | 14 |
| 91 | TPP-10282 | CDRH2 | GS | GS | 20 | 15 |
| 99 | TPP-10281 | CDRH3 | GS | GS | 10 | 3 |
| 100 | TPP-10280 | CDRH3 | GS | GS | 10 | 8 |
| 169 | TPP-10361 | CDRL2 | GS | GS | 19 | 17 |
| 184 | TPP-10776 | CDRL3 | GS | GS | 18 | 13 |
| 185 | TPP-10777 | CDRL3 | GS | GS | 18 | 13 |
| 189 | TPP-10356 | CDRL3 | GS | GS | 19 | 14 |
| 198 | TPP-10358 | CDRL3 | GS | GS | 20 | 15 |
| 18 | TPP-10767 | CDRH2 | PN | PN | 13 | 12 |
| 55 | TPP-10765 | CDRH2 | PN | PN | 17 | 14 |
| 93 | TPP-10286 | CDRH2 | PN | PN | 20 | 15 |
| 94 | TPP-10283 | CDRH2 | PN | PN | 20 | 15 |
| 111 | TPP-10289 | CDRH3 | PN | PN | 19 | 17 |
| 125 | TPP-10290 | CDRH3 | PN | PN | 20 | 18 |
| 191 | TPP-10355 | CDRL3 | PN | PN | 19 | 14 |
| 63 | TPP-10844 | CDRH2 | 2 | 3 | 18 | 13 |
| 80 | TPP-10845 | CDRH2 | 2 | 3 | 19 | 14 |
| 128 | TPP-10288 | CDRH3 | 2 | 3 | 20 | 18 |
| 61 | TPP-10847 | CDRH2 | 4 | 5 | 18 | 13 |
| 76 | TPP-10848 | CDRH2 | 4 | 5 | 19 | 14 |
| 156 | TPP-10571 | CDRL2 | 15 | 15 | 17 | 16 |
| 42 | TPP-13060 | CDRH2 | 9 | 20 | 17 | 11 |
| 43 | TPP-13061 | CDRH2 | 9 | 20 | 17 | 11 |
| 44 | TPP-13062 | CDRH2 | 9 | 20 | 17 | 11 |
| 46 | TPP-13064 | CDRH2 | 9 | 10 | 17 | 11 |

TABLE 9-continued

Ntls and Ctls effects on antibody purity (excerpt of Table 7)

| | | | | | | |
|---|---|---|---|---|---|---|
| 45 | TPP-13063 | CDRH2 | 9 | 10 | 17 | 11 |
| 40 | TPP-13058 | CDRH2 | 9 | 10 | 17 | 11 |
| 47 | TPP-13065 | CDRH2 | 9 | 10 | 17 | 11 |
| 41 | TPP-13059 | CDRH2 | 9 | 10 | 17 | 11 |
| 201 | TPP-10439 | CDRL3 | 11 | 12 | 21 | 15 |
| 194 | TPP-10440 | CDRL3 | 11 | 12 | 20 | 14 |
| 187 | TPP-10782 | CDRL3 | 11 | 12 | 19 | 13 |
| 126 | TPP-10445 | CDRH3 | 11 | 12 | 20 | 18 |
| 135 | TPP-10444 | CDRH3 | 11 | 12 | 22 | 20 |
| 50 | TPP-10452 | CDRH2 | 13 | 14 | 17 | 12 |
| 74 | TPP-10451 | CDRH2 | 13 | 14 | 19 | 14 |
| 26 | TPP-10772 | CDRH2 | 13 | 14 | 16 | 11 |
| 6 | TPP-10454 | CDRH1 | | | 19 | 17 |
| 7 | TPP-10453 | CDRH1 | | | 19 | 17 |
| 186 | TPP-10784 | CDRL3 | | | 18 | 14 |
| 195 | TPP-10442 | CDRL3 | | | 20 | 14 |
| 202 | TPP-10441 | CDRL3 | | | 21 | 15 |

| Cpd | N-terminal seequence[3] | C-terminal sequence[4] | µg/ml pcs | % purity pcs | qualit. actvity |
|---|---|---|---|---|---|
| 2 | SGFTFGSGSG (SEQ ID NO: 93) | GSGSGM (SEQ ID NO: 94) | 179 | 96 | - |
| 3 | SGFTFGSGSGSGS (SEQ ID NO: 95) | SGSGSGSGM (SEQ ID NO: 96) | 196 | 97 | ++ |
| 4 | SGFTFGSGSGSGGSGG (SEQ ID NO: 97) | GGSGGSGSGSG (SEQ ID NO: 39) | 214 | 96 | ++ |
| 5 | SGFTFGSGSGSGSGGGSGG (SEQ ID NO: 99) | GSGSGGSGSGM (SEQ ID NO: 100) | 229 | 93 | ++ |
| 9 | SGFTFGSGSGSGSGSGSPDGGSGG (SEQ ID NO: 105) | GSYGSGSGSGSGSGM (SEQ ID NO: 106) | 226 | 97 | ++ |
| 10 | SGFTFGSGSGSGSGSGSPDGGSGG (SEQ ID NO: 105) | GSYGSGSGSGSGSGM (SEQ ID NO: 106) | 265 | 96 | ++ |
| 91 | ISGSGSGSGSGSGSPDGGSGG (SEQ ID NO: 231) | GSYGSGSGSGSGSGST (SEQ ID NO: 221) | 275 | 99 | ++ |

TABLE 9-continued

Ntls and Ctls effects on antibody purity (excerpt of Table 7)

| | | | | | |
|---|---|---|---|---|---|
| 99 | CAKSPDGGSGG (SEQ ID NO: 244) | GSYG (SEQ ID NO: 245) | 257 | 100 | - |
| 100 | CAKSPDGGSGG (SEQ ID NO: 244) | GSYQHWGQG (SEQ ID NO: 246) | 188 | 99 | - |
| 169 | YGSGSGSGSGSPDGGSGG (SEQ ID NO: 364) | GSYGSGGSGSGSGNRPSG (SEQ ID NO: 365) | 78 | 99 | ++ |
| 184 | CGSGSGSGSGPDGGSGG (SEQ ID NO: 390) | GSGSGSGSGSGSGF (SEQ ID NO: 385) | 100 | 100 | y |
| 185 | CGSGSGSGSGSDGGSGG (SEQ ID NO: 391) | GSGSGSGSGSGSGF (SEQ ID NO: 385) | 81 | 100 | y |
| 189 | CGSGSGSGSGSGSPDGGSGG (SEQ ID NO: 398) | GSYGSGSGSGSGSGF (SEQ ID NO: 399) | 102 | 99 | y |
| 198 | CGGSGSGSGSGSGSPDGGSGG (SEQ ID NO: 412) | GSYGSGSGSGSGSGGF (SEQ ID NO: 413) | 57 | 100 | y |
| 18 | ISGPNPNKNPNPGG (SEQ ID NO: 121) | GSNENPNPNPGST (SEQ ID NO: 122) | 290 | 98 | + |
| 55 | ISGPNPNKNPNPNPGSGG (SEQ ID NO: 170) | GSNPNENPNPNPGST (SEQ ID NO: 134) | 271 | 95 | ++ |
| 93 | ISGPNPNKNPNPNSPDGGSGG (SEQ ID NO: 234) | GSYNPNENPNPNPGST (SEQ ID NO: 235) | 286 | 98 | +++ |
| 94 | ISGPNPNPNPNPNSPDGGSGG (SEQ ID NO: 236) | GSYNPNPNPNPNPGST (SEQ ID NO: 237) | 318 | 98 | +++ |
| 111 | CAKVHPNPNPNPNPDGGSGG (SEQ ID NO: 265) | GSNPNPNPNPHVDVWGQG (SEQ ID NO: 266) | 296 | 98 | ++ |
| 125 | CAKVHPNPNPNPNSPDGGSGG (SEQ ID NO: 286) | GSYNPNPNPNPHVDVWGQG (SEQ ID NO: 287) | 320 | 99 | ++ |
| 191 | CAAWNPNPNPNPNPNGGSGG (SEQ ID NO: 402) | GSNPNPNPNPNPNVF (SEQ ID NO: 403) | 248 | 99 | ++ |
| 63 | ISGTYISNVNHKPDGGSGG (SEQ ID NO: 185) | GSNTKVDKKVEGST (SEQ ID NO: 186) | 239 | 96 | ++ |
| 80 | ISGSTYISNVNHKPDGGSGG (SEQ ID NO: 211) | GSNTKVDKKVEGGST (SEQ ID NO: 212) | 214 | 95 | ++ |
| 128 | CAKTQTYISNVNHKPDGGSGG (SEQ ID NO: 291) | GSNTKVDKKAEYFQHWGQG (SEQ ID NO: 292) | 291 | 96 | y |
| 61 | ISGTSASLAITGPDGGSGG (SEQ ID NO: 181) | GSDRFSGSKSGGST (SEQ ID NO: 182) | 334 | 97 | ++ |
| 76 | ISGSTSASLAITGPDGGSGG (SEQ ID NO: 204) | GSDRFSGSKSGGGST (SEQ ID NO: 205) | 299 | 97 | ++ |
| 156 | YGVPKEKEKEKVSTAVGG (SEQ ID NO: 340) | GSAPLEVPKEKEKEKVG (SEQ ID NO: 341) | 64 | 98 | ++ |
| 42 | ISVVVTSHQSPTPGGSGG (SEQ ID NO: 154) | GGSTPLKSLAST (SEQ ID NO: 155) | 112 | 97 | ++ |
| 43 | ISVVVTSHQAPGEGGSGG (SEQ ID NO: 145) | GGSTPLKSLAST (SEQ ID NO: 155) | 141 | 96 | ++ |
| 44 | ISVVVTSHQAPGEGGSGG (SEQ ID NO: 145) | GSTPKLKSLAST (SEQ ID NO: 156) | 166 | 93 | +++ |
| 46 | ISVVVTSHPTPGEGGSGG (SEQ ID NO: 157) | GEKKKLKSLAST (SEQ ID NO: 146) | 166 | 92 | ++ |
| 45 | ISVVVTSHQSPTPGGSGG (SEQ ID NO: 154) | GEKKKLKSLAST (SEQ ID NO: 146) | 135 | 90 | ++ |
| 40 | ISVVVTSHQAPGSGGSGG (SEQ ID NO: 152) | GEKKKLKSLAST (SEQ ID NO: 146) | 154 | 85 | ++ |

TABLE 9-continued

Ntls and Ctls effects on antibody purity (excerpt of Table 7)

| | | | | | |
|---|---|---|---|---|---|
| 47 | ISVVVTSHQAPSPGSTGG (SEQ ID NO: 158) | GEKKKLKSLAST (SEQ ID NO: 146) | 123 | 83 | ++ |
| 41 | ISVVVTSHQAPTSGGSGG (SEQ ID NO: 153) | GEKKKLKSLAST (SEQ ID NO: 146) | 106 | 79 | n.d. |
| 201 | CQSYDQVKLELGHRAPDGGSGG (SEQ ID NO: 417) | GSVNHLRSEKLTGVVF (SEQ ID NO: 405) | 134 | 97 | ++ |
| 194 | CQSYDQVKLELGHRPDGGSGG (SEQ ID NO: 407) | GSNHLRSEKLTGVVF (SEQ ID NO: 408) | 98 | 97 | y |
| 187 | CQSYDKLELGHRAPDGGSGG (SEQ ID NO: 394) | GSVNHLRSEKGVVF (SEQ ID NO: 395) | 217 | 95 | +++ |
| 126 | CAKLTQVKLELGHRPDGGSGG (SEQ ID NO: 288) | GSNHLRSEKLTYFQHWGQG (SEQ ID NO: 289) | 203 | 90 | y |
| 135 | CAKLTAVQVKLELGHRPDGGSGG (SEQ ID NO: 303) | GSNHLRSEKLTFNYFQHWGQG (SEQ ID NO: 299) | 158 | 88 | ? |
| 50 | ISGSAVVNVRAPDGGSGG (SEQ ID NO: 160) | GSKGDKIAIGGST (SEQ ID NO: 161) | 87 | 97 | ++ |
| 74 | ISGSSGAVVNVRAPDGGSGG (SEQ ID NO: 201) | GSKGDKIAIWTTGST (SEQ ID NO: 202) | 142 | 97 | ++ |
| 26 | ISGSAVVNVRADGGSGG (SEQ ID NO: 135) | GSGDKIAIGGST (SEQ ID NO: 136) | 181 | 98 | - |
| 6 | SPAVVYIEILDRHPDGGSGG (SEQ ID NO: 101) | GSGREVPISNGSGFVVAM (SEQ ID NO: 102) | 150 | 76 | y |
| 7 | SGAVVYIEILDRHPDGGSGG (SEQ ID NO: 103) | GSGREVPISNGSGFVVAM (SEQ ID NO: 102) | 117 | 70 | y |
| 186 | CQSYDGFILPIEVYGGSGG (SEQ ID NO: 392) | GSKVRFDYDLFGVVF (SEQ ID NO: 393) | 77 | 96 | y |
| 195 | CQSYDGFILPIEVYPDGGSGG (SEQ ID NO: 409) | GSKVRFDYDLFGVVF (SEQ ID NO: 393) | 43 | 97 | y |
| 202 | CQSYDGFILPIEVYFPDGGSGG (SEQ ID NO: 418) | GSRKVRFDYDLFGVVF (SEQ ID NO: 419) | 29 | n.d. | y |

[1]The number of amino acid residues present between the respective N-terminal reference amino acid residue and the first amino acid of the inserted natriuretic peptide;
[2]The number of amino acid residues present between the last amino acid of the inserted natriuretic peptide and the respective C-terminal reference amino acid residue
[3]The N-terminal sequence corresponds to the nearest neighboring reference aa N-terminal from the inserted natriuretic peptide plus the amino acid stretch present between said reference aa and the first amino acid residue of the inserted natriuretic peptide
[4]The C-terminal sequence corresponds the amino acid stretch present between the last amino acid residue of the inserted natriuretic peptide and the nearest neighboring reference aa C-terminal from the inserted natriuretic peptide plus and said reference aa Example 7: IgG1, IgG2 and IgG4 Isotypes Provide Equally Suitable Antibody Scaffolds Compounds 9, 33, 65, 91, 127 and 191 (human IgG1 TPP-10294, TPP-10277, TPP-10279, TPP-10282, TPP-10269 and TPP-10355, respectively) were generated as different IgG isotypes. Purified compound samples were tested as described in Example 3 in quadruplets in dilution series on stable hNPRA-CHO k1 cells. The activities of ANP engrafted human IgG2 and IgG4 isotype constructs (e.g. compound 9 IgG4 TPP-10992) are similar to their corresponding IgG1 isotype as graphically depicted in FIG. 12.

Example 8: Human and Non-Human IgGs Provide Equally Suitable Antibody Scaffolds

Compound 9 (human IgG1 TPP-10294 and IgG4 TPP-10992) and compound 117 (human IgG1 TPP-5665) were generated as non-human IgG isotypes. Purified compound samples were tested as described in Example 3 in quadruplets in dilution series on stable hNPRA-CHO k1 cells. ANP engrafted rat and mouse isotype constructs, e.g. compound 9 rat IgG1 TPP-13992, showed activities similar to their corresponding human IgG isotype (FIG. 13).

Example 9: Human IgGs Comprising Varying Germline Sequences Provide Equally Suitable Antibody Scaffolds 22 additional ANP engrafted IgG4 antibodies (compounds A to S) were constructed. In each case ANP was incorporated within CDRH1. The heavy chains of these constructs comprise varying HV and CDRH3 sequences and were paired with varying lambda or kappa light chains. The structure of compounds A to S is summarized in Tables 10 and 11.

TABLE 10

Design of ANP engrafted antibody constructs A to S

| Cmpd. | Insertion Site | # aa N-term[1] | #aa C-term[2] | N-terminal sequence[3] | C-terminal sequence[4] |
|---|---|---|---|---|---|
| A-P | CDRH1 | 23 | 14 | SGFTFGSGSGSGSGSPDGGSGG (SEQ ID NO: 105) | GSYGSGSGSGSGSM (SEQ ID NO: 106) |
| Q-S | CDRH1 | 23 | 14 | SGYSFGSGSGSGSGSPDGGSGG (SEQ ID NO: 449) | GSYGSGSGSGSGSI (SEQ ID NO: 450) |

[1]The number of amino acid residues present between the respective N-terminal reference amino acid residue and the first amino acid of the inserted natriuretic peptide;
[2]The number of amino acid residues present between the last amino acid of the inserted natriuretic peptide and the respective C-terminal reference amino acid residue
[3]The N-terminal sequence corresponds to the nearest neighboring reference aa N-terminal from the inserted natriuretic peptide plus the amino acid stretch present between said reference aa and the first amino acid residue of the inserted natriuretic peptide
[4]The C-terminal sequence corresponds the amino acid stretch present between the last amino acid residue of the inserted natriuretic peptide and the nearest neighboring reference aa C-terminal from the inserted natriuretic peptide plus and said reference aa

TABLE 11

Design of ANP engrafted antibody constructs A to S

| Cmpd | TPP | HV | CDRH3 | LV/KV | Purity |
|---|---|---|---|---|---|
| 9 | TPP-10992 | HV3-23 | KLTGAEYFQHW (SEQ ID NO: 451) | LV1-40 | 99 |
| A | TPP-13944 | HV3-23 | KLTGAEYFQHW (SEQ ID NO: 452) | LV2-14 | 98 |
| B | TPP-13945 | HV3-23 | KLTGAEYFQHW (SEQ ID NO: 453) | LV3-21 | 93 |
| C | TPP-13941 | HV3-23 | KDYGDYAEYFQHW (SEQ ID NO: 454) | LV1-40 | 100 |
| D | TPP-13956 | HV3-23 | KLTGAEYFQHW (SEQ ID NO: 455) | KV1-5 | 99 |
| E | TPP-13955 | HV3-23 | KLTGAEYFQHW (SEQ ID NO: 456) | KV3-20 | 99 |
| F | TPP-13940 | HV3-23 | KVLRFLEWLLYAEYFQHW (SEQ ID NO: 457) | LV1-40 | 98 |
| G | TPP-13939 | HV3-23 | KVQLERAEYFQHW (SEQ ID NO: 458) | LV1-40 | 100 |
| H | TPP-13943 | HV3-23 | KYNRNHAEYFQHW (SEQ ID NO: 459) | LV1-40 | 54 |
| I | TPP-13942 | HV3-23 | KYNWNDAEYFQHW (SEQ ID NO: 460) | LV1-40 | 99 |
| J | TPP-14684 | HV3-23 | RGATFALDW (SEQ ID NO: 461) | KV3-20 | 97 |
| K | TPP-13958 | HV3-23 | RGRLPDVW (SEQ ID NO: 462) | KV1-5 | 99 |
| L | TPP-13957 | HV3-23 | RGRLPDVW (SEQ ID NO: 462) | KV3-20 | 97 |
| M | TPP-13948 | HV3-23 | RGRLPDVW (SEQ ID NO: 462) | LV1-40 | 98 |
| N | TPP-14289 | HV3-23 | RGRLPDVW (SEQ ID NO: 462) | LV1-47 | |
| O | TPP-13946 | HV3-23 | RGRLPDVW (SEQ ID NO: 462) | LV2-14 | 97 |
| P | TPP-13947 | HV3-23 | RGRLPDVW (SEQ ID NO: 462) | LV3-21 | 96 |

TABLE 11-continued

Design of ANP engrafted antibody constructs A to S

| Cmpd | TPP | HV | CDRH3 | LV/KV | Purity |
|------|-----|----|-------|-------|--------|
| Q | TPP-13952 | HV5-51 | RGRLPDVW (SEQ ID NO: 462) | LV2-14 | 99 |
| R | TPP-13953 | HV5-51 | RGRLPDVW (SEQ ID NO: 462) | LV3-21 | 98 |
| S | TPP-13962 | HV5-51 | RGRLPDVW (SEQ ID NO: 462) | KV1-5 | 99 |

Purified compound samples of IgG scaffold constructs A to S comprising varying germline sequences were tested as described in Example 3 in quadruplets in dilution series on stable hNPRA-CHO k1 cells. Exemplary activity data are graphically depicted in FIG. 14.

Example 10: CNP Engrafted IgG Protects Against Induced Endothelial Barrier Permeability Endothelial monolayer permeability was assayed by real-time impedance measurement with an xCELLigence RTCA system utilizing microtiter well plates covered with microelectrodes (E-Plates). Relative impedance changes are expressed as unitless Cell Index (CI) values.

Primary Human Pulmonary Artery Endothelial Cells (HPAECs) were seeded at low passages in collagen pre-coated E-Plates. After tight monolayer and cell barrier formation with constant CI values, HPAECs were pre-treated with the indicated concentrations of compound TPP-12899 or the respective negative control antibody construct TPP-5657, followed by compromising the EC barrier with the disruptive agonists LPS (200 ng/ml), IL-1I3 (0.5 ng/ml), or thrombin (2 U/ml). CI were recorded every 10 min to monitor effects on cell growth and monolayer permeability. All cell indices were normalized at the last recording point before test substance application (=normalized CI).

The experiments were performed with n=4 with 3 technical triplicates each. Results were expressed as mean±SEM. Data were statistically analyzed using one-way ANOVA followed by Sidak's multiple post-test; p-values<0.05 were considered as significant.

FIG. 15 graphically depicts the effects on endothelial monolayer permeability expressed as Cell Index values. As shown in FIG. 15, pre-treatment of human endothelial monolayer cultures with TPP-12899 protected against induced endothelial barrier permeability in a dose-dependent manner. This was independent of the applied barrier disruptive agent; both, with fast and strong acting thrombin as well as with long-lasting pro-inflammatory stimuli LPS and IL-1I3 significant effects were observed. The respective negative control showed no effect.

Example 11: Long Term Effects of ANP Engrafted IgG in a Chronic Heart Failure Rat Model (TGR(mRenR2)27

The TGR(mRenR2)27 rat model shows hypertension and endothelial dysfunction, as well as end-organ damage. Male renin-transgenic rats (Ganten D., Nature. 1990; 344(6266): 541-4) at the age of 8 weeks were used. The nonselective inhibitor of nitric oxide synthetases L-NAME (Nω-Nitro-L-arginine methyl ester) was chronically administered via the drinking water (20 mg/l) in all study groups to induce endothelial dysfunction. TPP-13992, the rat IgG1 counterpart of TPP-10294 used in Example 8 and TPP-10155, a rat IgG1 isotype control antibody were administered once weekly intraperitoneally. Body weight and survival were assessed. The placebo group was treated with vehicle (PBS) and the healthy control group was treated with captopril-food from weaning on. Food and water were given ad libitum. Daily observation of the behavior and general health status of the animals was performed. At the end of the experiment (week 14), the rats were anaesthetized. The rats were then exsanguinated and the heart was removed from the thoracic cavity for analysis. Urine was collected at the end of the study to determine different urine parameters, e.g. urinary protein creatinine ratio. FIG. 16 graphically depicts the therapeutic effects of TPP-13992 on survival, body weight gain, urinary protein/creatinine ratio and left atrial weight.

Example 12: Hemodynamic Effects of ANP Engrafted IgG in Healthy Beagle Dogs

The effects of TPP-10992 on cardiovascular and ECG parameters after single subcutaneous administration were assessed in a primary pharmacodynamic study in conscious telemetered beagle dogs.

Telemetry devices (DSI™, USA) were surgically implanted to measure blood pressure as well as heart rate, followed by a recovery period to allow wound closure. On the day of the study, telemetry sensors were activated for continuous hemodynamic measurements. The transmitted signals were collected by telemetry receivers located in the animal facility. All collected data were processed by a data acquisition program and averaged over a predefined period of 12 h. As vehicle for TPP-10992 NaCl (0.9%) was used and doses of 0.1 mg/kg, 0.3 mg/kg and 1.0 mg/kg bodyweight were applied via subcutaneous injection.

The results are graphically depicted in FIG. 17. In healthy dogs, TPP-10992 showed a dose-dependent and long-lasting (>5d) reduction in blood pressure which was significant at 1.0 mg/kg s.c. (compared to placebo). No effects on heart rate were observable.

The invention claimed is:

1. An antibody or a fragment thereof comprising a heterologous amino acid sequence incorporated within a CDR region of said antibody or fragment thereof,
   wherein said heterologous amino acid sequence comprises an N-terminal linker sequence (Ntls), a Brain Natriuretic Peptide (BNP), and a C-terminal linker sequence (Ctls),
   wherein the Ntls comprises at least 12 amino acid residues and the Ctls comprises at least 9 amino acid residues, wherein:
   (i) in case of incorporation of said heterologous amino acid sequence within CDRH1, the Ntls is present between amino acid residue HC res25 according to Kabat and the first amino acid residue of said BNP, and the Ctls is present between the last amino acid residue of said BNP and amino acid residue HC res35a according to Kabat, or
   (ii) in case of incorporation of said heterologous amino acid sequence within CDRH2, the Ntls is present between amino acid residue HC res51 according to Kabat and the first amino acid residue of said BNP, and the Ctls is present between amino acid residue HC res57 according to Kabat, or
   (iii) in case of incorporation of said heterologous amino acid sequence within CDRH3, the Ntls is present between amino acid residue HC res92 according to Kabat and the first amino acid residue of said BNP, and the Ctls is present between amino acid residue HC res106 according to Kabat, or
   (iv) in case of incorporation of said heterologous amino acid sequence within CDRL1, the Ntls is present between amino acid residue LC res26 according to Kabat, and the Ctls is present between amino acid residue LC res 32 according to Kabat, or
   (v) in case of incorporation of said heterologous amino acid sequence within CDRL2, the Ntls is present between amino acid residue LC res49 according to Kabat and the first amino acid residue of said BNP, and the Ctls is present between amino acid residue LC res57 according to Kabat, or
   (vi) in case of incorporation of said heterologous amino acid sequence within CDRL3, the Ntls is present between amino acid residue LC res88 according to Kabat and the first amino acid residue of said BNP, and the Ctls is present between amino acid residue LC res98 according to Kabat, and
   wherein:
   (i) said Ntls and said Ctls each comprise a GS linker sequence, or
   (ii) said Ntls and said Ctls each comprise a PN linker sequence, or
   (iii) said Ntls comprises the sequence of any one of SEQ ID NOs: 1, 2, or 4 and said Ctls comprises the sequence of any one of SEQ ID NOs: 1, 3, or 5, or
   (iv) said Ntls and said Ctls each comprise the sequence of SEQ ID NO: 6, or
   (v) said Ntls comprises the sequence of SEQ ID NO: 7 and said Ctls comprises the sequence of SEQ ID NO: 8, or
   (vi) said Ntls comprises the sequence of SEQ ID NO: 9 and said Ctls comprises the sequence of SEQ ID NO: 10, or
   (vii) said Ntls comprises the sequence of SEQ ID NO: 11 and said Ctls comprises the sequence of SEQ ID NO: 12, or
   (viii) said Ntls comprises the sequence of SEQ ID NO: 13 and said Ctls comprises the sequence of SEQ ID NO: 14, or
   (ix) said Ntls and said Ctls each comprise the sequence of SEQ ID NO: 15; or
   (x) said Ntls comprises the sequence of SEQ ID NO: 9 and said Ctls comprises the sequence of SEQ ID NO: 20, or
   (xi) said Ntls comprises the sequence of SEQ ID NO: 21 and said Ctls comprises the sequence of SEQ ID NO: 22, and
   wherein said antibody or fragment thereof is of the class IgG.

2. The antibody or fragment thereof according to claim 1, wherein said BNP is a human BNP comprising the sequence of SEQ ID NO: 24 or a BNP comprising at least 95% sequence identity therewith.

3. The antibody or fragment thereof according to claim 1, wherein said Ntls further comprises an anchoring element A1 at its C terminal end and/or said Ctls further comprises an anchoring element A2 at its N terminal end, and wherein at least 60% of the amino acid residues of A1 and/or A2, when present, are selected from glycine and serine residues.

4. The antibody or fragment thereof according to claim 1, wherein: the amino acid stretch present between
   (i) amino acid residue HC res25 according to Kabat and the first amino acid residue of the BNP in case of an incorporation of said heterologous amino acid sequence within CDRH1; or
   (ii) amino acid residue HC res51 according to Kabat and the first amino acid residue of the BNP in case of an incorporation of said heterologous amino acid sequence within CDRH2; or
   (iii) amino acid residue HC res92 according to Kabat and the first amino acid residue of the BNP in case of an incorporation of said heterologous amino acid sequence within CDRH3; or
   (iv) amino acid residue LC res26 according to Kabat and the first amino acid residue of the BNP in case of an incorporation of said heterologous amino acid sequence within CDRL1; or
   (v) amino acid residue LC res49 according to Kabat and the first amino acid residue of the BNP in case of an incorporation of said heterologous amino acid sequence within CDRL2; or
   (vi) amino acid residue LC res88 according to Kabat and the first amino acid residue of the BNP in case of an incorporation of said heterologous amino acid sequence within CDRL3 comprises the sequence of any one of SEQ ID NOs: 26 to 38; and
   wherein the amino acid stretch present between the last amino acid residue of said BNP and
   (i) amino acid residue HC res35a according to Kabat in case of an incorporation of said heterologous amino acid sequence within CDRH1; or
   (ii) amino acid residue HC res57 according to Kabat in case of an incorporation of said heterologous amino acid sequence within CDRH2; or
   (iii) amino acid residue HC res106 according to Kabat in case of an incorporation of said heterologous amino acid sequence within CDRH3; or
   (iv) amino acid residue LC res 32 according to Kabat in case of an incorporation of said heterologous amino acid sequence within CDRL1; or
   (v) amino acid residue LC res57 according to Kabat in case of an incorporation of said heterologous amino acid sequence within CDRL2; or (vi) amino acid residue LC res98 according to Kabat in case of an incorporation of said heterologous amino acid sequence within CDRL3 comprises the sequence of any one of SEQ ID NOs: 39 to 51.

5. The antibody or fragment thereof according to claim 1, wherein the amino acid stretch present between
   (i) amino acid residue HC res25 according to Kabat and amino acid residue HC res35a according to Kabat in case of an incorporation of said heterologous amino acid sequence within CDRH1; or
   (ii) amino acid residue HC res51 according to Kabat and amino acid residue HC res57 according to Kabat in case of an incorporation of said heterologous amino acid sequence within CDRH2; or
   (iii) amino acid residue HC res92 according to Kabat and amino acid residue HC res 106 according to Kabat in case of an incorporation of said heterologous amino acid sequence within CDRH3; or
   (iv) amino acid residue LC res26 according to Kabat and amino acid residue LC res 32 according to Kabat in case of an incorporation of said heterologous amino acid sequence within CDRL1; or
   (v) amino acid residue LC res49 according to Kabat and amino acid residue LC res57 according to Kabat in case of an incorporation of said heterologous amino acid sequence within CDRL2; or
   (vi) amino acid residue LC res88 according to Kabat and amino acid residue LC res98 according to Kabat in case of an incorporation of said heterologous amino acid sequence within CDRL3
comprises the sequence of any one of SEQ ID NOs: 52 to 64.

6. The antibody or fragment thereof according to claim 1, further comprising at least one further natriuretic peptide, wherein said BNP and said at least one further natriuretic peptide are incorporated within at least two separate CDR regions, and wherein said at least one further natriuretic peptide is selected from ANP and CNP.

7. The antibody or fragment thereof according to claim 1, wherein the light chain comprises or consists of the amino acid sequence of SEQ ID NO: 66 and the heavy chain comprises or consists of the amino acid sequence of any one of SEQ ID NOs: 442 to 444.

8. The antibody or fragment thereof according to claim 1, wherein said antibody fragment is selected from the group consisting of Fab, Fab', Fab'-SH, F(ab')2, Fv fragments, diabodies, single domain antibodies (Dabs), linear antibodies, single-chain antibody molecules (scFv), and disulfide-stabilized Fv antibody fragments (dsFv).

9. A composition comprising the antibody or fragment thereof according to claim 1 and a pharmaceutically acceptable carrier.

10. The antibody or fragment thereof according to claim 7, wherein the light chain comprises the amino acid sequence of SEQ ID NO: 66 and the heavy chain comprises the amino acid sequence of SEQ ID NO: 442.

11. The antibody or fragment thereof according to claim 7, wherein the light chain comprises the amino acid sequence of SEQ ID NO: 66 and the heavy chain comprises the amino acid sequence of SEQ ID NO: 443.

12. The antibody or fragment thereof according to claim 7, wherein the light chain comprises the amino acid sequence of SEQ ID NO: 66 and the heavy chain comprises the amino acid sequence of SEQ ID NO: 444.

13. The antibody or fragment thereof according to claim 1, wherein at least a portion of said CDR region is replaced by said heterologous amino acid sequence incorporated therein.

14. The antibody or fragment thereof according to claim 1, wherein:
   (i) the Ntls comprises the amino acid sequence of SEQ ID NO: 268 and the Ctls comprises the amino acid sequence of SEQ ID NO: 252; or
   (ii) the Ntls comprises the amino acid sequence of SEQ ID NO: 430 and the Ctls comprises the amino acid sequence of SEQ ID NO: 431; or
   (iii) the Ntls comprises the amino acid sequence of SEQ ID NO: 268 and the Ctls comprises the amino acid sequence of SEQ ID NO: 252; or
   (iv) the Ntls comprises the amino acid sequence of SEQ ID NO: 259 and the Ctls comprises the amino acid sequence of SEQ ID NO: 432; or
   (v) the Ntls comprises the amino acid sequence of SEQ ID NO: 189 and the Ctls comprises the amino acid sequence of SEQ ID NO: 190; or
   (vi) the Ntls comprises the amino acid sequence of SEQ ID NO: 105 and the Ctls comprises the amino acid sequence of SEQ ID NO: 106; or
   (vii) the Ntls comprises the amino acid sequence of SEQ ID NO: 211 and the Ctls comprises the amino acid sequence of SEQ ID NO: 212; or
   (viii) the Ntls comprises the amino acid sequence of SEQ ID NO: 236 and the Ctls comprises the amino acid sequence of SEQ ID NO: 237; or
   (ix) the Ntls comprises the amino acid sequence of SEQ ID NO: 281 and the Ctls comprises the amino acid sequence of SEQ ID NO: 282; or
   (x) the Ntls comprises the amino acid sequence of SEQ ID NO: 402 and the Ctls comprises the amino acid sequence of SEQ ID NO: 403.

15. A nucleic acid or a mixture of nucleic acids encoding an antibody or fragment thereof,
   wherein the antibody or the fragment thereof comprises at least one a heterologous amino acid sequence incorporated within a CDR region of said antibody or the fragment thereof,
   wherein said heterologous amino acid sequence comprises an N-terminal linker sequence (Ntls), a Brain Natriuretic Peptide (BNP), and a C-terminal linker sequence (Ctls),
   wherein the Ntls comprises at least 12 amino acid residues and the Ctls comprises at least 9 amino acid residues,
   wherein:
   (i) in case of an incorporation of said heterologous amino acid sequence within CDRH1, the Ntls is present between amino acid residue HC res25 according to Kabat and the first amino acid residue of said BNP, and the Ctls is present between the last amino acid residue of said BNP and amino acid residue HC res35a according to Kabat, or
   (ii) in case of an incorporation of said heterologous amino acid sequence within CDRH2, the Ntls is present between amino acid residue HC res51 according to Kabat and the first amino acid residue of said BNP, and the Ctls is present between amino acid residue HC res57 according to Kabat, or
   (iii) in case of an incorporation of said heterologous amino acid sequence within CDRH3, the Ntls is present between amino acid residue HC res92 according to Kabat and the first amino acid residue of said BNP, and the Ctls is present between amino acid residue HC res106 according to Kabat, or
   (iv) in case of an incorporation of said heterologous amino acid sequence within CDRL1, the Ntls is present between amino acid residue LC res26 according to Kabat, and the Ctls is present between amino acid residue LC res 32 according to Kabat, or
(v) in case of an incorporation of said heterologous amino acid sequence within CDRL2, the Ntls is present between amino acid residue LC res49 according to Kabat and the first amino acid residue of said BNP, and the Ctls is present between amino acid residue LC res57 according to Kabat, or
(vi) in case of an incorporation of said heterologous amino acid sequence within CDRL3, the Ntls is present between amino acid residue LC res88 according to Kabat and the first amino acid residue of said BNP, and the Ctls is present between amino acid residue LC res98 according to Kabat;
wherein:
  (i) said Ntls and said Ctls each comprise a GS linker sequence, or
  (ii) said Ntls and said Ctls each comprise a PN linker sequence, or
  (iii) said Ntls comprises the sequence of any one of SEQ ID NOs: 1, 2, or 4 and said Ctls comprises the sequence of any one of SEQ ID NOs: 1, 3, or 5, or
  (iv) said Ntls and said Ctls each comprise the sequence of SEQ ID NO: 6, or
  (v) said Ntls comprises the sequence of SEQ ID NO: 7 and said Ctls comprises the sequence of SEQ ID NO: 8, or
  (vi) said Ntls comprises the sequence of SEQ ID NO: 9 and said Ctls comprises the sequence of SEQ ID NO: 10, or
  (vii) said Ntls comprises the sequence of SEQ ID NO: 11 and said Ctls comprises the sequence of SEQ ID NO: 12, or
  (viii) said Ntls comprises the sequence of SEQ ID NO: 13 and said Ctls comprises the sequence of SEQ ID NO: 14, or
  (ix) said Ntls and said Ctls each comprise the sequence of SEQ ID NO: 15; or
  (x) said Ntls comprises the sequence of SEQ ID NO: 9 and said Ctls comprises the sequence of SEQ ID NO: 20, or
  xi) said Ntls comprises the sequence of SEQ ID NO: 21 and said Ctls comprises the sequence of SEQ ID NO: 22, and
wherein said antibody or fragment thereof is of the class IgG.

16. A host cell comprising the nucleic acid or the mixture of nucleic acids according to claim 15.

17. A process for producing an antibody or fragment thereof, comprising culturing the host cell according to claim 16 under conditions suitable for expression of the antibody or fragment thereof.

* * * * *

SEQUENCE LISTING

<160> NUMBER OF SEQ ID NOS: 462

<210> SEQ ID NO 1
<211> LENGTH: 10
<212> TYPE: PRT
<213> ORGANISM: artificial
<220> FEATURE:
<223> OTHER INFORMATION: linker sequence

<400> SEQUENCE: 1

Ser Tyr Ala Met Ser Trp Val Arg Gln Ala
1               5                   10

<210> SEQ ID NO 2
<211> LENGTH: 10
<212> TYPE: PRT
<213> ORGANISM: artificial
<220> FEATURE:
<223> OTHER INFORMATION: linker sequence

<400> SEQUENCE: 2

Thr Tyr Ile Ser Asn Val Asn His Lys Pro
1               5                   10

<210> SEQ ID NO 3
<211> LENGTH: 9
<212> TYPE: PRT
<213> ORGANISM: artificial
<220> FEATURE:
<223> OTHER INFORMATION: linker sequence

<400> SEQUENCE: 3

Ser Asn Thr Lys Val Asp Lys Lys Val
1               5

<210> SEQ ID NO 4
<211> LENGTH: 10
<212> TYPE: PRT
<213> ORGANISM: artificial
<220> FEATURE:
<223> OTHER INFORMATION: linker sequence

<400> SEQUENCE: 4

Gly Thr Ser Ala Ser Leu Ala Ile Thr Gly
1               5                   10

<210> SEQ ID NO 5
<211> LENGTH: 9
<212> TYPE: PRT
<213> ORGANISM: artificial
<220> FEATURE:
<223> OTHER INFORMATION: linker sequence

<400> SEQUENCE: 5

Asp Arg Phe Ser Gly Ser Lys Ser Gly
1               5

<210> SEQ ID NO 6
<211> LENGTH: 15
<212> TYPE: PRT
<213> ORGANISM: artificial
<220> FEATURE:
<223> OTHER INFORMATION: linker sequence

<400> SEQUENCE: 6

Ser Ala Leu Leu Lys Ser Lys Leu Arg Ala Leu Leu Thr Ala Pro
1               5                   10                  15

```
<210> SEQ ID NO 7
<211> LENGTH: 14
<212> TYPE: PRT
<213> ORGANISM: artificial
<220> FEATURE:
<223> OTHER INFORMATION: linker sequence

<400> SEQUENCE: 7

Val His Gln Glu Thr Lys Lys Tyr Gln Ser Ser Pro Asp Gly
1               5                   10

<210> SEQ ID NO 8
<211> LENGTH: 17
<212> TYPE: PRT
<213> ORGANISM: artificial
<220> FEATURE:
<223> OTHER INFORMATION: linker sequence

<400> SEQUENCE: 8

Ser Tyr Ser Tyr Thr Tyr Asn Tyr Glu Trp His Val Asp Val Trp Gly
1               5                   10                  15

Gln

<210> SEQ ID NO 9
<211> LENGTH: 12
<212> TYPE: PRT
<213> ORGANISM: artificial
<220> FEATURE:
<223> OTHER INFORMATION: linker sequence

<400> SEQUENCE: 9

Ser Val Val Val Thr Ser His Gln Ala Pro Gly Glu
1               5                   10

<210> SEQ ID NO 10
<211> LENGTH: 10
<212> TYPE: PRT
<213> ORGANISM: artificial
<220> FEATURE:
<223> OTHER INFORMATION: linker sequence

<400> SEQUENCE: 10

Gly Glu Lys Lys Lys Leu Lys Ser Leu Ala
1               5                   10

<210> SEQ ID NO 11
<211> LENGTH: 10
<212> TYPE: PRT
<213> ORGANISM: artificial
<220> FEATURE:
<223> OTHER INFORMATION: linker sequence

<400> SEQUENCE: 11

Gln Val Lys Leu Glu Leu Gly His Arg Ala
1               5                   10

<210> SEQ ID NO 12
<211> LENGTH: 10
<212> TYPE: PRT
<213> ORGANISM: artificial
<220> FEATURE:
<223> OTHER INFORMATION: linker sequence

<400> SEQUENCE: 12

Val Asn His Leu Arg Ser Glu Lys Leu Thr
```

```
1               5                   10
```

<210> SEQ ID NO 13
<211> LENGTH: 7
<212> TYPE: PRT
<213> ORGANISM: artificial
<220> FEATURE:
<223> OTHER INFORMATION: linker sequence

<400> SEQUENCE: 13

```
Ala Val Val Asn Val Arg Ala
1               5
```

<210> SEQ ID NO 14
<211> LENGTH: 7
<212> TYPE: PRT
<213> ORGANISM: artificial
<220> FEATURE:
<223> OTHER INFORMATION: linker sequence

<400> SEQUENCE: 14

```
Lys Gly Asp Lys Ile Ala Ile
1               5
```

<210> SEQ ID NO 15
<211> LENGTH: 10
<212> TYPE: PRT
<213> ORGANISM: artificial
<220> FEATURE:
<223> OTHER INFORMATION: linker sequence

<400> SEQUENCE: 15

```
Val Pro Lys Glu Lys Glu Lys Glu Lys Val
1               5                   10
```

<210> SEQ ID NO 16
<211> LENGTH: 12
<212> TYPE: PRT
<213> ORGANISM: artificial
<220> FEATURE:
<223> OTHER INFORMATION: linker sequence

<400> SEQUENCE: 16

```
Ala Thr Lys Ala Val Ser Val Leu Lys Gly Asp Gly
1               5                   10
```

<210> SEQ ID NO 17
<211> LENGTH: 9
<212> TYPE: PRT
<213> ORGANISM: artificial
<220> FEATURE:
<223> OTHER INFORMATION: linker sequence

<400> SEQUENCE: 17

```
Gln Gly Ile Ile Asn Phe Glu Gln Lys
1               5
```

<210> SEQ ID NO 18
<211> LENGTH: 11
<212> TYPE: PRT
<213> ORGANISM: artificial
<220> FEATURE:
<223> OTHER INFORMATION: linker sequence

<400> SEQUENCE: 18

```
Gly Pro Val Lys Val Trp Gly Ser Ile Lys Gly
1               5                   10
```

<210> SEQ ID NO 19
<211> LENGTH: 7
<212> TYPE: PRT
<213> ORGANISM: artificial
<220> FEATURE:
<223> OTHER INFORMATION: linker sequence

<400> SEQUENCE: 19

Tyr Glu Lys Glu Lys Glu Lys
1               5

<210> SEQ ID NO 20
<211> LENGTH: 10
<212> TYPE: PRT
<213> ORGANISM: artificial
<220> FEATURE:
<223> OTHER INFORMATION: linker sequence

<400> SEQUENCE: 20

Gly Gly Ser Thr Pro Leu Lys Ser Leu Ala
1               5                   10

<210> SEQ ID NO 21
<211> LENGTH: 14
<212> TYPE: PRT
<213> ORGANISM: artificial
<220> FEATURE:
<223> OTHER INFORMATION: linker sequence

<400> SEQUENCE: 21

Gly Ile Thr Gly Thr Lys Lys Tyr Gln Ser Ser Pro Asp Gly
1               5                   10

<210> SEQ ID NO 22
<211> LENGTH: 17
<212> TYPE: PRT
<213> ORGANISM: artificial
<220> FEATURE:
<223> OTHER INFORMATION: linker sequence

<400> SEQUENCE: 22

Ser Tyr Ser Tyr Thr Tyr Asn Tyr Ala Glu Tyr Phe Gln His Trp Gly
1               5                   10                  15

Gln

<210> SEQ ID NO 23
<211> LENGTH: 28
<212> TYPE: PRT
<213> ORGANISM: Homo sapiens

<400> SEQUENCE: 23

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 24
<211> LENGTH: 28
<212> TYPE: PRT
<213> ORGANISM: Homo sapiens

<400> SEQUENCE: 24

Met Val Gln Gly Ser Gly Cys Phe Gly Arg Lys Met Asp Arg Ile Ser
1               5                   10                  15

```
Ser Ser Ser Gly Leu Gly Cys Lys Val Leu Arg Arg
        20                  25
```

<210> SEQ ID NO 25
<211> LENGTH: 22
<212> TYPE: PRT
<213> ORGANISM: Homo sapiens

<400> SEQUENCE: 25

```
Gly Leu Ser Lys Gly Cys Phe Gly Leu Lys Leu Asp Arg Ile Gly Ser
1               5                   10                  15

Met Ser Gly Leu Gly Cys
            20
```

<210> SEQ ID NO 26
<211> LENGTH: 15
<212> TYPE: PRT
<213> ORGANISM: artificial
<220> FEATURE:
<223> OTHER INFORMATION: N-terminal Sequence (without ref aa)

<400> SEQUENCE: 26

```
Gly Phe Thr Phe Gly Ser Gly Ser Gly Ser Gly Ser Gly Ser Gly
1               5                   10                  15
```

<210> SEQ ID NO 27
<211> LENGTH: 23
<212> TYPE: PRT
<213> ORGANISM: artificial
<220> FEATURE:
<223> OTHER INFORMATION: N-terminal Sequence (without ref aa)

<400> SEQUENCE: 27

```
Gly Phe Thr Phe Gly Ser Gly Ser Gly Ser Gly Ser Gly Ser Gly Ser
1               5                   10                  15

Pro Asp Gly Gly Ser Gly Gly
            20
```

<210> SEQ ID NO 28
<211> LENGTH: 19
<212> TYPE: PRT
<213> ORGANISM: artificial
<220> FEATURE:
<223> OTHER INFORMATION: N-terminal Sequence (without ref aa)

<400> SEQUENCE: 28

```
Gly Ser Gly Ser Gly Ser Gly Ser Gly Ser Gly Ser Pro Asp Gly Gly
1               5                   10                  15

Ser Gly Gly
```

<210> SEQ ID NO 29
<211> LENGTH: 20
<212> TYPE: PRT
<213> ORGANISM: artificial
<220> FEATURE:
<223> OTHER INFORMATION: N-terminal Sequence (without ref aa)

<400> SEQUENCE: 29

```
Ser Gly Ser Gly Ser Gly Ser Gly Ser Gly Ser Gly Ser Pro Asp Gly
1               5                   10                  15

Gly Ser Gly Gly
            20
```

```
<210> SEQ ID NO 30
<211> LENGTH: 17
<212> TYPE: PRT
<213> ORGANISM: artificial
<220> FEATURE:
<223> OTHER INFORMATION: N-terminal Sequence (without ref aa)

<400> SEQUENCE: 30

Ser Gly Pro Asn Pro Asn Lys Asn Pro Asn Pro Asn Pro Gly Ser Gly
1               5                   10                  15
Gly

<210> SEQ ID NO 31
<211> LENGTH: 20
<212> TYPE: PRT
<213> ORGANISM: artificial
<220> FEATURE:
<223> OTHER INFORMATION: N-terminal Sequence (without ref aa)

<400> SEQUENCE: 31

Ser Gly Pro Asn Pro Asn Pro Asn Pro Asn Pro Asn Ser Pro Asp Gly
1               5                   10                  15
Gly Ser Gly Gly
            20

<210> SEQ ID NO 32
<211> LENGTH: 20
<212> TYPE: PRT
<213> ORGANISM: artificial
<220> FEATURE:
<223> OTHER INFORMATION: N-terminal Sequence (without ref aa)

<400> SEQUENCE: 32

Ala Lys Val His Pro Asn Pro Asn Pro Asn Pro Asn Ser Pro Asp Gly
1               5                   10                  15
Gly Ser Gly Gly
            20

<210> SEQ ID NO 33
<211> LENGTH: 19
<212> TYPE: PRT
<213> ORGANISM: artificial
<220> FEATURE:
<223> OTHER INFORMATION: N-terminal Sequence (without ref aa)

<400> SEQUENCE: 33

Ala Ala Trp Asn Pro Asn Pro Asn Pro Asn Pro Asn Gly Gly
1               5                   10                  15
Ser Gly Gly

<210> SEQ ID NO 34
<211> LENGTH: 20
<212> TYPE: PRT
<213> ORGANISM: artificial
<220> FEATURE:
<223> OTHER INFORMATION: N-terminal Sequence (without ref aa)

<400> SEQUENCE: 34

Ala Lys Gly Ile Thr Gly Thr Lys Lys Tyr Gln Ser Ser Pro Asp Gly
1               5                   10                  15
Gly Ser Gly Gly
            20

<210> SEQ ID NO 35
```

```
<211> LENGTH: 19
<212> TYPE: PRT
<213> ORGANISM: artificial
<220> FEATURE:
<223> OTHER INFORMATION: N-terminal Sequence (without ref aa)

<400> SEQUENCE: 35

Ser Gly Ser Thr Tyr Ile Ser Asn Val Asn His Lys Pro Asp Gly Gly
1               5                   10                  15
Ser Gly Gly

<210> SEQ ID NO 36
<211> LENGTH: 18
<212> TYPE: PRT
<213> ORGANISM: artificial
<220> FEATURE:
<223> OTHER INFORMATION: N-terminal Sequence (without ref aa)

<400> SEQUENCE: 36

Ser Gly Thr Ser Ala Ser Leu Ala Ile Thr Gly Pro Asp Gly Gly Ser
1               5                   10                  15
Gly Gly

<210> SEQ ID NO 37
<211> LENGTH: 17
<212> TYPE: PRT
<213> ORGANISM: artificial
<220> FEATURE:
<223> OTHER INFORMATION: N-terminal Sequence (without ref aa)

<400> SEQUENCE: 37

Gly Val Pro Lys Glu Lys Glu Lys Glu Lys Val Ser Thr Ala Val Gly
1               5                   10                  15
Gly

<210> SEQ ID NO 38
<211> LENGTH: 17
<212> TYPE: PRT
<213> ORGANISM: artificial
<220> FEATURE:
<223> OTHER INFORMATION: N-terminal Sequence (without ref aa)

<400> SEQUENCE: 38

Ser Val Val Val Thr Ser His Gln Ala Pro Gly Glu Gly Gly Ser Gly
1               5                   10                  15
Gly

<210> SEQ ID NO 39
<211> LENGTH: 11
<212> TYPE: PRT
<213> ORGANISM: artificial
<220> FEATURE:
<223> OTHER INFORMATION: C-terminal Sequence (without ref aa)

<400> SEQUENCE: 39

Gly Gly Ser Gly Gly Ser Gly Ser Gly Ser Gly
1               5                   10

<210> SEQ ID NO 40
<211> LENGTH: 14
<212> TYPE: PRT
<213> ORGANISM: artificial
<220> FEATURE:
<223> OTHER INFORMATION: C-terminal Sequence (without ref aa)
```

```
<400> SEQUENCE: 40

Gly Ser Tyr Gly Ser Gly Ser Gly Ser Gly Ser Gly
1               5                   10

<210> SEQ ID NO 41
<211> LENGTH: 17
<212> TYPE: PRT
<213> ORGANISM: artificial
<220> FEATURE:
<223> OTHER INFORMATION: C-terminal Sequence (without ref aa)

<400> SEQUENCE: 41

Gly Ser Tyr Gly Ser Gly Gly Ser Gly Ser Gly Ser Gly Asn Arg Pro
1               5                   10                  15

Ser

<210> SEQ ID NO 42
<211> LENGTH: 15
<212> TYPE: PRT
<213> ORGANISM: artificial
<220> FEATURE:
<223> OTHER INFORMATION: C-terminal Sequence (without ref aa)

<400> SEQUENCE: 42

Gly Ser Tyr Gly Ser Gly Ser Gly Ser Gly Ser Gly Ser Gly Ser
1               5                   10                  15

<210> SEQ ID NO 43
<211> LENGTH: 14
<212> TYPE: PRT
<213> ORGANISM: artificial
<220> FEATURE:
<223> OTHER INFORMATION: C-terminal Sequence (without ref aa)

<400> SEQUENCE: 43

Gly Ser Asn Pro Asn Glu Asn Pro Asn Pro Asn Pro Gly Ser
1               5                   10

<210> SEQ ID NO 44
<211> LENGTH: 15
<212> TYPE: PRT
<213> ORGANISM: artificial
<220> FEATURE:
<223> OTHER INFORMATION: C-terminal Sequence (without ref aa)

<400> SEQUENCE: 44

Gly Ser Tyr Asn Pro Asn Pro Asn Pro Asn Pro Asn Pro Gly Ser
1               5                   10                  15

<210> SEQ ID NO 45
<211> LENGTH: 18
<212> TYPE: PRT
<213> ORGANISM: artificial
<220> FEATURE:
<223> OTHER INFORMATION: C-terminal Sequence (without ref aa)

<400> SEQUENCE: 45

Gly Ser Tyr Asn Pro Asn Pro Asn Pro Asn Pro His Val Asp Val Trp
1               5                   10                  15

Gly Gln

<210> SEQ ID NO 46
<211> LENGTH: 14
<212> TYPE: PRT
<213> ORGANISM: artificial
```

```
<220> FEATURE:
<223> OTHER INFORMATION: C-terminal Sequence (without ref aa)

<400> SEQUENCE: 46

Gly Ser Asn Pro Asn Pro Asn Pro Asn Pro Asn Val
1               5                   10

<210> SEQ ID NO 47
<211> LENGTH: 18
<212> TYPE: PRT
<213> ORGANISM: artificial
<220> FEATURE:
<223> OTHER INFORMATION: C-terminal Sequence (without ref aa)

<400> SEQUENCE: 47

Gly Ser Tyr Ser Tyr Thr Tyr Asn Tyr Ala Glu Tyr Phe Gln His Trp
1               5                   10                  15

Gly Gln

<210> SEQ ID NO 48
<211> LENGTH: 14
<212> TYPE: PRT
<213> ORGANISM: artificial
<220> FEATURE:
<223> OTHER INFORMATION: C-terminal Sequence (without ref aa)

<400> SEQUENCE: 48

Gly Ser Asn Thr Lys Val Asp Lys Lys Val Glu Gly Gly Ser
1               5                   10

<210> SEQ ID NO 49
<211> LENGTH: 13
<212> TYPE: PRT
<213> ORGANISM: artificial
<220> FEATURE:
<223> OTHER INFORMATION: C-terminal Sequence (without ref aa)

<400> SEQUENCE: 49

Gly Ser Asp Arg Phe Ser Gly Ser Lys Ser Gly Gly Ser
1               5                   10

<210> SEQ ID NO 50
<211> LENGTH: 16
<212> TYPE: PRT
<213> ORGANISM: artificial
<220> FEATURE:
<223> OTHER INFORMATION: C-terminal Sequence (without ref aa)

<400> SEQUENCE: 50

Gly Ser Ala Pro Leu Glu Val Pro Lys Glu Lys Glu Lys Glu Lys Val
1               5                   10                  15

<210> SEQ ID NO 51
<211> LENGTH: 11
<212> TYPE: PRT
<213> ORGANISM: artificial
<220> FEATURE:
<223> OTHER INFORMATION: C-terminal Sequence (without ref aa)

<400> SEQUENCE: 51

Gly Gly Ser Thr Pro Leu Lys Ser Leu Ala Ser
1               5                   10

<210> SEQ ID NO 52
<211> LENGTH: 54
<212> TYPE: PRT
```

```
<213> ORGANISM: artificial
<220> FEATURE:
<223> OTHER INFORMATION: N-terminal Sequence-NP-C-terminal Sequence
      (without ref aas)

<400> SEQUENCE: 52

Gly Phe Thr Phe Gly Ser Gly Ser Gly Ser Gly Ser Gly Ser
1               5                   10                  15

Leu Arg Arg Ser Ser Cys Phe Gly Gly Arg Met Asp Arg Ile Gly Ala
            20                  25                  30

Gln Ser Gly Leu Gly Cys Asn Ser Phe Arg Tyr Gly Gly Ser Gly Gly
        35                  40                  45

Ser Gly Ser Gly Ser Gly
    50

<210> SEQ ID NO 53
<211> LENGTH: 65
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 53

Gly Phe Thr Phe Gly Ser Gly Ser Gly Ser Gly Ser Gly Ser
1               5                   10                  15

Pro Asp Gly Gly Ser Gly Gly Ser Leu Arg Arg Ser Ser Cys Phe Gly
            20                  25                  30

Gly Arg Met Asp Arg Ile Gly Ala Gln Ser Gly Leu Gly Cys Asn Ser
        35                  40                  45

Phe Arg Tyr Gly Ser Tyr Gly Ser Gly Ser Gly Ser Gly Ser
    50                  55                  60

Gly
65

<210> SEQ ID NO 54
<211> LENGTH: 64
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 54

Gly Ser Gly Ser Gly Ser Gly Ser Gly Ser Pro Asp Gly Gly
1               5                   10                  15

Ser Gly Gly Ser Leu Arg Arg Ser Ser Cys Phe Gly Gly Arg Met Asp
            20                  25                  30

Arg Ile Gly Ala Gln Ser Gly Leu Gly Cys Asn Ser Phe Arg Tyr Gly
        35                  40                  45

Ser Tyr Gly Ser Gly Gly Ser Gly Ser Gly Ser Gly Asn Arg Pro Ser
    50                  55                  60

<210> SEQ ID NO 55
<211> LENGTH: 63
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 55
```

Ser Gly Ser Gly Ser Gly Ser Gly Ser Gly Ser Pro Asp Gly
1               5                   10                  15

Gly Ser Gly Gly Ser Leu Arg Arg Ser Ser Cys Phe Gly Gly Arg Met
                20                  25                  30

Asp Arg Ile Gly Ala Gln Ser Gly Leu Gly Cys Asn Ser Phe Arg Tyr
            35                  40                  45

Gly Ser Tyr Gly Ser Gly Ser Gly Ser Gly Ser Gly Ser
        50                  55                  60

<210> SEQ ID NO 56
<211> LENGTH: 59
<212> TYPE: PRT
<213> ORGANISM: artificial
<220> FEATURE:
<223> OTHER INFORMATION: N-terminal Sequence-NP-C-terminal Sequence (wo
      ref aas)

<400> SEQUENCE: 56

Ser Gly Pro Asn Pro Asn Lys Asn Pro Asn Pro Asn Pro Gly Ser Gly
1               5                   10                  15

Gly Ser Leu Arg Arg Ser Ser Cys Phe Gly Gly Arg Met Asp Arg Ile
                20                  25                  30

Gly Ala Gln Ser Gly Leu Gly Cys Asn Ser Phe Arg Tyr Gly Ser Asn
            35                  40                  45

Pro Asn Glu Asn Pro Asn Pro Asn Pro Gly Ser
        50                  55

<210> SEQ ID NO 57
<211> LENGTH: 63
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 57

Ser Gly Pro Asn Pro Asn Pro Asn Pro Asn Pro Asn Ser Pro Asp Gly
1               5                   10                  15

Gly Ser Gly Gly Ser Leu Arg Arg Ser Ser Cys Phe Gly Gly Arg Met
                20                  25                  30

Asp Arg Ile Gly Ala Gln Ser Gly Leu Gly Cys Asn Ser Phe Arg Tyr
            35                  40                  45

Gly Ser Tyr Asn Pro Asn Pro Asn Pro Asn Pro Asn Pro Gly Ser
        50                  55                  60

<210> SEQ ID NO 58
<211> LENGTH: 66
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 58

Ala Lys Val His Pro Asn Pro Asn Pro Asn Pro Asn Ser Pro Asp Gly
1               5                   10                  15

Gly Ser Gly Gly Ser Leu Arg Arg Ser Ser Cys Phe Gly Gly Arg Met
                20                  25                  30

Asp Arg Ile Gly Ala Gln Ser Gly Leu Gly Cys Asn Ser Phe Arg Tyr
            35                  40                  45

Gly Ser Tyr Asn Pro Asn Pro Asn Pro Asn Pro His Val Asp Val Trp

-continued

```
                 50                  55                  60

Gly Gln
 65

<210> SEQ ID NO 59
<211> LENGTH: 61
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 59

Ala Ala Trp Asn Pro Asn Pro Asn Pro Asn Pro Asn Pro Asn Gly Gly
  1               5                  10                  15

Ser Gly Gly Ser Leu Arg Arg Ser Ser Cys Phe Gly Gly Arg Met Asp
                 20                  25                  30

Arg Ile Gly Ala Gln Ser Gly Leu Gly Cys Asn Ser Phe Arg Tyr Gly
             35                  40                  45

Ser Asn Pro Asn Pro Asn Pro Asn Pro Asn Val
         50                  55                  60

<210> SEQ ID NO 60
<211> LENGTH: 66
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 60

Ala Lys Gly Ile Thr Gly Thr Lys Lys Tyr Gln Ser Ser Pro Asp Gly
  1               5                  10                  15

Gly Ser Gly Gly Ser Leu Arg Arg Ser Ser Cys Phe Gly Gly Arg Met
                 20                  25                  30

Asp Arg Ile Gly Ala Gln Ser Gly Leu Gly Cys Asn Ser Phe Arg Tyr
             35                  40                  45

Gly Ser Tyr Ser Tyr Thr Tyr Asn Tyr Ala Glu Tyr Phe Gln His Trp
         50                  55                  60

Gly Gln
 65

<210> SEQ ID NO 61
<211> LENGTH: 61
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 61

Ser Gly Ser Thr Tyr Ile Ser Asn Val Asn His Lys Pro Asp Gly Gly
  1               5                  10                  15

Ser Gly Gly Ser Leu Arg Arg Ser Ser Cys Phe Gly Gly Arg Met Asp
                 20                  25                  30

Arg Ile Gly Ala Gln Ser Gly Leu Gly Cys Asn Ser Phe Arg Tyr Gly
             35                  40                  45

Ser Asn Thr Lys Val Asp Lys Lys Val Glu Gly Gly Ser
         50                  55                  60

<210> SEQ ID NO 62
```

<211> LENGTH: 59
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 62

Ser Gly Thr Ser Ala Ser Leu Ala Ile Thr Gly Pro Asp Gly Gly Ser
1               5                   10                  15

Gly Gly Ser Leu Arg Arg Ser Ser Cys Phe Gly Gly Arg Met Asp Arg
            20                  25                  30

Ile Gly Ala Gln Ser Gly Leu Gly Cys Asn Ser Phe Arg Tyr Gly Ser
        35                  40                  45

Asp Arg Phe Ser Gly Ser Lys Ser Gly Gly Ser
    50                  55

<210> SEQ ID NO 63
<211> LENGTH: 61
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 63

Gly Val Pro Lys Glu Lys Glu Lys Val Ser Thr Ala Val Gly
1               5                   10                  15

Gly Ser Leu Arg Arg Ser Ser Cys Phe Gly Gly Arg Met Asp Arg Ile
            20                  25                  30

Gly Ala Gln Ser Gly Leu Gly Cys Asn Ser Phe Arg Tyr Gly Ser Ala
        35                  40                  45

Pro Leu Glu Val Pro Lys Glu Lys Glu Lys Val
    50                  55                  60

<210> SEQ ID NO 64
<211> LENGTH: 56
<212> TYPE: PRT
<213> ORGANISM: artificial
<220> FEATURE:
<223> OTHER INFORMATION: N-terminal Sequence-NP-C-terminal Sequence
      (without ref aas)

<400> SEQUENCE: 64

Ser Val Val Val Thr Ser His Gln Ala Pro Glu Gly Gly Ser Gly
1               5                   10                  15

Gly Ser Leu Arg Arg Ser Ser Cys Phe Gly Gly Arg Met Asp Arg Ile
            20                  25                  30

Gly Ala Gln Ser Gly Leu Gly Cys Asn Ser Phe Arg Tyr Gly Ser
        35                  40                  45

Thr Pro Leu Lys Ser Leu Ala Ser
    50                  55

<210> SEQ ID NO 65
<211> LENGTH: 447
<212> TYPE: PRT
<213> ORGANISM: Homo sapiens

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
                    20              25              30
Ala Met Ser Trp Val Arg Gln Ala Pro Gly Lys Gly Leu Glu Trp Val
                35              40              45
Ser Ala Ile Ser Gly Ser Gly Gly Ser Thr Tyr Tyr Ala Asp Ser Val
            50              55              60
Lys Gly Arg Phe Thr Ile Ser Arg Asp Asn Ser Lys Asn Thr Leu Tyr
65              70              75              80
Leu Gln Met Asn Ser Leu Arg Ala Glu Asp Thr Ala Val Tyr Tyr Cys
                85              90              95
Ala Lys Leu Thr Gly Ala Glu Tyr Phe Gln His Trp Gly Gln Gly Thr
            100             105             110
Leu Val Thr Val Ser Ser Ala Ser Thr Lys Gly Pro Ser Val Phe Pro
        115             120             125
Leu Ala Pro Ser Ser Lys Ser Thr Ser Gly Gly Thr Ala Ala Leu Gly
    130             135             140
Cys Leu Val Lys Asp Tyr Phe Pro Glu Pro Val Thr Val Ser Trp Asn
145             150             155             160
Ser Gly Ala Leu Thr Ser Gly Val His Thr Phe Pro Ala Val Leu Gln
            165             170             175
Ser Ser Gly Leu Tyr Ser Leu Ser Ser Val Val Thr Val Pro Ser Ser
        180             185             190
Ser Leu Gly Thr Gln Thr Tyr Ile Cys Asn Val Asn His Lys Pro Ser
    195             200             205
Asn Thr Lys Val Asp Lys Lys Val Glu Pro Lys Ser Cys Asp Lys Thr
    210             215             220
His Thr Cys Pro Pro Cys Pro Ala Pro Glu Leu Leu Gly Gly Pro Ser
225             230             235             240
Val Phe Leu Phe Pro Pro Lys Pro Lys Asp Thr Leu Met Ile Ser Arg
            245             250             255
Thr Pro Glu Val Thr Cys Val Val Val Asp Val Ser His Glu Asp Pro
        260             265             270
Glu Val Lys Phe Asn Trp Tyr Val Asp Gly Val Glu Val His Asn Ala
    275             280             285
Lys Thr Lys Pro Arg Glu Glu Gln Tyr Asn Ser Thr Tyr Arg Val Val
    290             295             300
Ser Val Leu Thr Val Leu His Gln Asp Trp Leu Asn Gly Lys Glu Tyr
305             310             315             320
Lys Cys Lys Val Ser Asn Lys Ala Leu Pro Ala Pro Ile Glu Lys Thr
            325             330             335
Ile Ser Lys Ala Lys Gly Gln Pro Arg Glu Pro Gln Val Tyr Thr Leu
        340             345             350
Pro Pro Ser Arg Asp Glu Leu Thr Lys Asn Gln Val Ser Leu Thr Cys
    355             360             365
Leu Val Lys Gly Phe Tyr Pro Ser Asp Ile Ala Val Glu Trp Glu Ser
    370             375             380
Asn Gly Gln Pro Glu Asn Asn Tyr Lys Thr Thr Pro Pro Val Leu Asp
385             390             395             400
Ser Asp Gly Ser Phe Phe Leu Tyr Ser Lys Leu Thr Val Asp Lys Ser
            405             410             415
Arg Trp Gln Gln Gly Asn Val Phe Ser Cys Ser Val Met His Glu Ala
        420             425             430
Leu His Asn His Tyr Thr Gln Lys Ser Leu Ser Leu Ser Pro Gly
    435             440             445
```

<210> SEQ ID NO 66
<211> LENGTH: 217
<212> TYPE: PRT
<213> ORGANISM: Homo sapiens

<400> SEQUENCE: 66

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 67
<211> LENGTH: 499
<212> TYPE: PRT
<213> ORGANISM: artificial
<220> FEATURE:
<223> OTHER INFORMATION: NP engrafted HC

<400> SEQUENCE: 67

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Thr Ser Val His Gln Glu Thr Lys Lys Tyr Gln Ser Ser Pro Asp Gly
            100                 105                 110

Gly Ser Gly Gly Ser Leu Arg Arg Ser Ser Cys Phe Gly Gly Arg Ile
        115                 120                 125

Asp Arg Ile Gly Ala Gln Ser Gly Leu Gly Cys Asn Ser Phe Arg Tyr
    130                 135                 140

Gly Ser Tyr Ser Tyr Thr Tyr Asn Tyr Glu Trp His Val Asp Val Trp
145                 150                 155                 160

Gly Gln Gly Thr Leu Val Thr Val Ser Ser Ala Ser Thr Lys Gly Pro
                165                 170                 175

Ser Val Phe Pro Leu Ala Pro Ser Ser Lys Ser Thr Ser Gly Gly Thr
            180                 185                 190

Ala Ala Leu Gly Cys Leu Val Lys Asp Tyr Phe Pro Glu Pro Val Thr
        195                 200                 205

Val Ser Trp Asn Ser Gly Ala Leu Thr Ser Gly Val His Thr Phe Pro
    210                 215                 220

Ala Val Leu Gln Ser Ser Gly Leu Tyr Ser Leu Ser Ser Val Val Thr
225                 230                 235                 240

Val Pro Ser Ser Ser Leu Gly Thr Gln Thr Tyr Ile Cys Asn Val Asn
                245                 250                 255

His Lys Pro Ser Asn Thr Lys Val Asp Lys Lys Val Glu Pro Lys Ser
            260                 265                 270

Cys Asp Lys Thr His Thr Cys Pro Pro Cys Pro Ala Pro Glu Leu Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 68
```

```
<211> LENGTH: 499
<212> TYPE: PRT
<213> ORGANISM: artificial
<220> FEATURE:
<223> OTHER INFORMATION: NP engrafted HC

<400> SEQUENCE: 68
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Ser | Gly | Ser | Gly | Gly | Ser | Thr | Tyr | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Thr | Ser | Val | His | Gln | Glu | Thr | Lys | Lys | Tyr | Gln | Ser | Ser | Pro | Asp | Gly |
|---|---|---|---|---|---|---|---|---|---|---|---|---|---|---|---|
| | | | 100 | | | | | 105 | | | | | 110 | | |

| Gly | Ser | Gly | Gly | Ser | Leu | Arg | Arg | Ser | Ser | Cys | Phe | Gly | Gly | Arg | Met |
|---|---|---|---|---|---|---|---|---|---|---|---|---|---|---|---|
| | | 115 | | | | | 120 | | | | | 125 | | | |

| Asp | Arg | Ile | Gly | Ala | Gln | Ser | Gly | Leu | Gly | Cys | Asn | Ser | Phe | Arg | Tyr |
|---|---|---|---|---|---|---|---|---|---|---|---|---|---|---|---|
| | 130 | | | | | 135 | | | | | 140 | | | | |

| Gly | Ser | Tyr | Ser | Tyr | Thr | Tyr | Asn | Tyr | Glu | Trp | His | Val | Asp | Val | Trp |
|---|---|---|---|---|---|---|---|---|---|---|---|---|---|---|---|
| 145 | | | | | 150 | | | | | 155 | | | | | 160 |

| Gly | Gln | Gly | Thr | Leu | Val | Thr | Val | Ser | Ser | Ala | Ser | Thr | Lys | Gly | Pro |
|---|---|---|---|---|---|---|---|---|---|---|---|---|---|---|---|
| | | | | 165 | | | | | 170 | | | | | 175 | |

| Ser | Val | Phe | Pro | Leu | Ala | Pro | Ser | Ser | Lys | Ser | Thr | Ser | Gly | Gly | Thr |
|---|---|---|---|---|---|---|---|---|---|---|---|---|---|---|---|
| | | | 180 | | | | | 185 | | | | | 190 | | |

| Ala | Ala | Leu | Gly | Cys | Leu | Val | Lys | Asp | Tyr | Phe | Pro | Glu | Pro | Val | Thr |
|---|---|---|---|---|---|---|---|---|---|---|---|---|---|---|---|
| | | 195 | | | | | 200 | | | | | 205 | | | |

| Val | Ser | Trp | Asn | Ser | Gly | Ala | Leu | Thr | Ser | Gly | Val | His | Thr | Phe | Pro |
|---|---|---|---|---|---|---|---|---|---|---|---|---|---|---|---|
| | 210 | | | | | 215 | | | | | 220 | | | | |

| Ala | Val | Leu | Gln | Ser | Ser | Gly | Leu | Tyr | Ser | Leu | Ser | Ser | Val | Val | Thr |
|---|---|---|---|---|---|---|---|---|---|---|---|---|---|---|---|
| 225 | | | | | 230 | | | | | 235 | | | | | 240 |

| Val | Pro | Ser | Ser | Ser | Leu | Gly | Thr | Gln | Thr | Tyr | Ile | Cys | Asn | Val | Asn |
|---|---|---|---|---|---|---|---|---|---|---|---|---|---|---|---|
| | | | | 245 | | | | | 250 | | | | | 255 | |

| His | Lys | Pro | Ser | Asn | Thr | Lys | Val | Asp | Lys | Lys | Val | Glu | Pro | Lys | Ser |
|---|---|---|---|---|---|---|---|---|---|---|---|---|---|---|---|
| | | | 260 | | | | | 265 | | | | | 270 | | |

| Cys | Asp | Lys | Thr | His | Thr | Cys | Pro | Pro | Cys | Pro | Ala | Pro | Glu | Leu | Leu |
|---|---|---|---|---|---|---|---|---|---|---|---|---|---|---|---|
| | | 275 | | | | | 280 | | | | | 285 | | | |

| Gly | Gly | Pro | Ser | Val | Phe | Leu | Phe | Pro | Pro | Lys | Pro | Lys | Asp | Thr | Leu |
|---|---|---|---|---|---|---|---|---|---|---|---|---|---|---|---|
| | 290 | | | | | 295 | | | | | 300 | | | | |

| Met | Ile | Ser | Arg | Thr | Pro | Glu | Val | Thr | Cys | Val | Val | Val | Asp | Val | Ser |
|---|---|---|---|---|---|---|---|---|---|---|---|---|---|---|---|
| 305 | | | | | 310 | | | | | 315 | | | | | 320 |

| His | Glu | Asp | Pro | Glu | Val | Lys | Phe | Asn | Trp | Tyr | Val | Asp | Gly | Val | Glu |
|---|---|---|---|---|---|---|---|---|---|---|---|---|---|---|---|
| | | | | 325 | | | | | 330 | | | | | 335 | |

| Val | His | Asn | Ala | Lys | Thr | Lys | Pro | Arg | Glu | Glu | Gln | Tyr | Asn | Ser | Thr |
|---|---|---|---|---|---|---|---|---|---|---|---|---|---|---|---|
| | | | 340 | | | | | 345 | | | | | 350 | | |

| Tyr | Arg | Val | Val | Ser | Val | Leu | Thr | Val | Leu | His | Gln | Asp | Trp | Leu | Asn |
|---|---|---|---|---|---|---|---|---|---|---|---|---|---|---|---|
| | | 355 | | | | | 360 | | | | | 365 | | | |

| Gly | Lys | Glu | Tyr | Lys | Cys | Lys | Val | Ser | Asn | Lys | Ala | Leu | Pro | Ala | Pro |
|---|---|---|---|---|---|---|---|---|---|---|---|---|---|---|---|
| | 370 | | | | | 375 | | | | | 380 | | | | |

-continued

```
Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 69
<211> LENGTH: 504
<212> TYPE: PRT
<213> ORGANISM: artificial
<220> FEATURE:
<223> OTHER INFORMATION: NP engrafted HC

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Gly Ser Gly Ser Gly Ser Gly Ser
    50                  55                  60

Pro Asp Gly Gly Ser Gly Ser Leu Arg Arg Ser Ser Cys Phe Gly
65                  70                  75                  80

Gly Arg Met Asp Arg Ile Gly Ala Gln Ser Gly Leu Gly Cys Asn Ser
                85                  90                  95

Phe Arg Tyr Gly Ser Tyr Gly Ser Gly Ser Gly Ser Gly Ser Gly Ser
            100                 105                 110

Gly Ser Thr Tyr Tyr Ala Asp Ser Val Lys Gly Arg Phe Thr Ile Ser
        115                 120                 125

Arg Asp Asn Ser Lys Asn Thr Leu Tyr Leu Gln Met Asn Ser Leu Arg
130                 135                 140

Ala Glu Asp Thr Ala Val Tyr Tyr Cys Ala Lys Leu Thr Gly Ala Glu
145                 150                 155                 160

Tyr Phe Gln His Trp Gly Gln Gly Thr Leu Val Thr Val Ser Ser Ala
                165                 170                 175

Ser Thr Lys Gly Pro Ser Val Phe Pro Leu Ala Pro Ser Ser Lys Ser
            180                 185                 190

Thr Ser Gly Gly Thr Ala Ala Leu Gly Cys Leu Val Lys Asp Tyr Phe
        195                 200                 205

Pro Glu Pro Val Thr Val Ser Trp Asn Ser Gly Ala Leu Thr Ser Gly
    210                 215                 220

Val His Thr Phe Pro Ala Val Leu Gln Ser Ser Gly Leu Tyr Ser Leu
225                 230                 235                 240
```

```
Ser Ser Val Val Thr Val Pro Ser Ser Leu Gly Thr Gln Thr Tyr
            245                 250                 255

Ile Cys Asn Val Asn His Lys Pro Ser Asn Thr Lys Val Asp Lys Lys
            260                 265                 270

Val Glu Pro Lys Ser Cys Asp Lys Thr His Thr Cys Pro Pro Cys Pro
        275                 280                 285

Ala Pro Glu Leu Leu Gly Gly Pro Ser Val Phe Leu Phe Pro Pro Lys
    290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
    370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly
            500

<210> SEQ ID NO 70
<211> LENGTH: 504
<212> TYPE: PRT
<213> ORGANISM: artificial
<220> FEATURE:
<223> OTHER INFORMATION: NP engrafted HC

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Pro Asn Pro Asn Pro Asn Pro Asn Pro Asn Ser
    50                  55                  60

Pro Asp Gly Gly Ser Gly Ser Leu Arg Arg Ser Ser Cys Phe Gly
65                  70                  75                  80

Gly Arg Met Asp Ar

```
Phe Arg Tyr Gly Ser Tyr Asn Pro Asn Pro Asn Pro Asn Pro
                100             105             110

Gly Ser Thr Tyr Tyr Ala Asp Ser Val Lys Gly Arg Phe Thr Ile Ser
        115                 120                 125

Arg Asp Asn Ser Lys Asn Thr Leu Tyr Leu Gln Met Asn Ser Leu Arg
        130                 135                 140

Ala Glu Asp Thr Ala Val Tyr Tyr Cys Ala Lys Leu Thr Gly Ala Glu
145                 150                 155                 160

Tyr Phe Gln His Trp Gly Gln Gly Thr Leu Val Thr Val Ser Ser Ala
                165                 170                 175

Ser Thr Lys Gly Pro Ser Val Phe Pro Leu Ala Pro Ser Ser Lys Ser
            180                 185                 190

Thr Ser Gly Gly Thr Ala Ala Leu Gly Cys Leu Val Lys Asp Tyr Phe
            195                 200                 205

Pro Glu Pro Val Thr Val Ser Trp Asn Ser Gly Ala Leu Thr Ser Gly
        210                 215                 220

Val His Thr Phe Pro Ala Val Leu Gln Ser Ser Gly Leu Tyr Ser Leu
225                 230                 235                 240

Ser Ser Val Val Thr Val Pro Ser Ser Ser Leu Gly Thr Gln Thr Tyr
                245                 250                 255

Ile Cys Asn Val Asn His Lys Pro Ser Asn Thr Lys Val Asp Lys Lys
                260                 265                 270

Val Glu Pro Lys Ser Cys Asp Lys Thr His Thr Cys Pro Pro Cys Pro
            275                 280                 285

Ala Pro Glu Leu Leu Gly Gly Pro Ser Val Phe Leu Phe Pro Pro Lys
            290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
        370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
        450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly
            500
```

<210> SEQ ID NO 71
<211> LENGTH: 499
<212> TYPE: PRT
<213> ORGANISM: artificial
<220> FEATURE:
<223> OTHER INFORMATION: NP engrafted HC

<400> SEQUENCE: 71

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly |
| 1 | | | | 5 | | | | | 10 | | | | | 15 |
| Gly | Ser | Leu | Arg | Leu | Ser | Cys | Ala | Ala | Ser | Gly | Phe | Thr | Phe | Ser |
| | | | 20 | | | | | 25 | | | | | 30 | |
| Ser | Tyr | Ala | Met | Ser | Trp | Val | Arg | Gln | Ala | Pro | Gly | Lys | Gly | Leu |
| | | | 35 | | | | | 40 | | | | | 45 | |
| Glu | Trp | Val | Ser | Ala | Ile | Ser | Gly | Ser | Gly | Gly | Ser | Thr | Tyr | Tyr |
| | | | 50 | | | | | 55 | | | | | 60 | |
| Ala | Asp | Ser | Val | Lys | Gly | Arg | Phe | Thr | Ile | Ser | Arg | Asp | Asn | Ser |
| 65 | | | | | 70 | | | | | 75 | | | | | 80 |
| Lys | Asn | Thr | Leu | Tyr | Leu | Gln | Met | Asn | Ser | Leu | Arg | Ala | Glu | Asp |
| | | | | 85 | | | | | 90 | | | | | 95 |
| Thr | Ala | Val | Tyr | Tyr | Cys | Ala | Lys | Val | His | Pro | Asn | Pro | Asn | Pro |
| | | | | 100 | | | | | 105 | | | | | 110 |
| Asn | Pro | Asn | Ser | Pro | Asp | Gly | Gly | Ser | Gly | Gly | Ser | Leu | Arg | Arg |
| | | | | 115 | | | | | 120 | | | | | 125 |
| Ser | Ser | Cys | Phe | Gly | Gly | Arg | Met | Asp | Arg | Ile | Gly | Ala | Gln | Ser |
| | | | | 130 | | | | | 135 | | | | | 140 |
| Gly | Leu | Gly | Cys | Asn | Ser | Phe | Arg | Tyr | Gly | Ser | Tyr | Asn | Pro | Asn |
| 145 | | | | | 150 | | | | | 155 | | | | | 160 |
| Pro | Asn | Pro | Asn | Pro | His | Val | Asp | Val | Trp | Gly | Gln | Gly | Thr | Thr |
| | | | | 165 | | | | | 170 | | | | | 175 |
| Val | Thr | Val | Ser | Ser | Ala | Ser | Thr | Lys | Gly | Pro | Ser | Val | Phe | Pro |
| | | | | 180 | | | | | 185 | | | | | 190 |
| Leu | Ala | Pro | Ser | Ser | Lys | Ser | Thr | Ser | Gly | Gly | Thr | Ala | Ala | Leu |
| | | | | 195 | | | | | 200 | | | | | 205 |
| Gly | Cys | Leu | Val | Lys | Asp | Tyr | Phe | Pro | Glu | Pro | Val | Thr | Val | Ser |
| | | | | 210 | | | | | 215 | | | | | 220 |
| Trp | Asn | Ser | Gly | Ala | Leu | Thr | Ser | Gly | Val | His | Thr | Phe | Pro | Ala |
| 225 | | | | | 230 | | | | | 235 | | | | | 240 |
| Val | Leu | Gln | Ser | Ser | Gly | Leu | Tyr | Ser | Leu | Ser | Ser | Val | Val | Thr |
| | | | | 245 | | | | | 250 | | | | | 255 |
| Val | Pro | Ser | Ser | Ser | Leu | Gly | Thr | Gln | Thr | Tyr | Ile | Cys | Asn | Val |
| | | | | 260 | | | | | 265 | | | | | 270 |
| Asn | His | Lys | Pro | Ser | Asn | Thr | Lys | Val | Asp | Lys | Lys | Val | Glu | Pro |
| | | | | 275 | | | | | 280 | | | | | 285 |
| Lys | Ser | Cys | Asp | Lys | Thr | His | Thr | Cys | Pro | Pro | Cys | Pro | Ala | Pro |
| | | | | 290 | | | | | 295 | | | | | 300 |
| Glu | Leu | Leu | Gly | Gly | Pro | Ser | Val | Phe | Leu | Phe | Pro | Pro | Lys | Pro |
| 305 | | | | | 310 | | | | | 315 | | | | | 320 |
| Lys | Asp | Thr | Leu | Met | Ile | Ser | Arg | Thr | Pro | Glu | Val | Thr | Cys | Val |
| | | | | 325 | | | | | 330 | | | | | 335 |
| Val | Val | Asp | Val | Ser | His | Glu | Asp | Pro | Glu | Val | Lys | Phe | Asn | Trp |
| | | | | 340 | | | | | 345 | | | | | 350 |
| Tyr | Val | Asp | Gly | Val | Glu | Val | His | Asn | Ala | Lys | Thr | Lys | Pro | Arg |
| | | | | 355 | | | | | 360 | | | | | 365 |
| Glu | Glu | Gln | Tyr | Asn | Ser | Thr | Tyr | Arg | Val | Val | Ser | Val | Leu | Thr |
| | | | | | | | | | | | | | | |
| Val | Leu | His | Gln | Asp | Trp | Leu | Asn | Gly | Lys | Glu | Tyr | Lys | Cys | Lys |
| Val | Ser | Asn | Lys | Ala | Leu | Pro | Ala | Pro | | | | | | |

```
                370                 375                 380
Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
                420                 425                 430

Glu Trp Glu Ser Asn Gly Gln Pro Glu Asn Asn Tyr Lys Thr Thr Pro
                435                 440                 445

Pro Val Leu Asp Ser Asp Gly Ser Phe Phe Leu Tyr Ser Lys Leu Thr
                450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 72
<211> LENGTH: 504
<212> TYPE: PRT
<213> ORGANISM: artificial
<220> FEATURE:
<223> OTHER INFORMATION: NP engrafted HC

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Gly
                20                  25                  30

Ser Gly Ser Gly Ser Gly Ser Gly Ser Pro Asp Gly Ser Gly Ser Gly
                35                  40                  45

Ser Leu Arg Arg Ser Ser Cys Phe Gly Gly Arg Met Asp Arg Ile Gly
                50                  55                  60

Ala Gln Ser Gly Leu Gly Cys Asn Ser Phe Arg Tyr Gly Ser Tyr Gly
65              70                  75                  80

Ser Gly Ser Gly Ser Gly Ser Gly Met Ser Trp Val Arg Gln
                85                  90                  95

Ala Pro Gly Lys Gly Leu Glu Trp Val Ser Ala Ile Ser Gly Ser Gly
                100                 105                 110

Gly Ser Thr Tyr Tyr Ala Asp Ser Val Lys Gly Arg Phe Thr Ile Ser
                115                 120                 125

Arg Asp Asn Ser Lys Asn Thr Leu Tyr Leu Gln Met Asn Ser Leu Arg
                130                 135                 140

Ala Glu Asp Thr Ala Val Tyr Tyr Cys Ala Lys Leu Thr Gly Ala Glu
145                 150                 155                 160

Tyr Phe Gln His Trp Gly Gln Gly Thr Leu Val Thr Val Ser Ser Ala
                165                 170                 175

Ser Thr Lys Gly Pro Ser Val Phe Pro Leu Ala Pro Ser Ser Lys Ser
                180                 185                 190

Thr Ser Gly Gly Thr Ala Ala Leu Gly Cys Leu Val Lys Asp Tyr Phe
                195                 200                 205

Pro Glu Pro Val Thr Val Ser Trp Asn Ser Gly Ala Leu Thr Ser Gly
                210                 215                 220

Val His Thr Phe Pro Ala Val Leu Gln Ser Ser Gly Leu Tyr Ser Leu
225                 230                 235                 240
```

Ser Ser Val Val Thr Val Pro Ser Ser Leu Gly Thr Gln Thr Tyr
            245                 250                 255

Ile Cys Asn Val Asn His Lys Pro Ser Asn Thr Lys Val Asp Lys Lys
            260                 265                 270

Val Glu Pro Lys Ser Cys Asp Lys Thr His Thr Cys Pro Pro Cys Pro
            275                 280                 285

Ala Pro Glu Leu Leu Gly Gly Pro Ser Val Phe Leu Phe Pro Pro Lys
            290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
            325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
            355                 360                 365

Gln Asp Trp Leu Asn Gly Lys Glu Tyr Lys Cys Lys Val Ser Asn Lys
            370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Asp Glu Leu
            405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
            450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
            485                 490                 495

Lys Ser Leu Ser Leu Ser Pro Gly
            500

<210> SEQ ID NO 73
<211> LENGTH: 500
<212> TYPE: PRT
<213> ORGANISM: artificial
<220> FEATURE:
<223> OTHER INFORMATION: NP engrafted HC

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Pro Asn Pro Asn Lys Asn Pro Asn Pro Asn Pro
50 55 60

Gly Ser Gly Gly Ser Leu Arg Arg Ser Ser Cys Phe Gly Gly Arg Met
65 70 75 80

Asp Arg Ile Gly Ala Gln Ser Gly Leu Gly Cys Asn Ser Phe Arg Tyr
85 90 95

```
Gly Ser Asn Pro Asn Glu Asn Pro Asn Pro Gly Ser Thr Tyr
            100                 105                 110

Tyr Ala Asp Ser Val Lys Gly Arg Phe Thr Ile Ser Arg Asp Asn Ser
            115                 120                 125

Lys Asn Thr Leu Tyr Leu Gln Met Asn Ser Leu Arg Ala Glu Asp Thr
130                 135                 140

Ala Val Tyr Tyr Cys Ala Lys Leu Thr Gly Ala Glu Tyr Phe Gln His
145                 150                 155                 160

Trp Gly Gln Gly Thr Leu Val Thr Val Ser Ala Ser Thr Lys Gly
                165                 170                 175

Pro Ser Val Phe Pro Leu Ala Pro Ser Ser Lys Ser Thr Ser Gly Gly
                180                 185                 190

Thr Ala Ala Leu Gly Cys Leu Val Lys Asp Tyr Phe Pro Glu Pro Val
            195                 200                 205

Thr Val Ser Trp Asn Ser Gly Ala Leu Thr Ser Gly Val His Thr Phe
            210                 215                 220

Pro Ala Val Leu Gln Ser Ser Gly Leu Tyr Ser Leu Ser Ser Val Val
225                 230                 235                 240

Thr Val Pro Ser Ser Ser Leu Gly Thr Gln Thr Tyr Ile Cys Asn Val
                245                 250                 255

Asn His Lys Pro Ser Asn Thr Lys Val Asp Lys Lys Val Glu Pro Lys
                260                 265                 270

Ser Cys Asp Lys Thr His Thr Cys Pro Pro Cys Pro Ala Pro Glu Leu
            275                 280                 285

Leu Gly Gly Pro Ser Val Phe Leu Phe Pro Pro Lys Pro Lys Asp Thr
            290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
            355                 360                 365

Asn Gly Lys Glu Tyr Lys Cys Lys Val Ser Asn Lys Ala Leu Pro Ala
            370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Lys Asn Gln
                405                 410                 415

Val Ser Leu Thr Cys Leu Val Lys Gly Phe Tyr Pro Ser Asp Ile Ala
                420                 425                 430

Val Glu Trp Glu Ser Asn Gly Gln Pro Glu Asn Asn Tyr Lys Thr Thr
            435                 440                 445

Pro Pro Val Leu Asp Ser Asp Gly Ser Phe Phe Leu Tyr Ser Lys Leu
            450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly
                500
```

<210> SEQ ID NO 74
<211> LENGTH: 502
<212> TYPE: PRT
<213> ORGANISM: artificial
<220> FEATURE:
<223> OTHER INFORMATION: NP engrafted HC

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Thr Tyr Ile Ser Asn Val Asn His Lys Pro
    50                  55                  60

Asp Gly Gly Ser Gly Gly Ser Leu Arg Arg Ser Ser Cys Phe Gly Gly
65                  70                  75                  80

Arg Met Asp Arg Ile Gly Ala Gln Ser Gly Leu Gly Cys Asn Ser Phe
                85                  90                  95

Arg Tyr Gly Ser Asn Thr Lys Val Asp Lys Val Glu Gly Gly Ser
            100                 105                 110

Thr Tyr Tyr Ala Asp Ser Val Lys Gly Arg Phe Thr Ile Ser Arg Asp
        115                 120                 125

Asn Ser Lys Asn Thr Leu Tyr Leu Gln Met Asn Ser Leu Arg Ala Glu
    130                 135                 140

Asp Thr Ala Val Tyr Tyr Cys Ala Lys Leu Thr Gly Ala Glu Tyr Phe
145                 150                 155                 160

Gln His Trp Gly Gln Gly Thr Leu Val Thr Val Ser Ser Ala Ser Thr
                165                 170                 175

Lys Gly Pro Ser Val Phe Pro Leu Ala Pro Ser Ser Lys Ser Thr Ser
            180                 185                 190

Gly Gly Thr Ala Ala Leu Gly Cys Leu Val Lys Asp Tyr Phe Pro Glu
        195                 200                 205

Pro Val Thr Val Ser Trp Asn Ser Gly Ala Leu Thr Ser Gly Val His
    210                 215                 220

Thr Phe Pro Ala Val Leu Gln Ser Ser Gly Leu Tyr Ser Leu Ser Ser
225                 230                 235                 240

Val Val Thr Val Pro Ser Ser Ser Leu Gly Thr Gln Thr Tyr Ile Cys
                245                 250                 255

Asn Val Asn His Lys Pro Ser Asn Thr Lys Val Asp Lys Lys Val Glu
            260                 265                 270

Pro Lys Ser Cys Asp Lys Thr His Thr Cys Pro Pro Cys Pro Ala Pro
        275                 280                 285

Glu Leu Leu Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365
```

```
Trp Leu Asn Gly Lys Glu Tyr Lys Cys Lys Val Ser Asn Lys Ala Leu
    370                 375                 380
Pro Ala Pro Ile Glu Lys Thr Ile Ser Lys Ala Lys Gly Gln Pro Arg
385                 390                 395                 400
Glu Pro Gln Val Tyr Thr Leu Pro Pro Ser Arg Asp Glu Leu Thr Lys
                405                 410                 415
Asn Gln Val Ser Leu Thr Cys Leu Val Lys Gly Phe Tyr Pro Ser Asp
            420                 425                 430
Ile Ala Val Glu Trp Glu Ser Asn Gly Gln Pro Glu Asn Asn Tyr Lys
            435                 440                 445
Thr Thr Pro Pro Val Leu Asp Ser Asp Gly Ser Phe Phe Leu Tyr Ser
450                 455                 460
Lys Leu Thr Val Asp Lys Ser Arg Trp Gln Gln Gly Asn Val Phe Ser
465                 470                 475                 480
Cys Ser Val Met His Glu Ala Leu His Asn His Tyr Thr Gln Lys Ser
                485                 490                 495
Leu Ser Leu Ser Pro Gly
            500
```

<210> SEQ ID NO 75
<211> LENGTH: 500
<212> TYPE: PRT
<213> ORGANISM: artificial
<220> FEATURE:
<223> OTHER INFORMATION: NP engrafted HC

<400> SEQUENCE: 75

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val

```
Pro Ala Val Leu Gln Ser Gly Leu Tyr Ser Leu Ser Val Val
225                 230                 235                 240

Thr Val Pro Ser Ser Leu Gly Thr Gln Thr Tyr Ile Cys Asn Val
                245                 250                 255

Asn His Lys Pro Ser Asn Thr Lys Val Asp Lys Lys Val Glu Pro Lys
            260                 265                 270

Ser Cys Asp Lys Thr His Thr Cys Pro Pro Cys Pro Ala Pro Glu Leu
        275                 280                 285

Leu Gly Gly Pro Ser Val Phe Leu Phe Pro Pro Lys Pro Lys Asp Thr
        290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Lys Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Lys Leu
        450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly
            500

<210> SEQ ID NO 76
<211> LENGTH: 501
<212> TYPE: PRT
<213> ORGANISM: artificial
<220> FEATURE:
<223> OTHER INFORMATION: NP engrafted HC

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Gly
            20                  25                  30

Ser Gly Ser Gly Ser Gly Ser Gly Ser Pro Asp Gly Gly Ser Gly Gly
        35                  40                  45

Ser Leu Arg Arg Ser Ser Cys Phe Gly Gly Arg Met Asp Arg Ile Gly
    50                  55                  60

Ala Gln Ser Gly Leu Gly Cys Asn Ser Phe Arg Tyr Gly Ser Tyr Gly
65                  70                  75                  80
```

```
Ser Gly Ser Gly Ser Gly Ser Gly Met Ser Trp Val Arg Gln
                85              90              95
Ala Pro Gly Lys Gly Leu Glu Trp Val Ser Ala Ile Ser Gly Ser Gly
            100             105             110
Gly Ser Thr Tyr Tyr Ala Asp Ser Val Lys Gly Arg Phe Thr Ile Ser
        115             120             125
Arg Asp Asn Ser Lys Asn Thr Leu Tyr Leu Gln Met Asn Ser Leu Arg
    130             135             140
Ala Glu Asp Thr Ala Val Tyr Tyr Cys Ala Lys Leu Thr Gly Ala Glu
145             150             155             160
Tyr Phe Gln His Trp Gly Gln Gly Thr Leu Val Thr Val Ser Ser Ala
                165             170             175
Ser Thr Lys Gly Pro Ser Val Phe Pro Leu Ala Pro Cys Ser Arg Ser
            180             185             190
Thr Ser Glu Ser Thr Ala Ala Leu Gly Cys Leu Val Lys Asp Tyr Phe
        195             200             205
Pro Glu Pro Val Thr Val Ser Trp Asn Ser Gly Ala Leu Thr Ser Gly
    210             215             220
Val His Thr Phe Pro Ala Val Leu Gln Ser Ser Gly Leu Tyr Ser Leu
225             230             235             240
Ser Ser Val Val Thr Val Pro Ser Ser Ser Leu Gly Thr Lys Thr Tyr
                245             250             255
Thr Cys Asn Val Asp His Lys Pro Ser Asn Thr Lys Val Asp Lys Arg
            260             265             270
Val Glu Ser Lys Tyr Gly Pro Pro Cys Pro Pro Cys Pro Ala Pro Glu
        275             280             285
Phe Leu Gly Gly Pro Ser Val Phe Leu Phe Pro Pro Lys Pro Lys Asp
    290             295             300
Thr Leu Met Ile Ser Arg Thr Pro Glu Val Thr Cys Val Val Val Asp
305             310             315             320
Val Ser Gln Glu Asp Pro Glu Val Gln Phe Asn Trp Tyr Val Asp Gly
                325             330             335
Val Glu Val His Asn Ala Lys Thr Lys Pro Arg Glu Glu Gln Phe Asn
            340             345             350
Ser Thr Tyr Arg Val Val Ser Val Leu Thr Val Leu His Gln Asp Trp
        355             360             365
Leu Asn Gly Lys Glu Tyr Lys Cys Lys Val Ser Asn Lys Gly Leu Pro
    370             375             380
Ser Ser Ile Glu Lys Thr Ile Ser Lys Ala Lys Gly Gln Pro Arg Glu
385             390             395             400
Pro Gln Val Tyr Thr Leu Pro Pro Ser Gln Glu Glu Met Thr Lys Asn
                405             410             415
Gln Val Ser Leu Thr Cys Leu Val Lys Gly Phe Tyr Pro Ser Asp Ile
            420             425             430
Ala Val Glu Trp Glu Ser Asn Gly Gln Pro Glu Asn Asn Tyr Lys Thr
        435             440             445
Thr Pro Pro Val Leu Asp Ser Asp Gly Ser Phe Phe Leu Tyr Ser Arg
    450             455             460
Leu Thr Val Asp Lys Ser Arg Trp Gln Glu Gly Asn Val Phe Ser Cys
465             470             475             480
Ser Val Met His Glu Ala Leu His Asn His Tyr Thr Gln Lys Ser Leu
                485             490             495
Ser Leu Ser Leu Gly
```

<210> SEQ ID NO 77
<211> LENGTH: 493
<212> TYPE: PRT
<213> ORGANISM: artificial
<220> FEATURE:
<223> OTHER INFORMATION: NP engrafted HC

<400> SEQUENCE: 77

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Gly
            20                  25                  30

Ser Gly Ser Gly Gly Ser Gly Gly Ser Leu Arg Arg Ser Ser Cys Phe
        35                  40                  45

Gly Gly Arg Met Asp Arg Ile Gly Ala Gln Ser Gly Leu Gly Cys Asn
    50                  55                  60

Ser Phe Arg Tyr Gly Gly Ser Gly Gly Ser Gly Ser Gly Ser Gly Met
65                  70                  75                  80

Ser Trp Val Arg Gln Ala Pro Gly Lys Gly Leu Glu Trp Val Ser Ala
                85                  90                  95

Ile Ser Gly Ser Gly Gly Ser Thr Tyr Tyr Ala Asp Ser Val Lys Gly
            100                 105                 110

Arg Phe Thr Ile Ser Arg Asp Asn Ser Lys Asn Thr Leu Tyr Leu Gln
        115                 120                 125

Met Asn Ser Leu Arg Ala Glu Asp Thr Ala Val Tyr Tyr Cys Ala Lys
    130                 135                 140

Leu Thr Gly Ala Glu Tyr Phe Gln His Trp Gly Gln Gly Thr Leu Val
145                 150                 155                 160

Thr Val Ser Ser Ala Ser Thr Lys Gly Pro Ser Val Phe Pro Leu Ala
                165                 170                 175

Pro Ser Ser Lys Ser Thr Ser Gly Gly Thr Ala Ala Leu Gly Cys Leu
            180                 185                 190

Val Lys Asp Tyr Phe Pro Glu Pro Val Thr Val Ser Trp Asn Ser Gly
        195                 200                 205

Ala Leu Thr Ser Gly Val His Thr Phe Pro Ala Val Leu Gln Ser Ser
    210                 215                 220

Gly Leu Tyr Ser Leu Ser Ser Val Val Thr Val Pro Ser Ser Ser Leu
225                 230                 235                 240

Gly Thr Gln Thr Tyr Ile Cys Asn Val Asn His Lys Pro Ser Asn Thr
                245                 250                 255

Lys Val Asp Lys Lys Val Glu Pro Lys Ser Cys Asp Lys Thr His Thr
            260                 265                 270

Cys Pro Pro Cys Pro Ala Pro Glu Leu Leu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
```

```
            355                 360                 365
Lys Val Ser Asn Lys Ala Leu Pro Ala Pro Ile Glu Lys Thr Ile Ser
370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
                420                 425                 430

Gln Pro Glu Asn Asn Tyr Lys Thr Thr Pro Pro Val Leu Asp Ser Asp
                435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly
                485                 490

<210> SEQ ID NO 78
<211> LENGTH: 497
<212> TYPE: PRT
<213> ORGANISM: artificial
<220> FEATURE:
<223> OTHER INFORMATION: NP engrafted HC

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Val Val Val Thr Ser His Gln Ala Pro Gly Glu Gly
        50                  55                  60

Gly Ser Gly Gly Ser Leu Arg Arg Ser Ser Cys Phe Gly Gly Arg Met
65                  70                  75                  80

Asp Arg Ile Gly Ala Gln Ser Gly Leu Gly Cys Asn Ser Phe Arg Tyr
                85                  90                  95

Gly Gly Ser Thr Pro Leu Lys Ser Leu Ala Ser Thr Tyr Tyr Ala Asp
                100                 105                 110

Ser Val Lys Gly Arg Phe Thr Ile Ser Arg Asp Asn Ser Lys Asn Thr
            115                 120                 125

Leu Tyr Leu Gln Met Asn Ser Leu Arg Ala Glu Asp Thr Ala Val Tyr
        130                 135                 140

Tyr Cys Ala Lys Leu Thr Gly Ala Glu Tyr Phe Gln His Trp Gly Gln
145                 150                 155                 160

Gly Thr Leu Val Thr Val Ser Ser Ala Ser Thr Lys Gly Pro Ser Val
                165                 170                 175

Phe Pro Leu Ala Pro Ser Ser Lys Ser Thr Ser Gly Gly Thr Ala Ala
                180                 185                 190

Leu Gly Cys Leu Val Lys Asp Tyr Phe Pro Glu Pro Val Thr Val Ser
            195                 200                 205

Trp Asn Ser Gly Ala Leu Thr Ser Gly Val His Thr Phe Pro Ala Val
        210                 215                 220

Leu Gln Ser Ser Gly Leu Tyr Ser Leu Ser Ser Val Val Thr Val Pro
```

-continued

```
                225                 230                 235                 240
        Ser Ser Ser Leu Gly Thr Gln Thr Tyr Ile Cys Asn Val Asn His Lys
                        245                 250                 255

Pro Ser Asn Thr Lys Val Asp Lys Lys Val Glu Pro Lys Ser Cys Asp
                        260                 265                 270

Lys Thr His Thr Cys Pro Pro Cys Pro Ala Pro Glu Leu Leu Gly Gly
                        275                 280                 285

Pro Ser Val Phe Leu Phe Pro Pro Lys Pro Lys Asp Thr Leu Met Ile
                290                 295                 300

Ser Arg Thr Pro Glu Val Thr Cys Val Val Val Asp Val Ser His Glu
        305                 310                 315                 320

Asp Pro Glu Val Lys Phe Asn Trp Tyr Val Asp Gly Val Glu Val His
                                325                 330                 335

Asn Ala Lys Thr Lys Pro Arg Glu Glu Gln Tyr Asn Ser Thr Tyr Arg
                        340                 345                 350

Val Val Ser Val Leu Thr Val Leu His Gln Asp Trp Leu Asn Gly Lys
                        355                 360                 365

Glu Tyr Lys Cys Lys Val Ser Asn Lys Ala Leu Pro Ala Pro Ile Glu
                370                 375                 380

Lys Thr Ile Ser Lys Ala Lys Gly Gln Pro Arg Glu Pro Gln Val Tyr
        385                 390                 395                 400

Thr Leu Pro Pro Ser Arg Asp Glu Leu Thr Lys Asn Gln Val Ser Leu
                                405                 410                 415

Thr Cys Leu Val Lys Gly Phe Tyr Pro Ser Asp Ile Ala Val Glu Trp
                        420                 425                 430

Glu Ser Asn Gly Gln Pro Glu Asn Asn Tyr Lys Thr Thr Pro Pro Val
                        435                 440                 445

Leu Asp Ser Asp Gly Ser Phe Phe Leu Tyr Ser Lys Leu Thr Val Asp
                450                 455                 460

Lys Ser Arg Trp Gln Gln Gly Asn Val Phe Ser Cys Ser Val Met His
        465                 470                 475                 480

Glu Ala Leu His Asn His Tyr Thr Gln Lys Ser Leu Ser Leu Ser Pro
                                485                 490                 495

Gly

<210> SEQ ID NO 79
<211> LENGTH: 499
<212> TYPE: PRT
<213> ORGANISM: artificial
<220> FEATURE:
<223> OTHER INFORMATION: NP engrafted HC

<400> SEQUENCE: 79

Glu Val Gln Leu Leu Glu Ser Gly Gly Gly Leu Val Gln Pro Gly Gly
        1               5                   10                  15

Ser Leu Arg Leu Ser Cys Ala Ala Ser Gly Phe Thr Phe Ser Ser Tyr
                        20                  25                  30

Ala Met Ser Trp Val Arg Gln Ala Pro Gly Lys Gly Leu Glu Trp Val
                        35                  40                  45

Ser Ala Ile Ser Gly Ser Gly Gly Ser Thr Tyr Tyr Ala Asp Ser Val
                50                  55                  60

Lys Gly Arg Phe Thr Ile Ser Arg Asp Asn Ser Lys Asn Thr Leu Tyr
        65                  70                  75                  80

Leu Gln Met Asn Ser Leu Arg Ala Glu Asp Thr Ala Val Tyr Tyr Cys
                        85                  90                  95
```

```
Ala Lys Gly Ile Thr Gly Thr Lys Tyr Gln Ser Ser Pro Asp Gly
            100                 105                 110

Gly Ser Gly Gly Ser Leu Arg Arg Ser Ser Cys Phe Gly Arg Met
            115                 120                 125

Asp Arg Ile Gly Ala Gln Ser Gly Leu Gly Cys Asn Ser Phe Arg Tyr
            130                 135                 140

Gly Ser Tyr Ser Tyr Thr Tyr Asn Tyr Ala Glu Tyr Phe Gln His Trp
145                 150                 155                 160

Gly Gln Gly Thr Leu Val Thr Val Ser Ser Ala Ser Thr Lys Gly Pro
                165                 170                 175

Ser Val Phe Pro Leu Ala Pro Ser Ser Lys Ser Thr Ser Gly Gly Thr
            180                 185                 190

Ala Ala Leu Gly Cys Leu Val Lys Asp Tyr Phe Pro Glu Pro Val Thr
            195                 200                 205

Val Ser Trp Asn Ser Gly Ala Leu Thr Ser Gly Val His Thr Phe Pro
            210                 215                 220

Ala Val Leu Gln Ser Ser Gly Leu Tyr Ser Leu Ser Ser Val Val Thr
225                 230                 235                 240

Val Pro Ser Ser Ser Leu Gly Thr Gln Thr Tyr Ile Cys Asn Val Asn
                245                 250                 255

His Lys Pro Ser Asn Thr Lys Val Asp Lys Lys Val Glu Pro Lys Ser
            260                 265                 270

Cys Asp Lys Thr His Thr Cys Pro Pro Cys Pro Ala Pro Glu Leu Leu
            275                 280                 285

Gly Gly Pro Ser Val Phe Leu Phe Pro Pro Lys Pro Lys Asp Thr Leu
            290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
            355                 360                 365

Gly Lys Glu Tyr Lys Cys Lys Val Ser Asn Lys Ala Leu Pro Ala Pro
            370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
            435                 440                 445

Pro Val Leu Asp Ser Asp Gly Ser Phe Phe Leu Tyr Ser Lys Leu Thr
            450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly
```

-continued

```
<210> SEQ ID NO 80
<211> LENGTH: 267
<212> TYPE: PRT
<213> ORGANISM: artificial
<220> FEATURE:
<223> OTHER INFORMATION: NP engrafted LC

<400> SEQUENCE: 80

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ala Ala Trp Asn Pro Asn
                85                  90                  95

Pro Asn Pro Asn Pro Asn Gly Gly Ser Gly Gly Ser Leu Arg
            100                 105                 110

Arg Ser Ser Cys Phe Gly Gly Arg Met Asp Arg Ile Gly Ala Gln Ser
            115                 120                 125

Gly Leu Gly Cys Asn Ser Phe Arg Tyr Gly Ser Asn Pro Asn Pro Asn
        130                 135                 140

Pro Asn Pro Asn Pro Asn Val Phe Gly Ser Gly Thr Lys Val Thr Val
145                 150                 155                 160

Leu Gly Gln Pro Lys Ala Ala Pro Ser Val Thr Leu Phe Pro Pro Ser
                165                 170                 175

Ser Glu Glu Leu Gln Ala Asn Lys Ala Thr Leu Val Cys Leu Ile Ser
            180                 185                 190

Asp Phe Tyr Pro Gly Ala Val Thr Val Ala Trp Lys Ala Asp Ser Ser
            195                 200                 205

Pro Val Lys Ala Gly Val Glu Thr Thr Thr Pro Ser Lys Gln Ser Asn
        210                 215                 220

Asn Lys Tyr Ala Ala Ser Ser Tyr Leu Ser Leu Thr Pro Glu Gln Trp
225                 230                 235                 240

Lys Ser His Arg Ser Tyr Ser Cys Gln Val Thr His Glu Gly Ser Thr
                245                 250                 255

Val Glu Lys Thr Val Ala Pro Thr Glu Cys Ser
            260                 265

<210> SEQ ID NO 81
<211> LENGTH: 274
<212> TYPE: PRT
<213> ORGANISM: artificial
<220> FEATURE:
<223> OTHER INFORMATION: NP engrafted LC

<400> SEQUENCE: 81

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45
```

```
Leu Ile Tyr Gly Ser Gly Gly Ser Gly Ser Gly Ser Pro
         50              55              60

Asp Gly Gly Ser Gly Gly Ser Leu Arg Arg Ser Ser Cys Phe Gly Gly
 65              70                  75                  80

Arg Met Asp Arg Ile Gly Ala Gln Ser Gly Leu Gly Cys Asn Ser Phe
                 85                  90                  95

Arg Tyr Gly Ser Tyr Gly Ser Gly Gly Ser Gly Ser Gly Ser Gly Asn
             100                 105                 110

Arg Pro Ser Gly Val Pro Asp Arg Phe Ser Gly Ser Lys Ser Gly Thr
         115                 120                 125

Ser Ala Ser Leu Ala Ile Thr Gly Leu Gln Ala Glu Asp Glu Ala Asp
     130                 135                 140

Tyr Tyr Cys Gln Ser Tyr Asp Ser Ser Leu Ser Gly Val Val Phe Gly
145             150                 155                 160

Gly Gly Thr Lys Leu Thr Val Leu Gly Gln Pro Lys Ala Ala Pro Ser
                 165                 170                 175

Val Thr Leu Phe Pro Pro Ser Ser Glu Glu Leu Gln Ala Asn Lys Ala
             180                 185                 190

Thr Leu Val Cys Leu Ile Ser Asp Phe Tyr Pro Gly Ala Val Thr Val
         195                 200                 205

Ala Trp Lys Ala Asp Ser Ser Pro Val Lys Ala Gly Val Glu Thr Thr
     210                 215                 220

Thr Pro Ser Lys Gln Ser Asn Asn Lys Tyr Ala Ala Ser Ser Tyr Leu
225             230                 235                 240

Ser Leu Thr Pro Glu Gln Trp Lys Ser His Arg Ser Tyr Ser Cys Gln
                 245                 250                 255

Val Thr His Glu Gly Ser Thr Val Glu Lys Thr Val Ala Pro Thr Glu
             260                 265                 270

Cys Ser
```

<210> SEQ ID NO 82
<211> LENGTH: 366
<212> TYPE: DNA
<213> ORGANISM: artificial
<220> FEATURE:
<223> OTHER INFORMATION: NP engrafted HC encoding construct

<400> SEQUENCE: 82

```
gaagtgcagc tgctggaaag cggcggaggc ctggtgcagc ctggcggatc tctgagactg    60
agctgtgccg ccagcggctt caccttcagc agctacgcca tgagctgggt gcgccaggcc   120
cctggaaaag gcctggaatg ggtgtccgcc atctctggca gcggcggcag cacctactac   180
gccgattctg tgaagggccg gttcaccatc agccgggaca acagcaagaa caccctgtac   240
ctgcagatga acagcctgcg ggccgaggac accgccgtgt actactgtac aagcgtgcac   300
caggaaacaa agaagtacca gagcagcccc gacggcggca gtggcggaag tctgagaaga   360
agctcc                                                              366
```

<210> SEQ ID NO 83
<211> LENGTH: 525
<212> TYPE: DNA
<213> ORGANISM: artificial
<220> FEATURE:
<223> OTHER INFORMATION: NP engrafted HC encoding construct

<400> SEQUENCE: 83

```
gaagttcagc tgctggaatc tggcggcgga ctggttcaac tggcggatc tctgagactg     60
```

```
agctgtgccg ccagcggctt tacatttggc agcggctctg gatctggctc cggaagcgga    120
tctcctgatg gtggaagcgg aggcagcctg agaagaagca gctgtttcgg cggcagaatg    180
gacagaatcg gcgcccaatc tggcctgggc tgcaacagct ttagatacgg cagctacggc    240
tccggcagtg gttccggtag tggctctgga atgagctggg ttcgacaggc ccctggcaaa    300
ggccttgaat gggtgtccgc catttctggc agcggaggct ctacctacta cgccgatagc    360
gtgaagggca gattcaccat cagccgggac aacagcaaga cacccctgta cctgcagatg    420
aactccctga gagccgagga caccgccgtg tactattgcg ccaaactgac aggcgccgag    480
tacttccagc attggggaca gggaaccctg gtcacagtct cttca                     525
```

<210> SEQ ID NO 84
<211> LENGTH: 333
<212> TYPE: DNA
<213> ORGANISM: Homo sapiens

<400> SEQUENCE: 84

```
cagtctgtgc tgacacagcc tcctagtgtg tctggcgccc tggccagag agtgaccatc      60 agctgtaccg gcagcagctc caacatcgga gccggctatg acgtgcactg gtatcagcag    120
ctgcctggca ccgcccccaa actgctgatc tacggcaaca gcaaccggcc cagcggcgtg    180
cccgatagat tttccggcag caagagcggc accagcgcca gcctggctat tactggactg    240
caggccgagg acgaggccga ctactactgc cagagctacg acagcagcct gagcggcgtg    300
gtgtttggcg gcggaacaaa gctgaccgtg cta                                 333
```

<210> SEQ ID NO 85
<211> LENGTH: 98
<212> TYPE: PRT
<213> ORGANISM: Homo sapiens

<400> SEQUENCE: 85

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 86
<211> LENGTH: 17
<212> TYPE: PRT
<213> ORGANISM: Homo sapiens

<400> SEQUENCE: 86

```
Ala Glu Tyr Phe Gln His Trp Gly Gln Gly Thr Leu Val Thr Val Ser
1               5                   10                  15

Ser
```

-continued

```
<210> SEQ ID NO 87
<211> LENGTH: 329
<212> TYPE: PRT
<213> ORGANISM: Homo sapiens

<400> SEQUENCE: 87
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

```
<210> SEQ ID NO 88
<211> LENGTH: 99
<212> TYPE: PRT
<213> ORGANISM: Homo sapiens

<400> SEQUENCE: 88
```

Gln Ser Val Leu Thr Gln Pro Pro Ser Val Ser Gly Ala Pro Gly Gln

```
                1               5                  10                 15
            Arg Val Thr Ile Ser Cys Thr Gly Ser Ser Asn Ile Gly Ala Gly
                            20                  25                  30

Tyr Asp Val His Trp Tyr Gln Gln Leu Pro Gly Thr Ala Pro Lys Leu
                            35                  40                  45

Leu Ile Tyr Gly Asn Ser Asn Arg Pro Ser Gly Val Pro Asp Arg Phe
                            50                  55                  60

Ser Gly Ser Lys Ser Gly Thr Ser Ala Ser Leu Ala Ile Thr Gly Leu
             65                  70                  75                  80

Gln Ala Glu Asp Glu Ala Asp Tyr Tyr Cys Gln Ser Tyr Asp Ser Ser
                            85                  90                  95

Leu Ser Gly

<210> SEQ ID NO 89
<211> LENGTH: 12
<212> TYPE: PRT
<213> ORGANISM: Homo sapiens

<400> SEQUENCE: 89

Val Val Phe Gly Gly Gly Thr Lys Leu Thr Val Leu
1               5                   10

<210> SEQ ID NO 90
<211> LENGTH: 106
<212> TYPE: PRT
<213> ORGANISM: Homo sapiens

<400> SEQUENCE: 90

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
                35                  40                  45

Val Lys Ala Gly Val Glu Thr Thr Thr Pro Ser Lys Gln Ser Asn Asn
 50                 55                  60

Lys Tyr Ala Ala Ser Ser Tyr Leu Ser Leu Thr Pro Glu Gln Trp Lys
 65                 70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 91
<211> LENGTH: 18
<212> TYPE: PRT
<213> ORGANISM: artificial
<220> FEATURE:
<223> OTHER INFORMATION: NP variant
<220> FEATURE:
<221> NAME/KEY: VARIANT
<222> LOCATION: (1)..(1)
<223> OTHER INFORMATION: Xaa = Gly or Ser
<220> FEATURE:
<221> NAME/KEY: VARIANT
<222> LOCATION: (5)..(5)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: Xaa = Arg or Lys
<220> FEATURE:
```

```
<221> NAME/KEY: VARIANT
<222> LOCATION: (7)..(7)
<223> OTHER INFORMATION: Xaa can be any naturally occurring amino acid
<220> FEATURE:
<221> NAME/KEY: VARIANT
<222> LOCATION: (11)..(11)
<223> OTHER INFORMATION: Xaa = Gly or Ser
<220> FEATURE:
<221> NAME/KEY: VARIANT
<222> LOCATION: (12)..(12)
<223> OTHER INFORMATION: Xaa = Ala or Ser
<220> FEATURE:
<221> NAME/KEY: VARIANT
<222> LOCATION: (13)..(13)
<223> OTHER INFORMATION: Xaa can be any naturally occurring amino acid
<220> FEATURE:
<221> NAME/KEY: VARIANT
<222> LOCATION: (15)..(15)
<223> OTHER INFORMATION: Xaa can be any naturally occurring amino acid

<400> SEQUENCE: 91

Xaa Cys Phe Gly Xaa Xaa Xaa Asp Arg Ile Xaa Xaa Xaa Ser Xaa Leu
1               5                   10                  15

Gly Cys

<210> SEQ ID NO 92
<211> LENGTH: 7
<212> TYPE: PRT
<213> ORGANISM: artificial
<220> FEATURE:
<223> OTHER INFORMATION: N-terminal sequence (with ref aa)

<400> SEQUENCE: 92

Ser Gly Phe Thr Phe Ser Ser
1               5

<210> SEQ ID NO 93
<211> LENGTH: 10
<212> TYPE: PRT
<213> ORGANISM: artificial
<220> FEATURE:
<223> OTHER INFORMATION: N-terminal sequence (with ref aa)

<400> SEQUENCE: 93

Ser Gly Phe Thr Phe Gly Ser Gly Ser Gly
1               5                   10

<210> SEQ ID NO 94
<211> LENGTH: 6
<212> TYPE: PRT
<213> ORGANISM: artificial
<220> FEATURE:
<223> OTHER INFORMATION: C-terminal sequence (with ref aa)

<400> SEQUENCE: 94

Gly Ser Gly Ser Gly Met
1               5

<210> SEQ ID NO 95
<211> LENGTH: 13
<212> TYPE: PRT
<213> ORGANISM: artificial
<220> FEATURE:
<223> OTHER INFORMATION: N-terminal sequence (with ref aa)

<400> SEQUENCE: 95

Ser Gly Phe Thr Phe Gly Ser Gly Ser Gly Ser Gly Ser
1               5                   10
```

```
<210> SEQ ID NO 96
<211> LENGTH: 9
<212> TYPE: PRT
<213> ORGANISM: artificial
<220> FEATURE:
<223> OTHER INFORMATION: C-terminal sequence (with ref aa)

<400> SEQUENCE: 96

Ser Gly Ser Gly Ser Gly Ser Gly Met
1               5

<210> SEQ ID NO 97
<211> LENGTH: 16
<212> TYPE: PRT
<213> ORGANISM: artificial
<220> FEATURE:
<223> OTHER INFORMATION: N-terminal sequence (with ref aa)

<400> SEQUENCE: 97

Ser Gly Phe Thr Phe Gly Ser Gly Ser Gly Ser Gly Gly Ser Gly Gly
1               5                   10                  15

<210> SEQ ID NO 98
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 98

Gly Gly Ser Gly Gly Ser Gly Ser Gly Ser Gly Met
1               5                   10

<210> SEQ ID NO 99
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 99

Ser Gly Phe Thr Phe Gly Ser Gly Ser Gly Ser Gly Ser Gly Gly Gly
1               5                   10                  15

Ser Gly Gly

<210> SEQ ID NO 100
<211> LENGTH: 11
<212> TYPE: PRT
<213> ORGANISM: artificial
<220> FEATURE:
<223> OTHER INFORMATION: C-terminal sequence (with ref aa)

<400> SEQUENCE: 100

Gly Ser Gly Ser Gly Gly Ser Gly Ser Gly Met
1               5                   10

<210> SEQ ID NO 101
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 101

Ser Pro Ala Val Val Tyr Ile Glu Ile Leu Asp Arg His Pro Asp Gly
1               5                   10                  15
```

```
Gly Ser Gly Gly
        20

<210> SEQ ID NO 102
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 102

Gly Ser Gly Arg Glu Val Pro Ile Ser Asn Gly Ser Gly Phe Val Val
1               5                   10                  15

Ala Met

<210> SEQ ID NO 103
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 103

Ser Gly Ala Val Val Tyr Ile Glu Ile Leu Asp Arg His Pro Asp Gly
1               5                   10                  15

Gly Ser Gly Gly
        20

<210> SEQ ID NO 104
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 104

Ser Ser Ser Asp Arg Ser Ala Leu Leu Lys Ser Lys Leu Arg Ala Leu
1               5                   10                  15

Leu Thr Ala Pro Arg
        20

<210> SEQ ID NO 105
<211> LENGTH: 24
<212> TYPE: PRT
<213> ORGANISM: artificial
<220> FEATURE:
<223> OTHER INFORMATION: N-terminal sequence (with ref aa)

<400> SEQUENCE: 105

Ser Gly Phe Thr Phe Gly Ser Gly Ser Gly Ser Gly Ser Gly Ser Gly
1               5                   10                  15

Ser Pro Asp Gly Gly Ser Gly Gly
        20

<210> SEQ ID NO 106
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 106

Gly Ser Tyr Gly Ser Gly Ser Gly Ser Gly Ser Gly Ser Gly Met
1               5                   10                  15
```

```
<210> SEQ ID NO 107
<211> LENGTH: 25
<212> TYPE: PRT
<213> ORGANISM: artificial
<220> FEATURE:
<223> OTHER INFORMATION: N-terminal sequence (with ref aa)

<400> SEQUENCE: 107

Ser Gly Phe Thr Phe Ser Ser Asp Arg Ser Ala Leu Leu Lys Ser Lys
1               5                   10                  15

Leu Arg Ala Leu Leu Thr Ala Pro Arg
            20                  25

<210> SEQ ID NO 108
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 108

Gly Ser Gly Ser Gly Ser Gly Ser Gly Ser Gly Ser Gly Met
1               5                   10

<210> SEQ ID NO 109
<211> LENGTH: 4
<212> TYPE: PRT
<213> ORGANISM: artificial
<220> FEATURE:
<223> OTHER INFORMATION: N-terminal sequence (with ref aa)

<400> SEQUENCE: 109

Ile Ser Gly Ser
1

<210> SEQ ID NO 110
<211> LENGTH: 4
<212> TYPE: PRT
<213> ORGANISM: artificial
<220> FEATURE:
<223> OTHER INFORMATION: C-terminal sequence (with ref aa)

<400> SEQUENCE: 110

Gly Gly Ser Thr
1

<210> SEQ ID NO 111
<211> LENGTH: 8
<212> TYPE: PRT
<213> ORGANISM: artificial
<220> FEATURE:
<223> OTHER INFORMATION: N-terminal sequence (with ref aa)

<400> SEQUENCE: 111

Ile Ser Gly Ser Gly Ser Gly Ser
1               5

<210> SEQ ID NO 112
<211> LENGTH: 8
<212> TYPE: PRT
<213> ORGANISM: artificial
<220> FEATURE:
<223> OTHER INFORMATION: C-terminal sequence (with ref aa)

<400> SEQUENCE: 112
```

Gly Ser Gly Ser Gly Gly Ser Thr
1               5

<210> SEQ ID NO 113
<211> LENGTH: 9
<212> TYPE: PRT
<213> ORGANISM: artificial
<220> FEATURE:
<223> OTHER INFORMATION: N-terminal sequence (with ref aa)

<400> SEQUENCE: 113

Ile Ser Gly Ser Gly Ser Gly Ser Gly
1               5

<210> SEQ ID NO 114
<211> LENGTH: 10
<212> TYPE: PRT
<213> ORGANISM: artificial
<220> FEATURE:
<223> OTHER INFORMATION: C-terminal sequence (with ref aa)

<400> SEQUENCE: 114

Gly Ser Ser Gly Ser Gly Ser Gly Ser Thr
1               5                   10

<210> SEQ ID NO 115
<211> LENGTH: 11
<212> TYPE: PRT
<213> ORGANISM: artificial
<220> FEATURE:
<223> OTHER INFORMATION: N-terminal sequence (with ref aa)

<400> SEQUENCE: 115

Ile Ser Gly Ser Gly Ser Gly Ser Gly Ser Gly
1               5                   10

<210> SEQ ID NO 116
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 116

Gly Ser Ser Gly Ser Gly Ser Gly Ser Gly Ser Thr
1               5                   10

<210> SEQ ID NO 117
<211> LENGTH: 12
<212> TYPE: PRT
<213> ORGANISM: artificial
<220> FEATURE:
<223> OTHER INFORMATION: N-terminal sequence (with ref aa)

<400> SEQUENCE: 117

Ile Ser Gly Ser Gly Ser Gly Ser Gly Ser Gly Gly
1               5                   10

<210> SEQ ID NO 118
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 118

Gly Glu Lys Glu Lys Glu Lys Val Ser Thr Ala Val Gly Ser Thr

<210> SEQ ID NO 119
<211> LENGTH: 13
<212> TYPE: PRT
<213> ORGANISM: artificial
<220> FEATURE:
<223> OTHER INFORMATION: N-terminal sequence (with ref aa)

<400> SEQUENCE: 119

Ile Ser Gly Ser Ala Val Val Asn Gly Gly Ser Gly Gly
1               5                   10

<210> SEQ ID NO 120
<211> LENGTH: 9
<212> TYPE: PRT
<213> ORGANISM: artificial
<220> FEATURE:
<223> OTHER INFORMATION: C-terminal sequence (with ref aa)

<400> SEQUENCE: 120

Gly Lys Ile Ala Ile Gly Gly Ser Thr
1               5

<210> SEQ ID NO 121
<211> LENGTH: 14
<212> TYPE: PRT
<213> ORGANISM: artificial
<220> FEATURE:
<223> OTHER INFORMATION: N-terminal sequence (with ref aa)

<400> SEQUENCE: 121

Ile Ser Gly Pro Asn Pro Asn Lys Asn Pro Asn Pro Gly Gly
1               5                   10

<210> SEQ ID NO 122
<211> LENGTH: 13
<212> TYPE: PRT
<213> ORGANISM: artificial
<220> FEATURE:
<223> OTHER INFORMATION: C-terminal sequence (with ref aa)

<400> SEQUENCE: 122

Gly Ser Asn Glu Asn Pro Asn Pro Asn Pro Gly Ser Thr
1               5                   10

<210> SEQ ID NO 123
<211> LENGTH: 15
<212> TYPE: PRT
<213> ORGANISM: artificial
<220> FEATURE:
<223> OTHER INFORMATION: N-terminal sequence (with ref aa)

<400> SEQUENCE: 123

Ile Ser Gly Ser Val Val Val Thr Ser His Gly Gly Ser Gly Gly
1               5                   10                  15

<210> SEQ ID NO 124
<211> LENGTH: 10
<212> TYPE: PRT
<213> ORGANISM: artificial
<220> FEATURE:
<223> OTHER INFORMATION: C-terminal sequence (with ref aa)

<400> SEQUENCE: 124

Gly Gly Ser Gly Ser Gly Ser Gly Ser Thr
1               5                   10

<210> SEQ ID NO 125
<211> LENGTH: 15
<212> TYPE: PRT
<213> ORGANISM: artificial
<220> FEATURE:
<223> OTHER INFORMATION: N-terminal sequence (with ref aa)

<400> SEQUENCE: 125

Ile Ser Gly Ser Ala Val Val Asn Val Arg Gly Gly Ser Gly Gly
1               5                   10                  15

<210> SEQ ID NO 126
<211> LENGTH: 11
<212> TYPE: PRT
<213> ORGANISM: artificial
<220> FEATURE:
<223> OTHER INFORMATION: C-terminal sequence (with ref aa)

<400> SEQUENCE: 126

Gly Gly Asp Lys Ile Ala Ile Gly Gly Ser Thr
1               5                   10

<210> SEQ ID NO 127
<211> LENGTH: 15
<212> TYPE: PRT
<213> ORGANISM: artificial
<220> FEATURE:
<223> OTHER INFORMATION: N-terminal sequence (with ref aa)

<400> SEQUENCE: 127

Ile Ser Gly Ser Gly Ser Gly Ser Gly Ser Gly Ser Ser Gly Gly
1               5                   10                  15

<210> SEQ ID NO 128
<211> LENGTH: 15
<212> TYPE: PRT
<213> ORGANISM: artificial
<220> FEATURE:
<223> OTHER INFORMATION: N-terminal sequence (with ref aa)

<400> SEQUENCE: 128

Ile Ser Gly Leu Ala Val Gln Ile Arg Arg Gly Gly Ser Gly Gly
1               5                   10                  15

<210> SEQ ID NO 129
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 129

Gly Gly Ser Gly Arg Glu Thr Leu Thr Leu Tyr Val Gly Ser Thr
1               5                   10                  15

<210> SEQ ID NO 130
<211> LENGTH: 16
<212> TYPE: PRT
<213> ORGANISM: artificial
<220> FEATURE:
<223> OTHER INFORMATION: N-terminal sequence (with ref aa)

<400> SEQUENCE: 130

Ile Ser Gly Ser Ala Val Val Asn Val Arg Ala Gly Gly Ser Gly Gly
1               5                   10                  15

<210> SEQ ID NO 131
<211> LENGTH: 16
<212> TYPE: PRT
<213> ORGANISM: artificial
<220> FEATURE:
<223> OTHER INFORMATION: N-terminal sequence (with ref aa)

<400> SEQUENCE: 131

Ile Ser Gly Ser Tyr Ala Met Ser Trp Val Arg Gly Gly Ser Gly Gly
1               5                   10                  15

<210> SEQ ID NO 132
<211> LENGTH: 13
<212> TYPE: PRT
<213> ORGANISM: artificial
<220> FEATURE:
<223> OTHER INFORMATION: C-terminal sequence (with ref aa)

<400> SEQUENCE: 132

Gly Ser Tyr Ala Met Ser Trp Val Arg Gln Gly Ser Thr
1               5                   10

<210> SEQ ID NO 133
<211> LENGTH: 16
<212> TYPE: PRT
<213> ORGANISM: artificial
<220> FEATURE:
<223> OTHER INFORMATION: N-terminal sequence (with ref aa)

<400> SEQUENCE: 133

Ile Ser Gly Pro Asn Pro Asn Lys Asn Pro Asn Pro Asn Gly Gly
1               5                   10                  15

<210> SEQ ID NO 134
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 134

Gly Ser Asn Pro Asn Glu Asn Pro Asn Pro Asn Pro Gly Ser Thr
1               5                   10                  15

<210> SEQ ID NO 135
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 135

Ile Ser Gly Ser Ala Val Val Asn Val Arg Ala Asp Gly Gly Ser Gly
1               5                   10                  15
Gly

<210> SEQ ID NO 136
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 136

Gly Ser Gly Asp Lys Ile Ala Ile Gly Gly Ser Thr
1               5                   10

```
<210> SEQ ID NO 137
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 137

Ile Ser Gly Ser Gly Ser Gly Ser Gly Ser Pro Asp Gly Gly Ser Gly
1               5                   10                  15

Gly

<210> SEQ ID NO 138
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 138

Ile Ser Gly Ser Gly Ser Gly Ser Gly Ser Gly Ser Gly Gly Ser Gly
1               5                   10                  15

Gly

<210> SEQ ID NO 139
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 139

Ile Ser Gly Ser Val Val Val Thr Ser His Gln Ala Pro Gly Ser Gly
1               5                   10                  15

Gly

<210> SEQ ID NO 140
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 140

Gly Ser Gly Glu Lys Lys Lys Leu Lys Ser Leu Ala Tyr Gly Ser Thr
1               5                   10                  15

<210> SEQ ID NO 141
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 141

Ile Ser Gly Arg Tyr Asn Ile Leu Lys Ile Gln Lys Val Gly Ser Gly
1               5                   10                  15

Gly

<210> SEQ ID NO 142
<211> LENGTH: 16
<212> TYPE: PRT
<213> ORGANISM: artificial
```

```
<220> FEATURE:
<223> OTHER INFORMATION: C-terminal sequence (with ref aa)

<400> SEQUENCE: 142

Gly Gly Ser Gly Glu Tyr Leu Ile Thr Tyr Gln Ile Met Gly Ser Thr
1               5                   10                  15

<210> SEQ ID NO 143
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 143

Ile Ser Gly Arg Gln Leu Leu Phe Cys Arg Val Thr Leu Gly Ser Gly
1               5                   10                  15

Gly

<210> SEQ ID NO 144
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 144

Gly Gly Ser Gly Glu Gln Ala Tyr Pro Glu Tyr Leu Ile Thr Tyr Gly
1               5                   10                  15

Ser Thr

<210> SEQ ID NO 145
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 145

Ile Ser Val Val Val Thr Ser His Gln Ala Pro Gly Glu Gly Gly Ser
1               5                   10                  15

Gly Gly

<210> SEQ ID NO 146
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 146

Gly Glu Lys Lys Lys Leu Lys Ser Leu Ala Ser Thr
1               5                   10

<210> SEQ ID NO 147
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 147

Ile Ser Gly Val Val Thr Ser His Gln Ala Pro Gly Glu Gly Gly Ser
1               5                   10                  15
```

Gly Gly

<210> SEQ ID NO 148
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 148

Gly Glu Lys Lys Lys Leu Lys Ser Leu Gly Ser Thr
1               5                   10

<210> SEQ ID NO 149
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 149

Gly Glu Lys Lys Lys Leu Lys Ser Gly Gly Ser Thr
1               5                   10

<210> SEQ ID NO 150
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 150

Ile Ser Gly Ser Val Thr Ser His Gln Ala Pro Gly Glu Gly Gly Ser
1               5                   10                  15

Gly Gly

<210> SEQ ID NO 151
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 151

Gly Glu Lys Lys Lys Gly Lys Ser Gly Gly Ser Thr
1               5                   10

<210> SEQ ID NO 152
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 152

Ile Ser Val Val Val Thr Ser His Gln Ala Pro Gly Ser Gly Gly Ser
1               5                   10                  15

Gly Gly

<210> SEQ ID NO 153
<211> LENGTH: 18
<212> TYPE: PRT
<213> ORGANISM: artificial
<220> FEATURE:
<223> OTHER INFORMATION: N-terminal sequence (with ref aa)

```
<400> SEQUENCE: 153

Ile Ser Val Val Val Thr Ser His Gln Ala Pro Thr Ser Gly Gly Ser
1               5                   10                  15

Gly Gly

<210> SEQ ID NO 154
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 154

Ile Ser Val Val Val Thr Ser His Gln Ser Pro Thr Pro Gly Gly Ser
1               5                   10                  15

Gly Gly

<210> SEQ ID NO 155
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 155

Gly Gly Ser Thr Pro Leu Lys Ser Leu Ala Ser Thr
1               5                   10

<210> SEQ ID NO 156
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 156

Gly Ser Thr Pro Lys Leu Lys Ser Leu Ala Ser Thr
1               5                   10

<210> SEQ ID NO 157
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 157

Ile Ser Val Val Val Thr Ser His Pro Thr Pro Gly Glu Gly Gly Ser
1               5                   10                  15

Gly Gly

<210> SEQ ID NO 158
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 158

Ile Ser Val Val Val Thr Ser His Gln Ala Pro Ser Pro Gly Ser Thr
1               5                   10                  15

Gly Gly
```

```
<210> SEQ ID NO 159
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 159

Ile Ser Val Val Val Thr Ser His Gln Ala Asn Gly Ser Gly Gly Ser
1               5                   10                  15

Gly Gly

<210> SEQ ID NO 160
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 160

Ile Ser Gly Ser Ala Val Val Asn Val Arg Ala Pro Asp Gly Gly Ser
1               5                   10                  15

Gly Gly

<210> SEQ ID NO 161
<211> LENGTH: 13
<212> TYPE: PRT
<213> ORGANISM: artificial
<220> FEATURE:
<223> OTHER INFORMATION: C-terminal sequence (with ref aa)

<400> SEQUENCE: 161

Gly Ser Lys Gly Asp Lys Ile Ala Ile Gly Gly Ser Thr
1               5                   10

<210> SEQ ID NO 162
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 162

Ile Ser Thr Ser Ala Ser Leu Ala Ile Thr Gly Pro Asp Gly Gly Ser
1               5                   10                  15

Gly Gly

<210> SEQ ID NO 163
<211> LENGTH: 13
<212> TYPE: PRT
<213> ORGANISM: artificial
<220> FEATURE:
<223> OTHER INFORMATION: C-terminal sequence (with ref aa)

<400> SEQUENCE: 163

Gly Ser Asp Arg Phe Ser Gly Ser Lys Ser Gly Ser Thr
1               5                   10

<210> SEQ ID NO 164
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 164
```

Ile Ser Gly Phe Ile Leu Pro Ile Glu Val Tyr Pro Asp Gly Gly Ser
1               5                   10                  15

Gly Gly

<210> SEQ ID NO 165
<211> LENGTH: 13
<212> TYPE: PRT
<213> ORGANISM: artificial
<220> FEATURE:
<223> OTHER INFORMATION: C-terminal sequence (with ref aa)

<400> SEQUENCE: 165

Gly Ser Lys Val Arg Phe Asp Tyr Asp Leu Phe Ser Thr
1               5                   10

<210> SEQ ID NO 166
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 166

Ile Ser Ser Ala Leu Leu Lys Ser Lys Leu Arg Ala Leu Leu Thr Ala
1               5                   10                  15

Pro Gly

<210> SEQ ID NO 167
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 167

Gly Gly Ser Gly Ser Gly Ser Gly Ser Gly Ser Gly Ser Thr
1               5                   10

<210> SEQ ID NO 168
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 168

Ile Ser Gly Ser Tyr Ala Met Ser Trp Val Arg Gln Ala Gly Gly Ser
1               5                   10                  15

Gly Gly

<210> SEQ ID NO 169
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 169

Gly Ser Ser Ser Tyr Ala Met Ser Trp Val Arg Gln Gly Ser Thr
1               5                   10                  15

<210> SEQ ID NO 170
<211> LENGTH: 18
<212> TYPE: PRT

```
<213> ORGANISM: artificial
<220> FEATURE:
<223> OTHER INFORMATION: N-terminal sequence (with ref aa)

<400> SEQUENCE: 170

Ile Ser Gly Pro Asn Pro Asn Lys Asn Pro Asn Pro Asn Pro Gly Ser
1               5                   10                  15

Gly Gly

<210> SEQ ID NO 171
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 171

Ile His Pro Leu Gln Asn Arg Trp Ala Leu Trp Phe Phe Lys Gly Ser
1               5                   10                  15

Gly Gly

<210> SEQ ID NO 172
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 172

Gly Gly Ser Gly Asn Leu Arg Leu Ile Ser Lys Phe Asp Thr Val Thr
1               5                   10                  15

<210> SEQ ID NO 173
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 173

Ile Ser Gly Ser Val Thr Ile Phe Ser Leu Ala Thr Asn Glu Gly Ser
1               5                   10                  15

Gly Gly

<210> SEQ ID NO 174
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 174

Gly Gly Ser Gly Lys Thr Thr Trp His Arg Ile Ser Val Phe Gly Gly
1               5                   10                  15

Ser Thr

<210> SEQ ID NO 175
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 175
```

Ile Tyr Leu Glu Gly Lys Ile Asp Tyr Gly Glu Tyr Met Asp Gly Ser
1               5                   10                  15

Gly Gly

<210> SEQ ID NO 176
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 176

Gly Gly Ser Asn Val Arg Arg Gln Ala Thr Thr Ile Ile Ala Asp Asn
1               5                   10                  15

Ile Thr

<210> SEQ ID NO 177
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 177

Ile Ser Gly Ser Val Gln Gly Ile Ile Asn Phe Glu Gln Lys Gly Ser
1               5                   10                  15

Gly Gly

<210> SEQ ID NO 178
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 178

Gly Gly Ser Gly Pro Val Lys Val Trp Gly Ser Ile Lys Gly Gly
1               5                   10                  15

Ser Thr

<210> SEQ ID NO 179
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 179

Ile Ser Gly Val Val Thr Ser His Gln Ala Pro Gly Glu Gly Gly
1               5                   10                  15

Ser Gly Gly

<210> SEQ ID NO 180
<211> LENGTH: 13
<212> TYPE: PRT
<213> ORGANISM: artificial
<220> FEATURE:
<223> OTHER INFORMATION: C-terminal sequence (with ref aa)

<400> SEQUENCE: 180

Gly Glu Lys Lys Lys Leu Lys Ser Leu Ala Gly Ser Thr
1               5                   10

```
<210> SEQ ID NO 181
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 181

Ile Ser Gly Thr Ser Ala Ser Leu Ala Ile Thr Gly Pro Asp Gly Gly
1               5                   10                  15

Ser Gly Gly

<210> SEQ ID NO 182
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 182

Gly Ser Asp Arg Phe Ser Gly Ser Lys Ser Gly Gly Ser Thr
1               5                   10

<210> SEQ ID NO 183
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 183

Ile Ser Gly Ser Gly Ser Gly Ser Gly Ser Gly Ser Pro Asp Gly Gly
1               5                   10                  15

Ser Gly Gly

<210> SEQ ID NO 184
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 184

Gly Ser Ser Gly Ser Gly Ser Gly Ser Gly Ser Gly Ser Thr
1               5                   10

<210> SEQ ID NO 185
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 185

Ile Ser Gly Thr Tyr Ile Ser Asn Val Asn His Lys Pro Asp Gly Gly
1               5                   10                  15

Ser Gly Gly

<210> SEQ ID NO 186
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 186
```

Gly Ser Asn Thr Lys Val Asp Lys Lys Val Glu Gly Ser Thr
1               5                   10

<210> SEQ ID NO 187
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 187

Ile Ser Gly Gly Phe Ile Leu Pro Ile Glu Val Tyr Pro Asp Gly Gly
1               5                   10                  15

Ser Gly Gly

<210> SEQ ID NO 188
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 188

Gly Ser Lys Val Arg Phe Asp Tyr Asp Leu Phe Gly Ser Thr
1               5                   10

<210> SEQ ID NO 189
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 189

Ile Ser Gly Ser Val Val Val Thr Ser His Gln Ala Pro Gly Gly Gly
1               5                   10                  15

Ser Gly Gly

<210> SEQ ID NO 190
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 190

Gly Glu Lys Lys Lys Leu Lys Ser Leu Ala Tyr Gly Ser Thr
1               5                   10

<210> SEQ ID NO 191
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 191

Gly Glu Lys Pro Lys Pro Lys Pro Leu Ala Tyr Gly Ser Thr
1               5                   10

<210> SEQ ID NO 192
<211> LENGTH: 14
<212> TYPE: PRT
<213> ORGANISM: artificial
<220> FEATURE:

<223> OTHER INFORMATION: C-terminal sequence (with ref aa)

<400> SEQUENCE: 192

Gly Ser Gly Ser Gly Ser Gly Ser Gly Ser Gly Gly Ser Thr
1               5                   10

<210> SEQ ID NO 193
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 193

Ile Ser Gly Pro Asn Pro Asn Lys Asn Pro Asn Pro Asn Pro Gly Gly
1               5                   10                  15
Ser Gly Gly

<210> SEQ ID NO 194
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 194

Ile Ser Gly Asp Ile Tyr Leu Ala Ile Asn Ile Thr Asn Gly Glu Gly
1               5                   10                  15
Ser Gly Gly

<210> SEQ ID NO 195
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 195

Gly Gly Ser Gly Asp Ile Tyr Leu Ala Ile Asn Ile Thr Asn Gly Glu
1               5                   10                  15
Ser Thr

<210> SEQ ID NO 196
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 196

Ile Ser Gly Ser Ala Thr Lys Ala Val Ser Val Leu Lys Gly Asp Gly
1               5                   10                  15
Ser Gly Gly

<210> SEQ ID NO 197
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 197

Gly Gly Ser Gly Val Gln Gly Ile Ile Asn Phe Glu Gln Lys Gly Gly
1               5                   10                  15

Ser Thr

<210> SEQ ID NO 198
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 198

Ile Ser Gly Ser Val Pro Lys Glu Lys Glu Lys Val Ser Thr
1               5                   10                  15

Ala Val Gly Gly
            20

<210> SEQ ID NO 199
<211> LENGTH: 13
<212> TYPE: PRT
<213> ORGANISM: artificial
<220> FEATURE:
<223> OTHER INFORMATION: C-terminal sequence (with ref aa)

<400> SEQUENCE: 199

Gly Ser Gly Ser Gly Ser Gly Ser Gly Ser Gly Ser Thr
1               5                   10

<210> SEQ ID NO 200
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 200

Gly Ser Gly Ser Gly Ser Gly Ser Gly Ser Gly Ser Gly Ser Thr
1               5                   10                  15

<210> SEQ ID NO 201
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 201

Ile Ser Gly Ser Ser Gly Ala Val Val Asn Val Arg Ala Pro Asp Gly
1               5                   10                  15

Gly Ser Gly Gly
            20

<210> SEQ ID NO 202
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 202

Gly Ser Lys Gly Asp Lys Ile Ala Ile Trp Thr Thr Gly Ser Thr
1               5                   10                  15

<210> SEQ ID NO 203
<211> LENGTH: 20
<212> TYPE: PRT
<213> ORGANISM: artificial

```
<220> FEATURE:
<223> OTHER INFORMATION: N-terminal sequence (with ref aa)

<400> SEQUENCE: 203

Ile Ser Gly Ser Tyr Ala Met Ser Trp Val Arg Gln Ala Pro Asp Gly
1               5                   10                  15

Gly Ser Gly Gly
            20

<210> SEQ ID NO 204
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 204

Ile Ser Gly Ser Thr Ser Ala Ser Leu Ala Ile Thr Gly Pro Asp Gly
1               5                   10                  15

Gly Ser Gly Gly
            20

<210> SEQ ID NO 205
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 205

Gly Ser Asp Arg Phe Ser Gly Ser Lys Ser Gly Gly Ser Thr
1               5                   10              15

<210> SEQ ID NO 206
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 206

Ile Ser Gly Ser Gly Ser Gly Ser Gly Ser Gly Ser Gly Pro Asp Gly
1               5                   10                  15

Gly Ser Gly Gly
            20

<210> SEQ ID NO 207
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 207

Ser Gly Ser Gly Ser Gly Ser Gly Ser Gly Ser Ser Pro Asp Gly Gly
1               5                   10                  15

Ser Gly Gly

<210> SEQ ID NO 208
<211> LENGTH: 15
<212> TYPE: PRT
<213> ORGANISM: artificial
<220> FEATURE:
<223> OTHER INFORMATION: C-terminal sequence (with ref aa)
```

```
<400> SEQUENCE: 208

Gly Ser Tyr Ser Gly Ser Gly Ser Gly Ser Gly Ser Thr
1               5                   10                  15

<210> SEQ ID NO 209
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 209

Ile Ser Thr Gln Thr Tyr Ile Ser Asn Val Asn His Lys Pro Asp Gly
1               5                   10                  15

Gly Ser Gly Gly
            20

<210> SEQ ID NO 210
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 210

Gly Ser Asn Thr Lys Val Asp Lys Lys Val Glu Pro Lys Ser Thr
1               5                   10                  15

<210> SEQ ID NO 211
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 211

Ile Ser Gly Ser Thr Tyr Ile Ser Asn Val Asn His Lys Pro Asp Gly
1               5                   10                  15

Gly Ser Gly Gly
            20

<210> SEQ ID NO 212
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 212

Gly Ser Asn Thr Lys Val Asp Lys Lys Val Glu Gly Gly Ser Thr
1               5                   10                  15

<210> SEQ ID NO 213
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 213

Ile Ser Gly Pro Asn Pro Asn Pro Asn Pro Asn Pro Asn Pro Asp Gly
1               5                   10                  15

Gly Ser Gly Gly
            20
```

```
<210> SEQ ID NO 214
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 214

Gly Ser Asn Pro Asn Pro Asn Pro Asn Pro Asn Pro Gly Ser Thr
1               5                   10                  15

<210> SEQ ID NO 215
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 215

Ile Ser Ala Val Gln Val Lys Leu Glu Leu Gly His Arg Pro Asp Gly
1               5                   10                  15

Gly Ser Gly Gly
            20

<210> SEQ ID NO 216
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 216

Gly Ser Asn His Leu Arg Ser Glu Lys Leu Thr Phe Asn Ser Thr
1               5                   10                  15

<210> SEQ ID NO 217
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 217

Ile Ser Gly Phe Ile Leu Pro Ile Glu Val Tyr Phe Lys Pro Asp Gly
1               5                   10                  15

Gly Ser Gly Gly
            20

<210> SEQ ID NO 218
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 218

Gly Ser Pro Arg Lys Val Arg Phe Asp Tyr Asp Leu Phe Ser Thr
1               5                   10                  15

<210> SEQ ID NO 219
<211> LENGTH: 20
<212> TYPE: PRT
<213> ORGANISM: artificial
<220> FEATURE:
<223> OTHER INFORMATION: N-terminal sequence (with ref aa)
```

```
<400> SEQUENCE: 219

Ile Ser Gly Ser Gly Phe Ile Leu Pro Ile Glu Val Tyr Pro Asp Gly
1               5                   10                  15

Gly Ser Gly Gly
            20

<210> SEQ ID NO 220
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 220

Gly Ser Lys Val Arg Phe Asp Tyr Asp Leu Phe Gly Gly Ser Thr
1               5                   10                  15

<210> SEQ ID NO 221
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 221

Gly Ser Tyr Gly Ser Gly Ser Gly Ser Gly Ser Gly Ser Thr
1               5                   10                  15

<210> SEQ ID NO 222
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 222

Ile Ser Asp Arg Ser Ala Leu Leu Lys Ser Lys Leu Arg Ala Leu Leu
1               5                   10                  15

Thr Ala Pro Arg
            20

<210> SEQ ID NO 223
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 223

Gly Ser Asp Arg Ser Ala Leu Leu Lys Ser Lys Leu Arg Ala Ser Thr
1               5                   10                  15

<210> SEQ ID NO 224
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 224

Ile Ser Asp Arg Ser Ala Leu Leu Lys Ser Lys Leu Arg Ala Leu Leu
1               5                   10                  15

Thr Ala Pro Gly
            20
```

<210> SEQ ID NO 225
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 225

Gly Gly Ser Gly Ser Gly Ser Gly Ser Gly Ser Gly Ser Gly Ser Thr
1               5                   10                  15

<210> SEQ ID NO 226
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 226

Ile Ser Gly Ser Ser Asp Lys Thr His Thr Ser Pro Pro Ser Pro Asp
1               5                   10                  15

Gly Gly Ser Gly Gly
            20

<210> SEQ ID NO 227
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 227

Gly Ser Lys Thr His Thr Ser Pro Pro Ser Pro Gly Gly Ser Thr
1               5                   10                  15

<210> SEQ ID NO 228
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 228

Ile Ser Gly Ser Tyr Ala Met Ser Trp Val Arg Gln Ala Ser Pro Asp
1               5                   10                  15

Gly Gly Ser Gly Gly
            20

<210> SEQ ID NO 229
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 229

Gly Ser Tyr Ser Ser Tyr Ala Met Ser Trp Val Arg Gly Gly Ser Thr
1               5                   10                  15

<210> SEQ ID NO 230
<211> LENGTH: 16
<212> TYPE: PRT
<213> ORGANISM: artificial
<220> FEATURE:
<223> OTHER INFORMATION: C-terminal sequence (with ref aa)

```
<400> SEQUENCE: 230

Gly Ser Tyr Ser Ser Tyr Ala Met Ser Trp Val Arg Gln Gly Ser Thr
1               5                   10                  15

<210> SEQ ID NO 231
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 231

Ile Ser Gly Ser Gly Ser Gly Ser Gly Ser Gly Ser Pro Asp
1               5                   10                  15

Gly Gly Ser Gly Gly
            20

<210> SEQ ID NO 232
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 232

Ile Ser Gly Ser Pro Asn Pro Asn Pro Asn Pro Asn Pro Ser Pro Asp
1               5                   10                  15

Gly Gly Ser Gly Gly
            20

<210> SEQ ID NO 233
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 233

Gly Ser Tyr Pro Asn Pro Asn Pro Asn Pro Asn Pro Ser Gly Ser Thr
1               5                   10                  15

<210> SEQ ID NO 234
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 234

Ile Ser Gly Pro Asn Pro Asn Lys Asn Pro Asn Pro Asn Ser Pro Asp
1               5                   10                  15

Gly Gly Ser Gly Gly
            20

<210> SEQ ID NO 235
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 235

Gly Ser Tyr Asn Pro Asn Glu Asn Pro Asn Pro Asn Pro Gly Ser Thr
1               5                   10                  15
```

<210> SEQ ID NO 236
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 236

Ile Ser Gly Pro Asn Pro Asn Pro Asn Pro Asn Ser Pro Asp
1               5                   10                  15

Gly Gly Ser Gly Gly
            20

<210> SEQ ID NO 237
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 237

Gly Ser Tyr Asn Pro Asn Pro Asn Pro Asn Pro Gly Ser Thr
1               5                   10                  15

<210> SEQ ID NO 238
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 238

Ile Ser Gly Ser Val Val Val Thr Ser His Gln Ala Pro Gly Gly Ser
1               5                   10                  15

Gly Gly Ser Gly Gly
            20

<210> SEQ ID NO 239
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 239

Ile Ser Gly Ser Val Val Tyr Ile Glu Ile Leu Asp Arg His Pro Asp
1               5                   10                  15

Gly Gly Ser Gly Gly
            20

<210> SEQ ID NO 240
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 240

Gly Ser Gly Arg Glu Val Pro Ile Ser Asn Gly Ser Gly Gly Ser Thr
1               5                   10                  15

<210> SEQ ID NO 241
<211> LENGTH: 21
<212> TYPE: PRT
<213> ORGANISM: artificial

-continued

```
<220> FEATURE:
<223> OTHER INFORMATION: N-terminal sequence (with ref aa)

<400> SEQUENCE: 241

Ile Ser Gly Ala Val Val Tyr Ile Glu Ile Leu Asp Arg His Pro Asp
1               5                   10                  15

Gly Gly Ser Gly Gly
            20

<210> SEQ ID NO 242
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 242

Ile Ser Pro Ala Val Val Tyr Ile Glu Ile Leu Asp Arg His Pro Asp
1               5                   10                  15

Gly Gly Ser Gly Gly
            20

<210> SEQ ID NO 243
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 243

Gly Ser Gly Arg Glu Val Pro Ile Ser Asn Gly Ser Gly Phe Ser Thr
1               5                   10                  15

<210> SEQ ID NO 244
<211> LENGTH: 11
<212> TYPE: PRT
<213> ORGANISM: artificial
<220> FEATURE:
<223> OTHER INFORMATION: N-terminal sequence (with ref aa)

<400> SEQUENCE: 244

Cys Ala Lys Ser Pro Asp Gly Gly Ser Gly Gly
1               5                   10

<210> SEQ ID NO 245
<211> LENGTH: 4
<212> TYPE: PRT
<213> ORGANISM: artificial
<220> FEATURE:
<223> OTHER INFORMATION: C-terminal sequence (with ref aa)

<400> SEQUENCE: 245

Gly Ser Tyr Gly
1

<210> SEQ ID NO 246
<211> LENGTH: 9
<212> TYPE: PRT
<213> ORGANISM: artificial
<220> FEATURE:
<223> OTHER INFORMATION: C-terminal sequence (with ref aa)

<400> SEQUENCE: 246

Gly Ser Tyr Gln His Trp Gly Gln Gly
1               5
```

```
<210> SEQ ID NO 247
<211> LENGTH: 13
<212> TYPE: PRT
<213> ORGANISM: artificial
<220> FEATURE:
<223> OTHER INFORMATION: N-terminal sequence (with ref aa)

<400> SEQUENCE: 247

Cys Ala Lys Val His Gln Glu Thr Gly Gly Ser Gly Gly
1               5                   10

<210> SEQ ID NO 248
<211> LENGTH: 11
<212> TYPE: PRT
<213> ORGANISM: artificial
<220> FEATURE:
<223> OTHER INFORMATION: C-terminal sequence (with ref aa)

<400> SEQUENCE: 248

Gly Ser Trp His Val Gln His Trp Gly Gln Gly
1               5                   10

<210> SEQ ID NO 249
<211> LENGTH: 15
<212> TYPE: PRT
<213> ORGANISM: artificial
<220> FEATURE:
<223> OTHER INFORMATION: N-terminal sequence (with ref aa)

<400> SEQUENCE: 249

Cys Ala Lys Val His Gln Glu Thr Pro Asp Gly Gly Ser Gly Gly
1               5                   10                  15

<210> SEQ ID NO 250
<211> LENGTH: 13
<212> TYPE: PRT
<213> ORGANISM: artificial
<220> FEATURE:
<223> OTHER INFORMATION: C-terminal sequence (with ref aa)

<400> SEQUENCE: 250

Gly Ser Tyr Glu Trp His Val Gln His Trp Gly Gln Gly
1               5                   10

<210> SEQ ID NO 251
<211> LENGTH: 16
<212> TYPE: PRT
<213> ORGANISM: artificial
<220> FEATURE:
<223> OTHER INFORMATION: N-terminal sequence (with ref aa)

<400> SEQUENCE: 251

Cys Thr Ser Val His Gln Glu Thr Lys Lys Tyr Gln Ser Ser Gly Gly
1               5                   10                  15

<210> SEQ ID NO 252
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 252

Gly Ser Tyr Ser Tyr Thr Tyr Asn Tyr Glu Trp His Val Asp Val Trp
1               5                   10                  15

Gly Gln Gly
```

```
<210> SEQ ID NO 253
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 253

Cys Thr Ser Val His Gln Glu Thr Ser Ser Pro Asp Gly Gly Ser Gly
1               5                   10                  15

Gly

<210> SEQ ID NO 254
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 254

Gly Ser Tyr Ser Tyr Glu Trp His Val Asp Val Trp Gly Gln Gly
1               5                   10                  15

<210> SEQ ID NO 255
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 255

Cys Ala Lys Thr His Thr Ser Pro Pro Ser Pro Asp Gly Gly Ser Gly
1               5                   10                  15

Gly

<210> SEQ ID NO 256
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 256

Gly Ser Ser Pro Pro Ser Pro Tyr Phe Gln His Trp Gly Gln Gly
1               5                   10                  15

<210> SEQ ID NO 257
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 257

Cys Thr Ser Val His Gln Glu Thr Lys Ser Ser Pro Asp Gly Gly Ser
1               5                   10                  15

Gly Gly

<210> SEQ ID NO 258
<211> LENGTH: 16
<212> TYPE: PRT
<213> ORGANISM: artificial
<220> FEATURE:
<223> OTHER INFORMATION: C-terminal sequence (with ref aa)
```

```
<400> SEQUENCE: 258

Gly Ser Tyr Ser Asn Tyr Glu Trp His Val Asp Val Trp Gly Gln Gly
1               5                   10                  15

<210> SEQ ID NO 259
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 259

Cys Thr Ser Val His Gln Glu Thr Lys Lys Tyr Gln Ser Ser Pro Asp
1               5                   10                  15

Gly Gly

<210> SEQ ID NO 260
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 260

Cys Thr Ser Val His Gln Glu Thr Lys Lys Ser Ser Pro Asp Gly Gly
1               5                   10                  15

Ser Gly Gly

<210> SEQ ID NO 261
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 261

Gly Ser Tyr Ser Tyr Asn Tyr Glu Trp His Val Asp Val Trp Gly Gln
1               5                   10                  15

Gly

<210> SEQ ID NO 262
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 262

Cys Thr Ser Val His Gln Glu Thr Lys Lys Tyr Gln Ser Ser Gly Gly
1               5                   10                  15

Ser Gly Gly

<210> SEQ ID NO 263
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 263

Cys Thr Ser Val His Gln Glu Thr Lys Lys Gln Ser Ser Pro Asp Gly
1               5                   10                  15
```

```
Gly Ser Gly Gly
            20

<210> SEQ ID NO 264
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 264

Gly Ser Tyr Ser Tyr Tyr Asn Tyr Glu Trp His Val Asp Val Trp Gly
1               5                   10                  15

Gln Gly

<210> SEQ ID NO 265
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 265

Cys Ala Lys Val His Pro Asn Pro Asn Pro Asn Pro Asn Pro Asp Gly
1               5                   10                  15

Gly Ser Gly Gly
            20

<210> SEQ ID NO 266
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 266

Gly Ser Asn Pro Asn Pro Asn Pro Asn Pro His Val Asp Val Trp Gly
1               5                   10                  15

Gln Gly

<210> SEQ ID NO 267
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 267

Cys Thr Ser Val His Gln Glu Thr Lys Lys Tyr Gln Ser Ser Pro Asp
1               5                   10                  15

Gly Gly Ser Gly
            20

<210> SEQ ID NO 268
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 268

Cys Thr Ser Val His Gln Glu Thr Lys Lys Tyr Gln Ser Ser Pro Asp
1               5                   10                  15

Gly Gly Ser Gly Gly
```

```
                20

<210> SEQ ID NO 269
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 269

Cys Ala Lys Leu Thr Val Val Val Thr Ser His Gln Ala Pro Gly Glu
1               5                   10                  15

Gly Gly Ser Gly Gly
            20

<210> SEQ ID NO 270
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 270

Gly Glu Lys Lys Lys Leu Lys Ser Leu Ala Tyr Phe Gln His Trp Gly
1               5                   10                  15

Gln Gly

<210> SEQ ID NO 271
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 271

Cys Ala Lys Ser Ser Asp Lys Thr His Thr Ser Pro Pro Ser Pro Asp
1               5                   10                  15

Gly Gly Ser Gly Gly
            20

<210> SEQ ID NO 272
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 272

Gly Ser Lys Thr His Thr Ser Pro Pro Ser Pro Tyr Phe Gln His Trp
1               5                   10                  15

Gly Gln Gly

<210> SEQ ID NO 273
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 273

Cys Ala Lys Val Glu Thr Lys Lys Tyr Gln Ser Ser Pro Asp Gly Gly
1               5                   10                  15

Ser Gly Gly
```

```
<210> SEQ ID NO 274
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 274

Gly Ser Tyr Ser Tyr Thr Tyr Asn Tyr Glu Val Gln His Trp Gly Gln
1               5                   10                  15

Gly

<210> SEQ ID NO 275
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 275

Cys Ala Lys Val His Thr Lys Lys Tyr Gln Ser Ser Pro Asp Gly Gly
1               5                   10                  15

Ser Gly Gly

<210> SEQ ID NO 276
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 276

Gly Ser Tyr Ser Tyr Thr Tyr Asn Tyr His Val Gln His Trp Gly Gln
1               5                   10                  15

Gly

<210> SEQ ID NO 277
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 277

Cys Ala Lys Leu Thr Val Glu Thr Lys Lys Tyr Gln Ser Ser Pro Asp
1               5                   10                  15

Gly Gly Ser Gly Gly
            20

<210> SEQ ID NO 278
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 278

Gly Ser Tyr Ser Tyr Thr Tyr Asn Tyr Glu Trp His Val Gln His Trp
1               5                   10                  15

Gly Gln Gly

<210> SEQ ID NO 279
<211> LENGTH: 21
```

<212> TYPE: PRT
<213> ORGANISM: artificial
<220> FEATURE:
<223> OTHER INFORMATION: N-terminal sequence (with ref aa)

<400> SEQUENCE: 279

Cys Ala Lys Leu Thr Ala Glu Thr Lys Lys Tyr Gln Ser Ser Pro Asp
1               5                   10                  15

Gly Gly Ser Gly Gly
            20

<210> SEQ ID NO 280
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 280

Gly Ser Tyr Ser Tyr Thr Tyr Asn Tyr Glu Asn Tyr Phe Gln His Trp
1               5                   10                  15

Gly Gln Gly

<210> SEQ ID NO 281
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 281

Cys Ala Lys Gly Ile Thr Gly Thr Lys Lys Tyr Gln Ser Ser Pro Asp
1               5                   10                  15

Gly Gly Ser Gly Gly
            20

<210> SEQ ID NO 282
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 282

Gly Ser Tyr Ser Tyr Thr Tyr Asn Tyr Ala Glu Tyr Phe Gln His Trp
1               5                   10                  15

Gly Gln Gly

<210> SEQ ID NO 283
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 283

Gly Ser Tyr Asp Tyr Val Trp Gly Ser Tyr Ala Tyr Phe Gln His Trp
1               5                   10                  15

Gly Gln Gly

<210> SEQ ID NO 284
<211> LENGTH: 21
<212> TYPE: PRT
<213> ORGANISM: artificial

```
<220> FEATURE:
<223> OTHER INFORMATION: N-terminal sequence (with ref aa)

<400> SEQUENCE: 284

Cys Ala Lys Leu Thr Ser Val Val Thr Ser His Gln Ala Pro Gly
1               5                   10                  15

Gly Gly Ser Gly Gly
            20

<210> SEQ ID NO 285
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 285

Gly Glu Lys Lys Lys Leu Lys Ser Leu Ala Tyr Tyr Phe Gln His Trp
1               5                   10                  15

Gly Gln Gly

<210> SEQ ID NO 286
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 286

Cys Ala Lys Val His Pro Asn Pro Asn Pro Asn Pro Asn Ser Pro Asp
1               5                   10                  15

Gly Gly Ser Gly Gly
            20

<210> SEQ ID NO 287
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 287

Gly Ser Tyr Asn Pro Asn Pro Asn Pro Asn Pro His Val Asp Val Trp
1               5                   10                  15

Gly Gln Gly

<210> SEQ ID NO 288
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 288

Cys Ala Lys Leu Thr Gln Val Lys Leu Glu Leu Gly His Arg Pro Asp
1               5                   10                  15

Gly Gly Ser Gly Gly
            20

<210> SEQ ID NO 289
<211> LENGTH: 19
<212> TYPE: PRT
<213> ORGANISM: artificial
<220> FEATURE:
```

```
<223> OTHER INFORMATION: C-terminal sequence (with ref aa)

<400> SEQUENCE: 289

Gly Ser Asn His Leu Arg Ser Glu Lys Leu Thr Tyr Phe Gln His Trp
1               5                   10                  15

Gly Gln Gly

<210> SEQ ID NO 290
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 290

Cys Ala Lys Val His Gln Glu Thr Lys Lys Tyr Gln Ser Ser Pro Asp
1               5                   10                  15

Gly Gly Ser Gly Gly
            20

<210> SEQ ID NO 291
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 291

Cys Ala Lys Thr Gln Thr Tyr Ile Ser Asn Val Asn His Lys Pro Asp
1               5                   10                  15

Gly Gly Ser Gly Gly
            20

<210> SEQ ID NO 292
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 292

Gly Ser Asn Thr Lys Val Asp Lys Lys Ala Glu Tyr Phe Gln His Trp
1               5                   10                  15

Gly Gln Gly

<210> SEQ ID NO 293
<211> LENGTH: 20
<212> TYPE: PRT
<213> ORGANISM: artificial
<220> FEATURE:
<223> OTHER INFORMATION: C-terminal sequence (with ref aa)

<400> SEQUENCE: 293

Gly Ser Tyr Ser Tyr Thr Thr Tyr Asn Tyr Glu Trp His Val Asp Val
1               5                   10                  15

Trp Gly Gln Gly
            20

<210> SEQ ID NO 294
<211> LENGTH: 22
<212> TYPE: PRT
<213> ORGANISM: artificial
<220> FEATURE:
<223> OTHER INFORMATION: N-terminal sequence (with ref aa)
```

```
<400> SEQUENCE: 294

Cys Ala Thr Ser Val His Gln Glu Thr Lys Lys Tyr Gln Ser Ser Pro
1               5                   10                  15

Asp Gly Gly Ser Gly Gly
            20

<210> SEQ ID NO 295
<211> LENGTH: 20
<212> TYPE: PRT
<213> ORGANISM: artificial
<220> FEATURE:
<223> OTHER INFORMATION: C-terminal sequence (with ref aa)

<400> SEQUENCE: 295

Gly Ser Tyr Ser Tyr Thr Tyr Asn Tyr Glu Trp His Val Asp Val His
1               5                   10                  15

Trp Gly Gln Gly
            20

<210> SEQ ID NO 296
<211> LENGTH: 23
<212> TYPE: PRT
<213> ORGANISM: artificial
<220> FEATURE:
<223> OTHER INFORMATION: N-terminal sequence (with ref aa)

<400> SEQUENCE: 296

Cys Ala Lys Leu Thr Ala Glu Glu Trp Lys Lys Tyr Glu Lys Glu
1               5                   10                  15

Lys Glu Lys Asn Lys Gly Ser
            20

<210> SEQ ID NO 297
<211> LENGTH: 21
<212> TYPE: PRT
<213> ORGANISM: artificial
<220> FEATURE:
<223> OTHER INFORMATION: C-terminal sequence (with ref aa)

<400> SEQUENCE: 297

Gly Gly Ser Gly Gly Ser Gly Gly Ser Gly Gly Ala Glu Tyr Phe Gln
1               5                   10                  15

His Trp Gly Gln Gly
            20

<210> SEQ ID NO 298
<211> LENGTH: 23
<212> TYPE: PRT
<213> ORGANISM: artificial
<220> FEATURE:
<223> OTHER INFORMATION: N-terminal sequence (with ref aa)

<400> SEQUENCE: 298

Cys Ala Asp Ser Ser Asp Arg Ser Ala Leu Leu Lys Ser Lys Leu Arg
1               5                   10                  15

Ala Leu Leu Thr Ala Pro Arg
            20

<210> SEQ ID NO 299
<211> LENGTH: 21
<212> TYPE: PRT
<213> ORGANISM: artificial
<220> FEATURE:
```

<223> OTHER INFORMATION: C-terminal sequence (with ref aa)

<400> SEQUENCE: 299

Gly Ser Asn His Leu Arg Ser Glu Lys Leu Thr Phe Asn Tyr Phe Gln
1               5                   10                  15

His Trp Gly Gln Gly
            20

<210> SEQ ID NO 300
<211> LENGTH: 23
<212> TYPE: PRT
<213> ORGANISM: artificial
<220> FEATURE:
<223> OTHER INFORMATION: N-terminal sequence (with ref aa)

<400> SEQUENCE: 300

Cys Thr Ser Val His Gln Glu Thr Lys Lys Tyr Gln Tyr Gln Ser Ser
1               5                   10                  15

Pro Asp Gly Gly Ser Gly Gly
            20

<210> SEQ ID NO 301
<211> LENGTH: 21
<212> TYPE: PRT
<213> ORGANISM: artificial
<220> FEATURE:
<223> OTHER INFORMATION: C-terminal sequence (with ref aa)

<400> SEQUENCE: 301

Gly Ser Tyr Ser Tyr Thr Tyr Thr Tyr Asn Tyr Glu Trp His Val Asp
1               5                   10                  15

Val Trp Gly Gln Gly
            20

<210> SEQ ID NO 302
<211> LENGTH: 23
<212> TYPE: PRT
<213> ORGANISM: artificial
<220> FEATURE:
<223> OTHER INFORMATION: N-terminal sequence (with ref aa)

<400> SEQUENCE: 302

Cys Ala Lys Leu Thr Asp Arg Ser Ala Leu Leu Lys Ser Lys Leu Arg
1               5                   10                  15

Ala Leu Leu Thr Ala Pro Arg
            20

<210> SEQ ID NO 303
<211> LENGTH: 23
<212> TYPE: PRT
<213> ORGANISM: artificial
<220> FEATURE:
<223> OTHER INFORMATION: N-terminal sequence (with ref aa)

<400> SEQUENCE: 303

Cys Ala Lys Leu Thr Ala Val Gln Val Lys Leu Glu Leu Gly His Arg
1               5                   10                  15

Pro Asp Gly Gly Ser Gly Gly
            20

<210> SEQ ID NO 304
<211> LENGTH: 25
<212> TYPE: PRT
<213> ORGANISM: artificial

```
<220> FEATURE:
<223> OTHER INFORMATION: N-terminal sequence (with ref aa)

<400> SEQUENCE: 304

Cys Thr Ser Val His Gln Glu Thr Lys Lys Tyr Gln Ser Ser Tyr Gln
1               5                   10                  15

Ser Ser Pro Asp Gly Gly Ser Gly Gly
            20                  25

<210> SEQ ID NO 305
<211> LENGTH: 23
<212> TYPE: PRT
<213> ORGANISM: artificial
<220> FEATURE:
<223> OTHER INFORMATION: C-terminal sequence (with ref aa)

<400> SEQUENCE: 305

Gly Ser Tyr Ser Tyr Thr Tyr Ser Tyr Thr Tyr Asn Tyr Glu Trp His
1               5                   10                  15

Val Asp Val Trp Gly Gln Gly
            20

<210> SEQ ID NO 306
<211> LENGTH: 25
<212> TYPE: PRT
<213> ORGANISM: artificial
<220> FEATURE:
<223> OTHER INFORMATION: N-terminal sequence (with ref aa)

<400> SEQUENCE: 306

Cys Ala Lys Leu Thr Ala Val Gln Val Lys Leu Glu Leu Gly His Arg
1               5                   10                  15

Ala Gln Pro Asp Gly Gly Ser Gly Gly
            20                  25

<210> SEQ ID NO 307
<211> LENGTH: 23
<212> TYPE: PRT
<213> ORGANISM: artificial
<220> FEATURE:
<223> OTHER INFORMATION: C-terminal sequence (with ref aa)

<400> SEQUENCE: 307

Gly Ser Pro Val Asn His Leu Arg Ser Glu Lys Leu Thr Phe Asn Tyr
1               5                   10                  15

Phe Gln His Trp Gly Gln Gly
            20

<210> SEQ ID NO 308
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 308

Ser Ser Ser Asn Ile Gly Ser Lys Leu Arg Ala Leu Leu Thr Ala Pro
1               5                   10                  15

Arg

<210> SEQ ID NO 309
<211> LENGTH: 15
<212> TYPE: PRT
<213> ORGANISM: artificial
```

```
<220> FEATURE:
<223> OTHER INFORMATION: C-terminal sequence (with ref aa)

<400> SEQUENCE: 309

Gly Ser Gly Ser Gly Gly Ser Gly Gly Ser Gly Ser Gly Tyr Asp
1               5                   10                  15

<210> SEQ ID NO 310
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 310

Gly Ser Tyr Gly Ser Gly Gly Ser Gly Ser Gly Ser Gly Asp
1               5                   10

<210> SEQ ID NO 311
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 311

Ser Ser Leu Gly Gln Ile Gln Leu Thr Ile Arg His Ser Ser Pro Asp
1               5                   10                  15

Gly Gly Ser Gly Gly
            20

<210> SEQ ID NO 312
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 312

Gly Ser Asn Lys Leu Ile Val Val Val His Ala Ser Arg Asn Leu Ile
1               5                   10                  15

Gly Tyr Asp

<210> SEQ ID NO 313
<211> LENGTH: 22
<212> TYPE: PRT
<213> ORGANISM: artificial
<220> FEATURE:
<223> OTHER INFORMATION: N-terminal sequence (with ref aa)

<400> SEQUENCE: 313

Ser Pro Leu Gly Gln Ile Gln Leu Thr Ile Arg His Ser Ser Gln Pro
1               5                   10                  15

Asp Gly Gly Ser Gly Gly
            20

<210> SEQ ID NO 314
<211> LENGTH: 20
<212> TYPE: PRT
<213> ORGANISM: artificial
<220> FEATURE:
<223> OTHER INFORMATION: C-terminal sequence (with ref aa)

<400> SEQUENCE: 314

Gly Ser Arg Asn Lys Leu Ile Val Val Val His Ala Ser Arg Asn Leu
```

```
1               5                   10                  15

Ile Ala Tyr Asp
            20

<210> SEQ ID NO 315
<211> LENGTH: 22
<212> TYPE: PRT
<213> ORGANISM: artificial
<220> FEATURE:
<223> OTHER INFORMATION: N-terminal sequence (with ref aa)

<400> SEQUENCE: 315

Ser Ser Leu Gly Gln Ile Gln Leu Thr Ile Arg His Ser Ser Gln Pro
1               5                   10                  15

Asp Gly Gly Ser Gly Gly
            20

<210> SEQ ID NO 316
<211> LENGTH: 20
<212> TYPE: PRT
<213> ORGANISM: artificial
<220> FEATURE:
<223> OTHER INFORMATION: C-terminal sequence (with ref aa)

<400> SEQUENCE: 316

Gly Ser Arg Asn Lys Leu Ile Val Val His Ala Ser Arg Asn Leu
1               5                   10                  15

Ile Gly Tyr Asp
            20

<210> SEQ ID NO 317
<211> LENGTH: 22
<212> TYPE: PRT
<213> ORGANISM: artificial
<220> FEATURE:
<223> OTHER INFORMATION: N-terminal sequence (with ref aa)

<400> SEQUENCE: 317

Ser Ser Ser Asn Ile Gly Ser Ala Leu Leu Lys Ser Lys Leu Arg Ala
1               5                   10                  15

Leu Leu Thr Ala Pro Arg
            20

<210> SEQ ID NO 318
<211> LENGTH: 20
<212> TYPE: PRT
<213> ORGANISM: artificial
<220> FEATURE:
<223> OTHER INFORMATION: C-terminal sequence (with ref aa)

<400> SEQUENCE: 318

Gly Ser Ser Asp Arg Ser Ala Leu Leu Lys Ser Lys Leu Arg Ala Leu
1               5                   10                  15

Leu Thr Ala Asp
            20

<210> SEQ ID NO 319
<211> LENGTH: 20
<212> TYPE: PRT
<213> ORGANISM: artificial
<220> FEATURE:
<223> OTHER INFORMATION: C-terminal sequence (with ref aa)

<400> SEQUENCE: 319
```

```
Gly Ser Gly Ser Gly Gly Ser Gly Gly Ser Gly Ser Gly
1               5                   10                  15

Ser Gly Tyr Asp
            20

<210> SEQ ID NO 320
<211> LENGTH: 24
<212> TYPE: PRT
<213> ORGANISM: artificial
<220> FEATURE:
<223> OTHER INFORMATION: N-terminal sequence (with ref aa)

<400> SEQUENCE: 320

Ser Ser Ser Asn Ile Gly Ser Gly Ser Gly Ser Gly Ser Gly
1               5                   10                  15

Ser Pro Asp Gly Gly Ser Gly Gly
            20

<210> SEQ ID NO 321
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 321

Gly Ser Tyr Gly Ser Gly Gly Ser Gly Ser Gly Ser Gly Tyr Asp
1               5                   10                  15

<210> SEQ ID NO 322
<211> LENGTH: 7
<212> TYPE: PRT
<213> ORGANISM: artificial
<220> FEATURE:
<223> OTHER INFORMATION: C-terminal sequence (with ref aa)

<400> SEQUENCE: 322

Asn Ser Asn Arg Pro Ser Gly
1               5

<210> SEQ ID NO 323
<211> LENGTH: 6
<212> TYPE: PRT
<213> ORGANISM: artificial
<220> FEATURE:
<223> OTHER INFORMATION: N-terminal sequence (with ref aa)

<400> SEQUENCE: 323

Tyr Gly Gly Ser Gly Ser
1               5

<210> SEQ ID NO 324
<211> LENGTH: 11
<212> TYPE: PRT
<213> ORGANISM: artificial
<220> FEATURE:
<223> OTHER INFORMATION: C-terminal sequence (with ref aa)

<400> SEQUENCE: 324

Gly Ser Gly Ser Asn Ser Asn Arg Pro Ser Gly
1               5                   10

<210> SEQ ID NO 325
<211> LENGTH: 13
<212> TYPE: PRT
<213> ORGANISM: artificial
```

```
<220> FEATURE:
<223> OTHER INFORMATION: N-terminal sequence (with ref aa)

<400> SEQUENCE: 325

Tyr Gly Lys Thr His Thr Ser Pro Pro Ser Pro Gly Gly
1               5                   10

<210> SEQ ID NO 326
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 326

Gly Gly Lys Thr His Thr Ser Pro Pro Ser Pro Gly Asn Arg Pro Ser
1               5                   10                  15

Gly

<210> SEQ ID NO 327
<211> LENGTH: 14
<212> TYPE: PRT
<213> ORGANISM: artificial
<220> FEATURE:
<223> OTHER INFORMATION: N-terminal sequence (with ref aa)

<400> SEQUENCE: 327

Tyr Gly Ser Gly Ser Gly Ser Gly Ser Gly Ser Gly Gly Gly
1               5                   10

<210> SEQ ID NO 328
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 328

Gly Gly Lys Thr His Thr Ser Pro Pro Ser Pro Ser Gly Asn Arg Pro
1               5                   10                  15

Ser Gly

<210> SEQ ID NO 329
<211> LENGTH: 14
<212> TYPE: PRT
<213> ORGANISM: artificial
<220> FEATURE:
<223> OTHER INFORMATION: N-terminal sequence (with ref aa)

<400> SEQUENCE: 329

Tyr Gly Ser Lys Thr His Thr Ser Pro Pro Ser Pro Gly Gly
1               5                   10

<210> SEQ ID NO 330
<211> LENGTH: 15
<212> TYPE: PRT
<213> ORGANISM: artificial
<220> FEATURE:
<223> OTHER INFORMATION: N-terminal sequence (with ref aa)

<400> SEQUENCE: 330

Tyr Gly Ser Gly Ser Gly Ser Gly Gly Gly Ser Gly Gly
1               5                   10                  15

<210> SEQ ID NO 331
```

```
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 331

Gly Ser Gly Gly Ser Gly Ser Gly Ser Gly Asn Arg Pro Ser Gly
1               5                   10                  15

<210> SEQ ID NO 332
<211> LENGTH: 16
<212> TYPE: PRT
<213> ORGANISM: artificial
<220> FEATURE:
<223> OTHER INFORMATION: N-terminal sequence (with ref aa)

<400> SEQUENCE: 332

Tyr Gly Ser Ser Asp Lys Thr His Thr Ser Pro Pro Ser Pro Gly Gly
1               5                   10                  15

<210> SEQ ID NO 333
<211> LENGTH: 20
<212> TYPE: PRT
<213> ORGANISM: artificial
<220> FEATURE:
<223> OTHER INFORMATION: C-terminal sequence (with ref aa)

<400> SEQUENCE: 333

Gly Gly Ser Gly Ser Gly Ser Gly Gly Ser Gly Ser Gly Ser Gly Asn
1               5                   10                  15

Arg Pro Ser Gly
            20

<210> SEQ ID NO 334
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 334

Tyr Thr Ser Ala Ser Leu Ala Ile Thr Gly Pro Asp Gly Gly Ser Gly
1               5                   10                  15

Gly

<210> SEQ ID NO 335
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 335

Gly Ser Asp Arg Phe Ser Gly Ser Lys Ser Gly Asn Arg Pro Ser Gly
1               5                   10                  15

<210> SEQ ID NO 336
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 336

Tyr Gly Phe Ile Leu Pro Ile Glu Val Tyr Pro Asp Gly Gly Ser Gly
```

```
1               5                  10                  15
Gly

<210> SEQ ID NO 337
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 337

Gly Ser Lys Val Arg Phe Asp Tyr Asp Leu Phe Asn Arg Pro Ser Gly
1               5                  10                  15

<210> SEQ ID NO 338
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 338

Tyr Gly Ser Gly Ser Gly Ser Gly Ser Gly Ser Gly Gly Gly Ser Gly
1               5                  10                  15
Gly

<210> SEQ ID NO 339
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 339

Gly Ser Gly Ser Gly Gly Ser Gly Ser Gly Ser Gly Asn Arg Pro Ser
1               5                  10                  15
Gly

<210> SEQ ID NO 340
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 340

Tyr Gly Val Pro Lys Glu Lys Glu Lys Glu Lys Val Ser Thr Ala Val
1               5                  10                  15
Gly Gly

<210> SEQ ID NO 341
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 341

Gly Ser Ala Pro Leu Glu Val Pro Lys Glu Lys Glu Lys Glu Lys Val
1               5                  10                  15
Gly

<210> SEQ ID NO 342
```

```
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 342

Tyr Gly Thr Ser Ala Ser Leu Ala Ile Thr Gly Pro Asp Gly Gly Ser
1               5                   10                  15

Gly Gly

<210> SEQ ID NO 343
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 343

Gly Ser Asp Arg Phe Ser Gly Ser Lys Ser Gly Asn Arg Pro Ser
1               5                   10                  15

Gly

<210> SEQ ID NO 344
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 344

Tyr Gly Gly Ser Gly Ser Gly Ser Gly Pro Asp Gly Gly Ser
1               5                   10                  15

Gly Gly

<210> SEQ ID NO 345
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 345

Tyr Gly Ser Gly Ser Gly Ser Gly Ser Gly Ser Gly Ser Gly
1               5                   10                  15

Gly Gly

<210> SEQ ID NO 346
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 346

Gly Ser Tyr Glu Lys Glu Lys Glu Lys Asn Lys Thr Leu Lys Asn Val
1               5                   10                  15

Gly

<210> SEQ ID NO 347
<211> LENGTH: 18
<212> TYPE: PRT
<213> ORGANISM: artificial
<220> FEATURE:
```

```
<223> OTHER INFORMATION: N-terminal sequence (with ref aa)

<400> SEQUENCE: 347

Tyr Gly Thr Tyr Ile Ser Asn Val Asn His Lys Pro Asp Gly Gly Ser
1               5                   10                  15

Gly Gly

<210> SEQ ID NO 348
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 348

Gly Ser Asn Thr Lys Val Asp Lys Lys Val Glu Gly Asn Arg Pro Ser
1               5                   10                  15

Gly

<210> SEQ ID NO 349
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 349

Tyr Gly Ala Glu Glu Trp Lys Lys Tyr Glu Lys Glu Lys Glu Lys
1               5                   10                  15

Gly Gly

<210> SEQ ID NO 350
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 350

Gly Ser Gly Ser Gly Ser Gly Ser Gly Ser Gly Ser Gly Ser Gly Ser
1               5                   10                  15

Gly

<210> SEQ ID NO 351
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 351

Tyr Gly Gly Phe Ile Leu Pro Ile Glu Val Tyr Pro Asp Gly Gly Ser
1               5                   10                  15

Gly Gly

<210> SEQ ID NO 352
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 352
```

```
Gly Ser Lys Val Arg Phe Asp Tyr Asp Leu Phe Gly Asn Arg Pro Ser
1               5                   10                  15

Gly

<210> SEQ ID NO 353
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 353

Tyr Gly Ser Ala Leu Leu Lys Ser Lys Leu Arg Ala Leu Leu Thr Ala
1               5                   10                  15

Pro Gly

<210> SEQ ID NO 354
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 354

Gly Ser Asp Gly Ser Gly Gly Ser Gly Ser Gly Ser Gly Asn Arg Pro
1               5                   10                  15

Ser Gly

<210> SEQ ID NO 355
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 355

Tyr Gly Ser Gly Ser Gly Ser Gly Ser Gly Ser Gly Pro Asp Gly Gly
1               5                   10                  15

Ser Gly Gly

<210> SEQ ID NO 356
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 356

Tyr Gly Gly Thr Ser Ala Ser Leu Ala Ile Thr Gly Pro Asp Gly Gly
1               5                   10                  15

Ser Gly Gly

<210> SEQ ID NO 357
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 357

Gly Ser Asp Arg Phe Ser Gly Ser Lys Ser Gly Gly Gly Asn Arg Pro
1               5                   10                  15

Ser Gly
```

```
<210> SEQ ID NO 358
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 358

Tyr Gly Gly Thr Tyr Ile Ser Asn Val Asn His Lys Pro Asp Gly Gly
1               5                   10                  15

Ser Gly Gly

<210> SEQ ID NO 359
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 359

Gly Ser Asn Thr Lys Val Asp Lys Lys Val Glu Gly Gly Asn Arg Pro
1               5                   10                  15

Ser Gly

<210> SEQ ID NO 360
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 360

Tyr Thr Gln Thr Tyr Ile Ser Asn Val Asn His Lys Pro Asp Gly Gly
1               5                   10                  15

Ser Gly Gly

<210> SEQ ID NO 361
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 361

Gly Ser Asn Thr Lys Val Asp Lys Lys Val Glu Pro Lys Asn Arg Pro
1               5                   10                  15

Ser Gly

<210> SEQ ID NO 362
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 362

Tyr Gly Gly Gly Phe Ile Leu Pro Ile Glu Val Tyr Pro Asp Gly Gly
1               5                   10                  15

Ser Gly Gly

<210> SEQ ID NO 363
<211> LENGTH: 18
```

-continued

```
<212> TYPE: PRT
<213> ORGANISM: artificial
<220> FEATURE:
<223> OTHER INFORMATION: C-terminal sequence (with ref aa)

<400> SEQUENCE: 363

Gly Ser Lys Val Arg Phe Asp Tyr Asp Leu Phe Gly Gly Asn Arg Pro
1               5                   10                  15

Ser Gly

<210> SEQ ID NO 364
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 364

Tyr Gly Ser Gly Ser Gly Ser Gly Ser Gly Ser Gly Ser Pro Asp Gly
1               5                   10                  15

Gly Ser Gly Gly
            20

<210> SEQ ID NO 365
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 365

Gly Ser Tyr Gly Ser Gly Gly Ser Gly Ser Gly Ser Gly Asn Arg Pro
1               5                   10                  15

Ser Gly

<210> SEQ ID NO 366
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 366

Tyr Gly Ser Gln Val Lys Leu Glu Leu Gly His Arg Ala Pro Asp Gly
1               5                   10                  15

Gly Ser Gly Gly
            20

<210> SEQ ID NO 367
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 367

Gly Ser Val Asn His Leu Arg Ser Glu Lys Leu Thr Ser Gly Asn Arg
1               5                   10                  15

Pro Ser Gly

<210> SEQ ID NO 368
<211> LENGTH: 20
<212> TYPE: PRT
<213> ORGANISM: artificial
```

```
<220> FEATURE:
<223> OTHER INFORMATION: N-terminal sequence (with ref aa)

<400> SEQUENCE: 368

Tyr Pro Ala Val Val Tyr Ile Glu Ile Leu Asp Arg His Pro Asp Gly
1               5                   10                  15

Gly Ser Gly Gly
            20

<210> SEQ ID NO 369
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 369

Gly Ser Gly Arg Glu Val Pro Ile Ser Asn Gly Ser Gly Phe Asn Arg
1               5                   10                  15

Pro Ser Gly

<210> SEQ ID NO 370
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 370

Tyr Gly Gly Val Val Tyr Ile Glu Ile Leu Asp Arg His Pro Asp Gly
1               5                   10                  15

Gly Ser Gly Gly
            20

<210> SEQ ID NO 371
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 371

Gly Ser Gly Arg Glu Val Pro Ile Ser Asn Gly Ser Gly Gly Asn Arg
1               5                   10                  15

Pro Ser Gly

<210> SEQ ID NO 372
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 372

Tyr Gly Ala Val Val Tyr Ile Glu Ile Leu Asp Arg His Pro Asp Gly
1               5                   10                  15

Gly Ser Gly Gly
            20

<210> SEQ ID NO 373
<211> LENGTH: 20
<212> TYPE: PRT
<213> ORGANISM: artificial
<220> FEATURE:
```

-continued

<223> OTHER INFORMATION: N-terminal sequence (with ref aa)

<400> SEQUENCE: 373

Tyr Gly Ser Arg Ser Ala Leu Leu Lys Ser Lys Leu Arg Ala Leu Leu
1               5                   10                  15

Thr Ala Pro Arg
            20

<210> SEQ ID NO 374
<211> LENGTH: 20
<212> TYPE: PRT
<213> ORGANISM: artificial
<220> FEATURE:
<223> OTHER INFORMATION: C-terminal sequence (with ref aa)

<400> SEQUENCE: 374

Gly Ser Asp Gly Ser Gly Ser Gly Gly Ser Gly Ser Gly Ser Gly Asn
1               5                   10                  15

Arg Pro Ser Gly
            20

<210> SEQ ID NO 375
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 375

Tyr Gly Ser Arg Ser Ala Leu Leu Lys Ser Lys Leu Arg Ala Leu Leu
1               5                   10                  15

Thr Ala Pro Gly
            20

<210> SEQ ID NO 376
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 376

Tyr Gly Ser Ala Val Gln Val Lys Leu Glu Leu Gly His Arg Pro Asp
1               5                   10                  15

Gly Gly Ser Gly Gly
            20

<210> SEQ ID NO 377
<211> LENGTH: 20
<212> TYPE: PRT
<213> ORGANISM: artificial
<220> FEATURE:
<223> OTHER INFORMATION: C-terminal sequence (with ref aa)

<400> SEQUENCE: 377

Gly Ser Asn His Leu Arg Ser Glu Lys Leu Thr Phe Asn Ser Gly Asn
1               5                   10                  15

Arg Pro Ser Gly
            20

<210> SEQ ID NO 378
<211> LENGTH: 15
<212> TYPE: PRT
<213> ORGANISM: artificial

```
<220> FEATURE:
<223> OTHER INFORMATION: N-terminal sequence (with ref aa)

<400> SEQUENCE: 378

Cys Gly Ser Gly Ser Gly Ser Gly Pro Asp Gly Gly Ser Gly Gly
1               5                   10                  15

<210> SEQ ID NO 379
<211> LENGTH: 10
<212> TYPE: PRT
<213> ORGANISM: artificial
<220> FEATURE:
<223> OTHER INFORMATION: C-terminal sequence (with ref aa)

<400> SEQUENCE: 379

Gly Ser Gly Ser Gly Ser Gly Ser Gly Phe
1               5                   10

<210> SEQ ID NO 380
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 380

Cys Gln Ser Tyr Asp Ile Leu Pro Ile Glu Pro Asp Gly Gly Ser Gly
1               5                   10                  15

Gly

<210> SEQ ID NO 381
<211> LENGTH: 11
<212> TYPE: PRT
<213> ORGANISM: artificial
<220> FEATURE:
<223> OTHER INFORMATION: C-terminal sequence (with ref aa)

<400> SEQUENCE: 381

Gly Ser Arg Phe Asp Tyr Asp Gly Val Val Phe
1               5                   10

<210> SEQ ID NO 382
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 382

Cys Gly Ser Gly Ser Gly Ser Gly Ser Gly Pro Asp Gly Gly Ser Gly
1               5                   10                  15

Gly

<210> SEQ ID NO 383
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 383

Gly Ser Gly Ser Gly Ser Gly Ser Gly Ser Gly Phe
1               5                   10

<210> SEQ ID NO 384
```

```
<211> LENGTH: 17
<212> TYPE: PRT
<213> ORGANISM: artificial
<220> FEATURE:
<223> OTHER INFORMATION: N-terminal sequence (with ref aa)

<400> SEQUENCE: 384

Cys Gly Ser Gly Ser Gly Ser Gly Ser Gly Ser Gly Gly Gly Ser Gly
1               5                   10                  15

Gly

<210> SEQ ID NO 385
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 385

Gly Ser Gly Ser Gly Ser Gly Ser Gly Ser Gly Ser Gly Phe
1               5                   10

<210> SEQ ID NO 386
<211> LENGTH: 18
<212> TYPE: PRT
<213> ORGANISM: artificial
<220> FEATURE:
<223> OTHER INFORMATION: N-terminal sequence (with ref aa)

<400> SEQUENCE: 386

Cys Gln Ser Tyr Asp Lys Leu Glu Leu Gly His Pro Asp Gly Gly Ser
1               5                   10                  15

Gly Gly

<210> SEQ ID NO 387
<211> LENGTH: 12
<212> TYPE: PRT
<213> ORGANISM: artificial
<220> FEATURE:
<223> OTHER INFORMATION: C-terminal sequence (with ref aa)

<400> SEQUENCE: 387

Gly Ser His Leu Arg Ser Glu Lys Gly Val Val Phe
1               5                   10

<210> SEQ ID NO 388
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 388

Cys Gln Ser Tyr Asp Ile Leu Pro Ile Glu Val Tyr Pro Asp Gly Gly
1               5                   10                  15

Ser Gly Gly

<210> SEQ ID NO 389
<211> LENGTH: 13
<212> TYPE: PRT
<213> ORGANISM: artificial
<220> FEATURE:
<223> OTHER INFORMATION: C-terminal sequence (with ref aa)

<400> SEQUENCE: 389
```

```
Gly Ser Lys Val Arg Phe Asp Tyr Asp Gly Val Val Phe
1               5                  10
```

<210> SEQ ID NO 390
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 390

```
Cys Gly Ser Gly Ser Gly Ser Gly Ser Gly Ser Gly Pro Asp Gly Gly
1               5                  10                  15

Ser Gly Gly
```

<210> SEQ ID NO 391
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 391

```
Cys Gly Ser Gly Ser Gly Ser Gly Ser Gly Ser Gly Ser Asp Gly Gly
1               5                  10                  15

Ser Gly Gly
```

<210> SEQ ID NO 392
<211> LENGTH: 19
<212> TYPE: PRT
<213> ORGANISM: artificial
<220> FEATURE:
<223> OTHER INFORMATION: N-terminal sequence (with ref aa)

<400> SEQUENCE: 392

```
Cys Gln Ser Tyr Asp Gly Phe Ile Leu Pro Ile Glu Val Tyr Gly Gly
1               5                  10                  15

Ser Gly Gly
```

<210> SEQ ID NO 393
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 393

```
Gly Ser Lys Val Arg Phe Asp Tyr Asp Leu Phe Gly Val Val Phe
1               5                  10                  15
```

<210> SEQ ID NO 394
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 394

```
Cys Gln Ser Tyr Asp Lys Leu Glu Leu Gly His Arg Ala Pro Asp Gly
1               5                  10                  15

Gly Ser Gly Gly
            20
```

<210> SEQ ID NO 395

```
<211> LENGTH: 14
<212> TYPE: PRT
<213> ORGANISM: artificial
<220> FEATURE:
<223> OTHER INFORMATION: C-terminal sequence (with ref aa)

<400> SEQUENCE: 395

Gly Ser Val Asn His Leu Arg Ser Glu Lys Gly Val Val Phe
1               5                   10

<210> SEQ ID NO 396
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 396

Cys Gln Val His Gln Glu Thr Lys Lys Tyr Gln Ser Ser Pro Asp Gly
1               5                   10                  15

Gly Ser Gly Gly
            20

<210> SEQ ID NO 397
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 397

Gly Ser Tyr Ser Tyr Thr Tyr Asn Tyr Glu Trp His Val Val Phe
1               5                   10                  15

<210> SEQ ID NO 398
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 398

Cys Gly Ser Gly Ser Gly Ser Gly Ser Gly Ser Gly Ser Pro Asp Gly
1               5                   10                  15

Gly Ser Gly Gly
            20

<210> SEQ ID NO 399
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 399

Gly Ser Tyr Gly Ser Gly Ser Gly Ser Gly Ser Gly Ser Gly Phe
1               5                   10                  15

<210> SEQ ID NO 400
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 400
```

```
Cys Gln Ser Tyr Asp Pro Asn Pro Asn Pro Asn Pro Asn Pro Asp Gly
1               5                   10                  15

Gly Ser Gly Gly
            20

<210> SEQ ID NO 401
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 401

Gly Ser Asn Pro Asn Pro Asn Pro Asn Pro Ser Gly Val Val Phe
1               5                   10                  15

<210> SEQ ID NO 402
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 402

Cys Ala Ala Trp Asn Pro Asn Pro Asn Pro Asn Pro Asn Pro Asn Gly
1               5                   10                  15

Gly Ser Gly Gly
            20

<210> SEQ ID NO 403
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 403

Gly Ser Asn Pro Asn Pro Asn Pro Asn Pro Asn Pro Asn Val Phe
1               5                   10                  15

<210> SEQ ID NO 404
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 404

Cys Gln Ser Tyr Asp Gln Val Lys Leu Glu Leu Gly His Arg Ala Gly
1               5                   10                  15

Gly Ser Gly Gly
            20

<210> SEQ ID NO 405
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 405

Gly Ser Val Asn His Leu Arg Ser Glu Lys Leu Thr Gly Val Val Phe
1               5                   10                  15

<210> SEQ ID NO 406
```

```
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 406

Cys Gln Ser Val His Gln Glu Thr Lys Lys Tyr Gln Ser Ser Pro Asp
1               5                   10                  15

Gly Gly Ser Gly Gly
            20

<210> SEQ ID NO 407
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 407

Cys Gln Ser Tyr Asp Gln Val Lys Leu Glu Leu Gly His Arg Pro Asp
1               5                   10                  15

Gly Gly Ser Gly Gly
            20

<210> SEQ ID NO 408
<211> LENGTH: 15
<212> TYPE: PRT
<213> ORGANISM: artificial
<220> FEATURE:
<223> OTHER INFORMATION: C-terminal sequence (with ref aa)

<400> SEQUENCE: 408

Gly Ser Asn His Leu Arg Ser Glu Lys Leu Thr Gly Val Val Phe
1               5                   10                  15

<210> SEQ ID NO 409
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 409

Cys Gln Ser Tyr Asp Gly Phe Ile Leu Pro Ile Glu Val Tyr Pro Asp
1               5                   10                  15

Gly Gly Ser Gly Gly
            20

<210> SEQ ID NO 410
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 410

Gly Ser Tyr Ser Tyr Thr Tyr Asn Tyr Glu Trp His Val Asp Val Phe
1               5                   10                  15

<210> SEQ ID NO 411
<211> LENGTH: 16
<212> TYPE: PRT
<213> ORGANISM: artificial
<220> FEATURE:
<223> OTHER INFORMATION: C-terminal sequence (with ref aa)
```

```
<400> SEQUENCE: 411

Gly Ser Tyr Ser Tyr Thr Tyr Asn Tyr Glu Trp His Val Val Val Phe
1               5                   10                  15

<210> SEQ ID NO 412
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 412

Cys Gly Gly Ser Gly Ser Gly Ser Gly Ser Gly Ser Gly Ser Pro Asp
1               5                   10                  15

Gly Gly Ser Gly Gly
            20

<210> SEQ ID NO 413
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 413

Gly Ser Tyr Gly Ser Gly Ser Gly Ser Gly Ser Gly Ser Gly Gly Phe
1               5                   10                  15

<210> SEQ ID NO 414
<211> LENGTH: 22
<212> TYPE: PRT
<213> ORGANISM: artificial
<220> FEATURE:
<223> OTHER INFORMATION: N-terminal sequence (with ref aa)

<400> SEQUENCE: 414

Cys Gln Ser Tyr Asp Ser Ser Ala Leu Leu Lys Ser Lys Leu Arg Ala
1               5                   10                  15

Leu Leu Thr Ala Pro Arg
            20

<210> SEQ ID NO 415
<211> LENGTH: 22
<212> TYPE: PRT
<213> ORGANISM: artificial
<220> FEATURE:
<223> OTHER INFORMATION: N-terminal sequence (with ref aa)

<400> SEQUENCE: 415

Cys Gln Ser Ala Val Gln Val Lys Leu Glu Leu Gly His Arg Ala Pro
1               5                   10                  15

Asp Gly Gly Ser Gly Gly
            20

<210> SEQ ID NO 416
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 416

Gly Ser Val Asn His Leu Arg Ser Glu Lys Leu Thr Phe Asn Val Phe
1               5                   10                  15
```

<210> SEQ ID NO 417
<211> LENGTH: 22
<212> TYPE: PRT
<213> ORGANISM: artificial
<220> FEATURE:
<223> OTHER INFORMATION: N-terminal sequence (with ref aa)

<400> SEQUENCE: 417

Cys Gln Ser Tyr Asp Gln Val Lys Leu Glu Leu Gly His Arg Ala Pro
1               5                   10                  15

Asp Gly Gly Ser Gly Gly
            20

<210> SEQ ID NO 418
<211> LENGTH: 22
<212> TYPE: PRT
<213> ORGANISM: artificial
<220> FEATURE:
<223> OTHER INFORMATION: N-terminal sequence (with ref aa)

<400> SEQUENCE: 418

Cys Gln Ser Tyr Asp Gly Phe Ile Leu Pro Ile Glu Val Tyr Phe Pro
1               5                   10                  15

Asp Gly Gly Ser Gly Gly
            20

<210> SEQ ID NO 419
<211> LENGTH: 16
<212> TYPE: PRT
<213> ORGANISM: artificial
<220> FEATURE:
<223> OTHER INFORMATION: C-terminal sequence (with ref aa)

<400> SEQUENCE: 419

Gly Ser Arg Lys Val Arg Phe Asp Tyr Asp Leu Phe Gly Val Val Phe
1               5                   10                  15

<210> SEQ ID NO 420
<211> LENGTH: 22
<212> TYPE: PRT
<213> ORGANISM: artificial
<220> FEATURE:
<223> OTHER INFORMATION: N-terminal sequence (with ref aa)

<400> SEQUENCE: 420

Cys Gln Ser Tyr Val His Gln Glu Thr Lys Lys Tyr Gln Ser Ser Pro
1               5                   10                  15

Asp Gly Gly Ser Gly Gly
            20

<210> SEQ ID NO 421
<211> LENGTH: 17
<212> TYPE: PRT
<213> ORGANISM: artificial
<220> FEATURE:
<223> OTHER INFORMATION: C-terminal sequence (with ref aa)

<400> SEQUENCE: 421

Gly Ser Tyr Ser Tyr Thr Tyr Asn Tyr Glu Trp His Val Gly Val Val
1               5                   10                  15

Phe

<210> SEQ ID NO 422

```
<211> LENGTH: 23
<212> TYPE: PRT
<213> ORGANISM: artificial
<220> FEATURE:
<223> OTHER INFORMATION: N-terminal sequence (with ref aa)

<400> SEQUENCE: 422

Cys Gln Ser Tyr Asp Val His Gln Glu Thr Lys Lys Tyr Gln Ser Ser
1               5                   10                  15

Pro Asp Gly Gly Ser Gly Gly
            20

<210> SEQ ID NO 423
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 423

Gly Ser Tyr Ser Tyr Thr Tyr Asn Tyr Glu Trp His Val Ser Gly Val
1               5                   10                  15

Val Phe

<210> SEQ ID NO 424
<211> LENGTH: 24
<212> TYPE: PRT
<213> ORGANISM: artificial
<220> FEATURE:
<223> OTHER INFORMATION: N-terminal sequence (with ref aa)

<400> SEQUENCE: 424

Cys Gln Ser Tyr Asp Ala Val Gln Val Lys Leu Glu Leu Gly His Arg
1               5                   10                  15

Ala Pro Asp Gly Gly Ser Gly Gly
            20

<210> SEQ ID NO 425
<211> LENGTH: 18
<212> TYPE: PRT
<213> ORGANISM: artificial
<220> FEATURE:
<223> OTHER INFORMATION: C-terminal sequence (with ref aa)

<400> SEQUENCE: 425

Gly Ser Val Asn His Leu Arg Ser Glu Lys Leu Thr Phe Asn Gly Val
1               5                   10                  15

Val Phe

<210> SEQ ID NO 426
<211> LENGTH: 25
<212> TYPE: PRT
<213> ORGANISM: artificial
<220> FEATURE:
<223> OTHER INFORMATION: N-terminal sequence (with ref aa)

<400> SEQUENCE: 426

Cys Gln Ser Tyr Asp Ser Ser Asp Arg Ser Ala Leu Leu Lys Ser Lys
1               5                   10                  15

Leu Arg Ala Leu Leu Thr Ala Pro Arg
            20                  25

<210> SEQ ID NO 427
<211> LENGTH: 19
```

```
<212> TYPE: PRT
<213> ORGANISM: artificial
<220> FEATURE:
<223> OTHER INFORMATION: C-terminal sequence (with ref aa)

<400> SEQUENCE: 427

Gly Ser Gly Gly Ser Val Asn His Leu Arg Ser Glu Lys Leu Thr Gly
1               5                   10                  15

Val Val Phe

<210> SEQ ID NO 428
<211> LENGTH: 21
<212> TYPE: PRT
<213> ORGANISM: artificial
<220> FEATURE:
<223> OTHER INFORMATION: C-terminal sequence (with ref aa)

<400> SEQUENCE: 428

Gly Ser Asp Arg Ser Ala Leu Leu Lys Ser Lys Leu Arg Ala Leu Leu
1               5                   10                  15

Thr Ala Val Val Phe
            20

<210> SEQ ID NO 429
<211> LENGTH: 25
<212> TYPE: PRT
<213> ORGANISM: artificial
<220> FEATURE:
<223> OTHER INFORMATION: N-terminal sequence (with ref aa)

<400> SEQUENCE: 429

Cys Gln Ser Tyr Asp Ser Ser Asp Arg Ser Ala Leu Leu Lys Ser Lys
1               5                   10                  15

Leu Arg Ala Leu Leu Thr Ala Pro Glu
            20                  25

<210> SEQ ID NO 430
<211> LENGTH: 23
<212> TYPE: PRT
<213> ORGANISM: artificial
<220> FEATURE:
<223> OTHER INFORMATION: N-terminal sequence (with ref aa)

<400> SEQUENCE: 430

Cys Thr Ser Val His Gln Glu Thr Lys Lys Tyr Gln Ser Ser Pro Asp
1               5                   10                  15

Gly Gly Ser Gly Gly Ser Gly
            20

<210> SEQ ID NO 431
<211> LENGTH: 20
<212> TYPE: PRT
<213> ORGANISM: artificial
<220> FEATURE:
<223> OTHER INFORMATION: C-terminal sequence (with ref aa)

<400> SEQUENCE: 431

Gly Gly Ser Tyr Ser Tyr Thr Tyr Asn Tyr Glu Trp His Val Asp Val
1               5                   10                  15

Trp Gly Gln Gly
            20

<210> SEQ ID NO 432
<211> LENGTH: 18
```

```
<212> TYPE: PRT
<213> ORGANISM: artificial
<220> FEATURE:
<223> OTHER INFORMATION: C-terminal sequence (with ref aa)

<400> SEQUENCE: 432

Ser Tyr Ser Tyr Thr Tyr Asn Tyr Glu Trp His Val Asp Val Trp Gly
1               5                   10                  15

Gln Gly

<210> SEQ ID NO 433
<211> LENGTH: 22
<212> TYPE: PRT
<213> ORGANISM: artificial
<220> FEATURE:
<223> OTHER INFORMATION: N-terminal sequence (with ref aa)

<400> SEQUENCE: 433

Cys Thr Ser Val His Gln Glu Thr Lys Lys Tyr Gln Ser Ser Pro Asp
1               5                   10                  15

Gly Gly Ser Gly Gly Ser
            20

<210> SEQ ID NO 434
<211> LENGTH: 24
<212> TYPE: PRT
<213> ORGANISM: artificial
<220> FEATURE:
<223> OTHER INFORMATION: C-terminal sequence (with ref aa)

<400> SEQUENCE: 434

Gly Ser Gly Gly Tyr Gly Ser Tyr Ser Tyr Thr Tyr Asn Tyr Glu Trp
1               5                   10                  15

His Val Asp Val Trp Gly Gln Gly
            20

<210> SEQ ID NO 435
<211> LENGTH: 21
<212> TYPE: PRT
<213> ORGANISM: artificial
<220> FEATURE:
<223> OTHER INFORMATION: N-terminal sequence (with ref aa)

<400> SEQUENCE: 435

Cys Gln Ser Tyr Asp Gln Val Lys Leu Glu Leu Gly His Arg Ala Gly
1               5                   10                  15

Gly Ser Gly Gly Ser
            20

<210> SEQ ID NO 436
<211> LENGTH: 21
<212> TYPE: PRT
<213> ORGANISM: artificial
<220> FEATURE:
<223> OTHER INFORMATION: C-terminal sequence (with ref aa)

<400> SEQUENCE: 436

Gly Ser Gly Gly Ser Gly Ser Val Asn His Leu Arg Ser Glu Lys Leu
1               5                   10                  15

Thr Gly Val Val Phe
            20

<210> SEQ ID NO 437
<211> LENGTH: 24
```

```
<212> TYPE: PRT
<213> ORGANISM: artificial
<220> FEATURE:
<223> OTHER INFORMATION: C-terminal sequence (with ref aa)

<400> SEQUENCE: 437

Gly Ser Gly Gly Ser Gly Ser Tyr Ser Tyr Thr Tyr Asn Tyr Glu Trp
1               5                   10                  15

His Val Asp Val Trp Gly Gln Gly
            20

<210> SEQ ID NO 438
<211> LENGTH: 23
<212> TYPE: PRT
<213> ORGANISM: artificial
<220> FEATURE:
<223> OTHER INFORMATION: C-terminal sequence (with ref aa)

<400> SEQUENCE: 438

Gly Gly Gly Ser Gly Ser Tyr Ser Tyr Thr Tyr Asn Tyr Glu Trp His
1               5                   10                  15

Val Asp Val Trp Gly Gln Gly
            20

<210> SEQ ID NO 439
<211> LENGTH: 22
<212> TYPE: PRT
<213> ORGANISM: artificial
<220> FEATURE:
<223> OTHER INFORMATION: N-terminal sequence (with ref aa)

<400> SEQUENCE: 439

Cys Thr Ser Val His Gln Glu Thr Lys Lys Tyr Gln Ser Ser Pro Tyr
1               5                   10                  15

Lys Gly Ala Asn Lys Lys
            20

<210> SEQ ID NO 440
<211> LENGTH: 20
<212> TYPE: PRT
<213> ORGANISM: artificial
<220> FEATURE:
<223> OTHER INFORMATION: N-terminal sequence (with ref aa)

<400> SEQUENCE: 440

Ile Ser Gly Ser Val Val Val Thr Ser His Gln Ala Pro Gly Gly Gly
1               5                   10                  15

Ser Gly Gly Ser
            20

<210> SEQ ID NO 441
<211> LENGTH: 19
<212> TYPE: PRT
<213> ORGANISM: artificial
<220> FEATURE:
<223> OTHER INFORMATION: C-terminal sequence (with ref aa)

<400> SEQUENCE: 441

Gly Ser Gly Gly Ser Gly Glu Lys Lys Lys Leu Lys Ser Leu Ala Tyr
1               5                   10                  15

Gly Ser Thr

<210> SEQ ID NO 442
<211> LENGTH: 499
```

```
<212> TYPE: PRT
<213> ORGANISM: artificial
<220> FEATURE:
<223> OTHER INFORMATION: NP engrafted HC

<400> SEQUENCE: 442
```

| | | | | | | | | | | | | | |
|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 |
| Ala | Met | Ser | Trp | Val | Arg | Gln | Ala | Pro | Gly | Lys | Gly | Leu | Glu | Trp | Val |
| | | 35 | | | | | 40 | | | | | 45 |
| Ser | Ala | Ile | Ser | Gly | Ser | Gly | Ser | Thr | Tyr | Tyr | Ala | Asp | Ser | Val |
| 50 | | | | | 55 | | | | | 60 |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 |
| Thr | Ser | Val | His | Gln | Glu | Thr | Lys | Lys | Tyr | Gln | Ser | Ser | Pro | Asp | Gly |
| | | | 100 | | | | | 105 | | | | | 110 |
| Gly | Ser | Gly | Gly | Met | Val | Gln | Gly | Ser | Gly | Cys | Phe | Gly | Arg | Lys | Met |
| | | | 115 | | | | | 120 | | | | | 125 |
| Asp | Arg | Ile | Ser | Ser | Ser | Ser | Gly | Leu | Gly | Cys | Lys | Val | Leu | Arg | Arg |
| | | 130 | | | | | 135 | | | | | 140 |
| Gly | Ser | Tyr | Ser | Tyr | Thr | Tyr | Asn | Tyr | Glu | Trp | His | Val | Asp | Val | Trp |
| 145 | | | | | 150 | | | | | 155 | | | | | 160 |
| Gly | Gln | Gly | Thr | Leu | Val | Thr | Val | Ser | Ser | Ala | Ser | Thr | Lys | Gly | Pro |
| | | | | 165 | | | | | 170 | | | | | 175 |
| Ser | Val | Phe | Pro | Leu | Ala | Pro | Ser | Ser | Lys | Ser | Thr | Ser | Gly | Gly | Thr |
| | | | 180 | | | | | 185 | | | | | 190 |
| Ala | Ala | Leu | Gly | Cys | Leu | Val | Lys | Asp | Tyr | Phe | Pro | Glu | Pro | Val | Thr |
| | | | 195 | | | | | 200 | | | | | 205 |
| Val | Ser | Trp | Asn | Ser | Gly | Ala | Leu | Thr | Ser | Gly | Val | His | Thr | Phe | Pro |
| | 210 | | | | | 215 | | | | | 220 |
| Ala | Val | Leu | Gln | Ser | Ser | Gly | Leu | Tyr | Ser | Leu | Ser | Ser | Val | Val | Thr |
| 225 | | | | | 230 | | | | | 235 | | | | | 240 |
| Val | Pro | Ser | Ser | Ser | Leu | Gly | Thr | Gln | Thr | Tyr | Ile | Cys | Asn | Val | Asn |
| | | | | 245 | | | | | 250 | | | | | 255 |
| His | Lys | Pro | Ser | Asn | Thr | Lys | Val | Asp | Lys | Lys | Val | Glu | Pro | Lys | Ser |
| | | | 260 | | | | | 265 | | | | | 270 |
| Cys | Asp | Lys | Thr | His | Thr | Cys | Pro | Pro | Cys | Pro | Ala | Pro | Glu | Leu | Leu |
| | | 275 | | | | | 280 | | | | | 285 |
| Gly | Gly | Pro | Ser | Val | Phe | Leu | Phe | Pro | Pro | Lys | Pro | Lys | Asp | Thr | Leu |
| | 290 | | | | | 295 | | | | | 300 |
| Met | Ile | Ser | Arg | Thr | Pro | Glu | Val | Thr | Cys | Val | Val | Val | Asp | Val | Ser |
| 305 | | | | | 310 | | | | | 315 | | | | | 320 |
| His | Glu | Asp | Pro | Glu | Val | Lys | Phe | Asn | Trp | Tyr | Val | Asp | Gly | Val | Glu |
| | | | | 325 | | | | | 330 | | | | | 335 |
| Val | His | Asn | Ala | Lys | Thr | Lys | Pro | Arg | Glu | Glu | Gln | Tyr | Asn | Ser | Thr |
| | | | 340 | | | | | 345 | | | | | 350 |
| Tyr | Arg | Val | Val | Ser | Val | Leu | Thr | Val | Leu | His | Gln | Asp | Trp | Leu | Asn |
| | | 355 | | | | | 360 | | | | | 365 |
| Gly | Lys | Glu | Tyr | Lys | Cys | Lys | Val | Ser | Asn | Lys | Ala | Leu | Pro | Ala | Pro |
| 370 | | | | | 375 | | | | | 380 |

```
Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 443
<211> LENGTH: 500
<212> TYPE: PRT
<213> ORGANISM: artificial
<220> FEATURE:
<223> OTHER INFORMATION: NP engrafted HC

<400> SEQUENCE: 443

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Tr

```
                        245                 250                 255
Asn His Lys Pro Ser Asn Thr Lys Val Asp Lys Val Glu Pro Lys
                260                 265                 270

Ser Cys Asp Lys Thr His Thr Cys Pro Pro Cys Pro Ala Pro Glu Leu
            275                 280                 285

Leu Gly Gly Pro Ser Val Phe Leu Phe Pro Pro Lys Pro Lys Asp Thr
        290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
            325                 330                 335

Glu Val His Asn Ala Lys Thr Lys Pro Arg Glu Glu Gln Tyr Asn Ser
        340                 345                 350

Thr Tyr Arg Val Val Ser Val Leu Thr Val Leu His Gln Asp Trp Leu
    355                 360                 365

Asn Gly Lys Glu Tyr Lys Cys Lys Val Ser Asn Lys Ala Leu Pro Ala
370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Lys Asn Gln
            405                 410                 415

Val Ser Leu Thr Cys Leu Val Lys Gly Phe Tyr Pro Ser Asp Ile Ala
        420                 425                 430

Val Glu Trp Glu Ser Asn Gly Gln Pro Glu Asn Asn Tyr Lys Thr Thr
    435                 440                 445

Pro Pro Val Leu Asp Ser Asp Gly Ser Phe Phe Leu Tyr Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
            485                 490                 495

Leu Ser Pro Gly
            500

<210> SEQ ID NO 444
<211> LENGTH: 499
<212> TYPE: PRT
<213> ORGANISM: artificial
<220> FEATURE:
<223> OTHER INFORMATION: NP engrafted HC

<400> SEQUENCE: 444

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser

```
            100                 105                 110
Gly Ser Gly Gly Met Val Gln Gly Ser Gly Cys Phe Gly Arg Lys Met
        115                 120                 125
Asp Arg Ile Ser Ser Ser Gly Leu Gly Cys Lys Val Leu Arg Arg
    130                 135                 140
Gly Ser Tyr Ser Tyr Thr Tyr Asn Tyr Ala Glu Tyr Phe Gln His Trp
145                 150                 155                 160
Gly Gln Gly Thr Leu Val Thr Val Ser Ala Ser Thr Lys Gly Pro
                165                 170                 175
Ser Val Phe Pro Leu Ala Pro Ser Ser Lys Ser Thr Ser Gly Gly Thr
                180                 185                 190
Ala Ala Leu Gly Cys Leu Val Lys Asp Tyr Phe Pro Glu Pro Val Thr
            195                 200                 205
Val Ser Trp Asn Ser Gly Ala Leu Thr Ser Gly Val His Thr Phe Pro
    210                 215                 220
Ala Val Leu Gln Ser Ser Gly Leu Tyr Ser Leu Ser Ser Val Val Thr
225                 230                 235                 240
Val Pro Ser Ser Ser Leu Gly Thr Gln Thr Tyr Ile Cys Asn Val Asn
                245                 250                 255
His Lys Pro Ser Asn Thr Lys Val Asp Lys Lys Val Glu Pro Lys Ser
                260                 265                 270
Cys Asp Lys Thr His Thr Cys Pro Pro Cys Pro Ala Pro Glu Leu Leu
            275                 280                 285
Gly Gly Pro Ser Val Phe Leu Phe Pro Pro Lys Pro Lys Asp Thr Leu
    290                 295                 300
Met Ile Ser Arg Thr Pro Glu Val Thr Cys Val Val Val Asp Val Ser
305                 310                 315                 320
His Glu Asp Pro Glu Val Lys Phe Asn Trp Tyr Val Asp Gly Val Glu
                325                 330                 335
Val His Asn Ala Lys Thr Lys Pro Arg Glu Glu Gln Tyr Asn Ser Thr
                340                 345                 350
Tyr Arg Val Val Ser Val Leu Thr Val Leu His Gln Asp Trp Leu Asn
            355                 360                 365
Gly Lys Glu Tyr Lys Cys Lys Val Ser Asn Lys Ala Leu Pro Ala Pro
    370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Arg Asp Glu Leu Thr Lys Asn Gln Val
                405                 410                 415
Ser Leu Thr Cys Leu Val Lys Gly Phe Tyr Pro Ser Asp Ile Ala Val
                420                 425                 430
Glu Trp Glu Ser Asn Gly Gln Pro Glu Asn Asn Tyr Lys Thr Thr Pro
            435                 440                 445
Pro Val Leu Asp Ser Asp Gly Ser Phe Phe Leu Tyr Ser Lys Leu Thr
    450                 455                 460
Val Asp Lys Ser Arg Trp Gln Gln Gly Asn Val Phe Ser Cys Ser Val
465                 470                 475                 480
Met His Glu Ala Leu His Asn His Tyr Thr Gln Lys Ser Leu Ser Leu
                485                 490                 495
Ser Pro Gly

<210> SEQ ID NO 445
<211> LENGTH: 499
```

```
<212> TYPE: PRT
<213> ORGANISM: artificial
<220> FEATURE:
<223> OTHER INFORMATION: NP engrafted HC

<400> SEQUENCE: 445
```

| | | | | | | | | | | | | | |
|---|---|---|---|---|---|---|---|---|---|---|---|---|---|
| Glu | Val | Gln | Leu | Leu | Glu | Ser | Gly | Gly | Gly | Leu | Val | Gln | Pro | Gly | Gly |
| 1 | | | | 5 | | | | | 10 | | | | | 15 |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
| | | 35 | | | | | 40 | | | | | 45 | | | |

| Ser | Ala | Ile | Ser | Gly | Ser | Gly | Ser | Thr | Tyr | Tyr | Ala | Asp | Ser | Val |
| 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
| 65 | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |

| Thr | Ser | Val | His | Gln | Glu | Thr | Lys | Lys | Tyr | Gln | Ser | Ser | Pro | Tyr | Lys |
| | | | 100 | | | | | 105 | | | | | 110 | | |

| Gly | Ala | Asn | Lys | Lys | Gly | Leu | Ser | Lys | Gly | Cys | Phe | Gly | Leu | Lys | Leu |
| | | | 115 | | | | | 120 | | | | | 125 | | |

| Asp | Arg | Ile | Gly | Ser | Met | Ser | Gly | Leu | Gly | Cys | Gly | Ser | Gly | Gly | Ser |
| | 130 | | | | | 135 | | | | | 140 | | | | |

| Gly | Ser | Tyr | Ser | Tyr | Thr | Tyr | Asn | Tyr | Glu | Trp | His | Val | Asp | Val | Trp |
| 145 | | | | | 150 | | | | | 155 | | | | | 160 |

| Gly | Gln | Gly | Thr | Leu | Val | Thr | Val | Ser | Ser | Ala | Ser | Thr | Lys | Gly | Pro |
| | | | | 165 | | | | | 170 | | | | | 175 | |

| Ser | Val | Phe | Pro | Leu | Ala | Pro | Ser | Ser | Lys | Ser | Thr | Ser | Gly | Gly | Thr |
| | | | 180 | | | | | 185 | | | | | 190 | | |

| Ala | Ala | Leu | Gly | Cys | Leu | Val | Lys | Asp | Tyr | Phe | Pro | Glu | Pro | Val | Thr |
| | | 195 | | | | | 200 | | | | | 205 | | | |

| Val | Ser | Trp | Asn | Ser | Gly | Ala | Leu | Thr | Ser | Gly | Val | His | Thr | Phe | Pro |
| | 210 | | | | | 215 | | | | | 220 | | | | |

| Ala | Val | Leu | Gln | Ser | Ser | Gly | Leu | Tyr | Ser | Leu | Ser | Ser | Val | Val | Thr |
| 225 | | | | | 230 | | | | | 235 | | | | | 240 |

| Val | Pro | Ser | Ser | Ser | Leu | Gly | Thr | Gln | Thr | Tyr | Ile | Cys | Asn | Val | Asn |
| | | | | 245 | | | | | 250 | | | | | 255 | |

| His | Lys | Pro | Ser | Asn | Thr | Lys | Val | Asp | Lys | Lys | Val | Glu | Pro | Lys | Ser |
| | | | 260 | | | | | 265 | | | | | 270 | | |

| Cys | Asp | Lys | Thr | His | Thr | Cys | Pro | Pro | Cys | Pro | Ala | Pro | Glu | Leu | Leu |
| | | 275 | | | | | 280 | | | | | 285 | | | |

| Gly | Gly | Pro | Ser | Val | Phe | Leu | Phe | Pro | Pro | Lys | Pro | Lys | Asp | Thr | Leu |
| | 290 | | | | | 295 | | | | | 300 | | | | |

| Met | Ile | Ser | Arg | Thr | Pro | Glu | Val | Thr | Cys | Val | Val | Val | Asp | Val | Ser |
| 305 | | | | | 310 | | | | | 315 | | | | | 320 |

| His | Glu | Asp | Pro | Glu | Val | Lys | Phe | Asn | Trp | Tyr | Val | Asp | Gly | Val | Glu |
| | | | | 325 | | | | | 330 | | | | | 335 | |

| Val | His | Asn | Ala | Lys | Thr | Lys | Pro | Arg | Glu | Glu | Gln | Tyr | Asn | Ser | Thr |
| | | | 340 | | | | | 345 | | | | | 350 | | |

| Tyr | Arg | Val | Val | Ser | Val | Leu | Thr | Val | Leu | His | Gln | Asp | Trp | Leu | Asn |
| | | 355 | | | | | 360 | | | | | 365 | | | |

| Gly | Lys | Glu | Tyr | Lys | Cys | Lys | Val | Ser | Asn | Lys | Ala | Leu | Pro | Ala | Pro |
| | 370 | | | | | 375 | | | | | 380 | | | | |

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 446
<211> LENGTH: 499
<212> TYPE: PRT
<213> ORGANISM: artificial
<220> FEATURE:
<223> OTHER INFORMATION: NP engrafted HC

<400> SEQUENCE: 446

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ser Val His Gln Glu Thr Lys Lys Tyr Gln Ser Ser Pro Asp Gly
            100                 105                 110

Gly Ser Gly Gly Ser Gly Leu Ser Lys Gly Cys Phe Gly Leu Lys Leu
        115                 120                 125

Asp Arg Ile Gly Ser Met Ser Gly Leu Gly Cys Gly Ser Gly Gly Tyr
    130                 135                 140

Gly Ser Tyr Ser Tyr Thr Tyr Asn Tyr Glu Trp His Val Asp Val Trp
145                 150                 155                 160

Gly Gln Gly Thr Leu Val Thr Val Ser Ser Ala Ser Thr Lys Gly Pro
                165                 170                 175

Ser Val Phe Pro Leu Ala Pro Ser Ser Lys Ser Thr Ser Gly Gly Thr
180 185 190

Ala Ala Leu Gly Cys Leu Val Lys Asp Tyr Phe Pro Glu Pro Val Thr
195 200 205

Val Ser Trp Asn Ser Gly Ala Leu Thr Ser Gly Val His Thr Phe Pro
210 215 220

Ala Val Leu Gln Ser Ser Gly Leu Tyr Ser Leu Ser Ser Val Val Thr
225 230 235 240

Val Pro Ser Ser Ser Leu Gly Thr Gln Thr Tyr Ile Cys Asn Val Asn

```
                   245                 250                 255
His Lys Pro Ser Asn Thr Lys Val Asp Lys Val Glu Pro Lys Ser
                260                 265                 270

Cys Asp Lys Thr His Thr Cys Pro Pro Cys Pro Ala Pro Glu Leu Leu
            275                 280                 285

Gly Gly Pro Ser Val Phe Leu Phe Pro Pro Lys Pro Lys Asp Thr Leu
        290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Arg Asp Glu Leu Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 447
<211> LENGTH: 217
<212> TYPE: PRT
<213> ORGANISM: Homo sapiens

<400> SEQUENCE: 447

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Asp Gly Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
```

```
                    115                 120                 125
Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
                195                 200                 205

Lys Thr Val Ala Pro Thr Glu Cys Ser
            210                 215

<210> SEQ ID NO 448
<211> LENGTH: 20
<212> TYPE: PRT
<213> ORGANISM: Artificial Sequence
<220> FEATURE:
<223> OTHER INFORMATION: Synthetic Construct

<400> SEQUENCE: 448

Ile Ser Gly Ser Gly Ser Gly Ser Gly Ser Ser Pro Asp Gly
1               5                   10                  15

Gly Ser Gly Gly
            20

<210> SEQ ID NO 449
<211> LENGTH: 24
<212> TYPE: PRT
<213> ORGANISM: Artificial Sequence
<220> FEATURE:
<223> OTHER INFORMATION: Synthetic Construct

<400> SEQUENCE: 449

Ser Gly Tyr Ser Phe Gly Ser Gly Ser Gly Ser Gly Ser Gly
1               5                   10                  15

Ser Pro Asp Gly Gly Ser Gly Gly
            20

<210> SEQ ID NO 450
<211> LENGTH: 15
<212> TYPE: PRT
<213> ORGANISM: Artificial Sequence
<220> FEATURE:
<223> OTHER INFORMATION: Synthetic Construct

<400> SEQUENCE: 450

Gly Ser Tyr Gly Ser Gly Ser Gly Ser Gly Ser Gly Ile
1               5                   10                  15

<210> SEQ ID NO 451
<211> LENGTH: 11
<212> TYPE: PRT
<213> ORGANISM: Artificial Sequence
<220> FEATURE:
<223> OTHER INFORMATION: Synthetic Construct

<400> SEQUENCE: 451

Lys Leu Thr Gly Ala Glu Tyr Phe Gln His Trp
1               5                   10
```

```
<210> SEQ ID NO 452
<211> LENGTH: 11
<212> TYPE: PRT
<213> ORGANISM: Artificial Sequence
<220> FEATURE:
<223> OTHER INFORMATION: Synthetic Construct

<400> SEQUENCE: 452

Lys Leu Thr Gly Ala Glu Tyr Phe Gln His Trp
1               5                   10

<210> SEQ ID NO 453
<211> LENGTH: 11
<212> TYPE: PRT
<213> ORGANISM: Artificial Sequence
<220> FEATURE:
<223> OTHER INFORMATION: Synthetic Construct

<400> SEQUENCE: 453

Lys Leu Thr Gly Ala Glu Tyr Phe Gln His Trp
1               5                   10

<210> SEQ ID NO 454
<211> LENGTH: 13
<212> TYPE: PRT
<213> ORGANISM: Artificial Sequence
<220> FEATURE:
<223> OTHER INFORMATION: Synthetic Construct

<400> SEQUENCE: 454

Lys Asp Tyr Gly Asp Tyr Ala Glu Tyr Phe Gln His Trp
1               5                   10

<210> SEQ ID NO 455
<211> LENGTH: 11
<212> TYPE: PRT
<213> ORGANISM: Artificial Sequence
<220> FEATURE:
<223> OTHER INFORMATION: Synthetic Construct

<400> SEQUENCE: 455

Lys Leu Thr Gly Ala Glu Tyr Phe Gln His Trp
1               5                   10

<210> SEQ ID NO 456
<211> LENGTH: 11
<212> TYPE: PRT
<213> ORGANISM: Artificial Sequence
<220> FEATURE:
<223> OTHER INFORMATION: Synthetic Construct

<400> SEQUENCE: 456

Lys Leu Thr Gly Ala Glu Tyr Phe Gln His Trp
1               5                   10

<210> SEQ ID NO 457
<211> LENGTH: 18
<212> TYPE: PRT
<213> ORGANISM: Artificial Sequence
<220> FEATURE:
<223> OTHER INFORMATION: Synthetic Construct

<400> SEQUENCE: 457

Lys Val Leu Arg Phe Leu Glu Trp Leu Leu Tyr Ala Glu Tyr Phe Gln
1               5                   10                  15

His Trp
```

<210> SEQ ID NO 458
<211> LENGTH: 13
<212> TYPE: PRT
<213> ORGANISM: Artificial Sequence
<220> FEATURE:
<223> OTHER INFORMATION: Synthetic Construct

<400> SEQUENCE: 458

Lys Val Gln Leu Glu Arg Ala Glu Tyr Phe Gln His Trp
1               5                   10

<210> SEQ ID NO 459
<211> LENGTH: 13
<212> TYPE: PRT
<213> ORGANISM: Artificial Sequence
<220> FEATURE:
<223> OTHER INFORMATION: Synthetic Construct

<400> SEQUENCE: 459

Lys Tyr Asn Arg Asn His Ala Glu Tyr Phe Gln His Trp
1               5                   10

<210> SEQ ID NO 460
<211> LENGTH: 13
<212> TYPE: PRT
<213> ORGANISM: Artificial Sequence
<220> FEATURE:
<223> OTHER INFORMATION: Synthetic Construct

<400> SEQUENCE: 460

Lys Tyr Asn Trp Asn Asp Ala Glu Tyr Phe Gln His Trp
1               5                   10

<210> SEQ ID NO 461
<211> LENGTH: 9
<212> TYPE: PRT
<213> ORGANISM: Artificial Sequence
<220> FEATURE:
<223> OTHER INFORMATION: Synthetic Construct

<400> SEQUENCE: 461

Arg Gly Ala Thr Phe Ala Leu Asp Trp
1               5

<210> SEQ ID NO 462
<211> LENGTH: 8
<212> TYPE: PRT
<213> ORGANISM: Artificial Sequence
<220> FEATURE:
<223> OTHER INFORMATION: Synthetic Construct

<400> SEQUENCE: 462

Arg Gly Arg Leu Pro Asp Val Trp
1               5